(12) United States Patent
Narine et al.

(10) Patent No.: US 11,160,280 B2
(45) Date of Patent: Nov. 2, 2021

(54) PESTICIAL COMPOUNDS

(71) Applicant: BASF SE, Ludwigshafen am Rhein (DE)

(72) Inventors: Arun Narine, Ludwigshafen (DE); Ashokkumar Adisechan, Navi Mumbai (IN); Devendra Vyas, Navi Mumbai (IN); Gopal Krishna Datta, Goettingen (DE); Ramakrishnan Vallinayagam, Mumbai (IN); Rupsha Chaudhuri, Navi Mumbai (IN); Sunderraman Sambasivan, Navi Mumbai (IN)

(73) Assignee: BASF SE, Ludwigshafen (DE)

(*) Notice: Subject to any disclaimer, the term of this patent is extended or adjusted under 35 U.S.C. 154(b) by 0 days.

(21) Appl. No.: 16/498,623

(22) PCT Filed: Mar. 19, 2018

(86) PCT No.: PCT/EP2018/056787
§ 371 (c)(1),
(2) Date: Sep. 27, 2019

(87) PCT Pub. No.: WO2018/177781
PCT Pub. Date: Oct. 4, 2018

(65) Prior Publication Data
US 2020/0029566 A1    Jan. 30, 2020

(30) Foreign Application Priority Data
Mar. 28, 2017 (EP) ..................................... 17163239

(51) Int. Cl.
| | | |
|---|---|---|
| *A01N 43/56* | (2006.01) | |
| *A01N 43/76* | (2006.01) | |
| *A01N 43/80* | (2006.01) | |
| *A01N 43/90* | (2006.01) | |
| *A01N 47/18* | (2006.01) | |
| *A01N 47/24* | (2006.01) | |
| *C07D 231/24* | (2006.01) | |
| *C07D 487/04* | (2006.01) | |
| *C07D 498/04* | (2006.01) | |
| *C07D 231/56* | (2006.01) | |

(52) U.S. Cl.
CPC .............. *A01N 43/56* (2013.01); *A01N 43/76* (2013.01); *A01N 43/80* (2013.01); *A01N 43/90* (2013.01); *A01N 47/18* (2013.01); *A01N 47/24* (2013.01); *C07D 231/56* (2013.01); *C07D 487/04* (2013.01); *C07D 498/04* (2013.01)

(58) Field of Classification Search
None
See application file for complete search history.

(56) References Cited

U.S. PATENT DOCUMENTS

2019/0104738 A1    4/2019 Narine et al.

FOREIGN PATENT DOCUMENTS

| CN | 102134234 | * | 7/2011 |
|---|---|---|---|
| CN | 102134234 A | * | 7/2011 |
| EP | 0726266 A1 | | 8/1996 |
| WO | WO-2014/052563 A2 | | 4/2014 |
| WO | WO-2014/052566 A1 | | 4/2014 |
| WO | WO-2016/116445 A1 | | 7/2016 |
| WO | WO-2016/156076 A1 | | 10/2016 |
| WO | WO-2017/167832 A1 | | 10/2017 |
| WO | WO-2018/108671 A1 | | 6/2018 |
| WO | WO-2018/177781 A1 | | 10/2018 |

OTHER PUBLICATIONS

European Search Report for EP Application No. 17163239.1, dated Jul. 12, 2017, 3 pages.
International Application No. PCT/EP2018/056787, International Search Report and Written Opinion, dated Jul. 10, 2018.

* cited by examiner

*Primary Examiner* — Alton N Pryor
(74) *Attorney, Agent, or Firm* — Marshall, Gerstein & Borun LLP

(57) ABSTRACT

The present invention relates to the compounds of formula (I), and the N-oxides, stereoisomers, tautomers and agriculturally or veterinarily acceptable salts thereof wherein the variables are defined according to the description,

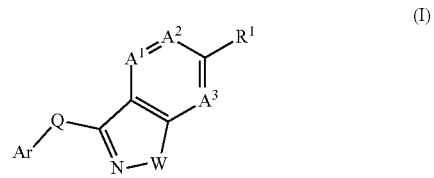

The compounds of formula (I), as well as the N-oxides, stereoisomers, tautomers and agriculturally or veterinarily acceptable salts thereof, are useful for combating or controlling invertebrate pests, in particular arthropod pests and nematodes. The invention also relates to a method for controlling invertebrate pests by using these compounds and to plant propagation material and to an agricultural and a veterinary composition comprising said compounds.

20 Claims, No Drawings

PESTICIAL COMPOUNDS

This application is a National Stage application of International Application No. PCT/EP2018/056787 filed Mar. 19, 2018. This application also claims priority under 35 U.S.C. § 119 to European Patent Application No. 17163239.1, filed Mar. 28, 2017.

Invertebrate pests and in particular insects, arachnids and nematodes destroy growing and harvested crops and attack wooden dwelling and commercial structures, thereby causing large economic loss to the food supply and to property. Accordingly, there is an ongoing need for new agents for combating invertebrate pests.

Carbamoylated and thiocarbamoylated oxime derivatives are known for pesticidal use, for example, in patent publications WO 2016/156076, semi-carbazones and thiosemicarbazones derivatives are known for pesticidal use in patent publication WO 2016/116445.

Due to the ability of target pests to develop resistance to pesticidally-active agents, there is an ongoing need to identify further compounds, which are suitable for combating invertebrate pests such as insects, arachnids and nematodes. Furthermore, there is a need for new compounds having a high pesticidal activity and showing a broad activity spectrum against a large number of different invertebrate pests, especially against difficult to control insects, arachnids and nematodes.

It is therefore an object of the present invention to identify and provide compounds, which exhibit a high pesticidal activity and have a broad activity spectrum against invertebrate pests.

It has been found that these objects can be achieved by substituted bicyclic compounds of formula I, as depicted and defined below, including their stereoisomers, their salts, in particular their agriculturally or veterinarily acceptable salts, their tautomers and their N-oxides.

In a first aspect, the present invention relates to the compounds of formula I,

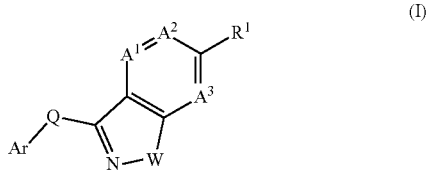

(I)

wherein $A^1$ is N or $CR^A$;
$A^2$ is N or $CR^B$;
$A^3$ is N or $CR^{B1}$;
W is O, $S(=O)_m$, or $NR^6$;
$R^A$, $R^B$ and $R^{B1}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, C(=O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(=O)—$NR^bR^c$, C(=O)—$R^d$, $SO_2NR^bR^c$, or $S(=O)_mR^e$, phenyl, phenoxy, phenylcarbonyl, phenylthio, or —$CH_2$-phenyl, wherein the phenyl rings are unsubstituted or substituted with $R^f$;

Q is —$C(R^4R^5)$—O—, —C(=O)—O—, —$S(=O)_m$—C($R^7R^8$)—, —$N(R^2)$—$S(=O)_m$—, —$N(R^2)$—C($R^9R^{10}$)—, —C(=O)C($R^{19}R^{20}$)—, —$N(R^2)$—C(=O)—, —C($R^{13}R^{14}$)—C($R^{15}R^{16}$)—, or —C($R^{17}$)=C($R^{18}$)—; wherein Ar is bound to either side of Q;

m is 0, 1, or 2;

$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

$R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, or —$CH_2$-phenyl, wherein the phenyl rings are unsubstituted or substituted with $R^f$;

$R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, $S(=O)_mR^e$, phenyl, —$CH_2$—C(=O)—$OR^a$, or —$CH_2$-phenyl, wherein the phenyl rings are unsubstituted or substituted with $R^f$;

Ar is phenyl or 5- or 6-membered hetaryl, which are unsubstituted or substituted with $R^{Ar}$, wherein $R^{Ar}$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, C(=O)—$NR^bR^c$, C(=O)—$R^d$, $SO_2NR^bR^c$, or $S(=O)_mR^e$, phenyl, phenoxy, phenylcarbonyl, phenylthio or —$CH_2$-phenyl, wherein phenyl rings are unsubstituted or substituted with $R^f$;

$R^1$ is a moiety of formula Y—Z-T-$R^{11}$ or Y—Z-T-$R^{12}$; wherein

Y is —$CR^{ya}$=N—, wherein the N is bound to Z;
—$NR^{yc}$—C(=O)—, wherein C(=O) is bound to Z; or
—$NR^{yc}$—C(=S)—, wherein C(=S) is bound to Z;

Z is a single bond;
—$NR^{zc}$—C(=O)—, wherein C(=O) is bound to T;
—$NR^{zc}$—C(=S)—, wherein C(=S) is bound to T;
—N=C(S—$R^{za}$)—, wherein T is bound to the carbon atom;

—O—C(=O)—, wherein T is bound to the carbon atom, or

—$NR^{zc}$—C(S—$R^{za}$)=, wherein T is bound to the carbon atom;

T is O, N or N—$R^T$;

$R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C_1$-$C_6$-alkylene-$NR^bR^c$, $C_1$-$C_6$-alkylene-CN, C(=O)—$NR^bR^c$, C(=O)—$R^d$, aryl, aryl-carbonyl, aryl-$C_1$-$C_4$-alkyl, aryloxy-$C_1$-$C_4$-alkyl, hetaryl, carbonyl-hetaryl, hetaryl-$C_1$-$C_4$-alkyl or hetaryloxy-$C_1$-$C_4$-alkyl, wherein the phenyl rings are unsubstituted or substituted with $R^g$ and wherein the hetaryl is a 5- or 6-membered monocyclic hetaryl or a 8-, 9- or 10-membered bicyclic hetaryl;

$R^{12}$ is a radical of the formula $A^1$;

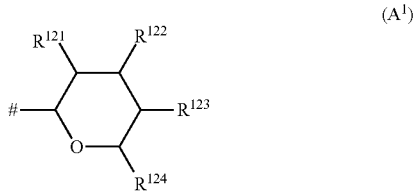

wherein # indicates the point of attachment to T;

$R^{121}$, $R^{122}$, $R^{123}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonlyoxy, $C_1$-$C_6$-alkenylcarbonlyoxy, $C_3$-$C_6$-cycloalkylcarbonlyoxy, wherein the alkyl, alkoxy, alkenyl, alkenyloxy, alkynyl, alkynyloxy and cycloalkyl moieties are unsubstituted or substituted with halogen, or $NR^bR^c$, or one of $R^{121}$, $R^{122}$, $R^{123}$ may also be oxo;

$R^{124}$ is H, $C_1$-$C_6$-alkyl, $C_1$-$C_6$-alkoxy-$C_1$-$C_4$-alkyl, $C_1$-$C_6$-alkoxy, or $C_2$-$C_6$-alkenyloxy, wherein the alkyl, alkoxy, alkenyl and alkenyloxy moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen,
C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, S(=O)$_mR^e$, phenyl, or —$CH_2$-phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, S(=O)$_mR^e$, phenyl, or —$CH_2$-phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C=N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, $C_1$-$C_4$-alkyl-$C_3$-$C_6$-cycloalkyl, wherein the alkyl, alkoxy, alkenyl, alkynyl, cycloalkyl and cycloalkoxy moieties are unsubstituted or substituted with halogen,
$C_1$-$C_6$-alkylene-$NR^bR^c$, $C_1$-$C_6$-alkylene-CN, C(=O)—$NR^bR^c$, C(=O)—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C=N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$ and $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
$C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, wherein the alkyl, cycloalkyl moieties are unsubstituted or substituted with halogen,
phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen,
C(=O)—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-NR$^b$R$^c$, C(=O)—NR$^b$R$^c$, C(=O)—R$^d$, SO$_2$NR$^b$R$^c$, or S(=O)$_m$R$^e$;

R$^g$ is halogen, N$_3$, OH, CN, NO$_2$, —SCN, —SF$_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(=O)—OR$^a$, NR$^b$R$^c$, $C_1$-$C_6$-alkylene-NR$^b$R$^c$, O—$C_1$-$C_6$-alkylene-NR$^b$R$^c$, $C_1$-$C_6$-alkylene-CN, NH—$C_1$-$C_6$-alkylene-NR$^b$R$^c$, C(=O)—NR$^b$R$^c$, C(=O)—R$^d$, SO$_2$NR$^b$R$^c$, or S(=O)$_m$R$^e$;

R$^h$ is halogen, OH, $C_1$-$C_6$-alkyl, $C_3$-$C_6$-cycloalkyl, or CN; with a proviso that when Z is a single bond, R$^T$ is other than H;

and the N-oxides, stereoisomers, tautomers and agriculturally or veterinarily acceptable salts thereof.

Moreover, the present invention also relates to processes and intermediates for preparing compounds of formula I and to active compound combinations comprising them. Moreover, the present invention relates to agricultural or veterinary compositions comprising the compounds of formula I, and to the use of the compounds of formula I or compositions comprising them for combating or controlling invertebrate pests and/or for protecting crops, plants, plant propagation material and/or growing plants from attack and/or infestation by invertebrate pests. The present invention also relates to methods of applying the compounds of formula I. Furthermore, the present invention relates to seed comprising compounds of formula I. Wherein the compounds of formula I includes N-oxides, stereoisomers, tautomers and agriculturally or veterinarily acceptable salts thereof.

General Procedure:

With due modification of the starting compounds, the compounds of formula I can be prepared by procedures as given in below schemes.

The compounds of the formula (I) can be prepared by methods of organic chemistry, e.g., by the methods described herein after in schemes 1 to 26 and in the synthesis description of the examples. In the schemes 1 to 26, the radicals Ar, A$^1$, A$^2$, A$^3$ and R$^1$, R$^2$, R$^4$, R$^5$, R$^6$, R$^7$, R$^8$, R$^9$, R$^{10}$, R$^{ya}$, R$^{zc}$, R$^{yc}$, R$^{11}$, R$^{12}$, R$^{13}$, R$^{14}$, R$^{15}$, R$^{16}$, R$^{17}$, R$^{18}$, R$^{19}$ and R$^{20}$ are as defined above for formula (1), unless otherwise specified.

Compounds of formula (I), wherein Z is a single bond or —NR$^{zc}$—C(=S)— or —NR$^{zc}$—C(=O)— and T is O, N or N—R$^T$, are the compounds of formula (Ia) and can be prepared by analogy to the methods described in WO 2011/017504 or WO 2015/007682 or methods described in Scheme 1.

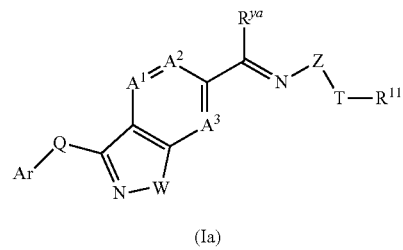

(Ia)

In one embodiment of Scheme 1, an aldehyde or ketone of the formula (II) is reacted with a compound of formula (E1) wherein Z is —NR$^{zc}$—C(=S)— or —NR$^{zc}$—C(=O)— and T is N, in the presence or in the absence of a solvent. Suitable solvents are polar protic solvents. If the reaction is performed in the absence of a solvent, the compound of the formula (E1) usually also act as solvent. Compounds of the formula (E1) are commercially available or can be prepared using organic reactions analogy to method as described in March's Advanced Organic Chemistry 6th edition, Michael B. Smith and Jerry March.

According to another embodiment of Scheme 1, an aldehyde or ketone compound of the formula (II) is first reacted with a hydrazine of the formula R$^{zc}$NHNH$_2$ followed by the reaction with an isocyanate of the formula R$^{11}$—NCO or with an isothiocyanate R$^{11}$—NCS to yield a compound of the formula (Ia), wherein Z is —N(R$^{zc}$)—C(=O) or —N(R$^{zc}$)—C(=S) and T is N.

According to another embodiment of Scheme 1, an aldehyde or ketone compound of the formula (II) is first reacted with a hydroxylamine followed by the reaction with a compound R$^{12}$-L, where L is a suitable leaving group, such as halogen or activated OH. Thereby, a compound of the formula (Ia) will result, wherein Z is a single bond and T is O.

According to another embodiment of the above reaction, an aldehyde or ketone compound of formula (II) is first reacted with a hydroxylamine followed by reaction with an isocyanate of the formula R$^{11}$—NCO or with an isothiocyanate R$^{11}$—NCS to yield a compound of the formula (Ia), wherein Z is —O—C(=O)— or —O—C(=S)— and T is N.

Compounds of formula (Ib) wherein Z is —NR$^{zc}$—C(=S)— or —NR$^{zc}$—C(=O)—, wherein C(=S) or C(=O) is bound to T and T is O, N or N—R$^T$, can be prepared by analogy to the method described in Synthesis, 2010, 2990-296 or as shown in Scheme 2.

Scheme 1

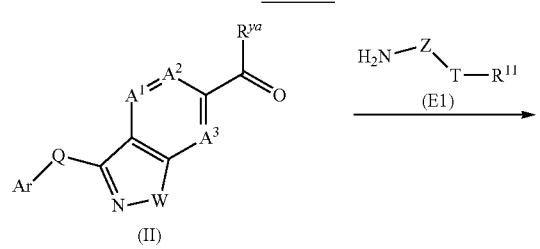

Scheme 2

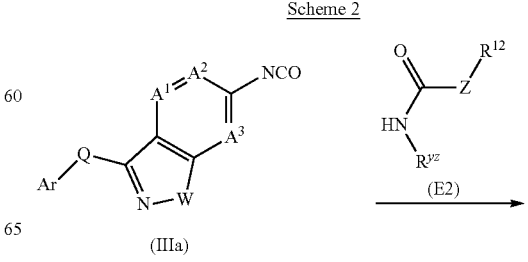

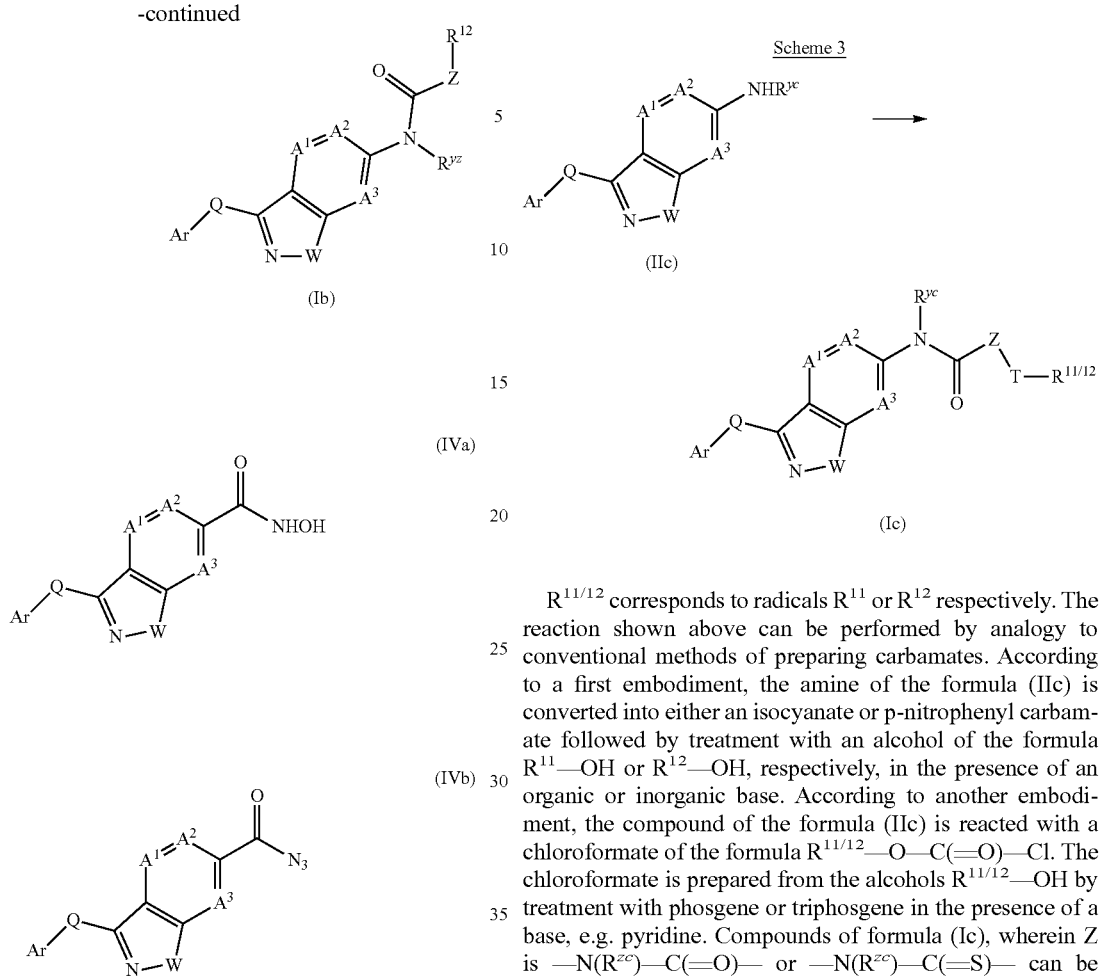

According to the method depicted in scheme 2, an isocyanate compound of the formula (IIIa) is reacted with the compound of formula (E2) by methods of isocyanate chemistry. The isocyanate of the formula (IIIa) can be obtained e.g. via Lossen rearrangement of the corresponding hydroxamic acid (IVa). The hydroxamic acid (IVa) is reacted with 1-propanephosphonic acid cyclic anhydride (T3P) in the presence of a base. The base is preferably N-methylmorpholine. The isocyanate of the formula (IIIa) may also be obtained via Curtius rearrangement of the corresponding azide of the formula (IVb), e.g. by analogy to the method described in WO 2014/204622.

For converting compounds of formula (Ia) and (Ib) wherein $R^{yz}$ or $R^{zc}$ is H into compounds (I) wherein $R^{yz}$ or $R^{zc}$ is different from H, compounds of formula (Ia) and (Ib) wherein $R^{yz}$ or $R^{zc}$ is H can be reacted with compounds of formulae $R^{yz}$-Lg or $R^{zc}$-Lg wherein $R^{yz}$ or $R^{zc}$ is not H and Lg is a leaving group, such as a bromine, chlorine or iodine atom or a tosylate, mesylate or triflate, to yield compounds of formula (Ia) and (Ib), wherein $R^{yz}$ or $R^{zc}$ is different from H. The reaction is suitably carried out in the presence of a base such as sodium hydride or potassium hydride, suitably in a polar aprotic solvent such as N,N-dimethylformamide, tetrahydrofuran, dioxane, acetonitrile, dimethylsulfoxide or pyridine, or mixtures of these solvents, in a temperature range of from 0° C. and 100° C.

Compounds of the formula (Ic) can be prepared from compounds of formula (IIc) by the reactions shown below.

$R^{11/12}$ corresponds to radicals $R^{11}$ or $R^{12}$ respectively. The reaction shown above can be performed by analogy to conventional methods of preparing carbamates. According to a first embodiment, the amine of the formula (IIc) is converted into either an isocyanate or p-nitrophenyl carbamate followed by treatment with an alcohol of the formula $R^{11}$—OH or $R^{12}$—OH, respectively, in the presence of an organic or inorganic base. According to another embodiment, the compound of the formula (IIc) is reacted with a chloroformate of the formula $R^{11/12}$—O—C(=O)—Cl. The chloroformate is prepared from the alcohols $R^{11/12}$—OH by treatment with phosgene or triphosgene in the presence of a base, e.g. pyridine. Compounds of formula (Ic), wherein Z is —N($R^{zc}$)—C(=O)— or —N($R^{zc}$)—C(=S)— can be prepared by analogy to the methods described in WO 2013/009791 or by analogy to methods described in US 2012/0202687.

Compounds of formula (IIb) and (IIc) can be prepared from compounds of formula (IIa) by the reactions shown below.

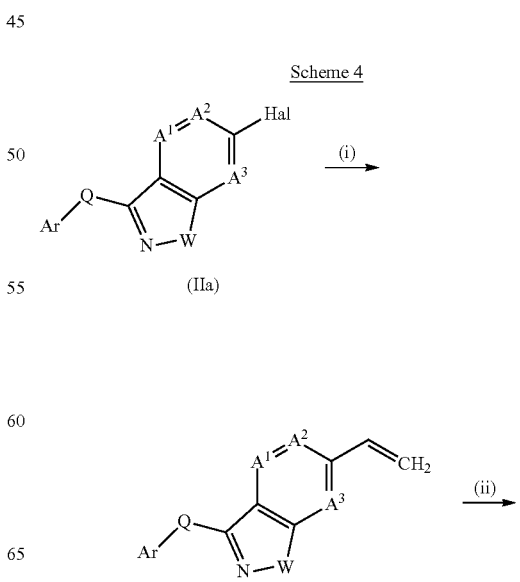

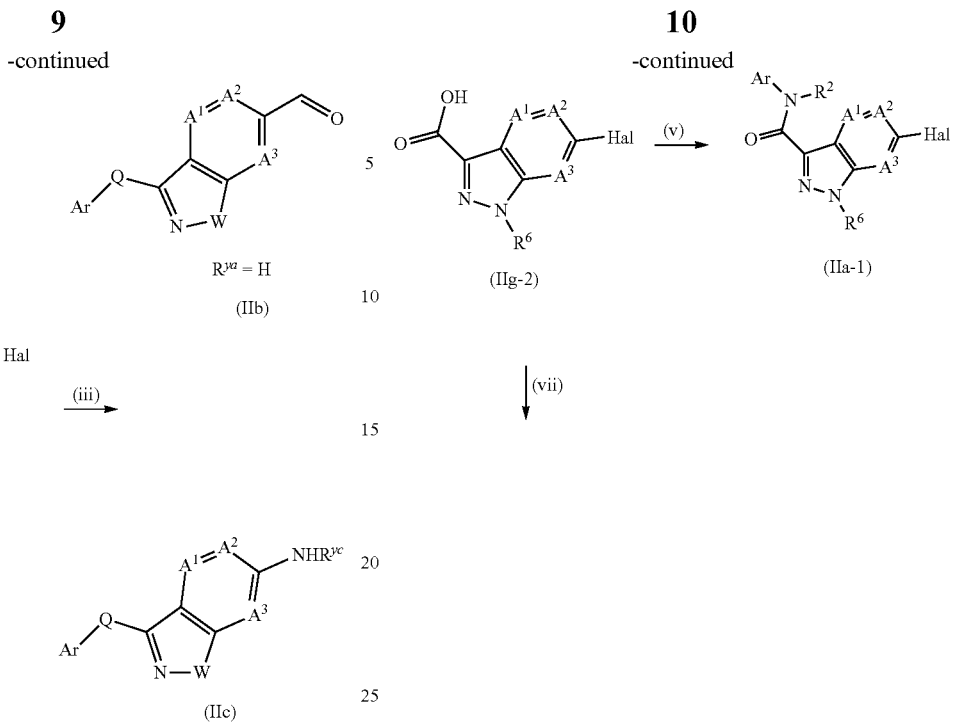

In the above reactions, -Hal is bromine, chlorine or iodine atom or a tosylate, mesylate or triflate. Reaction step (i) cab be performed by analogy to method described in WO 2015/051341. Reaction step (ii) cab be performed by analogy to method described in European Journal of Medicinal Chemistry, 49, 310-323, 2012. Compounds of the formula (IIc) (reaction step (iii) of the above reaction) can be prepared by reacting compounds of the formula (IIa) with ammonia or amines of the formula $R^{yc}NH_2$ in the presence of a metal catalyst or its salts, preferably copper or its salts as described in Chem. Commun., 2009, 3035-3037.

Compounds of formula (IIa-1) and (IIa-2), where Q is —N($R^2$)—C(=O)— or O—C(=O) and W is N($R^6$) can be prepared by the reactions shown below.

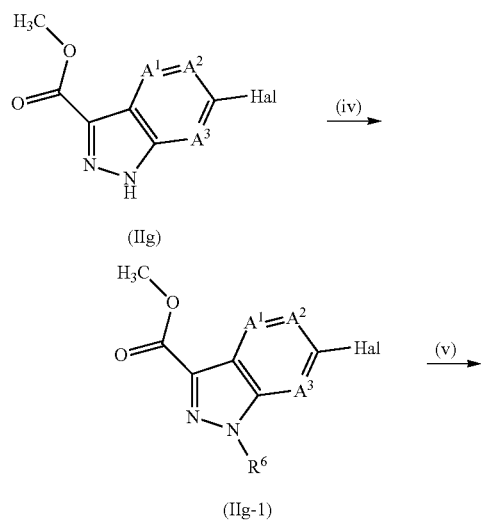

In the above reactions, -Hal is bromine, chlorine or iodine atom or a tosylate, mesylate or triflate, preferably bromine. Compounds of formula (IIa-1) can be prepared from a common intermediate of formula (IIg-2) via amide formation by reacting the compounds of formula (IIg-2) with Ar—$NH_2$. in presence of suitable coupling reagent like HATU and base like DIPEA. Compounds of formula (IIa-2) can be prepared from a common intermediate of formula (IIg-2) via esterification by reacting the compound of formula (IIg-2) with ArOH in presence of acid. Steps (vi) and (vii) can be performed analogous to process as described in March's Advanced Organic Chemistry 6th edition, Michael B. Smith and Jerry March.

Compounds of formula (IIg-2) can be prepared from compounds of formula (IIg) in two steps. Step (iv) can be performed by reacting the compounds of formula (IIg) with alkyl halides in presence of suitable bases like potassium carbonate as described in WO 2011/050245. Step (v) involves ester hydrolysis with suitable base like LiOH, NaOH, as mentioned in WO 2011/050245.

Compounds of formula (IIg) are commercially available and can also be prepared from compounds of formula (IId) by the reactions shown below. Compounds of formula (IId) are commercially available.

Scheme 6

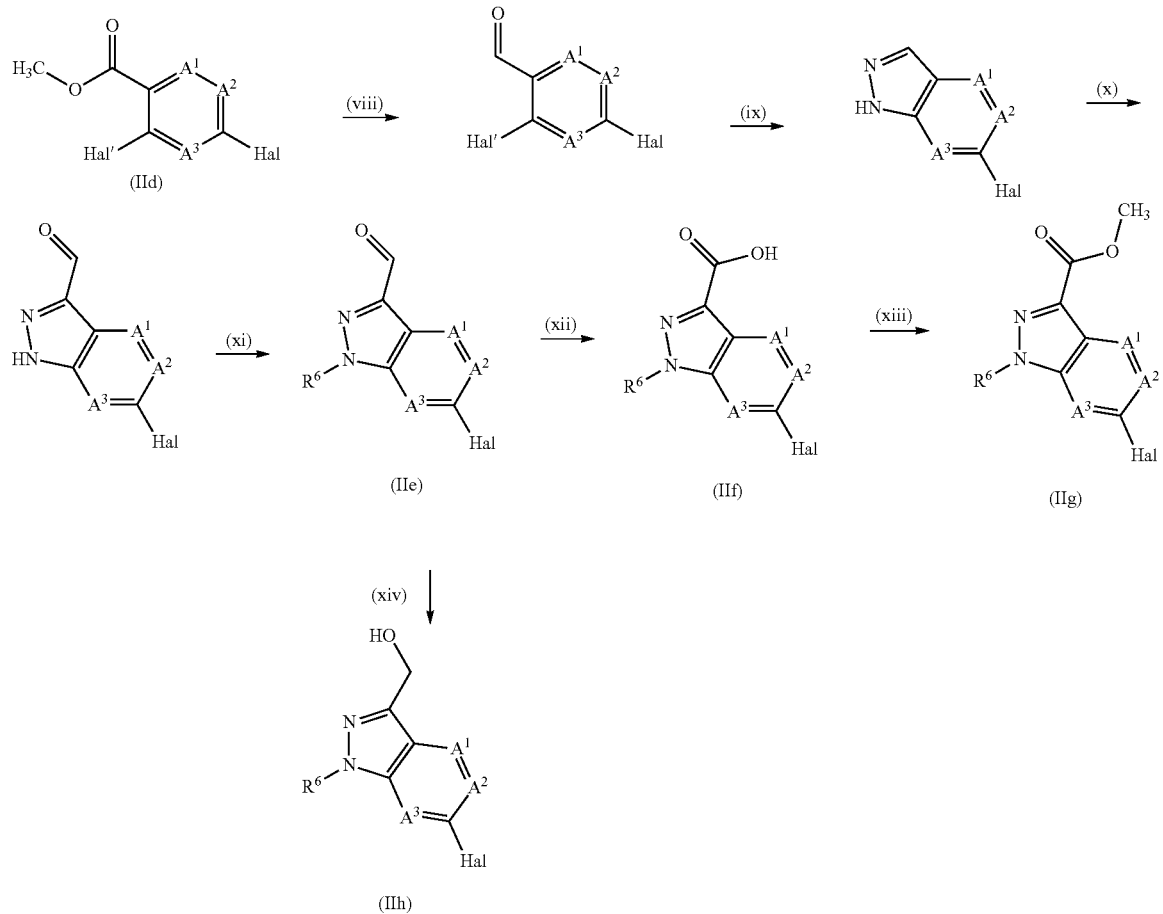

In the above reactions, -Hal' is bromine, chlorine, fluorine or iodine atom, preferably fluorine or chlorine. -Hal is bromine, chlorine or iodine atom or a tosylate, mesylate or triflate, preferably bromine. The compounds of formula (IIe) can be prepared from compounds of formula (IId) via 4 step sequence. Step (viii) involves ester reduction to aldehyde using DIBAL as reducing agent, as described in Tetrahedron Letters, 48(29), 5061-5064, 2007. Step (ix) involves cyclization by refluxing with hydrazine in DMF as described in Journal of Organic Chemistry, 71(21), 8166-8172, 2006. Step (x) involves introduction of formyl group at position 3 in accordance with the methods described in WO 2016/057834. Step (xi) involves N-alkylation using respective alkyl halides with suitable bases like potassium carbonate, as described in WO 2011/050245. Compounds of formula (IIf) can be prepared by oxidation of compounds of formula (IIe) using KMnO$_4$ and compounds of formula (IIh) can be prepared by reduction of compounds of formula (IIe) using NaBH$_4$, as described in March's Advanced Organic Chemistry 6th edition, Michael B. Smith and Jerry March. Compounds of formula (IIg) can be prepared from compounds of formula (IIe) by esterification process analogy to as method as described in March's Advanced Organic Chemistry 6th edition, Michael B. Smith and Jerry March.

Compounds of formula (IIa-3), where Q is —C(R$^{19}$R$^{20}$)—C(=O)— and W is N(R$^6$) can be prepared from compounds of formula (IIf) as per below reactions.

Scheme 7

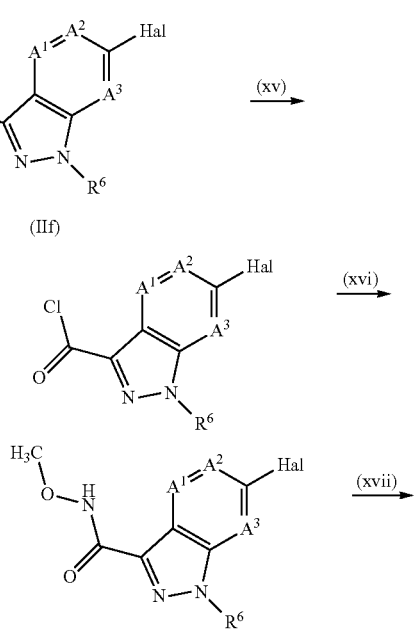

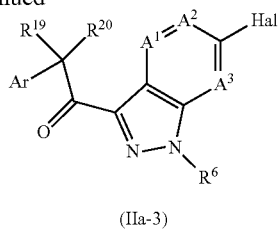

(IIa-3)

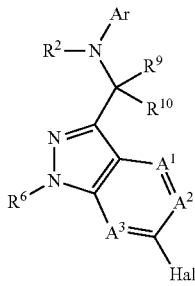

(IIa-5)

In the above reactions, -Hal is bromine, chlorine or iodine atom, preferably bromine. Compounds of formula (IIa-3) can be prepared from compounds of formula (IIf) by analogy to methods described in Organic Letters 2016, 18(23), 6026-6029.

Compounds of formula (IIa-4), (IIa-5) and (IIa-6) can be prepared from compounds of formula (IIi) by below method.

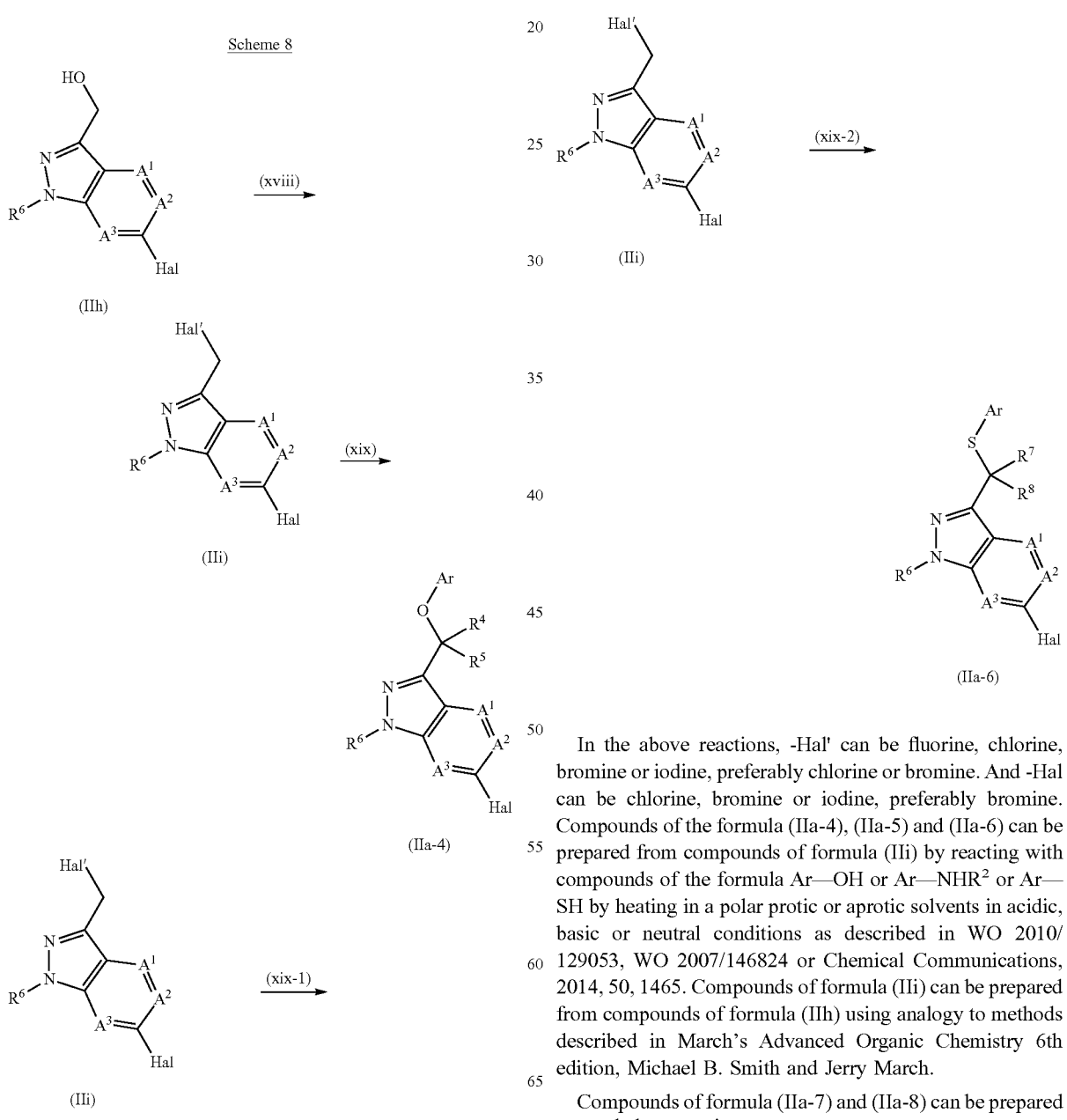

In the above reactions, -Hal' can be fluorine, chlorine, bromine or iodine, preferably chlorine or bromine. And -Hal can be chlorine, bromine or iodine, preferably bromine. Compounds of the formula (IIa-4), (IIa-5) and (IIa-6) can be prepared from compounds of formula (IIi) by reacting with compounds of the formula Ar—OH or Ar—NHR$^2$ or Ar—SH by heating in a polar protic or aprotic solvents in acidic, basic or neutral conditions as described in WO 2010/129053, WO 2007/146824 or Chemical Communications, 2014, 50, 1465. Compounds of formula (IIi) can be prepared from compounds of formula (IIh) using analogy to methods described in March's Advanced Organic Chemistry 6th edition, Michael B. Smith and Jerry March.

Compounds of formula (IIa-7) and (IIa-8) can be prepared as per below reactions.

Scheme 9

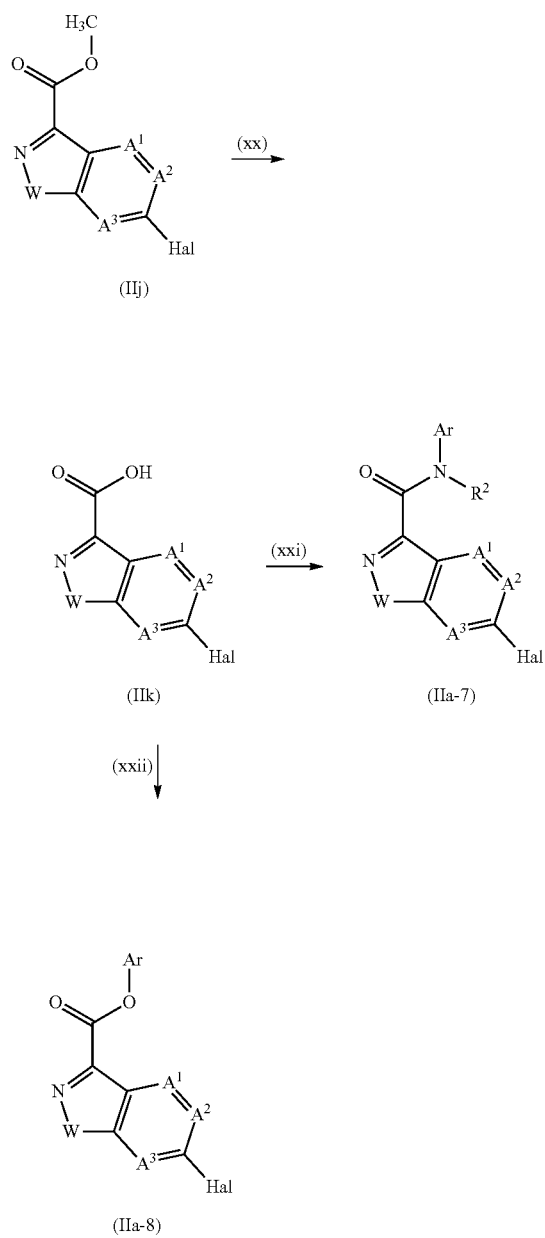

Scheme 10

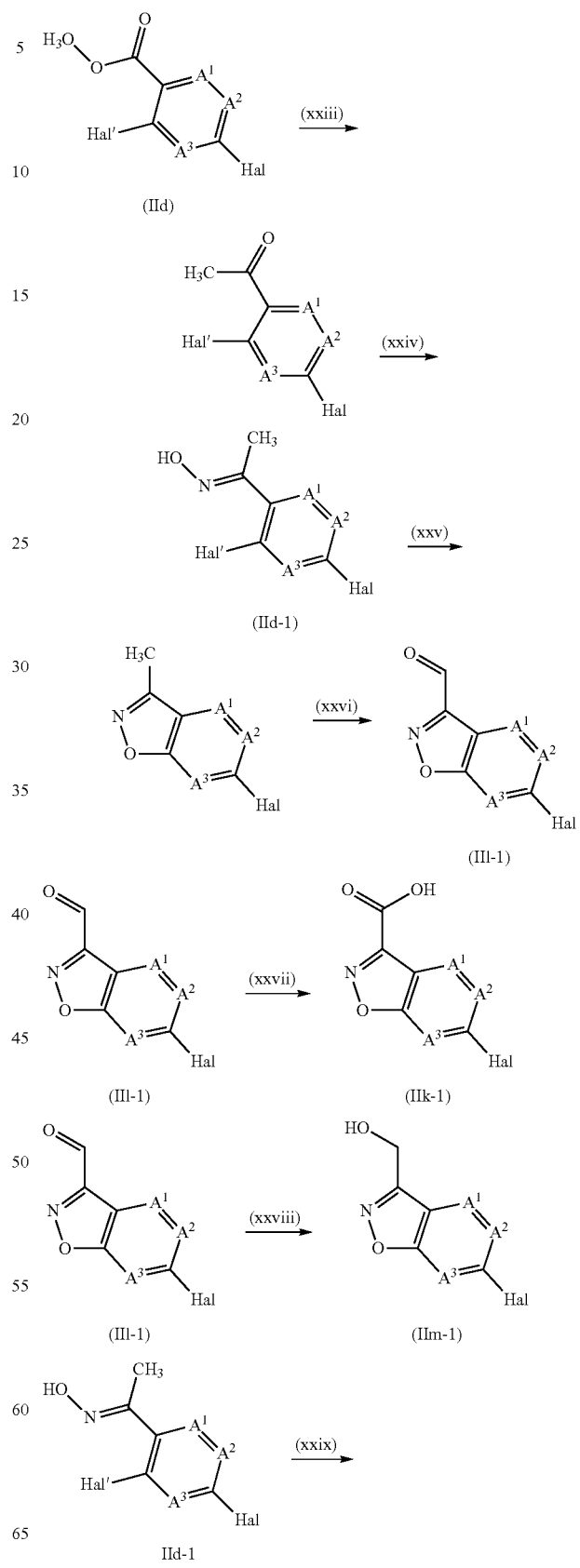

In the above scheme, -Hal is fluorine, chlorine, bromine or iodine, preferably bromine. Step (xx) involves ester hydrolysis with suitable base like LiOH, NaOH as mentioned in WO 2011/050245. Step (xxi) involves amide formation by reacting the compounds of formula (IIk) with Ar—NH$_2$. in presence of suitable coupling reagent like HATU and base like DIPEA. Step (xxii) involves esterification by reacting the compound of formula (IIk) with ArOH in presence of acid. Steps (xxi) and (xxii) can be performed by analogy to method as described in March's Advanced Organic Chemistry 6th edition, Michael B. Smith and Jerry March.

Compounds of formula (IIj) are commercially available and can also be prepared from compounds of formula (IId) by the reactions shown below. Compounds of formula (IId) are commercially available.

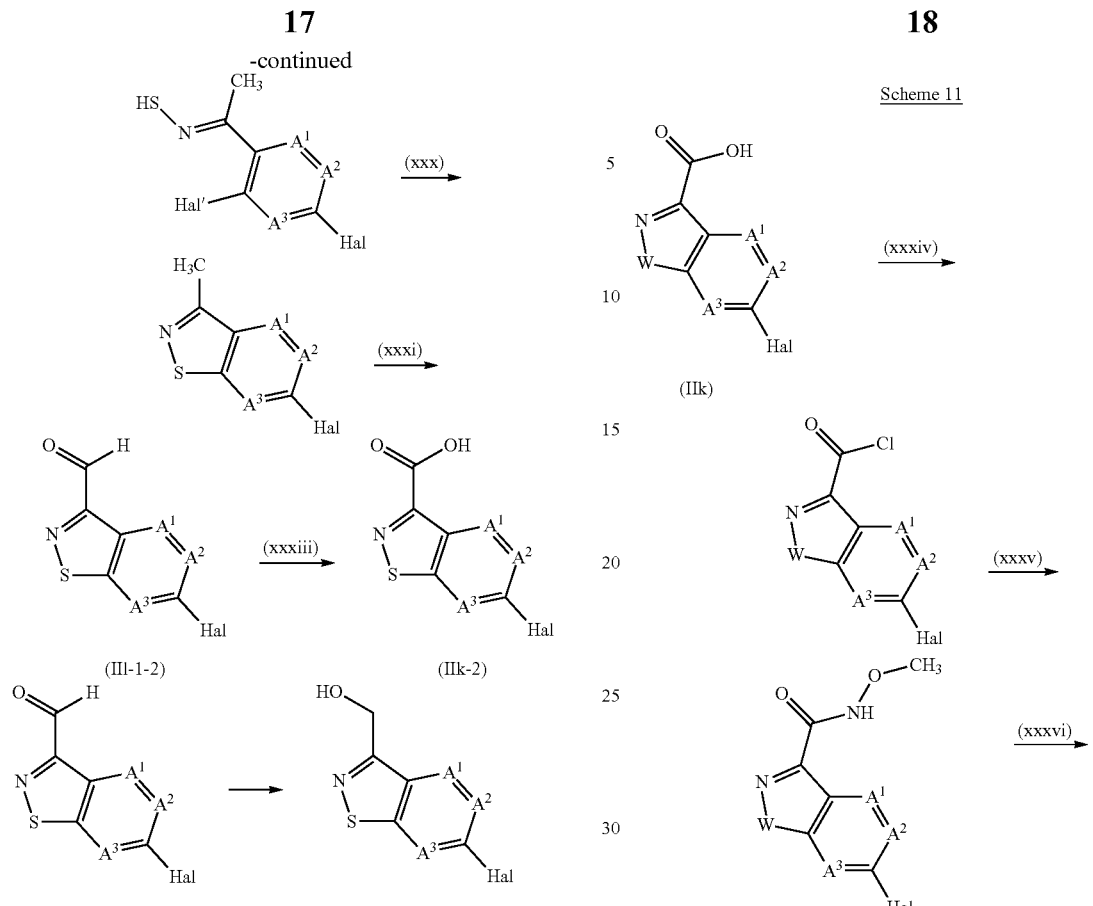

In the above reactions, -Hal is fluorine, chlorine, bromine or iodine, preferably bromine. And -Hal' is fluorine, chlorine, bromine or iodine, preferably fluorine. In the above scheme, step (xxiii) involves transformation of ester to methyl ketone using the organic reactions analogous to the method, as mentioned in March's Advanced Organic Chemistry 6th edition, Michael B. Smith and Jerry March. Step (xxiv) involves oxime formation by refluxing ketone with $NH_2OH \cdot HCl$ in protic solvent like MeOH analogous to the method, as described in Medicinal Chemistry Research, 25(3), 449-455, 2016. Step (xxv) involves base catalysed cyclization analogous to the method, as described in WO 2015/042397. Step (xxvi) involves $SeO_2$ oxidation of methyl group to aldehyde as described in European Journal of Medicinal Chemistry, 84, 42-50, 2014. Steps (xxvii) and (xxviii) involve oxidation and reduction reactions analogous to the methods, as described in March's Advanced Organic Chemistry 6th edition, Michael B. Smith and Jerry March. Step (xxix) involves transformation of oxime to thioxime using Lawesson's reagent as described in Phosphorus, Sulfur and Silicon and the Related Elements, 184(9), 2408-2426, 2009. Steps (xxx), (xxxi), (xxxii) and (xxxiii) can be performed analogous to steps (xxv), (xxvi), (xxvii) and (xxviii). Compounds of formula (IIj) can be prepared from compounds of formula (IIk-1) and (IIk-2) by using esterification by analogy to method as described in March's Advanced Organic Chemistry 6th edition, Michael B. Smith and Jerry March.

Compounds of formula (IIa-9), W is S or O can be prepared from compounds of formula (IIk) as per below reactions.

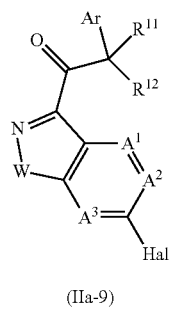

Compounds of formula (IIa-9) can be obtained from compounds of formula (IIk) by analogy to methods described in Organic Letters 2016, 18(23), 6026-6029.

Compounds of formula (IIa-10), (IIa-11) and (IIa-12), where W is S or O can be prepared from compounds of formula (IIm) as per below reactions.

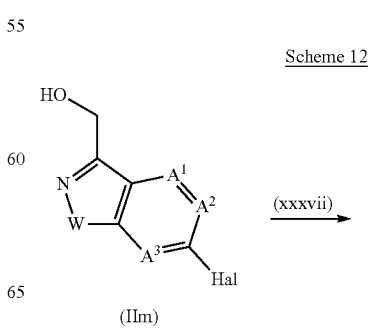

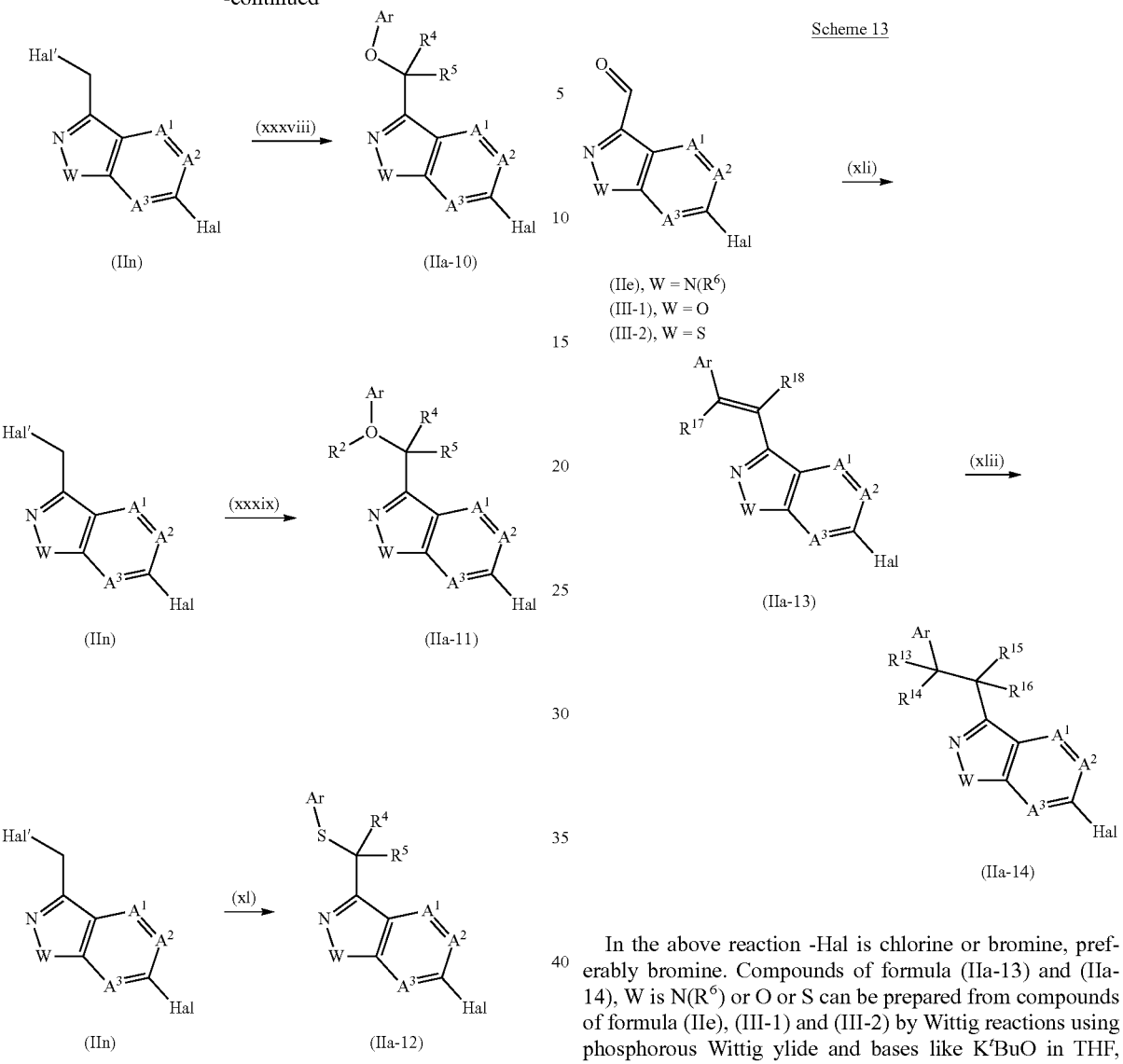

In the above reaction, Hal' can be fluorine, chlorine, bromine or iodine, preferably chlorine or bromine. Hal can be chlorine, bromine or iodine, preferably bromine or tosylate, mesylate or triflate. Compounds of the formula (IIa-10), (IIa-11) and (IIa-12) can be prepared from compounds of formula (IIn) by reacting with compounds of the formula Ar—OH or Ar—NHR$^2$ or Ar—SH by heating in a polar protic or aprotic solvents in acidic, basic or neutral conditions as described in WO 2010/129053, WO 2007/146824 or Chemical Communications, 2014, 50, 1465. Compounds of formula (IIn) can be prepared from compounds of formula (IIm), using the organic reactions analogy to method as described in March's Advanced Organic Chemistry 6th edition, Michael B. Smith and Jerry March. Compounds of formula (IIa-12) can be further oxidised using mCPBA for preparing compounds with different oxidation states on sulphur, as described in March's Advanced Organic Chemistry 6th edition, Michael B. Smith and Jerry March.

Compounds of formula (IIa-13) and (IIa-14), W is N(R$^6$) or O or S can be prepared from compounds of formula (IIe), (III-1) and (III-2) as per below reactions.

In the above reaction -Hal is chlorine or bromine, preferably bromine. Compounds of formula (IIa-13) and (IIa-14), W is N(R$^6$) or O or S can be prepared from compounds of formula (IIe), (III-1) and (III-2) by Wittig reactions using phosphorous Wittig ylide and bases like K$^t$BuO in THF, followed by hydrogenation process known in organic chemistry such as using hydrogen gas and a suitable metal catalyst as described in March's Advanced Organic Chemistry 6th edition, Michael B. Smith and Jerry March.

Compounds of formula (IIa-15) can be prepared from commercially available compounds of formula (IIId) as per below reactions.

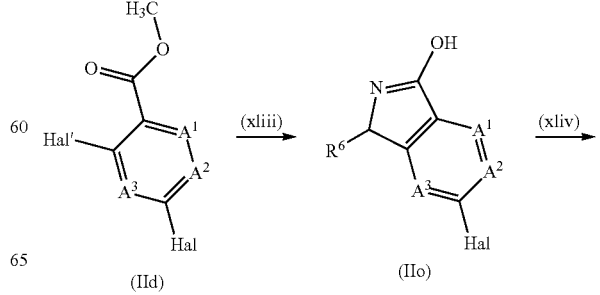

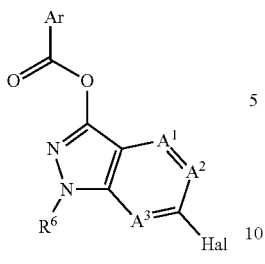

(IIa-15)

In the above reaction -Hal' is chlorine, fluorine, bromine or iodine, preferably fluorine and chlorine. And -Hal is chlorine, bromine or iodine, preferably bromine. Compounds of formula (IIo) can be prepared from (IId) by reacting it with substituted hydrazines in protic solvents like EtOH and irradiating in microwave as described in WO 2010/054279. Compounds of formula (IIa-15) can be prepared from (IIo) by esterification process analogous to as described in March's Advanced Organic Chemistry 6th edition, Michael B. Smith and Jerry March.

Compounds of formula (IIa-16) and (IIa-17), can be prepared from compounds of formula (IIo) and (IIp) as per below reactions.

Scheme 16

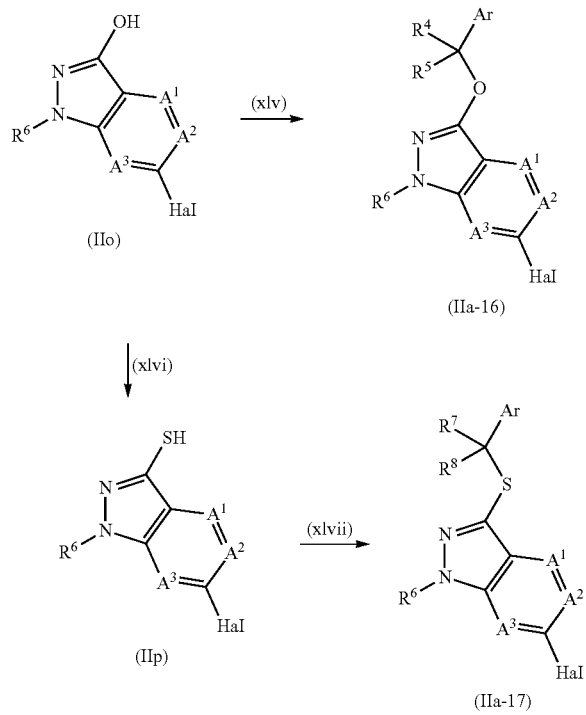

In the above reaction -Hal is chlorine, bromine or iodine, preferably bromine. Compounds of formula (IIa-16) and (IIa-17) can be prepared by heating compounds of formula Ar—C($R^4R^5$)-Lg and Ar—C($R^7R^8$)-Lg (where Lg can be bromine, chlorine, tosylate, mesylate) in a polar protic or aprotic solvents with compounds of formula (IIo) and (IIp) in acidic, basic or neutral conditions analogous to as described in WO 2010/129053, WO 2007/146824 or Chemical Communications, 2014, 50, 1465. Step (xlvi) involves transformation of hydroxyl group to thiol group using Lawesson's reagent. Compounds of formula (IIa-17) can be further oxidised using mCPBA for preparing compounds with different oxidation states on sulphur analogous to as described in March's Advanced Organic Chemistry 6th edition, Michael B. Smith and Jerry March.

Compounds of formula (IIa-18), (IIa-19) and (IIa-20) can be prepared as per below reactions.

Scheme 17

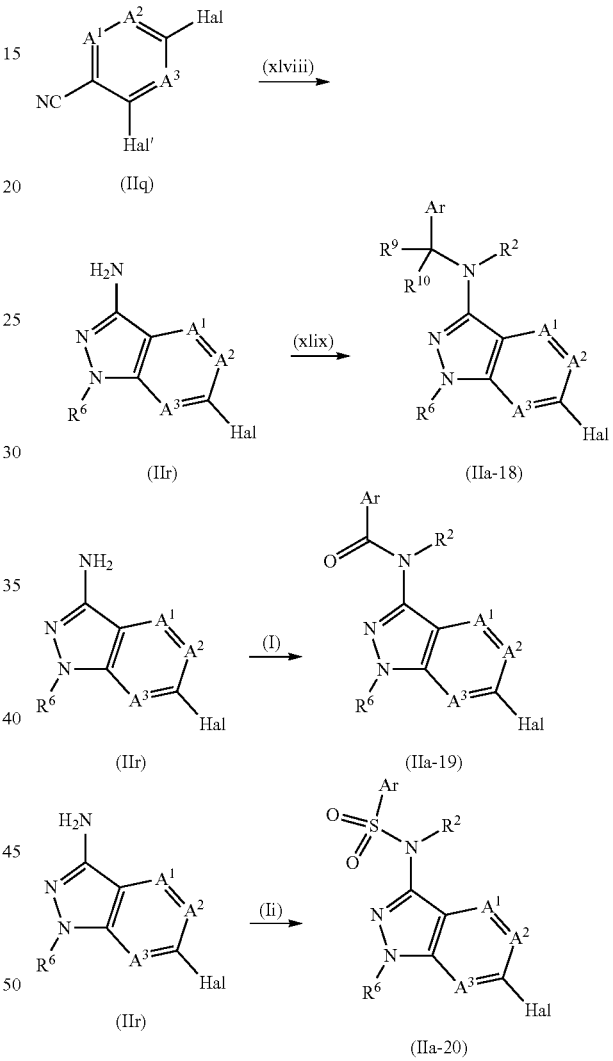

In the above reaction -Hal is chlorine, bromine or iodine, preferably bromine. And -Hal' is chlorine, fluorine, bromine or iodine, preferably fluorine or chlorine. Compounds of formula (IIa-18), (IIa-19) and (IIa-20) can be prepared from commercially available compounds of formula (IIq) in two steps. By reacting compound (IIq) with substituted hydrazines in protic solvents like EtOH and irradiating in microwave as described in WO 2010/054279 can produce compounds of formula (IIr). Compounds of formula (IIa-18) can be prepared by heating compounds of the formula Ar—C($R^9R^{10}$)-Lg (where Lg can be bromine, chlorine, tosylate, mesylate) with compounds of formula (IIr) in a polar protic or aprotic solvents in an acidic, basic, or neutral conditions analogous to as described in WO 2010/129053, WO 2007/0146824 or Chemical Communications, 2014, 50, 1465, shown in step (xlix). Compounds of formula (IIa-19) can be prepared from compounds of formula (IIr) by using amide coupling reactions analogous to as described in March's Advanced Organic Chemistry 6th edition, Michael B. Smith and Jerry March, shown in step (I). Compounds of formula (IIa-20) can be prepared from compounds of formula (IIr) by treating with suitable Ar—SO₃Cl in presence of bases like pyridine and coupling reagents like DMAP, as described in Chemistry—A European Journal, 20(1), 317-322, 2014 (step (Ii)).

Compounds of formula (IIa-21) (IIa-22) and (IIa-23) can be prepared as per below reactions.

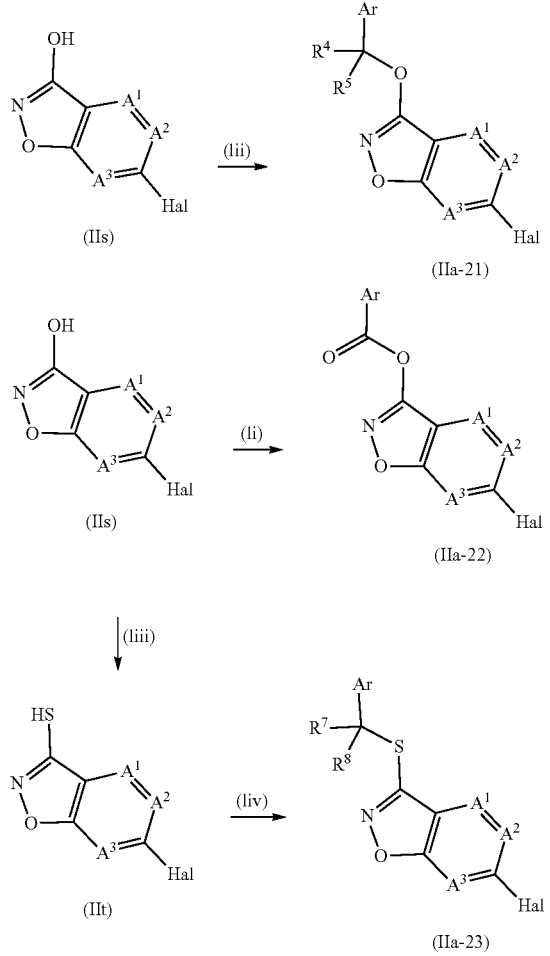

In the above reaction -Hal is chlorine, bromine or iodine, preferably bromine. Compounds of formula (IIa-21) and (IIa-23) can be prepared by heating compounds of the formula Ar—C(R⁴R⁵)-Lg and Ar—C(R⁷R⁸)-Lg (where Lg can be bromine, chlorine, tosylate, mesylate) with compounds of formula (IIs) and (IIt) in a polar protic or aprotic solvents in an acidic, basic, or neutral conditions as described in WO 2010/129053, WO 2007/146824 or Chemical Communications, 2014, 50, 1465, shown in steps (Iii) and (Iiv). Compounds of formula (IIa-22) can be prepared from compounds of formula (IIs) by using esterification process as described in March's Advanced Organic Chemistry 6th edition, Michael B. Smith and Jerry March, shown in step (Ii). Step (Iiii) involves transformation of hydroxyl group to thiol group using Lawesson's reagent. Compounds of formula (IIa-23) can be further oxidised using mCPBA for preparing compounds with different oxidation states on sulphur, as described in March's Advanced Organic Chemistry 6th edition, Michael B. Smith and Jerry March.

Compounds of formula (IIs) are commercially available or can be prepared from commercially available compounds of formula (IId') by the reactions shown below.

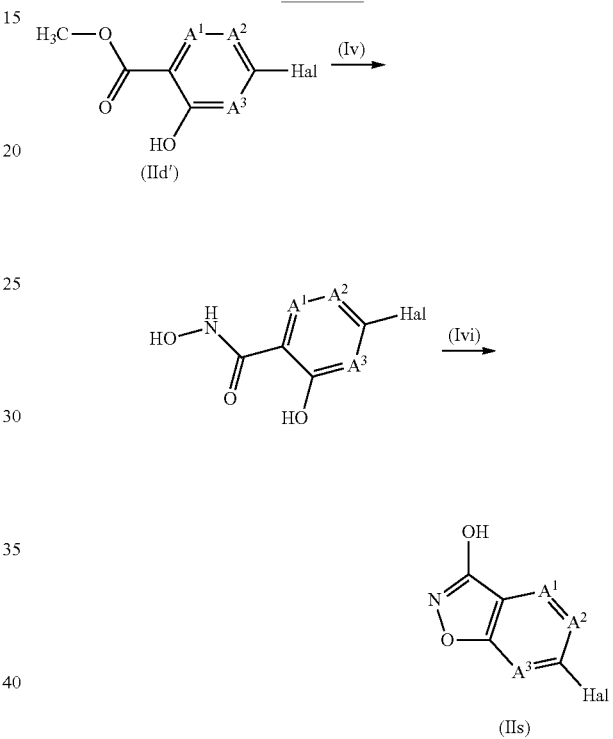

In the above reaction -Hal is chlorine, bromine or iodine, preferably bromine. Suitable reaction conditions for performing the above reaction steps are described in Organic Process Research & Development, 2016, 20, 233-241.

Compounds of formula (IIa-24), (IIa-25) and (IIa-26) can be prepared as per below reactions.

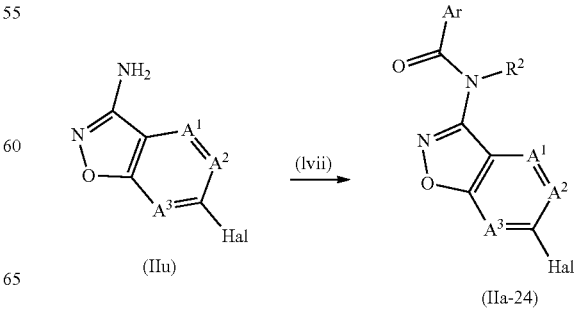

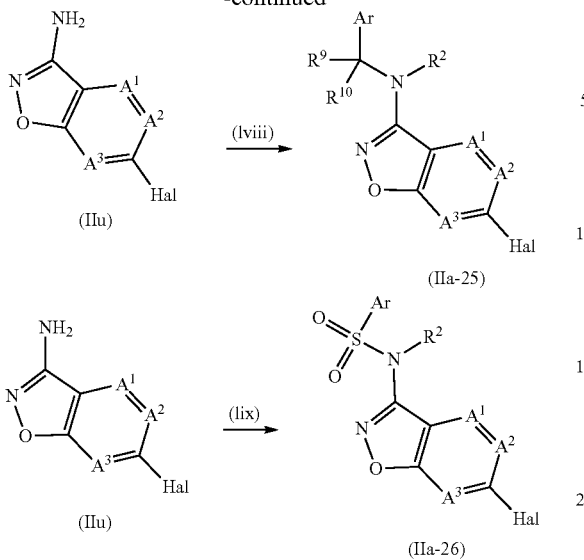

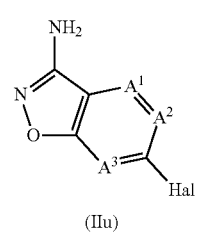

In the above reaction -Hal is chlorine, bromine or iodine, preferably bromine. Compounds of formula (IIa-25) can be prepared by heating compounds of the formula Ar—C($R^9R^{10}$)-Lg (where Lg can be bromine, chlorine, tosylate, mesylate) with compounds of formula (IIu) in a polar protic or aprotic solvents in an acidic, basic, or neutral conditions as described in WO 2010/129053, WO 2007/146824 or Chemical Communications, 2014, 50, 1465, shown in step (lviii). Compounds of formula (IIa-24) can be prepared from compounds of formula (IIu) by using amide coupling reactions analogous to as described in March's Advanced Organic Chemistry 6th edition, Michael B. Smith and Jerry March, shown in step (lvii). Compounds of formula (IIa-26) can be prepared from compounds of formula (IIu) by treating with suitable Ar—$SO_3Cl$ in presence of bases like pyridine and coupling reagents like DMAP, as described in Chemistry—A European Journal, 20(1), 317-322, 2014 (step (lix)).

Compounds of formula (IIu) are commercially available or can be prepared from commercially available compounds of formula (IId) as per below reactions.

Scheme 21

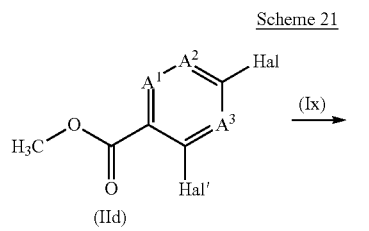

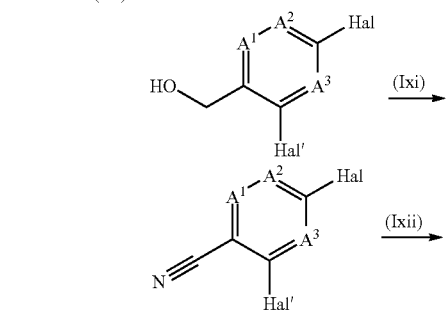

In the above reaction -Hal is chlorine, bromine or iodine, preferably bromine. And -Hal' is chlorine, fluorine, bromine or iodine, preferably fluorine or chlorine. Compounds of formula (IIu) can be prepared from commercially available compounds of formula (IId). Step (lx) involves reduction protocol using $NaBH_4$ as described in March's Advanced Organic Chemistry 6th edition, Michael B. Smith and Jerry March. Step (lxi) involves transformation of alcohols to nitriles by treating alcohols with tert-butyl hypochlorite in the presence of (2,2,6,6-tetramethylpiperidin-1-yl)oxidanyl (TEMPO) as described in Synthesis, 2013, 45, 2155-2164. Step (lxii) involves one-pot cyclization of ortho substituted benzonitriles to 3-amino-1,2-benzisoxazoles as described in Tetrahedron Letters, Vol. 37, No. 17, 2885-2886, 1996.

Compounds of formula (IIa-27), (IIa-28) and (IIa-29), can be prepared as per below reactions.

Scheme 22

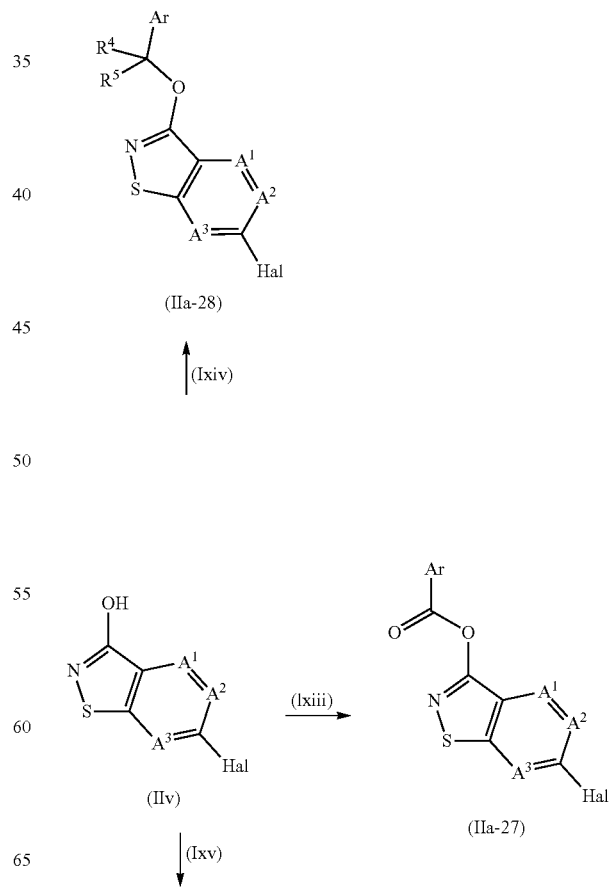

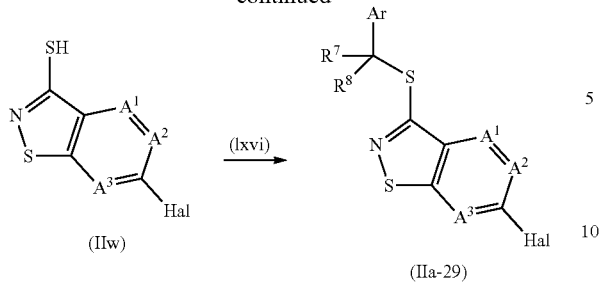

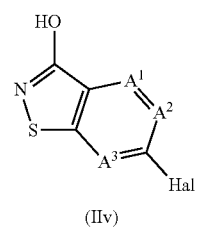

In the above reaction -Hal is chlorine, bromine or iodine, preferably bromine. Compounds of formula (IIa-28) and (IIa-29) can be prepared by heating compounds of the formula Ar—C(R$^4$R$^5$)-Lg and Ar—C(R$^7$R$^8$)-Lg ((where Lg can be bromine, chloride, tosylate, mesylate) with compounds of formula (IIv) and (IIw) in a polar protic or aprotic solvents in acidic, basic or neutral conditions as described in WO 2010/129053, WO 2007/146824 or Chemical Communications, 2014, 50, 1465, as shown in steps (Ixiv) and (Ixvi). Compounds of formula (IIa-27) can be prepared from compounds of formula (IIv) by using esterification process analogous to as described in March's Advanced Organic Chemistry 6th edition, Michael B. Smith and Jerry March, as shown in step (Ixiii). Step (Ixv) involves transformation of hydroxyl group to thiol group using Lawesson's reagent. Compounds of formula (IIa-29) can be further oxidised using mCPBA for preparing compounds with different oxidation states on sulphur, analogous to as described in March's Advanced Organic Chemistry 6th edition, Michael B. Smith and Jerry March.

Compounds of formula (IIv) are commercially available or can be prepared from commercially available compounds of formula (IId) as per reactions below.

Scheme 23

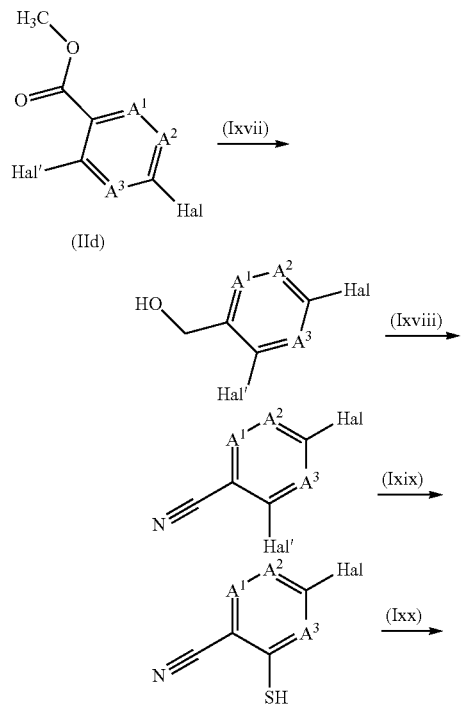

In the above reaction -Hal is chlorine, bromine or iodine, preferably bromine. And -Hal' is chlorine, fluorine, bromine or iodine, preferably fluorine or chlorine. Compounds of formula (IIv) can be prepared from commercially available compounds of formula (IId). Step (Ixvii) involves reduction process using NaBH$_4$ as described in March's Advanced Organic Chemistry 6th edition, Michael B. Smith and Jerry March. Step (Ixviii) involves transformation of alcohols to nitriles by treating alcohols with tert-butyl hypochlorite in the presence of (2,2,6,6-tetramethylpiperidin-1-yl)oxidanyl (TEMPO) as described in Synthesis, 2013, 45, 2155-2164. Steps (Ixix) and (Ixx) involve sequential selective substitution of halide with Na$_2$S followed by oxidative cyclization as described in Journal of Medicinal Chemistry, 2016, 59, 9906-9918.

Compounds of formula (IIa-30), (IIa-31) and (IIa-32) can be prepared as per below reactions.

Scheme 24

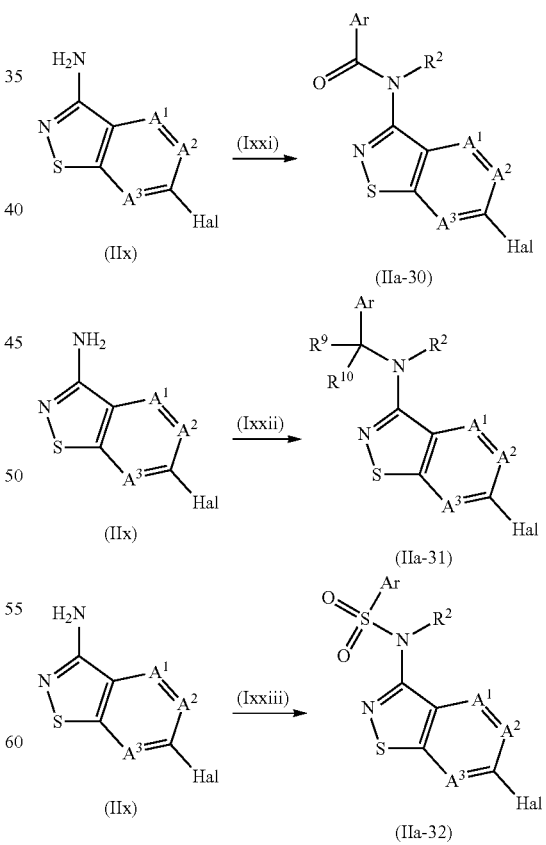

In the above reaction -Hal is chlorine, bromine or iodine, preferably bromine. Compounds of formula (IIa-31) can be prepared by heating compounds of the formula Ar—C(R$^9$R$^{10}$)-Lg (where Lg is bromine, chlorine, tosylate, or mesylate) with compounds of formula (IIx) in a polar protic or aprotic solvents in an acidic, basic, or neutral conditions as described in WO 2010/129053, WO 2007/146824 or Chemical Communications, 2014, 50, 1465, shown in step (lxxii). Compounds of formula (IIa-30) can be prepared from compounds of formula (IIx) by using amide coupling reactions analogous to as described in March's Advanced Organic Chemistry 6th edition, Michael B. Smith and Jerry March, shown in step (lxxi). Compounds of formula (IIa-32) can be prepared from compounds of formula (IIx) by treating with suitable Ar—SO$_3$Cl in presence of bases like pyridine and coupling reagents like DMAP, as described in Chemistry—A European Journal, 20(1), 317-322, 2014 (step (lxxiii)).

Compounds of formula (IIx) can be prepared from compounds of formula (IIv) as per below reactions.

Scheme 25

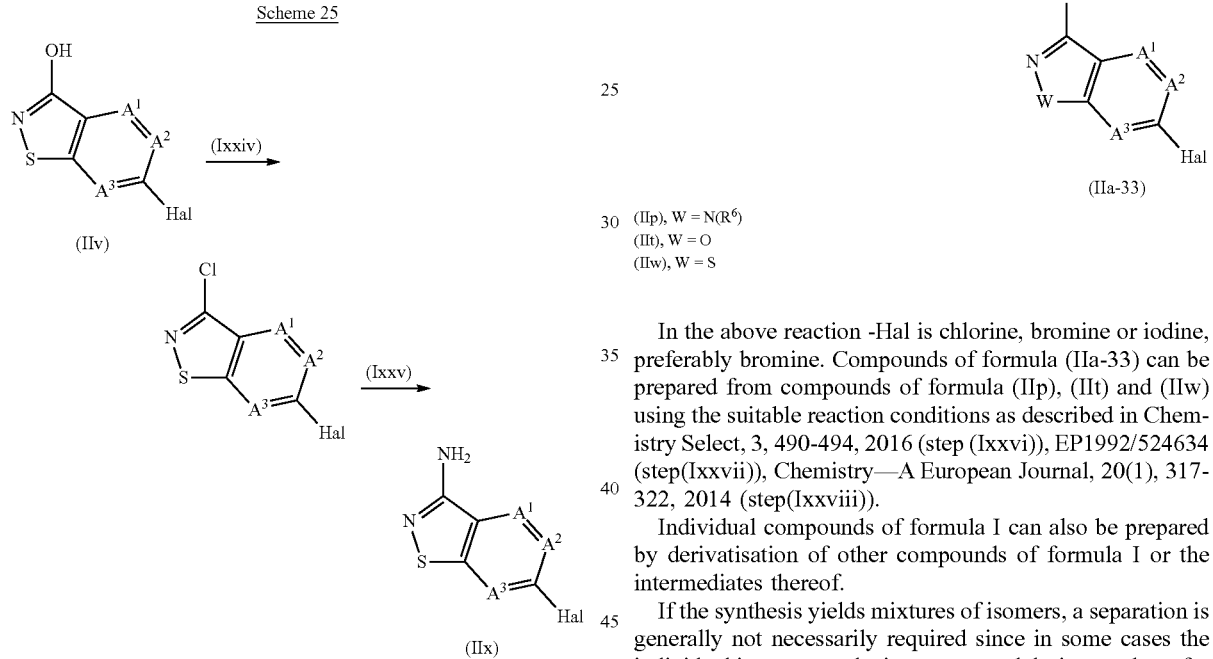

In the above reaction -Hal is chlorine, bromine or iodine, preferably bromine. Step (lxxiv) involves halogenation as described in European Journal of Medicinal Chemistry, 123 (2016) 332-353. Step (lxxv) involves amination as described in Chemistry A European Journal, 2015, 21, 3701-3707.

Compounds of formula (IIa-33) can be prepared as per below reactions.

Scheme 26

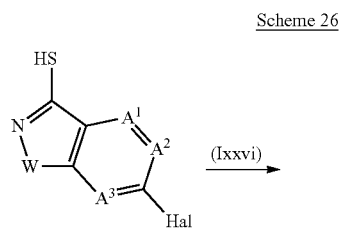

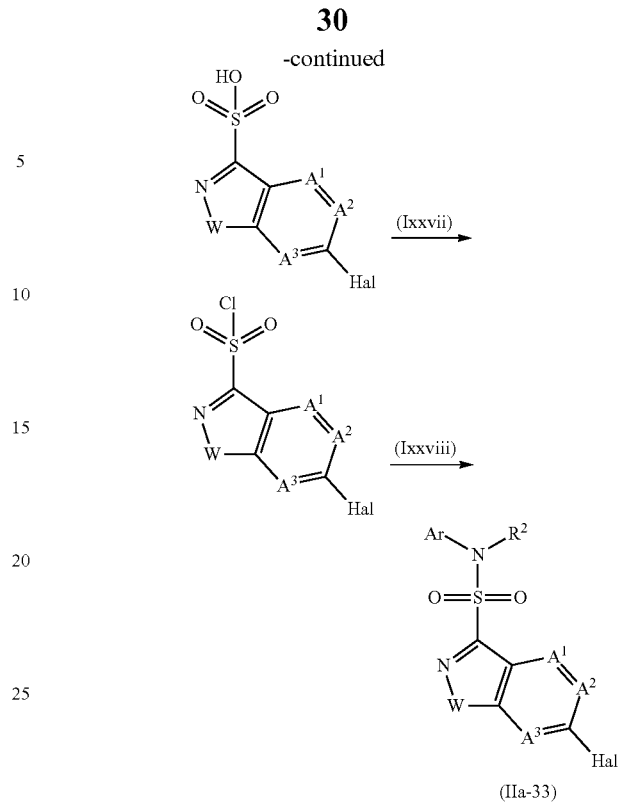

(IIp), W = N(R$^6$)
(IIt), W = O
(IIw), W = S

In the above reaction -Hal is chlorine, bromine or iodine, preferably bromine. Compounds of formula (IIa-33) can be prepared from compounds of formula (IIp), (IIt) and (IIw) using the suitable reaction conditions as described in Chemistry Select, 3, 490-494, 2016 (step (lxxvi)), EP1992/524634 (step(lxxvii)), Chemistry—A European Journal, 20(1), 317-322, 2014 (step(lxxviii)).

Individual compounds of formula I can also be prepared by derivatisation of other compounds of formula I or the intermediates thereof.

If the synthesis yields mixtures of isomers, a separation is generally not necessarily required since in some cases the individual isomers can be interconverted during work-up for use or during application (for example under the action of light, acids or bases). Such conversions may also take place after use, for example in the treatment of plants in the treated plant, or in the harmful fungus to be controlled.

A skilled person will readily understand that the preferences for the substituents, also in particular the ones given in the tables below for the respective substituents, given herein in connection with compounds I apply for the intermediates accordingly. Thereby, the substituents in each case have independently of each other or more preferably in combination the meanings as defined herein.

Unless otherwise indicated, the term "compound(s) according to the invention" or "compound(s) of the invention" or "compound(s) of formula (I)", refers to the compounds of formula I.

The term "compound(s) according to the invention", or "compounds of formula I" comprises the compound(s) as defined herein as well as a stereoisomer, salt, tautomer or N-oxide thereof. The term "compound(s) of the present invention" is to be understood as equivalent to the term "compound(s) according to the invention", therefore also comprising a stereoisomer, salt, tautomer or N-oxide thereof.

The term "composition(s) according to the invention" or "composition(s) of the present invention" encompasses composition(s) comprising at least one compound of formula I according to the invention as defined above. The compositions of the invention are preferably agricultural or veterinary compositions.

Depending on the substitution pattern, the compounds according to the invention may have one or more centers of chirality, in which case they are present as mixtures of enantiomers or diastereomers. The invention provides both the single pure enantiomers or pure diastereomers of the compounds according to the invention, and their mixtures and the use according to the invention of the pure enantiomers or pure diastereomers of the compounds according to the invention or their mixtures. Suitable compounds according to the invention also include all possible geometrical stereoisomers (cis/trans isomers) and mixtures thereof. Cis/trans isomers may be present with respect to an alkene, carbon-nitrogen double-bond or amide group. The term "stereoisomer(s)" encompasses both optical isomers, such as enantiomers or diastereomers, the latter existing due to more than one center of chirality in the molecule, as well as geometrical isomers (cis/trans isomers). The present invention relates to every possible stereoisomer of the compounds of formula I, i.e. to single enantiomers or diastereomers, as well as to mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

The term "tautomers" encompasses isomers, which are derived from the compounds of formula I by the shift of an H-atom involving at least one H-atom located at a nitrogen, oxygen or sulphur atom. Examples of tautomeric forms are keto-enol forms, imine-enamine forms, urea-isourea forms, thiourea-isothiourea forms, (thio)amide-(thio)imidate forms etc.

The term "stereoisomers" encompasses both optical isomers, such as enantiomers or diastereomers, the latter existing due to more than one center of chirality in the molecule, as well as geometrical isomers (cis/trans isomers).

Depending on the substitution pattern, the compounds of the formula I may have one or more centers of chirality, in which case they are present as mixtures of enantiomers or diastereomers. One center of chirality is the carbon ring atom of the isothiazoline ring carrying radical $R^1$. The invention provides both the pure enantiomers or diastereomers and their mixtures and the use according to the invention of the pure enantiomers or diastereomers of the compound I or its mixtures. Suitable compounds of the formula I also include all possible geometrical stereoisomers (cis/trans isomers) and mixtures thereof.

The term N-oxides relates to a form of compounds I in which at least one nitrogen atom is present in oxidized form (as NO). To be more precise, it relates to any compound of the present invention which has at least one tertiary nitrogen atom that is oxidized to an N-oxide moiety. N-oxides of compounds I can in particular be prepared by oxidizing e.g. the ring nitrogen atom of an N-heterocycle, e.g. a pyridine or pyrimidine ring present in Ar or $R^{11}$, or an imino-nitrogen present in central tricyclic core, with a suitable oxidizing agent, such as peroxo carboxylic acids or other peroxides. The person skilled in the art knows if and in which positions compounds of the present invention may form N-oxides.

Salts of the compounds of the formula I are preferably agriculturally and veterinarily acceptable salts. They can be formed in a customary method, e.g. by reacting the compound with an acid of the anion in question if the compound of formula I has a basic functionality or by reacting an acidic compound of formula I with a suitable base.

Suitable agriculturally or veterinarily acceptable salts are especially the salts of those cations or the acid addition salts of those acids whose cations and anions, which are known and accepted in the art for the formation of salts for agricultural or veterinary use respectively, and do not have any adverse effect on the action of the compounds according to the present invention. Suitable cations are in particular the ions of the alkali metals, preferably lithium, sodium and potassium, of the alkaline earth metals, preferably calcium, magnesium and barium, and of the transition metals, preferably manganese, copper, zinc and iron, and also ammonium ($NH^{4+}$) and substituted ammonium in which one to four of the hydrogen atoms are replaced by $C_1$-$C_4$-alkyl, $C_1$-$C_4$-hydroxyalkyl, $C_1$-$C_4$-alkoxy, $C_1$-$C_4$-alkoxy-$C_1$-$C_4$-alkyl, hydroxy-$C_1$-$C_4$-alkoxy-$C_1$-$C_4$-alkyl, phenyl or —$CH_2$-phenyl. Examples of substituted ammonium ions comprise methylammonium, isopropylammonium, dimethylammonium, diisopropylammonium, trimethylammonium, tetramethylammonium, tetraethylammonium, tetrabutylammonium, 2-hydroxyethylammonium, 2-(2-hydroxyethoxy)ethylammonium, bis(2-hydroxyethyl)ammonium, benzyltrimethylammonium and benzyl-triethylammonium, furthermore phosphonium ions, sulfonium ions, preferably tri($C_1$-$C_4$-alkyl)sulfonium, and sulfoxonium ions, preferably tri($C_1$-$C_4$-alkyl)sulfoxonium. Suitable acid addition veterinarily acceptable salts, e.g. formed by compounds of formula I containing a basic nitrogen atom, e.g. an amino group, include salts with inorganic acids, for example hydrochlorides, sulphates, phosphates, and nitrates and salts of organic acids for example acetic acid, maleic acid, dimaleic acid, fumaric acid, difumaric acid, methane sulfenic acid, methane sulfonic acid, and succinic acid.

Anions of useful acid addition salts are primarily chloride, bromide, fluoride, hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting a compound of formulae I with an acid of the corresponding anion, preferably of hydrochloric acid, hydrobromic acid, sulfuric acid, phosphoric acid or nitric acid.

The term "invertebrate pest" as used herein encompasses animal populations, such as insects, arachnids and nematodes, which may attack plants, thereby causing substantial damage to the plants attacked, as well as ectoparasites which may infest animals, in particular warm blooded animals such as e.g. mammals or birds, or other higher animals such as reptiles, amphibians or fish, thereby causing substantial damage to the animals infested.

The term "plant propagation material" is to be understood to denote all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants, including seedlings and young plants, which are to be transplanted after germination or after emergence from soil. The plant propagation materials may be treated prophylactically with a plant protection compound either at or before planting or transplanting. Said young plants may also be protected before transplantation by a total or partial treatment by immersion or pouring.

The term "plants" comprises any types of plants including "modified plants" and in particular "cultivated plants".

The term "modified plants" refers to any wild type species or related species or related genera of a cultivated plant.

The term "cultivated plants" is to be understood as including plants which have been modified by breeding, mutagenesis or genetic engineering including but not limiting to agricultural biotech products on the market or in development (cf. http://www.bio.org/speeches/pubs/er/agri_products.asp). Genetically modified plants are plants, which genetic material has been so modified by the use of recombinant DNA techniques that under natural circumstances cannot readily be obtained by cross breeding, mutations or natural recombination. Typically, one or more genes have been integrated into the genetic material of a genetically modified plant in order to improve certain properties of the plant. Such genetic modifications also include but are not limited to targeted post-translational modification of protein (s), oligo- or polypeptides e. g. by glycosylation or polymer additions such as prenylated, acetylated or farnesylated moieties or PEG moieties.

Plants that have been modified by breeding, mutagenesis or genetic engineering, e. g. have been rendered tolerant to applications of specific classes of herbicides, such as auxin herbicides such as dicamba or 2,4-D; bleacher herbicides such as hydroxylphenylpyruvate dioxygenase (HPPD) inhibitors or phytoene desaturase (PDS) inhibittors; acetolactate synthase (ALS) inhibitors such as sulfonyl ureas or imidazolinones; enolpyruvylshikimate-3-phosphate synthase (EPSPS) inhibitors, such as glyphosate; glutamine synthetase (GS) inhibitors such as glufosinate; protoporphyrinogen-IX oxidase inhibitors; lipid biosynthesis inhibitors such as acetyl CoA carboxylase (ACCase) inhibitors; or oxynil (i. e. bromoxynil or ioxynil) herbicides as a result of conventional methods of breeding or genetic engineering. Furthermore, plants have been made resistant to multiple classes of herbicides through multiple genetic modifications, such as resistance to both glyphosate and glufosinate or to both glyphosate and a herbicide from another class such as ALS inhibitors, HPPD inhibitors, auxin herbicides, or ACCase inhibitors. These herbicide resistance technologies are e. g. described in Pest Managem. Sci. 61, 2005, 246; 61, 2005, 258; 61, 2005, 277; 61, 2005, 269; 61, 2005, 286; 64, 2008, 326; 64, 2008, 332; Weed Sci. 57, 2009, 108; Austral. J. Agricult. Res. 58, 2007, 708; Science 316, 2007, 1185; and references quoted therein. Several cultivated plants have been rendered tolerant to herbicides by conventional methods of breeding (mutagenesis), e. g. Clearfield® summer rape (Canola, BASF SE, Germany) being tolerant to imidazolinones, e. g. imazamox, or ExpressSun® sunflowers (DuPont, USA) being tolerant to sulfonyl ureas, e. g. tribenuron. Genetic engineering methods have been used to render cultivated plants such as soybean, cotton, corn, beets and rape, tolerant to herbicides such as glyphosate and glufosinate, some of which are commercially available under the trade names RoundupReady® (glyphosate-tolerant, Monsanto, U.S.A.), Cultivance® (imidazolinone tolerant, BASF SE, Germany) and LibertyLink® (glufosinate-tolerant, Bayer CropScience, Germany).

Furthermore, plants are also covered that are by the use of recombinant DNA techniques capable to synthesize one or more insecticidal proteins, especially those known from the bacterial genus *Bacillus*, particularly from *Bacillus thuringiensis*, such as δ-endotoxins, e. g. CryIA(b), CryIA(c), CryIF, CryIF(a2), CryIIA(b), CryIIIA, CryIIIB(b1) or Cry9c; vegetative insecticidal proteins (VIP), e. g. VIP1, VIP2, VIP3 or VIP3A; insecticidal proteins of bacteria colonizing nematodes, e. g. *Photorhabdus* spp. or *Xenorhabdus* spp.; toxins produced by animals, such as scorpion toxins, arachnid toxins, wasp toxins, or other insect-specific neurotoxins; toxins produced by fungi, such Streptomycetes toxins, plant lectins, such as pea or barley lectins; agglutinins; proteinase inhibitors, such as trypsin inhibitors, serine protease inhibitors, patatin, cystatin or papain inhibitors; ribosome-inactivating proteins (RIP), such as ricin, maize-RIP, abrin, luffin, saporin or bryodin; steroid metabolism enzymes, such as 3-hydroxysteroid oxidase, ecdysteroid-IDP-glycosyl-transferase, cholesterol oxidases, ecdysone inhibitors or HMG-CoA-reductase; ion channel blockers, such as blockers of sodium or calcium channels; juvenile hormone esterase; diuretic hormone receptors (helicokinin receptors); stilben synthase, bibenzyl synthase, chitinases or glucanases. In the context of the present invention these insecticidal proteins or toxins are to be understood expressly also as pre-toxins, hybrid proteins, truncated or otherwise modified proteins. Hybrid proteins are characterized by a new combination of protein domains, (see, e. g. WO 02/015701). Further examples of such toxins or genetically modified plants capable of synthesizing such toxins are disclosed, e. g., in EP-A 374 753, WO 93/007278, WO 95/34656, EP-A 427 529, EP-A 451 878, WO 03/18810 und WO 03/52073. The methods for producing such genetically modified plants are generally known to the person skilled in the art and are described, e. g. in the publications mentioned above. These insecticidal proteins contained in the genetically modified plants impart to the plants producing these proteins tolerance to harmful pests from all taxonomic groups of athropods, especially to beetles (Coeloptera), two-winged insects (Diptera), and moths (Lepidoptera) and to nematodes (Nematoda). Genetically modified plants capable to synthesize one or more insecticidal proteins are, e. g., described in the publications mentioned above, and some of which are commercially available such as YieldGard® (corn cultivars producing the Cry1Ab toxin), YieldGard® Plus (corn cultivars producing Cry1Ab and Cry3Bb1 toxins), Starlink® (corn cultivars producing the Cry9c toxin), Herculex® RW (corn cultivars producing Cry34Ab1, Cry35Ab1 and the enzyme Phosphinothricin-N-Acetyltransferase [PAT]); NuCOTN® 33B (cotton cultivars producing the Cry1Ac toxin), Bollgard® I (cotton cultivars producing the Cry1Ac toxin), Bollgard® II (cotton cultivars producing Cry1Ac and Cry2Ab2 toxins); VIPCOT® (cotton cultivars producing a VIP-toxin); NewLeaf® (potato cultivars producing the Cry3A toxin); Bt-Xtra®, NatureGard®, KnockOut®, BiteGard®, Protecta®, Bt11 (e. g. Agrisure® CB) and Bt176 from Syngenta Seeds SAS, France, (corn cultivars producing the Cry1Ab toxin and PAT enyzme), MIR604 from Syngenta Seeds SAS, France (corn cultivars producing a modified version of the Cry3A toxin, c.f. WO 03/018810), MON 863 from Monsanto Europe S.A., Belgium (corn cultivars producing the Cry3Bb1 toxin), IPC 531 from Monsanto Europe S.A., Belgium (cotton cultivars producing a modified version of the Cry1Ac toxin) and 1507 from Pioneer Overseas Corporation, Belgium (corn cultivars producing the Cry1F toxin and PAT enzyme).

Furthermore, plants are also covered that are by the use of recombinant DNA techniques capable to synthesize one or more proteins to increase the resistance or tolerance of those plants to bacterial, viral or fungal pathogens. Examples of such proteins are the so-called "pathogenesis-related proteins" (PR proteins, see, e. g. EP-A 392 225), plant disease resistance genes (e. g. potato cultivars, which express resistance genes acting against *Phytophthora* infestans derived from the mexican wild potato *Solanum bulbocastanum*) or T4-lysozym (e. g. potato cultivars capable of synthesizing these proteins with increased resistance against bacteria such as *Erwinia amylvora*). The methods for producing such genetically modified plants are generally known to the person skilled in the art and are described, e. g. in the publications mentioned above.

Furthermore, plants are also covered that are by the use of recombinant DNA techniques capable to synthesize one or more proteins to increase the productivity (e. g. bio mass production, grain yield, starch content, oil content or protein content), tolerance to drought, salinity or other growth-limiting environmental factors or tolerance to pests and fungal, bacterial or viral pathogens of those plants.

Furthermore, plants are also covered that contain by the use of recombinant DNA techniques a modified amount of substances of content or new substances of content, specifically to improve human or animal nutrition, e. g. oil crops that produce health-promoting long-chain omega-3 fatty acids or unsaturated omega-9 fatty acids (e. g. Nexera® rape, DOW Agro Sciences, Canada).

Furthermore, plants are also covered that contain by the use of recombinant DNA techniques a modified amount of substances of content or new substances of content, specifically to improve raw material production, e. g. potatoes that produce increased amounts of amylopectin (e. g. Amflora® potato, BASF SE, Germany).

The organic moieties mentioned in the above definitions of the variables are—like the term halogen—collective terms for individual listings of the individual members. The prefix $C_n$-$C_m$ indicates in each case the possible number of carbon atoms in the group.

The term halogen denotes in each case F, Br, Cl or I, in particular F, Cl or Br.

The term "alkyl" as used herein and in the alkyl moieties of alkoxy, alkylthio, and the like refers to saturated straight-chain or branched hydrocarbon radicals having 1 to 2 ("$C_1$-$C_2$-alkyl"), 1 to 3 ("$C_1$-$C_3$-alkyl"), 1 to 4 ("$C_1$-$C_4$-alkyl") or 1 to 6 ("$C_1$-$C_6$-alkyl") carbon atoms. $C_1$-$C_2$-Alkyl is $CH_3$ or $C_2H_5$. $C_1$-$C_3$-Alkyl is additionally propyl and isopropyl. $C_1$-$C_4$-Alkyl is additionally butyl, 1-methylpropyl (sec-butyl), 2-methylpropyl (isobutyl) or 1,1-dimethylethyl (tert-butyl). $C_1$-$C_6$-Alkyl is additionally also, for example, pentyl, 1-methylbutyl, 2-methylbutyl, 3-methylbutyl, 2,2-dimethylpropyl, 1-ethylpropyl, 1,1-dimethylpropyl, 1,2-dimethylpropyl, hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, or 1-ethyl-2-methylpropyl.

The term "haloalkyl" as used herein, which is also expressed as "alkyl which is partially or fully halogenated", refers to straight-chain or branched alkyl groups having 1 to 2 ("$C_1$-$C_2$-haloalkyl"), 1 to 3 ("$C_1$-$C_3$-haloalkyl"), 1 to 4 ("$C_1$-$C_4$-haloalkyl") or 1 to 6 ("$C_1$-$C_6$-haloalkyl") carbon atoms (as mentioned above), where some or all of the hydrogen atoms in these groups are replaced by halogen atoms as mentioned above: in particular $C_1$-$C_2$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl or pentafluoroethyl. $C_1$-$C_3$-haloalkyl is additionally, for example, 1-fluoropropyl, 2-fluoropropyl, 3-fluoropropyl, 1,1-difluoropropyl, 2,2-difluoropropyl, 1,2-difluoropropyl, 3,3-difluoropropyl, 3,3,3-trifluoropropyl, heptafluoropropyl, 1,1,1-trifluoroprop-2-yl, 3-chloropropyl and the like. Examples for $C_1$-$C_4$-haloalkyl are, apart those mentioned for $C_1$-$C_3$-haloalkyl, 4-chlorobutyl and the like.

The term "alkylene" (or alkanediyl) as used herein in each case denotes an alkyl radical as defined above, wherein one hydrogen atom at any position of the carbon backbone is replaced by one further binding site, thus forming a bivalent moiety. Alkylene has preferably 1 to 6 carbon atoms ($C_1$-$C_6$-alkylene), 2 to 6 carbon atoms ($C_2$-$C_6$-alkylene), in particular 1 to 4 carbon atoms ($C_1$-$C_4$-alkylene) or 2 to 4 carbon atoms ($C_2$-$C_4$-alkylene). Examples of alkylene are methylene (CH2), 1,1-ethandiyl, 1,2-ethandiyl, 1,3-propandiyl, 1,2-propandiyl, 2,2-propandiyl, 1,4-butandiyl, 1,2-butandiyl, 1,3-butandiyl, 2,3-butandiyl, 2,2-butandiyl, 1,5-pentandiyl, 2,2-dimethylpropan-1,3-diyl, 1,3-dimethyl-1,3-propandiyl, 1,6-hexandiyl etc.

The term "alkenyl" as used herein refers to monounsaturated straight-chain or branched hydrocarbon radicals having 2 to 3 ("$C_2$-$C_3$-alkenyl"), 2 to 4 ("$C_2$-$C_4$-alkenyl") or 2 to 6 ("$C_2$-$C_6$-alkenyl) carbon atoms and a double bond in any position, for example $C_2$-$C_3$-alkenyl, such as ethenyl, 1-propenyl, 2-propenyl or 1-methylethenyl; $C_2$-$C_4$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl or 2-methyl-2-propenyl; $C_2$-$C_6$-alkenyl, such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, 1-ethyl-2-methyl-2-propenyl and the like.

The term "alkynyl" as used herein refers to straight-chain or branched hydrocarbon groups having 2 to 3 ("$C_2$-$C_3$-alkynyl"), 2 to 4 ("$C_2$-$C_4$-alkynyl") or 2 to 6 ("$C_2$-$C_6$-alkynyl") carbon atoms and one or two triple bonds in any position, for example $C_2$-$C_3$-alkynyl, such as ethynyl, 1-propynyl or 2-propynyl; $C_2$-$C_4$-alkynyl, such as ethynyl, 1-propynyl, 2-propynyl, 1-butynyl, 2-butynyl, 3-butynyl, 1-methyl-2-propynyl and the like, $C_2$-$C_6$-alkynyl, such as ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 1-ethyl-2-propynyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, 1-ethyl-1-methyl-2-propynyl and the like;

The term "cycloalkyl" as used herein refers to mono- or bi- or polycyclic saturated hydrocarbon radicals having in particular 3 to 6 ("$C_3$-$C_6$-cycloalkyl") or 3 to 5 ("$C_3$-$C_5$-cycloalkyl") or 3 to 4 ("$C_3$-$C_4$-cycloalkyl") carbon atoms. Examples of monocyclic radicals having 3 to 4 carbon atoms comprise cyclopropyl and cyclobutyl. Examples of monocyclic radicals having 3 to 5 carbon atoms comprise cyclopropyl, cyclobutyl and cyclopentyl. Examples of monocyclic radicals having 3 to 6 carbon atoms comprise cyclopropyl, cyclobutyl, cyclopentyl and cyclohexyl. Examples of monocyclic radicals having 3 to 8 carbon atoms comprise cyclopropyl, cyclobutyl, cyclopentyl, cyclohexyl, cycloheptyl and cyclooctyl. Examples of bicyclic radicals having 7 or 8 carbon atoms comprise bicyclo[2.2.1]heptyl, bicyclo[3.1.1]heptyl, bicyclo[2.2.2]octyl and bicyclo[3.2.1]octyl. Preferably, the term cycloalkyl denotes a monocyclic saturated hydrocarbon radical.

The term "cycloalkoxy" as used herein refers to a cycloalkyl radical, in particular a monocyclic cycloalkyl radical, as defined above having in particular 3 to 6 ("$C_3$-$C_6$-cycloalkoxy") or 3 to 5 ("$C_3$-$C_5$-cycloalkoxy") or 3 to 4 ("$C_3$-$C_4$-cycloalksoxy") carbon atoms, which is bound via an oxygen atom to the remainder of the molecule.

The term "cycloalkyl-$C_1$-$C_4$-alkyl" refers to a $C_3$-$C_8$-cycloalkyl ("$C_3$-$C_8$-cycloalkyl-$C_1$-$C_4$-alkyl"), preferably a $C_3$-$C_6$-cycloalkyl ("$C_3$-$C_6$-cycloalkyl-$C_1$-$C_4$-alkyl"), more preferably a $C_3$-$C_4$-cycloalkyl ("$C_3$-$C_4$-cycloalkyl-$C_1$-$C_4$-alkyl") as defined above (preferably a monocyclic cycloalkyl group) which is bound to the remainder of the molecule via a $C_1$-$C_4$-alkyl group, as defined above. Examples for $C_3$-$C_4$-cycloalkyl-$C_1$-$C_4$-alkyl are cyclopropylmethyl, cyclopropylethyl, cyclopropylpropyl, cyclobutylmethyl, cyclobutylethyl and cyclobutylpropyl, Examples for $C_3$-$C_6$-cycloalkyl-$C_1$-$C_4$-alkyl, apart those mentioned for $C_3$-$C_4$-cycloalkyl-$C_1$-$C_4$-alkyl, are cyclopentylmethyl, cyclopentylethyl, cyclopentylpropyl, cyclohexylmethyl, cyclohexylethyl and cyclohexylpropyl.

The term "$C_1$-$C_2$-alkoxy" is a $C_1$-$C_2$-alkyl group, as defined above, attached via an oxygen atom. The term "$C_1$-$C_3$-alkoxy" is a $C_1$-$C_3$-alkyl group, as defined above, attached via an oxygen atom. The term "$C_1$-$C_4$-alkoxy" is a $C_1$-$C_4$-alkyl group, as defined above, attached via an oxygen atom. The term "$C_1$-$C_6$-alkoxy" is a $C_1$-$C_6$-alkyl group, as defined above, attached via an oxygen atom. The term "$C_1$-$C_{10}$-alkoxy" is a $C_1$-$C_{10}$-alkyl group, as defined above, attached via an oxygen atom. $C_1$-$C_2$-Alkoxy is $OCH_3$ or $OC_2H_5$. $C_1$-$C_3$-Alkoxy is additionally, for example, n-propoxy and 1-methylethoxy (isopropoxy). $C_1$-$C_4$-Alkoxy is additionally, for example, butoxy, 1-methylpropoxy (sec-butoxy), 2-methylpropoxy (isobutoxy) or 1,1-dimethyl- ethoxy (tert-butoxy). $C_1$-$C_6$-Alkoxy is additionally, for example, pentoxy, 1-methylbutoxy, 2-methylbutoxy, 3-methylbutoxy, 1,1-dimethylpropoxy, 1,2-dimethylpropoxy, 2,2-dimethylpropoxy, 1-ethylpropoxy, hexoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy or 1-ethyl-2-methylpropoxy. $C_1$-$C_8$-Alkoxy is additionally, for example, heptyloxy, octyloxy, 2-ethylhexyloxy and positional isomers thereof. $C_1$-$C_{10}$-Alkoxy is additionally, for example, nonyloxy, decyloxy and positional isomers thereof.

The term "$C_1$-$C_2$-haloalkoxy" is a $C_1$-$C_2$-haloalkyl group, as defined above, attached via an oxygen atom. The term "$C_1$-$C_3$-haloalkoxy" is a $C_1$-$C_3$-haloalkyl group, as defined above, attached via an oxygen atom. The term "$C_1$-$C_4$-haloalkoxy" is a $C_1$-$C_4$-haloalkyl group, as defined above, attached via an oxygen atom. The term "$C_1$-$C_6$-haloalkoxy" is a $C_1$-$C_6$-haloalkyl group, as defined above, attached via an oxygen atom. $C_1$-$C_2$-Haloalkoxy is, for example, $OCH_2F$, $OCHF_2$, $OCF_3$, $OCH_2Cl$, $OCHCl_2$, $OCCl_3$, chlorofluoromethoxy, dichlorofluoromethoxy, chlorodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy or $OC_2F_5$. $C_1$-$C_3$-Haloalkoxy is additionally, for example, 2-fluoropropoxy, 3-fluoropropoxy, 2,2-difluoropropoxy, 2,3-difluoropropoxy, 2-chloropropoxy, 3-chloropropoxy, 2,3-dichloropropoxy, 2-bromopropoxy, 3-bromopropoxy, 3,3,3-trifluoropropoxy, 3,3,3-trichloropropoxy, $OCH_2$—$C_2F_5$, $OCF_2$—$C_2F_5$, 1-($CH_2F$)-2-fluoroethoxy, 1-($CH_2Cl$)-2-chloroethoxy or 1-($CH_2Br$)-2-bromoethoxy. $C_1$-$C_4$-Haloalkoxy is additionally, for example, 4-fluorobutoxy, 4-chlorobutoxy, 4-bromobutoxy or nonafluorobutoxy. $C_1$-$C_6$-Haloalkoxy is additionally, for example, 5-fluoropentoxy, 5-chloropentoxy, 5-brompentoxy, 5-iodopentoxy, undecafluoropentoxy, 6-fluorohexoxy, 6-chlorohexoxy, 6-bromohexoxy, 6-iodohexoxy or dodecafluorohexoxy.

The term "$C_1$-$C_6$-alkoxy-$C_1$-$C_4$-alkyl" as used herein, refers to a straight-chain or branched alkyl having 1 to 4 carbon atoms, as defined above, where one hydrogen atom is replaced by a $C_1$-$C_6$-alkoxy group, as defined above. Examples are methoxymethyl, ethoxymethyl, propoxymethyl, isopropoxymethyl, n-butoxymethyl, sec-butoxymethyl, isobutoxymethyl, tertbutoxymethyl, 1-methoxyethyl, 1-ethoxyethyl, 1-propoxyethyl, 1-isopropoxyethyl, 1-n-butoxyethyl, 1-sec-butoxyethyl, 1-isobutoxyethyl, 1-tert-butoxyethyl, 2-methoxyethyl, 2-ethoxyethyl, 2-propoxyethyl, 2-isopropoxyethyl, 2-n-butoxyethyl, 2-sec-butoxyethyl, 2-isobutoxyethyl, 2-tertbutoxyethyl, 1-methoxypropyl, 1-ethoxypropyl, 1-propoxypropyl, 1-isopropoxypropyl, 1-n-butoxypropyl, 1-sec-butoxypropyl, 1-isobutoxypropyl, 1-tert-butoxypropyl, 2-methoxypropyl, 2-ethoxypropyl, 2-propoxypropyl, 2-isopropoxypropyl, 2-n-butoxypropyl, 2-sec-butoxypropyl, 2-isobutoxypropyl, 2-tert-butoxypropyl, 3-methoxypropyl, 3-ethoxypropyl, 3-propoxypropyl, 3-isopropoxypropyl, 3-n-butoxypropyl, 3-sec-butoxypropyl, 3-isobutoxypropyl, 3-tert-butoxypropyl and the like.

The term "alkoxyalkoxy" as used herein refers to an alkoxyalkyl radical, in particular a $C_1$-$C_6$-alkoxy-$C_1$-$C_4$-alkyl radical, as defined above, which is bound via an oxygen atom to the remainder of the molecule. Examples thereof are $OCH_2$—$OCH_3$, $OCH_2$—$OC_2H_5$, n-propoxymethoxy, $OCH_2$—$OCH(CH_3)_2$, n-butoxymethoxy, (1-methylpropoxy)methoxy, (2-methylpropoxy) methoxy, $OCH_2$—$OC(CH_3)_3$, 2-(methoxy)ethoxy, 2-(ethoxy)ethoxy, 2-(n-propoxy)ethoxy, 2-(1-methylethoxy) ethoxy, 2-(n-butoxy)ethoxy, 2-(1-methylpropoxy)ethoxy, 2-(2-methylpropoxy)ethoxy, 2-(1,1-dimethylethoxy)ethoxy, etc.

The substituent "oxo" replaces a $CH_2$ by a $C(=O)$ group.

The term "aryl" relates to phenyl and bi- or polycyclic carbocycles having at least one fused phenylene ring, which is bound to the remainder of the molecule. Examples of bi- or polycyclic carbocycles having at least one phenylene ring include naphthyl, tetrahydronaphthyl, indanyl, indenyl, anthracenyl, fluorenyl etc.

The term "aryl-$C_1$-$C_4$-alkyl" relates to $C_1$-$C_4$-alkyl, as defined above, wherein one hydrogen atom has been replaced by an aryl radical, in particular a phenyl radical. Particular examples of aryl-$C_1$-$C_4$-alkyl include —$CH_2$-phenyl, 1-phenethyl, 2-phenetyl, 1-phenylpropyl, 2-phenylpropyl, 3-phenyl-1-propyl and 2-phenyl-2-propyl.

The term "aryloxy-$C_1$-$C_4$-alkyl" relates to $C_1$-$C_4$-alkyl, as defined above, wherein one hydrogen atom has been replaced by an aryloxy radical, in particular a phenoxy radical. Particular examples of aryloxy-$C_1$-$C_4$-alkyl include phenoxymethyl, 1-phenoxyethyl, 2-phenoxyetyl, 1-phenoxypropyl, 2-phenoxypropyl, 3-phenoxy-1-propyl and 2-phenoxy-2-propyl.

The term "aryl-$C_1$-$C_4$-carbonyl" relates to aryl as defined above, in particular a phenyl radical, which is bound by a carbonyl to the remainder of the molecule. Particular examples of arylcarbonyl include benzoyl, 1-naphthoyl and 2-naphthoyl.

The term "hetaryl" relates to aromatic heterocycles having either 5 or 6 ring atoms (5- or 6-membered hetaryl) and being monocyclic or 8, 9 or 10 ring atoms and bing bicyclic. Hetaryl will generally have at least one ring atom selected from O, S and N, which in case of N may be an imino-nitrogen or an amino-nitrogen, which carries hydrogen or a radical different from hydrogen. Hetaryl may have 1, 2, 3 or 4 further nitrogen atoms as ring members, which are imino nitrogens. Examples of 5- or 6-membered hetaryl include 2-furyl, 3-furyl, 2-thienyl, 3-thienyl, 1-pyrrolyl, 2-pyrrolyl, 3-pyrrolyl, 1-pyrazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 1-imidazolyl, 2-imidazolyl, 4-imidazolyl, 1,3,4-triazol-1-yl, 1,3,4-triazol-2-yl, 1,3,4-oxadiazolyl-2-yl, 1,3,4-thiadiazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl and 1,3,5-triazin-2-yl. Examples of 8-, 9- or 10-membered hetaryl include, for example, quinolinyl, isoquinolinyl, cinnolinyl, indolyl, indolizynyl, isoindolyl, indazolyl, benzofuryl, benzothienyl, benzo[b]thiazolyl, benzoxazolyl, benzthiazolyl, benzimidazolyl, imidazo[1,2-a]pyridine-2-yl, thieno[3,2-b]pyridine-5-yl, imidazo-[2,1-b]-thiazol-6-yl and 1,2,4-triazolo[1,5-a]pyridine-2-yl.

Examples of N-bound 5-, 6-, 7 or 8-membered saturated heterocycles include: pyrrolidin-1-yl, pyrazolidin-1-yl, imidazolidin-1-yl, oxazolidin-3-yl, isoxazolidin-2-yl, thiazolidin-3-yl, isothiazolidin-2-yl, piperidin-1-yl, piperazin-1-yl, morpholin-4-yl, thiomorpholin-4-yl, 1-oxothiomorpholin-4-yl, 1,1-dioxothiomorpholin-4-yl, azepan-1-yl and the like.

The term "hetaryl-$C_1$-$C_4$-alkyl" relates to $C_1$-$C_4$-alkyl, as defined above, wherein one hydrogen atom has been replaced by a hetaryl radical, in particular a pyridyl radical. Particular examples of hetaryl-$C_1$-$C_4$-alkyl include 2-pyridylmethyl, 3-pyridylmethyl, 4-pyridylmethyl, 1-(2-pyridyl)ethyl, 2-(2-pyridyl)ethyl, 1-(3-pyridyl)ethyl, 2-(3-pyridyl)ethyl, 1-(4-pyridyl)ethyl, 2-(4-pyridyl)ethyl etc.

The term "hetaryloxy-$C_1$-$C_4$-alkyl" relates to $C_1$-$C_4$-alkyl, as defined above, wherein one hydrogen atom has been replaced by an hetaryloxy radical, in particular a pyridyloxy radical.

Particular examples of hetaryloxy-$C_1$-$C_4$-alkyl include 2-pyridyloxymethyl, 3-pyridyloxymethyl, 4-pyridyloxymethyl, 1-(2-pyridyloxy)ethyl, 2-(2-pyridyloxy)ethyl, 1-(3-pyridyloxy)ethyl, 2-(3-pyridyloxy)ethyl, 1-(4-pyridyloxy) ethyl, 2-(4-pyridyloxy)ethyl etc.

The term "hetaryl-$C_1$-$C_4$-carbonyl" relates to hetaryl as defined above, in particular a C-bound hetaryl radical, e.g. 2-, 3- or 4-pyridyl, 2- or 3-thienyl, 2- or 3-furyl, 1-, 2- or 3-pyrrolyl, 2- or 4-pyrimidinyl, pyridazinyl, 1-, 3- or 4-pyrazolyl, 1-, 2- or 4-imidazolyl radical, which is bound by a carbonyl to the remainder of the molecule.

The term "substituted" if not specified otherwise refers to substituted with 1, 2 or maximum possible number of substituents. If substituents as defined in compounds of formula I are more than one then they are independently from each other are same or different if not mentioned otherwise.

With respect to the variables, the embodiments of the compounds of the formula I are, In one preferred embodiment, W is O.

In another preferred embodiment, W is $NR^6$.

In another preferred embodiment, W is $S(=O)_m$.

In one preferred embodiment, $A^1$ is $CR^A$.

In another preferred embodiment, $A^1$ is N.

In one preferred embodiment, $A^2$ is $CR^B$.

In another preferred embodiment, $A^2$ is N.

In one preferred embodiment, $A^3$ is $CR^{B1}$.

In another preferred embodiment, $A^3$ is N.

In one preferred embodiment, W is O, $A^1$ is $CR^A$, $A^2$ is $CR^B$, and $A^3$ is N.

In another preferred embodiment, W is O, $A^1$ is $CR^A$, $A^2$ is $CR^B$, and $A^3$ is $CR^{B1}$.

In another preferred embodiment, W is O, $A^1$ is N, $A^2$ is N, and $A^3$ is $R^{B1}$.

In another preferred embodiment, W is O, $A^1$ is $CR^A$, $A^2$ is N, and $A^3$ is $R^{B1}$.

In another preferred embodiment, W is O, $A^1$ is N, $A^2$ is $CR^B$, and $A^3$ is $R^{B1}$.

In another preferred embodiment, W is O, $A^1$ is $CR^A$, $A^2$ is N, and $A^3$ is N.

In another preferred embodiment, W is N, $A^1$ is $CR^A$, $A^2$ is $CR^B$, and $A^3$ is N.

In another preferred embodiment, W is N, $A^1$ is $CR^A$, $A^2$ is $CR^B$, and $A^3$ is $CR^{B1}$.

In another preferred embodiment, W is N, $A^1$ is N, $A^2$ is N, and $A^3$ is $CR^{B1}$.

In another preferred embodiment, W is N, $A^1$ is $CR^A$, $A^2$ is N, and $A^3$ is $R^{B1}$.

In another preferred embodiment, W is N, $A^1$ is N, $A^2$ is $CR^B$, and $A^3$ is $R^{B1}$.

In another preferred embodiment, W is N, $A^1$ is $CR^A$, $A^2$ is N, and $A^3$ is N.

In another preferred embodiment, W is $S(=O)_m$, $A^1$ is $CR^A$, $A^2$ is $CR^B$, and $A^3$ is N.

In another preferred embodiment, W is $S(=O)_m$, $A^1$ is $CR^A$, $A^2$ is $CR^B$, and $A^3$ is $CR^{B1}$.

In another preferred embodiment, W is $S(=O)_m$, $A^1$ is N, $A^2$ is N, and $A^3$ is $R^{B1}$.

In another preferred embodiment, W is $S(=O)_m$, $A^1$ is $CR^A$, $A^2$ is N, and $A^3$ is $R^{B1}$.

In another preferred embodiment, W is $S(=O)_m$, $A^1$ is N, $A^2$ is $CR^B$, and $A^3$ is $R^{B1}$.

In another preferred embodiment, W is $S(=O)_m$, $A^1$ is $CR^A$, $A^2$ is N, and $A^3$ is N.

In one preferred embodiment, $R^A$ is H, halogen, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In more preferred embodiment, $R^A$ is H, halogen, OH, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In most preferred embodiment, $R^A$ is H, Cl, Br, F, OH, CN, $CH_3$, $C_2H_5$, n-$C_3H_7$, isopropyl, cyclopropyl, allyl and propargyl, $CH_2F$, $CHF_2$, $CF_3$, $OCH_3$, $OC_2H_5$, $OCH_2F$, $OCHF_2$, $OCF_3$, $OCH_2CH_2CF_3$, $OCH_2CF_2CHF_2$, or $OCH_2CF_2CF_3$.

In one preferred embodiment, $R^B$ is H, halogen, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In more preferred embodiment, $R^B$ is H, halogen, OH, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In most preferred embodiment, $R^B$ is H, Cl, Br, F, OH, CN, $CH_3$, $C_2H_5$, n-$C_3H_7$, isopropyl, cyclopropyl, allyl and propargyl, $CH_2F$, $CHF_2$, $CF_3$, $OCH_3$, $OC_2H_5$, $OCH_2F$, $OCHF_2$, $OCF_3$, $OCH_2CH_2CF_3$, $OCH_2CF_2CHF_2$, or $OCH_2CF_2CF_3$.

In one preferred embodiment, $R^{B1}$ is H, halogen, OH, CN, $NO_2$, —SCN, —$SF_5$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In more preferred embodiment, $R^{B1}$ is H, halogen, OH, CN, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, or tri-$C_1$-$C_6$-alkylsilyl.

In most preferred embodiment, $R^{B1}$ is H, Cl, Br, F, OH, CN, $CH_3$, $C_2H_5$, n-$C_3H_7$, isopropyl, cyclopropyl, allyl and propargyl, $CH_2F$, $CHF_2$, $CF_3$, $OCH_3$, $OC_2H_5$, $OCH_2F$, $OCHF_2$, $OCF_3$, $OCH_2CH_2CF_3$, $OCH_2CF_2CHF_2$, or $OCH_2CF_2CF_3$.

In one preferred embodiment, Q is —$C(R^4R^5)$—O—, wherein C is bound to Ar.

In another preferred embodiment, Q is —$C(R^4R^5)$—O—, wherein O is bound to Ar.

In another preferred embodiment, Q is —$C(=O)$—O—, wherein C is bound to Ar.

In another preferred embodiment, Q is —$C(=O)$—O—, wherein O is bound to Ar.

In another preferred embodiment, Q is —$S(=O)_m$—$C(R^7R^8)$—, wherein S is bound to Ar.

In another preferred embodiment, Q is —$S(=O)_m$—$C(R^7R^8)$—, wherein C is bound to Ar.

In another preferred embodiment, Q is —$N(R^2)$—$S(=O)_m$—, wherein N is bound to Ar.

In another preferred embodiment, Q is —$N(R^2)$—$S(=O)_m$—, wherein S is bound to Ar.

In another preferred embodiment, Q is —$N(R^2)$—$C(R^9R^{10})$—, wherein N is bound to Ar.

In another preferred embodiment, Q is —$N(R^2)$—$C(R^9R^{10})$—, wherein C is bound to Ar.

In another preferred embodiment, Q is —$C(=O)$—$C(R^{19}R^{20})$—, wherein $C(=O)$ is bound to Ar.

In another preferred embodiment, Q is —$C(=O)$—$C(R^{19}R^{20})$—, wherein $C(R^{19}R^{20})$ is bound to Ar.

In another preferred embodiment, Q is —$N(R^2)$—$C(=O)$—, wherein N is bound to Ar.

In another preferred embodiment, Q is —$N(R^2)$—$C(=O)$—, wherein C is bound to Ar.

In another preferred embodiment, Q is —$C(R^{13}R^{14})$—$C(R^{15}R^{16})$—.

In another preferred embodiment, Q is —$C(R^{17})$=$C(R^{18})$—.

In one preferred embodiment, $R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)$—$OR^a$, $C_1$-$C_6$-alkylene-$NR^bR^c$, $C_1$-$C_6$-alkylene-CN, $C(=O)$—$NR^bR^c$, $C(=O)$—$R^d$, $SO_2NR^bR^c$, $S(=O)_mR^e$, phenyl, or —$CH_2$-phenyl, wherein the phenyl rings are unsubstituted or substituted with $R^f$;

In another preferred embodiment, $R^6$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, In another preferred embodiment, $R^6$ is $C(=O)$—$OR^a$, $C_1$-$C_6$-alkylene-$NR^bR^c$, $C_1$-$C_6$-alkylene-CN, $C(=O)$—$NR^bR^c$, $C(=O)$—$R^d$, $SO_2NR^bR^c$, $S(=O)_mR^e$, phenyl, or —$CH_2$-phenyl, wherein the phenyl rings are unsubstituted or substituted with $R^f$; In another preferred embodiment, $R^6$ is H, $C_1$-$C_6$-alkyl, $C_1$-$C_6$-haloalkyl, —$CH_2$—$C(=O)$—$OR^a$, or —$CH_2$-phenyl;

In another preferred embodiment, $R^6$ is H, $C_1$-$C_6$-alkyl, $C_1$-$C_6$-haloalkyl, or —$CH_2$-phenyl;

In another preferred embodiment, $R^6$ is H, $C_1$-$C_6$-alkyl, $C_1$-$C_6$-haloalkyl, or —$CH_2$—$C(=O)$—$OR^a$;

In another preferred embodiment, $R^6$ is H, or $C_1$-$C_6$-alkyl;

In another preferred embodiment, $R^6$ is H;

In another preferred embodiment, $R^6$ is $C_1$-$C_6$-alkyl;

In one preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_1$-$C_6$-haloalkylalkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-halocycloalkyl, $C_3$-$C_6$-cycloalkyl-$C_1$-$C_4$-alkyl, $C_3$-$C_6$-cycloalkoxy-$C_1$-$C_4$-alkyl, $C(=O)$—$OR^a$, $C(=O)$—$NR^bR^c$, $C(=O)$—$R^d$, $SO_2NR^bR^c$, $S(=O)_mR^e$, phenyl, or —$CH_2$-phenyl, wherein the phenyl rings are unsubstituted or substituted with $R^f$;

In more preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, $C_1$-$C_6$-haloalkylalkyl, $C_3$-$C_6$-cycloalkyl, $C_3$-$C_6$-halocycloalkyl, $C(=O)$—$OR^a$, $C(=O)$—$NR^bR^c$, $C(=O)$—$R^d$, phenyl, or —$CH_2$-phenyl, wherein the phenyl rings are unsubstituted or substituted with $R^f$;

In most preferred embodiment, $R^4$, $R^5$, $R^7$, $R^8$, $R^9$, $R^{10}$, $R^{13}$, $R^{14}$, $R^{15}$, $R^{16}$, $R^{17}$, $R^{18}$, $R^{19}$, $R^{20}$ are, identical or different, H, halogen, $C_1$-$C_6$-alkyl, or $C_1$-$C_6$-haloalkylalkyl;

In one preferred embodiment, Ar is phenyl which is unsubstituted or substituted with $R^{Ar}$.

In another preferred embodiment, Ar is 5- or 6-membered hetaryl, which is unsubstituted or substituted with $R^{Ar}$.

In more preferred embodiment, Ar is phenyl, pyrimidinyl, pyridazinyl, or pyridyl, which are unsubstituted or substituted with $R^{Ar}$.

In one preferred embodiment, $R^{Ar}$ is halogen, OH, CN, $NO_2$, SCN, $C_1$-$C_6$-alkyl, $C_1$-$C_6$-haloalkyl, $C_1$-$C_6$-alkoxy, $C_1$-$C_6$-haloalkoxy, or S—$R^e$.

In more preferred embodiment, $R^{Ar}$ is F, $C_1$, Br, OH, CN, $NO_2$, SCN, $CH_3$, $C_2H_5$, n-$C_3H_7$, isopropyl, $CH_2F$, $CHF_2$, CF$_3$, CH$_2$CF$_3$, CF$_2$CHF$_2$, C$_2$F$_5$, CH$_2$CH$_2$CF$_3$, CH$_2$CF$_2$CHF$_2$, CH$_2$CF$_2$CF$_3$, OCH$_3$, OC$_2$H$_5$, n-propyloxy, isopropyloxy, OCH$_2$F, OCHF$_2$, OCF$_3$, OCH$_2$CF$_3$, OCF$_2$CHF$_2$, OC$_2$F$_5$, OCH$_2$CH$_2$CF$_3$, OCH$_2$CF$_2$CHF$_2$, OCH$_2$CF$_2$CF$_3$, or S—R$^e$, where R$^e$ is C$_1$-C$_6$-alkyl, in particular C$_1$-C$_3$-alkyl such as CH$_3$, C$_2$H$_5$, n-C$_3$H$_7$ or isopropyl, or C$_1$-C$_6$-haloalkyl, in particular fluorinated C$_1$-C$_3$-alkyl such as CH$_2$F, CHF$_2$, CF$_3$, CH$_2$CF$_3$, CF$_2$CHF$_2$, C$_2$F$_5$, CH$_2$CH$_2$CF$_3$, CH$_2$CF$_2$CHF$_2$ or CH$_2$CF$_2$CF$_3$.

Particularly preferred Ar are listed in Table A below.

TABLE A

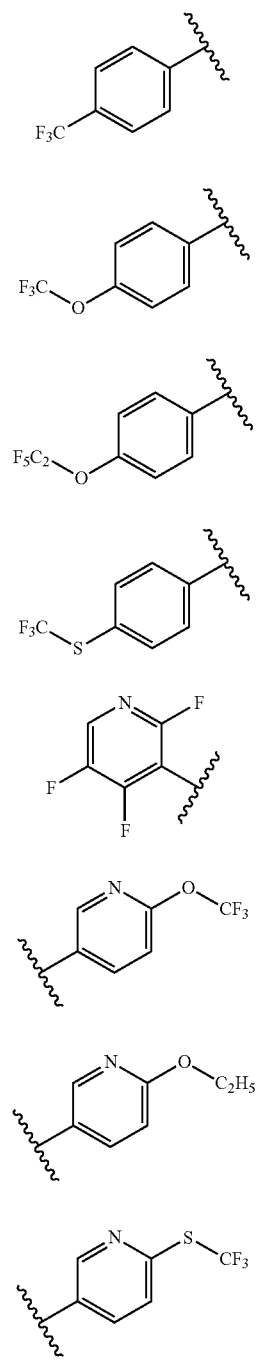

TABLE A-continued

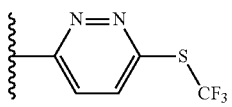
Ar-9

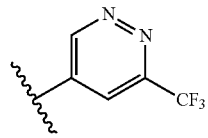 [SMILES: *c1cnnc(C(F)(F)F)c1]
Ar-10

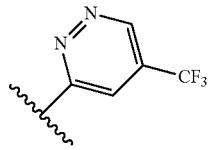 [SMILES: *c1cc(C(F)(F)F)cnn1]
Ar-11

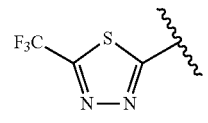
Ar-12

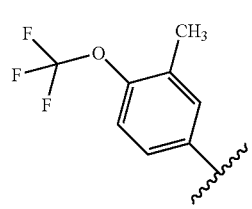 [SMILES: *c1ccc(OC(F)(F)F)c(C)c1]
Ar-13

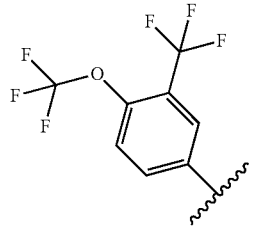 [SMILES: *c1ccc(OC(F)(F)F)c(C(F)(F)F)c1]
Ar-14

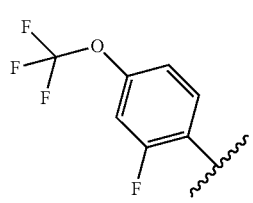 [SMILES: *c1ccc(OC(F)(F)F)cc1F]
Ar-15

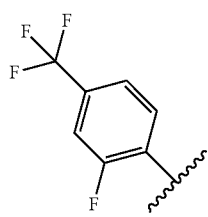 [SMILES: *c1ccc(C(F)(F)F)cc1F]
Ar-16

Particularly preferred Ar is selected from Ar-1 to Ar-16; also particularly preferred Ar is selected from Ar-1 to Ar-13;

In one preferred embodiment, R$^1$ is Y—Z-T-R$^{11}$.

In another preferred embodiment, R$^1$ is Y—Z-T-R$^{12}$.

In one preferred embodiment, Y is —$CR^{ya}$═N—, wherein the N is bound to Z.

In another preferred embodiment, Y is —$NR^{yc}$—C(═S)—, wherein C(═S) is bound to Z.

In another preferred embodiment, Y is —$NR^{yc}$—C(═O)—, wherein C(═O) is bound to Z.

In one preferred embodiment, Z is a single bond;
—$NR^{zc}$—C(═O)—, wherein C(═O) is bound to T;
—$NR^{zc}$—C(═S)—, wherein C(═S) is bound to T;
—N═C(S—$R^{za}$)—, wherein T is bound to the carbon atom; or
—$NR^{zc}$—C(S—$R^{za}$)═, wherein T is bound to the carbon atom;

In another preferred embodiment, Z is —$NR^{zc}$—C(═S)—, wherein C(═S) is bound to T.

In another preferred embodiment, Z is —$NR^{zc}$—C(═O)—, wherein C(═O) is bound to T.

In another preferred embodiment, Z is —N═C(S—$R^{za}$)—, wherein T is bound to the carbon atom.

In another preferred embodiment, Z is —$NR^{zc}$—C(S—$R^{za}$)═, wherein T is bound to the carbon atom.

In another preferred embodiment, Z is —O—C(═O)—, wherein T is bound to the carbon atom;

In another preferred embodiment, Z is a single bond.

In one preferred embodiment, T is O.

In another preferred embodiment, T is N—$R^T$.

In another preferred embodiment, T is N.

In one preferred embodiment, $R^{ya}$ is H, halogen, $C_1$-$C_6$-alkyl, $C_1$-$C_6$-alkoxy, which are unsubstituted or substituted with halogen,
phenyl, or —$CH_2$-phenyl, wherein the phenyl rings are unsubstituted or substituted with $R^f$.

In more preferred embodiment, $R^{ya}$ is H, halogen, $C_1$-$C_6$-alkyl, $C_1$-$C_6$-alkoxy, which are unsubstituted or substituted with halogen,
or phenyl which is unsubstituted or substituted with $R^f$.

In most preferred embodiment, $R^{ya}$ is H, F, Cl, Br, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, $OCH_3$, $OC_2H_5$, n-propyloxy, isopropyloxy, $OCH_2F$, $OCHF_2$, $OCF_3$, $OCH_2CF_3$, $OCF_2CHF_2$, $OC_2F_5$, $OCH_2CH_2CF_3$, $OCH_2CF_2CHF_2$, $OCH_2CF_2CF_3$, or phenyl which is unsubstituted or substituted with $R^f$.

In further most preferred embodiment, $R^{ya}$ is H or $CH_3$;

In one embodiment, $R^{yc}$, $R^{zc}$ are H, $C_1$-$C_6$-alkyl, $C_3$-$C_6$-cycloalkyl, which are unsubstituted or substituted with halogen,
phenyl, or —$CH_2$-phenyl, wherein the rings are unsubstituted or substituted with $R^f$.

In more preferred embodiment, $R^{yc}$ and $R^{zc}$ are H, $C_1$-$C_6$-alkyl, $C_1$-$C_6$-haloalkyl, or phenyl which is unsubstituted or substituted with $R^f$.

In most preferred embodiment, $R^{yc}$ and $R^{zc}$ are H, $CH_3$, $C_2H_5$, n-$C_3H_7$, isopropyl, $CH_2F$, $CHF_2$, $CF_3$, $CH_2CF_3$, $CF_2CHF_2$, $C_2F_5$, $CH_2CH_2CF_3$, $CH_2CF_2CHF_2$, $CH_2CF_2CF_3$, or phenyl which is unsubstituted or substituted with $R^f$.

In further most preferred embodiment, $R^{yc}$ and $R^{zc}$ are H or $CH_3$;

In one preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen,
C(═O)—$NR^bR^c$, C(═O)—$R^d$, $SO_2NR^bR^c$, S(═O)$_m R^e$, phenyl, or —$CH_2$-phenyl, wherein the phenyl rings are unsubstituted or substituted with $R^f$.

In more preferred embodiment, $R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, which are unsubstituted or substituted with halogen.

In most preferred embodiment, $R^T$ is H or $C_1$-$C_6$-alkyl.

In another preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{zc}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In one preferred embodiment, $R^{za}$ is H, $C_1$-$C_6$-alkyl, $C_1$-$C_6$-haloalkyl, $C_1$-$C_6$-alkylene-$NR^bR^c$, $C_1$-$C_6$—C(═O)—$R^d$, phenyl, phenylcarbonyl, or —$CH_2$-phenyl, wherein the phenyl rings are unsubstituted or substituted with $R^f$;

In more preferred embodiment, $R^{za}$ is H, $C_1$-$C_6$-alkyl, or $C_1$-$C_6$-haloalkyl;

In most preferred embodiment, $R^{za}$ is H, $C_1$-$C_6$-alkyl.

In another preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C═N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

In more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a carbonyl group.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety is replaced by a C═N—R' and wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$.

In another more preferred embodiment, $R^{za}$ together with $R^T$ if present, forms $C_1$-$C_6$-alkylene or a linear $C_2$-$C_6$-alkenylene group, where in the linear $C_1$-$C_6$-alkylene and the linear $C_2$-$C_6$-alkenylene 1 or 2 $CH_2$ moieties are replaced by O or S and/or wherein the linear $C_1$-$C_6$-alkylene and the linear $C_2$-$C_6$-alkenylene may be unsubstituted or substituted with $R^h$.

In a preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen, $C_1$-$C_6$-alkylene-CN, phenyl, or —$CH_2$-phenyl, wherein the phenyl rings are unsubstituted or substituted with $R^f$;

In more preferred embodiment, $R^a$, $R^b$ and $R^c$ are H, $C_1$-$C_6$-alkyl, $C_2$-$C_6$-alkenyl, $C_2$-$C_6$-alkynyl, which are unsubstituted or substituted with halogen,
phenyl, or —$CH_2$-phenyl, wherein the phenyl rings are unsubstituted or substituted with $R^f$.

In a preferred embodiment, $R^d$ is H, $C_1$-$C_6$-alkyl, $C_2$-$C_6$-alkenyl, $C_2$-$C_6$-alkynyl, which are unsubstituted or substituted with halogen, phenyl, or —$CH_2$-phenyl, wherein the phenyl rings are unsubstituted or substituted with $R^f$.

In more preferred embodiment, $R^d$ is H, $C_1$-$C_6$-alkyl, $C_1$-$C_6$-haloalkyl, or phenyl which is unsubstituted or substituted with $R^f$.

In one preferred embodiment, $R^e$ is $C_1$-$C_6$-alkyl, $C_1$-$C_6$-haloalkyl, $C_3$-$C_6$-cycloalkyl, $C_3$-$C_6$-halocycloalkyl, phenyl, or —$CH_2$-phenyl, wherein the phenyl rings are unsubstituted or substituted with $R^f$.

In more preferred embodiment, $R^e$ is H, $C_1$-$C_6$-alkyl, $C_1$-$C_6$-haloalkyl, or phenyl unsubstituted or substituted with $R^f$.

In one preferred embodiment, $R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen,
C(=O)—$OR^a$, $NR^bR^c$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, or $S(=O)_mR^e$.

In more preferred embodiment, $R^f$ is halogen, $N_3$, OH, CN, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen,
C(=O)—$OR^a$, $NR^bR^c$, $C_1$-$C_6$-alkylene-$NR^bR^c$, $C_1$-$C_6$-alkylene-CN, C(=O)—$NR^bR^c$, C(=O)—$R^d$, $SO_2NR^bR^c$, or $S(=O)_mR^e$.

In a preferred embodiment, $R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, $C_2$-$C_6$-alkynyl, $C_3$-$C_6$-cycloalkyl, $C_3$-$C_6$-cycloalkoxy, which are unsubstituted or substituted with halogen,
C(=O)—$OR^a$, $NR^bR^c$, $C_1$-$C_6$-alkylene-$NR^bR^c$, NH—$C_1$-$C_6$-alkylene-$NR^bR^c$, C(=O)—$NR^bR^c$, C(=O)—$R^d$, $SO_2NR^bR^c$, or $S(=O)_mR^e$.

In more preferred embodiment, $R^g$ is halogen, $N_3$, OH, CN, $NO_2$, $C_1$-$C_6$-alkyl, $C_1$-$C_6$-alkoxy, $C_2$-$C_6$-alkenyl, $C_3$-$C_6$-cycloalkyl, $C_3$-$C_6$-cycloalkoxy, which are unsubstituted or substituted with halogen,
C(=O)—$OR^a$, $NR^bR^c$, $C_1$-$C_6$-alkylene-$NR^bR^c$, C(=O)—$NR^bR^c$, C(=O)—$R^d$, $SO_2NR^bR^c$, or $S(=O)_mR^e$.

In one embodiment, m is 0.
In another embodiment, m is 1.
In another embodiment, m is 2. L
In more preferred embodiment, $R^1$ are formulas Y-1 to Y-9 wherein

denotes attachment to the 9 membered hetaryl, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

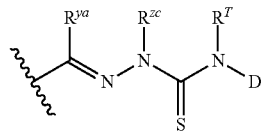 Y-1

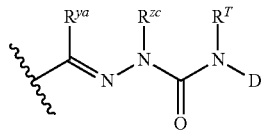 Y-2

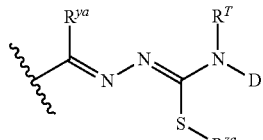 Y-3

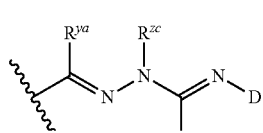 Y-4

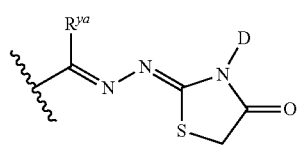 Y-5

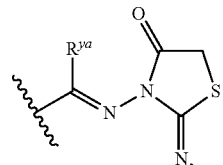 Y-6

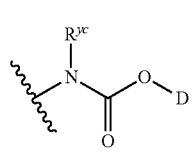 Y-7

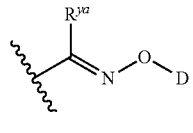 Y-8

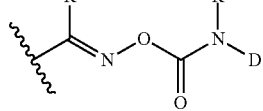 Y-9

In more preferred embodiment, $R^1$ are formulas Y-1 to Y-8 wherein denotes attachment to the 9 membered hetaryl, D is $R^{11}$ or $R^{12}$ and wherein $R^T$, $R^{11}$, $R^{12}$, $R^{ya}$, $R^{yc}$, $R^{za}$ and $R^{zc}$ are as defined in compounds of formula I.

In another more preferred embodiment, $R^1$ are formulas YZT-1 to YZT-9, wherein

denotes attachment to the 9 membered hetaryl and $R^{11}$, $R^{12}$, $R^T$, $R^{ya}$, $R^{za}$ and $R^Z$ are as defined in compounds of formula I.

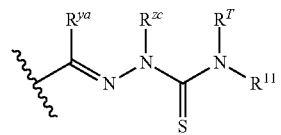
YZT-1

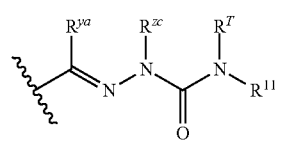
YZT-2

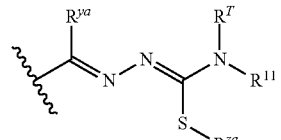
YZT-3

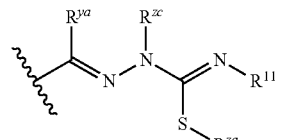
YZT-4

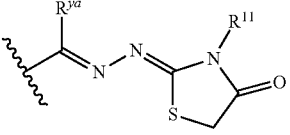
YZT-5

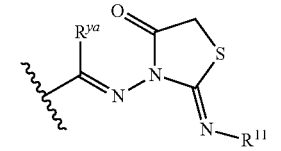
YZT-6

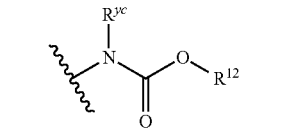
YZT-7

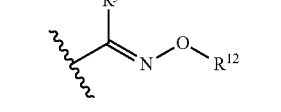
YZT-8

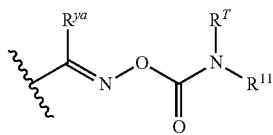
YZT-9

In another more preferred embodiment, $R^1$ are formulas YZT-1 to YZT-8, wherein

denotes attachment to the 9 membered hetaryl and $R^{11}$, $R^{12}$, $R^T$, $R^{ya}$, $R^{za}$ and $R^{zc}$ are as defined in compounds of formula I. 1

In most preferred embodiment, $R^1$ are formulas Y-1A to Y-9A, wherein

denotes attachment to the 9 membered hetaryl, D is $R^{11}$ or $R^{12}$.

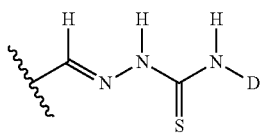
Y-1A

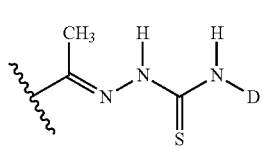
Y-1B

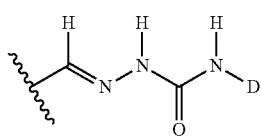
Y-2A

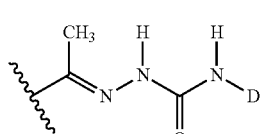
Y-2B

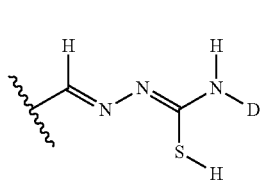
Y-3A

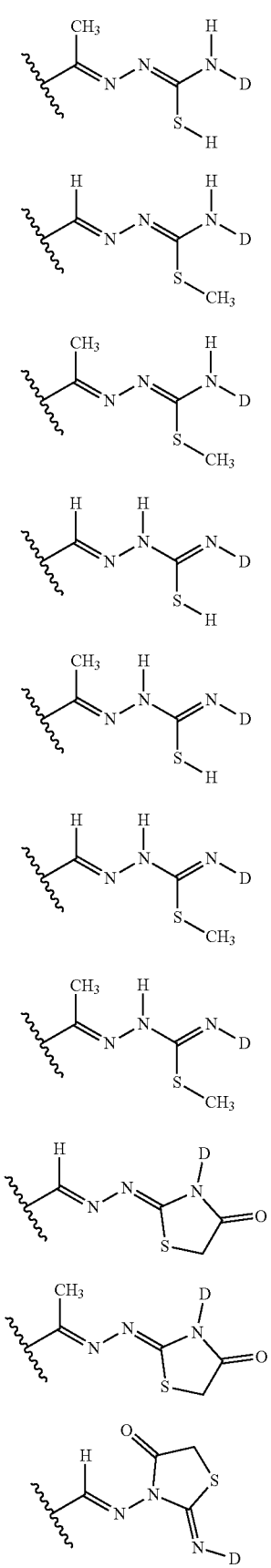
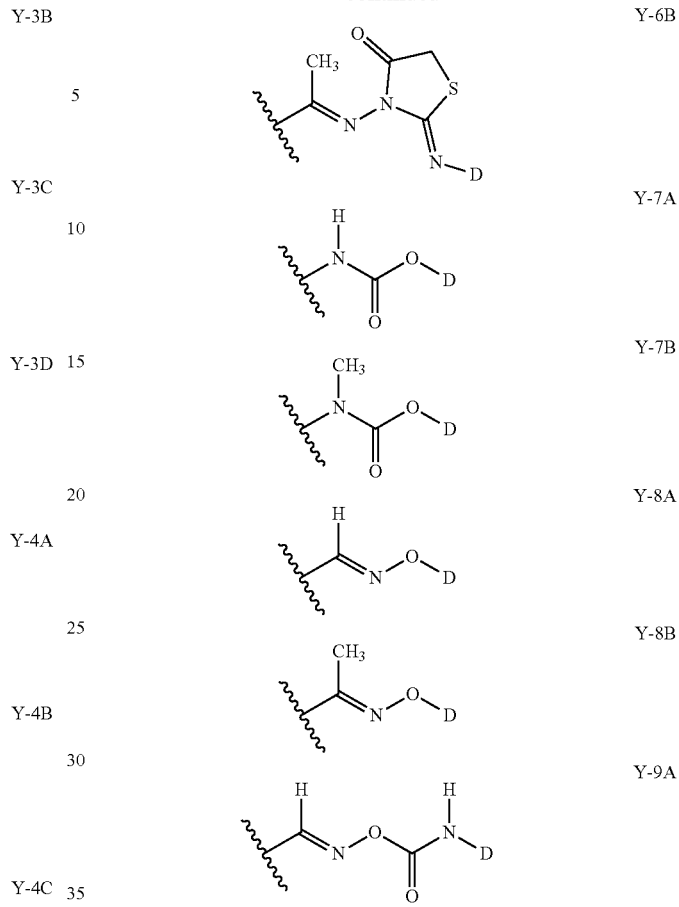

In most preferred embodiment, $R^1$ are formulas Y-1A to Y-8B, wherein denotes attachment to the 9 membered hetaryl, D is $R^{11}$ or $R^{12}$.

In one preferred embodiment, $R^{11}$ is $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_1$-$C_4$-alkyl-$C_3$-$C_6$-cycloalkoxy, which are unsubstituted or substituted with halogen, aryl, arylcarbonyl, aryl-$C_1$-$C_4$-alkyl, aryloxy-$C_1$-$C_4$-alkyl, hetaryl, carbonylhetaryl, $C_1$-$C_4$-alkyl-hetaryl and $C_1$-$C_4$-alkyl-hetaryloxy, wherein the aryl or hetaryl rings are unsubstituted or substituted with $R^g$ and wherein the hetaryl is a 5- or 6-membered monocyclic hetaryl or a 8-, 9- or 10-membered bicyclic hetaryl.

In more preferred embodiment, $R^{11}$ is $C_1$-$C_6$-alkyl, $C_2$-$C_6$-alkenyl, $C_2$-$C_6$-alkynyl, $C_3$-$C_6$-cycloalkyl, which are unsubstituted or substituted with halogen, aryl, arylcarbonyl, aryl-$C_1$-$C_4$-alkyl, aryloxy-$C_1$-$C_4$-alkyl, hetaryl, carbonylhetaryl, $C_1$-$C_4$-alkyl-hetaryl and $C_1$-$C_4$-alkyl-hetaryloxy, where the rings are unsubstituted or substituted with $R^g$ and wherein the hetaryl is a 5- or 6-membered monocyclic hetaryl or a 8-, 9- or 10-membered bicyclic hetaryl.

In most preferred embodiment, $R^{11}$ is aryl, aryl-$C_1$-$C_4$-alkyl, hetaryl, or hetaryl-$C_1$-$C_4$-alkyl, wherein the rings are unsubstituted or substituted with $R^g$ and where hetaryl in hetaryl or hetaryl-$C_1$-$C_4$-alkyl, is preferably a 5- or 6-membered monocyclic hetaryl such as pyridyl, pyrimidinyl, pyridazinyl, pyrrolyl, pyrazolyl, imidazolyl, oxazolyl, thiazolyl, isoxazolyl or isothiazolyl which is unsubstituted or substituted with $R^9$.

Examples of particularly preferred radicals $R^{11}$ are the radicals $R^{11}$-1 to $R^{11}$-29 summarized in Table A-1 below.

TABLE A-1

| | |
|---|---|
| 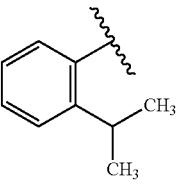 | $R^{11}$-1 |
| 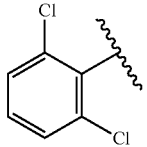 | $R^{11}$-2 |
| 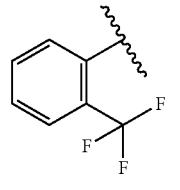 [SMILES: *c1ccccc1C(F)(F)F] | $R^{11}$-3 |
|  | $R^{11}$-4 |
| 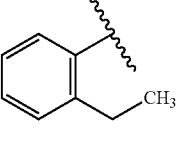 | $R^{11}$-5 |
| 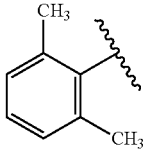 | $R^{11}$-6 |
| 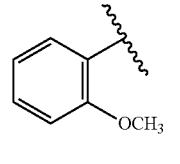 | $R^{11}$-7 |

TABLE A-1-continued

| | |
|---|---|
| 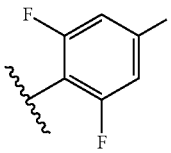 | $R^{11}$-8 |
| 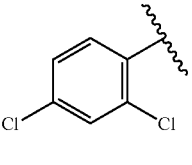 [SMILES: *c1ccc(Cl)cc1Cl] | $R^{11}$-9 |
| 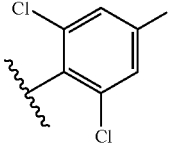 | $R^{11}$-10 |
| 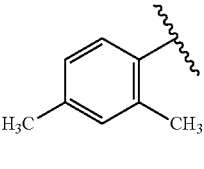 | $R^{11}$-11 |
| 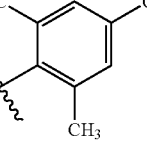 | $R^{11}$-12 |
| 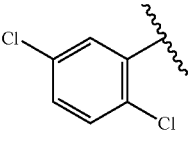 [SMILES: *c1cc(Cl)ccc1Cl] | $R^{11}$-13 |
| 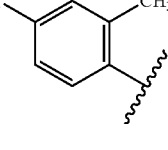 | $R^{11}$-14 |
| 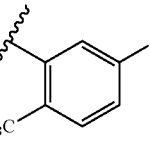 | $R^{11}$-15 |
| 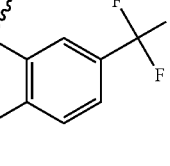 | $R^{11}$-16 |

TABLE A-1-continued

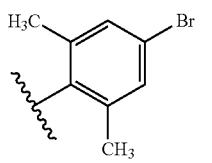 R11-17

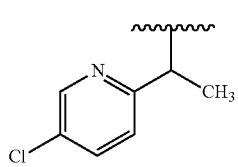 [SMILES: *C(C)c1ccc(Cl)cn1] R11-18

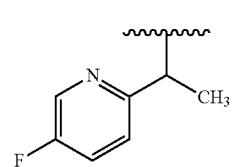 [SMILES: *C(C)c1ccc(F)cn1] R11-19

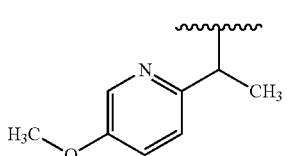 R11-20

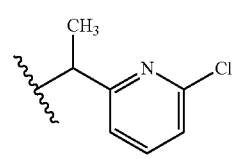 [SMILES: *C(C)c1cccc(Cl)n1] R11-21

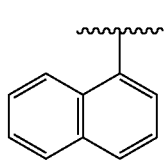 [SMILES: *c1cccc2ccccc12] R11-22

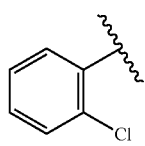 R11-23

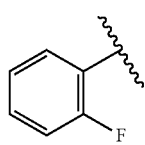 [SMILES: *c1ccccc1F] R11-24

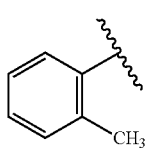 [SMILES: *c1ccccc1C] R11-25

TABLE A-1-continued

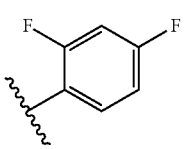 [SMILES: *c1ccc(F)cc1F] R11-26

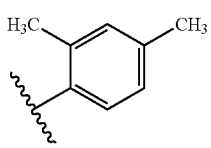 [SMILES: *c1ccc(C)cc1C] R11-27

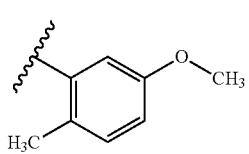 R11-28

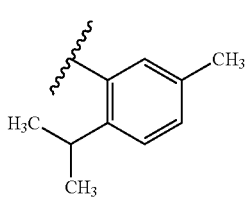 R11-29

In one embodiment, $R^{12}$ is a radical of the formula $(A^1)$,

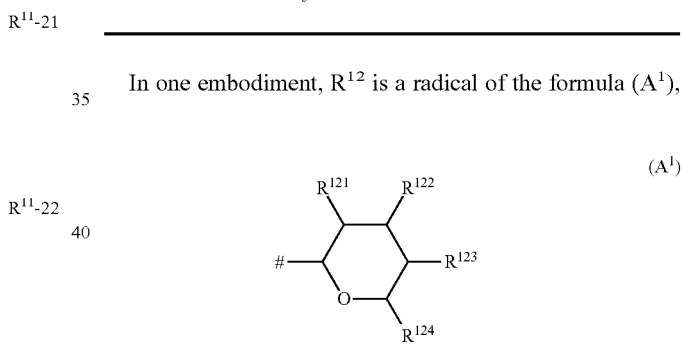

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$, $OC_2H_5$;

$R^{122}$ is $C_1$-$C_4$-alkoxy, such as $OCH_3$, $OC_2H_5$, n-propoxy or isopropoxy, or $C_3$-$C_4$-alkenyloxy, such as allyloxy, with $R^{122}$ in particular being $OCH_3$, $OC_2H_5$, or n-propoxy;

$R^{123}$ is OH, $C_1$-$C_4$-alkoxy, such as $OCH_3$, $OC_2H_5$, or $C_3$-$C_4$-alkenyloxy, such as allyloxy, with $R^{123}$ in particular being $OCH_3$, $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

In more preferred embodiment, $R^{12}$ is in particular a radical of the formula $(A^{11})$, e.g. $(A^{11}$-a) or $(A^{11}$-b)

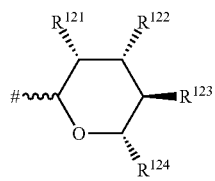
(A<sup>11</sup>)

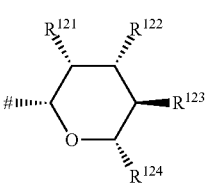
(A<sup>11</sup>-a)

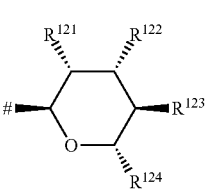
(A<sup>11</sup>-b)

wherein # indicates the point of attachment to T and wherein $R^{121}$, $R^{122}$, $R^{123}$ and $R^{124}$ are as defined above and wherein $R^{121}$, $R^{122}$, $R^{123}$ and $R^{124}$ independently of each other and especially in combination preferably have the following meanings:

$R^{121}$ is $C_1$-$C_4$-alkoxy, in particular $OCH_3$ or $OC_2H_5$;

$R^{122}$ is $C_1$-$C_4$-alkoxy, such as $OCH_3$, $OC_2H_5$, n-propoxy or isopropoxy, or $C_3$-$C_4$-alkenyloxy, such as allyloxy, with $R^{122}$ in particular being $OCH_3$, $OC_2H_5$ or n-propoxy;

$R^{123}$ is OH, $C_1$-$C_4$-alkoxy, such as $OCH_3$ or $OC_2H_5$, or $C_3$-$C_4$-alkenyloxy, such as allyloxy, with $R^{123}$ in particular being $OCH_3$ or $OC_2H_5$;

$R^{124}$ is $C_1$-$C_4$-alkyl, such as $CH_3$ or $C_2H_5$, or $C_1$-$C_4$-alkoxy-$C_1$-$C_4$-alkyl, such as methoxymethyl, ethoxymethyl, 2-methoxyethyl or 2-ethoxyethyl, with $R^{124}$ in particular being methyl.

Particular examples of radicals $R^{12}$ are the following radicals $A^{11}$-1, $A^{11}$-1a, $A^{11}$-1 b, $A^{11}$-2, $A^{11}$-2a, $A^{11}$-2b, $A^{11}$-3, $A^{11}$-3a and $A^{11}$-3b:

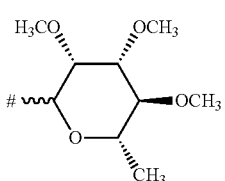
(A<sup>11</sup>-1)

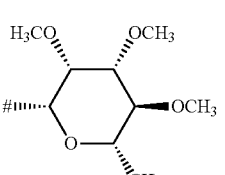
(A<sup>11</sup>-1a)

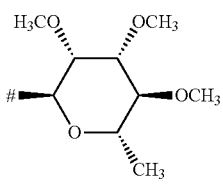
(A<sup>11</sup>-1b)

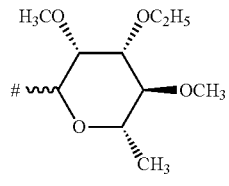
(A<sup>11</sup>-2)

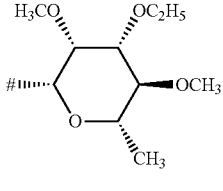
(A<sup>11</sup>-2a)

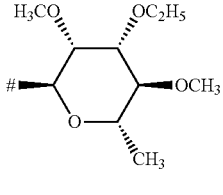
(A<sup>11</sup>-2b)

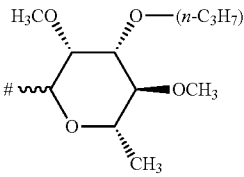
(A<sup>11</sup>-3)

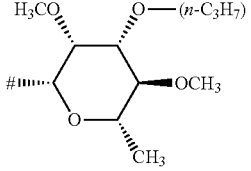
(A<sup>11</sup>-3a)

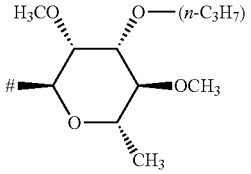
(A<sup>11</sup>-3b)

In a more preferred embodiment compounds of formula I are selected from compounds of formula I.A to I.V.

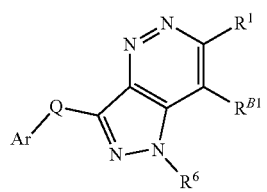 I.A
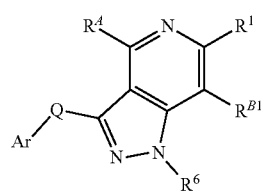 I.B
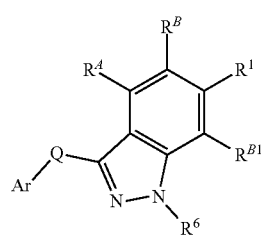 I.C
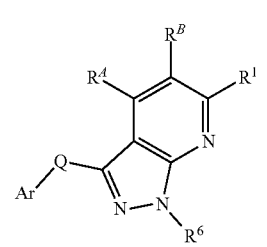 I.D
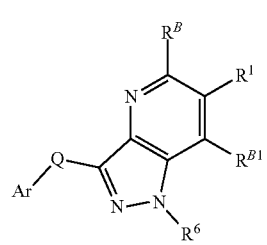 I.E
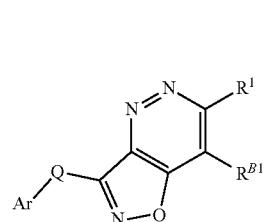 I.F
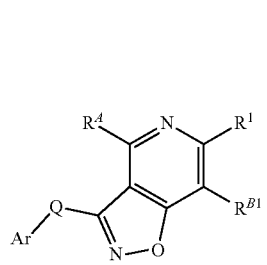 I.G
-continued
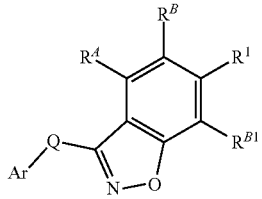 I.H
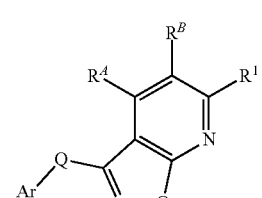 I.I
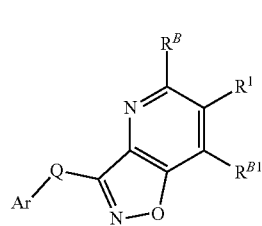 I.J
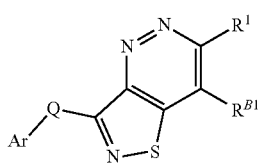 I.K
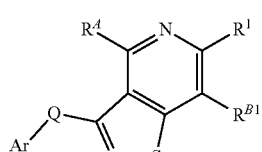 I.L
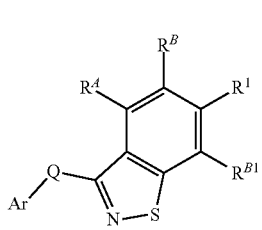 I.O
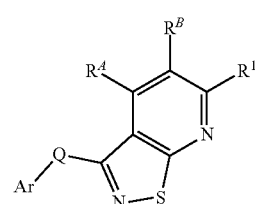 I.P
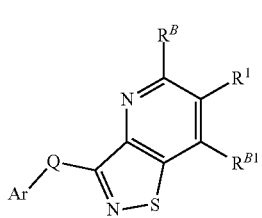 I.Q -continued I.R
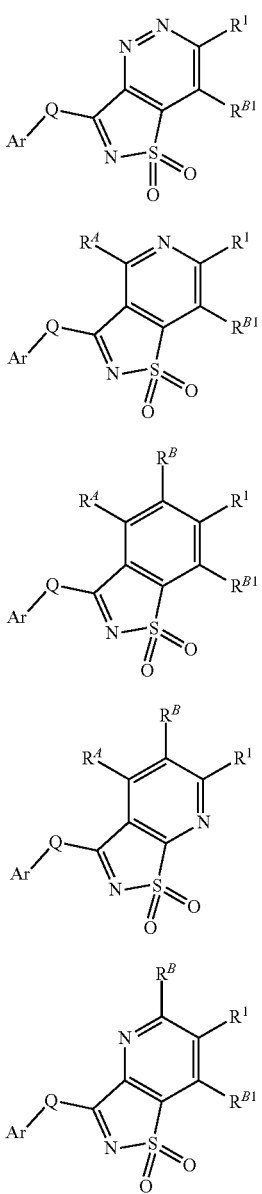

I.S

I.T

I.U

I.V wherein, Ar is phenyl or 5- or 6-membered hetaryl ring which is substituted with $R^{Ar}$;

$R^{Ar}$ is halogen, OH, CN, $NO_2$, SCN, $C_1$-$C_6$-alkyl, $C_1$-$C_6$-alkoxy, or S—$R^e$, wherein the alkyl and alkoxy are unsubstituted or substituted with halogen;

$R^2$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, or $C_3$-$C_6$-cycloalkyl, which are unsubstituted or substituted with halogen,
and phenyl which is unsubstituted or substituted with $R^f$;

Q is —C($R^4R^5$)—O—, —C(=O)—O—, —S(=O)$_m$—C($R^7R^8$)—, —N($R^2$)—S(=O)$_m$—, —N($R^2$)—C($R^9R^{10}$)—, —C(=O)C($R^{19}R^{20}$)—, —N($R^2$)—C(=O)—, —C($R^{13}R^{14}$)—C($R^{15}R^{16}$)—, or —C($R^{17}$)=C($R^{18}$)—;
wherein Ar is bound to either side of Q;

$R^4$ is H, halogen, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, or $C_2$-$C_6$-alkenyl;

$R^B$ is H, halogen, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, or $C_2$-$C_6$-alkenyl;

$R^{B1}$ is H, halogen, OH, CN, $NO_2$, —SCN, —SF$_5$, $C_1$-$C_6$-alkyl, $C_1$-$C_6$-haloalkyl, $C_1$-$C_6$-alkoxy, $C_1$-$C_6$-haloalkoxy, or $C_2$-$C_6$-alkenyl;

and $R^1$ is Y—Z-T-$R^{11}$ or Y—Z-T-$R^{12}$, as defined in formula I.

more preferred compounds of formula I are compounds of formula I.1 to I.24, wherein $R^1$ is selected from Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-7A, Y-7B, Y-8A, and Y-8B; wherein D is $R^{11}$ or $R^{12}$, and other variables are as defined herein.

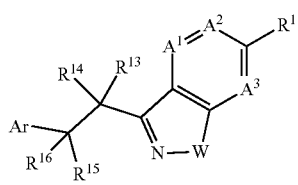
I.1

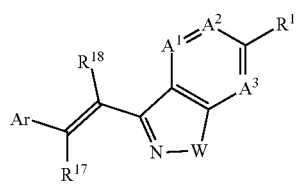
I.2

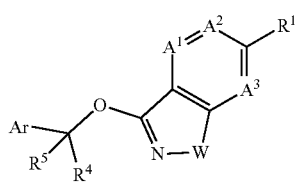
I.3

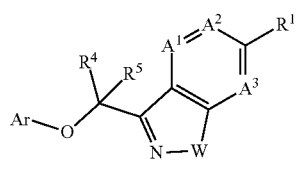
I.4

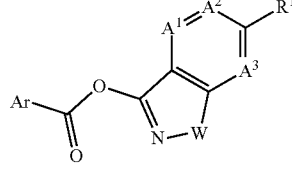
I.5

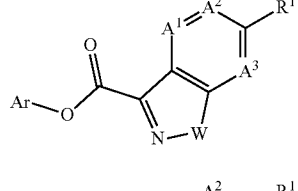
I.6

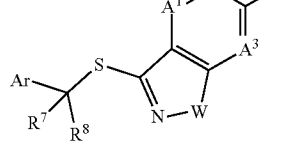
I.7

-continued
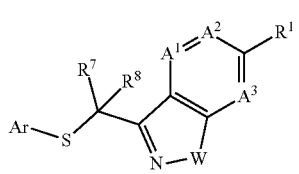 I.8
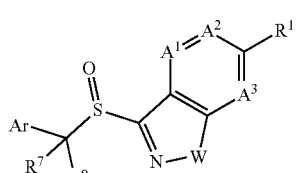 I.9
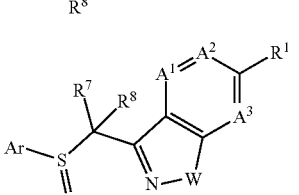 I.10
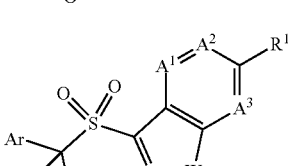 I.11
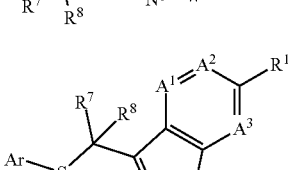 I.12
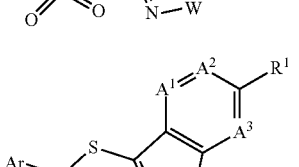 I.13
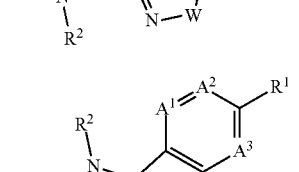 I.14
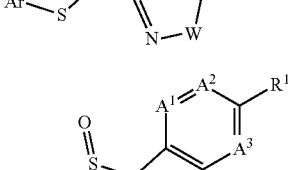 I.15
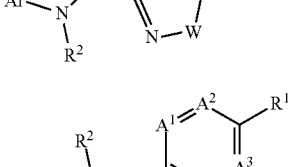 I.16
-continued
I.17
I.18
I.19
I.20
I.21
I.22
I.23
I.24
Also more preferred are the compound of formula I, wherein
$A^1$ $CR^A$;
$A^2$ is N or $R^B$;

$A^3$ is $OR^{B1}$;

W is O, $S(=O)_m$, or $NR^6$;

$R^A$, $R^B$ and $R^{B1}$ independently of each other are H or halogen;

Q is $—C(R^4R^5)—O—$, $—S(=O)_m—C(R^7R^8)—$, $—N(R^2)—C(R^9R^{10})—$, $—N(R^2)—C(=O)—$, or $—C(R^{17})=C(R^{18})—$; wherein Ar is bound to either side of Q;

m is 0, 1, or 2;

$R^2$ is H or $C_1$-$C_6$-alkyl;

$R^4$, $R^5$, $R^7$, $R^8$, $R^9$, $R^{10}$, $R^{17}$, $R^{18}$ are, identical or different H or $C_1$-$C_6$-alkyl;

$R^6$ is H, $C_1$-$C_6$-alkyl, $C_1$-$C_6$-haloalkyl, or $—CH_2$-phenyl;

Ar is Ar-2, Ar-3, Ar-10, Ar-13, or Ar-14;

$R^1$ is Y-1A, Y-3C, Y-5A, Y-6A, Y-7A, Y-8A, or Y-9A;

D is $R^{11}$ or $R^{12}$;

$R^{11}$ is $R^{11}$—I or $R^{11}$-10;

$R^{12}$ is $A^{11}$-1b or $A^{11}$-3b;

Also more preferred are the compound of formula I, where $A^1$ $CR^A$;

$A^2$ is N or $CR^B$;

$A^3$ is $CR^{B1}$;

W is O, S, NH, N—$CH_3$, N—$CH(CH_3)_2$, N—$CH_2(C_6H_5)$, N—$CH_2CHF_2$, or N—$C_2H_5$;

$R^A$, $R^B$ and $R^{B1}$ independently of each other are H or halogen, preferably H or F;

Q is $—CH_2—O—$, $—CH=CH—$, $—CH(CH_3)—O—$, $—S(=O)_2—CH_2—$, $—S—CH_2—$, $—S—CH(C_4H_9)—$, $—NH—CH_2—$, $—NH—C(=O)—$, or $—N(CH_3)—C(=O)—$; wherein Ar is bound to either side of Q;

Ar is Ar-2, Ar-3, Ar-10, Ar-13 or Ar-14

$R^1$ is Y-1A, Y-3C, Y-5A, Y-6A, Y-7A, Y-8A or Y-9A

D is $R^{11}$ or $R^{12}$;

$R^{11}$ is $R^{11}$—I and $R^{11}$-10

$R^{12}$ is $A^{11}$-1b and $A^{11}$-3b

Also more preferred are the compound of formula I, wherein $A^1$ is N or $CR^A$;

$A^2$ is N or $CR^B$;

$A^3$ is $CR^{B1}$

W is $NR^6$;

$R^A$, $R^B$ and $R^{B1}$ independently of each other are H, halogen, $C_1$-$C_6$-alkyl, or $S(=O)_m R^e$, wherein the $C_1$-$C_6$-alkyl is unsubstituted or substituted with halogen;

Q is $—O—C(R^4R^5)—$, $—N(R^2)—C(R^9R^{10})—$, $—N(R^2)—C(=O)—$, or $—C(R^{17})=C(R^{18})$;

m is 0, 1, or 2;

$R^2$ is H or $C_1$-$C_6$-alkyl;

$R^4$, $R^5$, $R^9$, $R^{10}$, $R^{17}$, $R^{18}$ are, identical or different, H and $C_1$-$C_6$-alkyl, or $C_1$-$C_6$-alkoxy-$C_1$-$C_4$-alkyl, wherein the alkyl, alkoxy moieties are unsubstituted or substituted with halogen $R^6$ is H, $C_1$-$C_6$-alkyl, wherein the alkyl, is unsubstituted or substituted with halogen, or $—CH_2—C(=O)—OR^a$;

Ar is Ar-1, Ar-2, Ar-3, Ar-4, Ar-10, Ar-12, Ar-13, Ar-14, Ar-15, or Ar-16;

$R^1$ is Y-1A, Y-5A, Y-6A, Y-7A, or Y-8A; D is $R^{11}$ or $R^{12}$;

$R^{11}$ is $R^{11}$-1, $R^{11}$-10, or $R^{11}$-29;

$R^{12}$ is $A^{11}$-1b, $A^{11}$-2b, or $A^{11}$-3b

Also more preferred are the compound of formula I, wherein $A^1$ is N or $CR^A$;

$A^2$ is N or $CR^B$;

$A^3$ is $CR^{B1}$;

W is $NR^6$;

$R^A$, $R^B$ and $R^{B1}$ independently of each other are H, halogen, or $C_1$-$C_6$-alkyl, wherein the alkyl is unsubstituted or substituted with halogen;

Q is $—O—C(R^4R^5)—$, $—N(R^2)—C(R^9R^{10})—$, or $—N(R^2)—C(=O)—$;

m is 0, 1, or 2;

$R^2$ is H or $C_1$-$C_6$-alkyl;

$R^4$, $R^5$, $R^9$, $R^{10}$ are, identical or different, H or $C_1$-$C_6$-alkyl wherein the alkyl is unsubstituted or substituted with halogen;

$R^6$ is $C_1$-$C_6$-alkyl;

Ar is Ar-2;

$R^1$ is Y-1A, Y-5A, Y-6A, or Y-7A;

D is $R^{11}$ or $R^{12}$;

$R^{11}$ is $R^{11}$-1;

$R^{12}$ is $A^{11}$-1b or $A^{11}$-3b;

most preferred compounds of formula I are compounds of formula I.1 to I.24, wherein Ar is $Ar^1$, $Ar^2$, $Ar^3$, $Ar^4$, $Ar^5$, $Ar^6$, $Ar^7$, $Ar^8$, $Ar^9$, $Ar^{10}$, $Ar^{11}$, or $Ar^{12}$;

$A^1$ is N, CH, or $CH_3$;

$A^2$ is N, CH, or $CH_3$;

$A^3$ is N, CH, or $CH_3$;

W is N, O, or S;

$R^1$ is Y-1A, Y-1B, Y-2A, Y-2B, Y-3A, Y-3B, Y-3C, Y-3D, Y-4A, Y-4B, Y-4C, Y-4D, Y-5A, Y-5B, Y-6A, Y-6B, Y-7A, Y-7B, Y-8A, or Y-8B; wherein D is $R^{11}$ or $R^{12}$;

$R^{11}$ is $R^{11}$-1, $R^{11}$-2, $R^{11}$-3, $R^{11}$-5, $R^{11}$-6, $R^{11}$-7, $R^{11}$-8, $R^{11}$-9, $R^{11}$-10, $R^{11}$-11, $R^{11}$-12, $R^{11}$-13, $R^{11}$-14, $R^{11}$-15, $R^{11}$-16, $R^{11}$-17, $R^{11}$-18, $R^{11}$-19, $R^{11}$-20, $R^{11}$-21, $R^{11}$-22, $R^{11}$-23, $R^{11}$-25, $R^{11}$-26, $R^{11}$-27, $R^{11}$-28, or $R^{11}$-29;

$R^{12}$ is $(A^{11}$-1$)$, $(A^{11}$-2$)$, or $(A^{11}$-3$)$.

As used herein, the term "compound(s) of the present invention" or "compound(s) according to the invention" refers to the compound(s) of formula (I) as defined above, which are also referred to as "compound(s) of formula I" or "compound(s) I" or "formula I compound(s)", and includes their salts, tautomers, stereoisomers, and N-oxides.

The present invention also relates to a mixture of at least one compound of the present invention with at least one mixing partner as defined herein after. Preferred are binary mixtures of one compound of the present invention as component I with one mixing partner as defined herein after as component II. Preferred weight ratios for such binary mixtures are from 5000:1 to 1:5000, preferably from 1000:1 to 1:1000, more preferably from 100:1 to 1:100, particularly preferably from 10:1 to 1:10. In such binary mixtures, components I and II may be used in equal amounts, or an excess of component I, or an excess of component II may be used.

Mixing partners can be selected from pesticides, in particular insecticides, nematicides, and acaricides, fungicides, herbicides, plant growth regulators, fertilizers, and the like. Preferred mixing partners are insecticides, nematicides and fungicides.

The following list M of pesticides, grouped and numbered according the Mode of Action Classification of the Insecticide Resistance Action Committee (IRAC), together with which the compounds of the present invention can be used and with which potential synergistic effects might be produced, is intended to illustrate the possible combinations, but not to impose any limitation:

M.1 Acetylcholine esterase (AChE) inhibitors from the class of: M.1A carbamates, for example aldicarb, alanycarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, trimethacarb, XMC, xylylcarb and triazamate; or from the class of M.1B organophosphates, for example acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos/DDVP, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl O-(methoxyaminothio-phosphoryl) salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimfos, temephos, terbufos, tetrachlorvinphos, thiometon, triazophos, trichlorfon and vamidothion;

M.2. GABA-gated chloride channel antagonists such as: M.2A cyclodiene organochlorine compounds, as for example endosulfan or chlordane; or M.2B fiproles (phenylpyrazoles), as for example ethiprole, fipronil, flufiprole, pyrafluprole and pyriprole;

M.3 Sodium channel modulators from the class of M.3A pyrethroids, for example acrinathrin, allethrin, d-cis-trans allethrin, d-trans allethrin, bifenthrin, bioallethrin, bioallethrin S-cylclopentenyl, bioresmethrin, cycloprothrin, cyfluthrin, beta-cyfluthrin, cyhalothrin, lambda-cyhalothrin, gamma-cyhalothrin, cypermethrin, alpha-cypermethrin, beta-cypermethrin, theta-cypermethrin, zeta-cypermethrin, cyphenothrin, deltamethrin, empenthrin, esfenvalerate, etofenprox, fenpropathrin, fenvalerate, flucythrinate, flumethrin, tau-fluvalinate, halfenprox, heptafluthrin, imiprothrin, meperfluthrin,metofluthrin, momfluorothrin, permethrin, phenothrin, prallethrin, profluthrin, pyrethrin (pyrethrum), resmethrin, silafluofen, tefluthrin, tetramethylfluthrin, tetramethrin, tralomethrin and transfluthrin; or M.3B sodium channel modulators such as DDT or methoxychlor;

M.4 Nicotinic acetylcholine receptor agonists (nAChR) from the class of M.4A neonicotinoids, for example acetamiprid, clothianidin, cycloxaprid, dinotefuran, imidacloprid, nitenpyram, thiacloprid and thiamethoxam; or the compounds M.4A.2: (2E-)-1-[(6-Chloropyridin-3-yl)methyl]-N'-nitro-2-pentylidenehydrazinecarboximidamide; or M4.A.3: 1-[(6-Chloropyridin-3-yl)methyl]-7-methyl-8-nitro-5-propoxy-1,2,3,5,6,7-hexahydroimidazo[1,2-a]pyridine; or from the class M.4B nicotine;

M.5 Nicotinic acetylcholine receptor allosteric activators from the class of spinosyns, for example spinosad or spinetoram;

M.6 Chloride channel activators from the class of avermectins and milbemycins, for example abamectin, emamectin benzoate, ivermectin, lepimectin or milbemectin;

M.7 Juvenile hormone mimics, such as M.7A juvenile hormone analogues as hydroprene, kinoprene and methoprene; or others as M.7B fenoxycarb or M.7C pyriproxyfen;

M.8 miscellaneous non-specific (multi-site) inhibitors, for example M.8A alkyl halides as methyl bromide and other alkyl halides, or M.8B chloropicrin, or M.8C sulfuryl fluoride, or M.8D borax, or M.8E tartar emetic;

M.9 Selective homopteran feeding blockers, for example M.9B pymetrozine, or M.9C flonicamid;

M.10 Mite growth inhibitors, for example M.10A clofentezine, hexythiazox and diflovidazin, or M.10B etoxazole;

M.11 Microbial disruptors of insect midgut membranes, for example *Bacillus thuringiensis* or *Bacillus sphaericus* and the insecticdal proteins they produce such as *Bacillus thuringiensis* subsp. *israelensis, Bacillus sphaericus, Bacillus thuringiensis* subsp. *aizawai, Bacillus thuringiensis* subsp. *kurstaki* and *Bacillus thuringiensis* subsp. *tenebrionis*, or the Bt crop proteins: Cry1Ab, Cry1Ac, Cry1Fa, Cry2Ab, mCry3A, Cry3Ab, Cry3Bb and Cry34/35Ab1;

M.12 Inhibitors of mitochondrial ATP synthase, for example M.12A diafenthiuron, or M.12B organotin miticides such as azocyclotin, cyhexatin or fenbutatin oxide, or M.12C propargite, or M.12D tetradifon;

M.13 Uncouplers of oxidative phosphorylation via disruption of the proton gradient, for example chlorfenapyr, DNOC or sulfluramid;

M.14 Nicotinic acetylcholine receptor (nAChR) channel blockers, for example nereistoxin analogues as bensultap, cartap hydrochloride, thiocyclam or thiosultap sodium;

M.15 Inhibitors of the chitin biosynthesis type 0, such as benzoylureas as for example bistrifluron, chlorfluazuron, diflubenzuron, flucycloxuron, flufenoxuron, hexaflumuron, lufenuron, novaluron, noviflumuron, teflubenzuron or triflumuron;

M.16 Inhibitors of the chitin biosynthesis type 1, as for example buprofezin;

M.17 Moulting disruptors, Dipteran, as for example cyromazine;

M.18 Ecdyson receptor agonists such as diacylhydrazines, for example methoxyfenozide, tebufenozide, halofenozide, fufenozide or chromafenozide;

M.19 Octopamin receptor agonists, as for example amitraz;

M.20 Mitochondrial complex III electron transport inhibitors, for example M.20A hydramethylnon, or M.20B acequinocyl, or M.20C fluacrypyrim;

M.21 Mitochondrial complex I electron transport inhibitors, for example M.21A METI acaricides and insecticides such as fenazaquin, fenpyroximate, pyrimidifen, pyridaben, tebufenpyrad or tolfenpyrad, or M.21B rotenone;

M.22 Voltage-dependent sodium channel blockers, for example M.22A indoxacarb, or M.22B metaflumizone, or M.22B.1: 2-[2-(4-Cyanophenyl)-1-[3-(trifluoromethyl)phenyl]ethylidene]-N-[4-(difluoromethoxy)phenyl]-hydrazinecarboxamide or M.22B.2: N-(3-Chloro-2-methylphenyl)-2-[(4-chlorophenyl)[4-[methyl(methylsulfonyl)amino] phenyl]methylene]-hydrazinecarboxamide;

M.23 Inhibitors of the of acetyl CoA carboxylase, such as Tetronic and Tetramic acid derivatives, for example spirodiclofen, spiromesifen or spirotetramat;

M.24 Mitochondrial complex IV electron transport inhibitors, for example M.24A phosphine such as aluminium phosphide, calcium phosphide, phosphine or zinc phosphide, or M.24B cyanide;

M.25 Mitochondrial complex II electron transport inhibitors, such as beta-ketonitrile derivatives, for example cyenopyrafen or cyflumetofen;

M.28 Ryanodine receptor-modulators from the class of diamides, as for example flubendiamide, chlorantraniliprole (Rynaxypyr®), cyantraniliprole (Cyazypyr®), tetraniliprole, or the phthalamide compounds M.28.1: (R)-3-Chlor-N1-{2-methyl-4-[1,2,2,2-tetrafluor-1-(trifluormethyl)ethyl]phenyl}-N2-(1-methyl-2-methylsulfonylethyl)phthalamid and M.28.2: (S)-3-Chlor-N-1-{2-methyl-4-[1,2,2,2-tetrafluor-1-(trifluormethyl)ethyl]phenyl}-N2-(1-methyl-2-methylsulfonylethyl)phthalamid, or the compound M.28.3: 3-bromo-N-{2-bromo-4-chloro-6-[(1-cyclopropylethyl)carbamoyl]phenyl}-1-(3-chloropyridin-2-yl)-1H-pyrazole-5- carboxamide (proposed ISO name: cyclaniliprole), or the compound M.28.4: methyl-2-[3,5-dibromo-2-({[3-bromo-1-(3-chlorpyridin-2-yl)-1H-pyrazol-5-yl]carbonyl}amino) benzoyl]-1,2-dimethylhydrazinecarboxylate; or a compound selected from M.28.5a) to M.28.5d) and M.28.5h) to M.28.5l): M.28.5a) N-[4,6-dichloro-2-[(diethyl-lambda-4-sulfanylidene)carbamoyl]-phenyl]-2-(3-chloro-2-pyridyl)-5-(trifluoromethyl)pyrazole-3-carboxamide; M.28.5b) N-[4-chloro-2-[(diethyl-lambda-4-sulfanylidene)carbamoyl]-6-methyl-phenyl]-2-(3-chloro-2-pyridyl)-5-(trifluoromethyl) pyrazole-3-carboxamide; M.28.5c) N-[4-chloro-2-[(di-2-propyl-lambda-4-sulfanylidene)carbamoyl]-6-methyl-phenyl]-2-(3-chloro-2-pyridyl)-5-(trifluoromethyl) pyrazole-3-carboxamide; M.28.5d) N-[4,6-dichloro-2-[(di-2-propyl-lambda-4-sulfanylidene)carbamoyl]-phenyl]-2-(3-chloro-2-pyridyl)-5-(trifluoromethyl)pyrazole-3-carboxamide; M.28.5h) N-[4,6-dibromo-2-[(diethyl-lambda-4-sulfanylidene)carbamoyl]-phenyl]-2-(3-chloro-2-pyridyl)-5-(trifluoromethyl)pyrazole-3-carboxamide; M.28.5i) N-[2-(5-Amino-1,3,4-thiadiazol-2-yl)-4-chloro-6-methylphenyl]-3-bromo-1-(3-chloro-2-pyridinyl)-1H-pyrazole-5-carboxamide; M.28.5j) 3-Chloro-1-(3-chloro-2-pyridinyl)-N-[2,4-dichloro-6-[[(1-cyano-1-methylethyl) amino]carbonyl]phenyl]-1H-pyrazole-5-carboxamide; M.28.5k) 3-Bromo-N-[2,4-dichloro-6-(methylcarbamoyl) phenyl]-1-(3,5-dichloro-2-pyridyl)-1H-pyrazole-5-carboxamide; M.28.5l) N-[4-Chloro-2-[[(1,1-dimethylethyl) amino]carbonyl]-6-methylphenyl]-1-(3-chloro-2-pyridinyl)-3-(fluoromethoxy)-1H-pyrazole-5-carboxamide; or M.28.6: cyhalodiamide; or;

M.29. insecticidal active compounds of unknown or uncertain mode of action, as for example afidopyropen, afoxolaner, azadirachtin, amidoflumet, benzoximate, bifenazate, broflanilide, bromopropylate, chinomethionat, cryolite, dicloromezotiaz, dicofol, flufenerim, flometoquin, fluensulfone, fluhexafon, fluopyram, flupyradifurone, fluralaner, metoxadiazone, piperonyl butoxide, pyflubumide, pyridalyl, pyrifluquinazon, sulfoxaflor, tioxazafen, triflumezopyrim, or the compounds M.29.3: 11-(4-chloro-2,6-dimethylphenyl)-12-hydroxy-1,4-dioxa-9-azadispiro[4.2.4.2]-tetradec-11-en-10-one, or the compound M.29.4: 3-(4'-fluoro-2,4-dimethylbiphenyl-3-yl)-4-hydroxy-8-oxa-1-azaspiro[4.5]dec-3-en-2-one, or the compound M.29.5: 1-[2-fluoro-4-methyl-5-[(2,2,2-trifluoroethyl) sulfinyl]phenyl]-3-(trifluoromethyl)-1H-1,2,4-triazole-5-amine, or actives on basis of *Bacillus firmus* (Votivo, 1-1582); or a compound selected from the of M.29.6, wherein the compound M.29.6a) to M.29.6k): M.29.6a) (E/Z)—N-[1-[(6-chloro-3-pyridyl)methyl]-2-pyridylidene]-2,2,2-trifluoro-acetamide; M.29.6b) (E/Z)—N-[1-[(6-chloro-5-fluoro-3-pyridyl)methyl]-2-pyridylidene]-2,2,2-trifluoro-acetamide; M.29.6c) (E/Z)-2,2,2-trifluoro-N-[1-[(6-fluoro-3-pyridyl)methyl]-2-pyridylidene]acetamide; M.29.6d) (E/Z)—N-[1-[(6-bromo-3-pyridyl)methyl]-2-pyridylidene]-2,2,2-trifluoro-acetamide; M.29.6e) (E/Z)—N-[1-[1-(6-chloro-3-pyridyl)ethyl]-2-pyridylidene]-2,2,2-trifluoro-acetamide; M.29.6f) (E/Z)—N-[1-[(6-chloro-3-pyridyl)methyl]-2-pyridylidene]-2,2-difluoro-acetamide; M.29.6g) (E/Z)-2-chloro-N-[1-[(6-chloro-3-pyridyl) methyl]-2-pyridylidene]-2,2-difluoro-acetamide; M.29.6h) (E/Z)—N-[1-[(2-chloropyrimidin-5-yl)methyl]-2-pyridylidene]-2,2,2-trifluoro-acetamide; M.29.6i) (E/Z)—N-[1-[(6-chloro-3-pyridyl)methyl]-2-pyridylidene]-2,2,3,3,3-pentafluoro-propanamide.); M.29.6j) N-[1-[(6-chloro-3-pyridyl)methyl]-2-pyridylidene]-2,2,2-trifluoro-thioacetamide; or M.29.6k) N-[1-[(6-chloro-3-pyridyl) methyl]-2-pyridylidene]-2,2,2-trifluoro-N'-isopropyl-acetamidine; or the compounds M.29.8: fluazaindolizine; or the compounds M.29.9.a): 4-[5-(3,5-dichlorophenyl)-5-(trifluoromethyl)-4H-isoxazol-3-yl]-2-methyl-N-(1-oxothietan-3-yl)benzamide; or M.29.9.b): fluxametamide; or M.29.10: 5-[3-[2,6-dichloro-4-(3,3-dichloroallyloxy)phenoxy]propoxy]-1H-pyrazole; or a compound selected from the of M.29.11, wherein the compound M.29.11 b) to M.29.11p): M.29.11.b) 3-(benzoylmethylamino)-N-[2-bromo-4-[1,2,2,3,3,3-hexafluoro-1-(trifluoromethyl)propyl]-6-(trifluoromethyl)phenyl]-2-fluoro-benzamide; M.29.11.c) 3-(benzoylmethylamino)-2-fluoro-N-[2-iodo-4-[1,2,2,2-tetrafluoro-1-(trifluoromethyl) ethyl]-6-(trifluoromethyl)phenyl]-benzamide; M.29.11.d) N-[3-[[[2-iodo-4-[1,2,2,2-tetrafluoro-1-(trifluoromethyl) ethyl]-6-(trifluoromethyl)phenyl]amino]carbonyl]phenyl]-N-methyl-benzamide; M.29.11.e) N-[3-[[[2-bromo-4-[1,2,2,2-tetrafluoro-1-(trifluoromethyl)ethyl]-6-(trifluoromethyl) phenyl]amino]carbonyl]-2-fluorophenyl]-4-fluoro-N-methyl-benzamide; M.29.11.f) 4-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11.g) 3-fluoro-N-[2-fluoro-3-[[[2-iodo-4-[1,2,2,2-tetrafluoro-1-(trifluoromethyl)ethyl]-6-(trifluoromethyl)phenyl]amino]carbonyl]phenyl]-N-methyl-benzamide; M.29.11. h) 2-chloro-N-[3-[[[2-iodo-4-[1,2,2,2-tetrafluoro-1-(trifluoromethyl)ethyl]-6-(trifluoromethyl)phenyl]amino]carbonyl]phenyl]-3-pyridinecarboxamide; M.29.11.i) 4-cyano-N-[2-cyano-5-[[2,6-dibromo-4-[1,2,2,3,3,3-hexafluoro-1-(trifluoromethyl) propyl]phenyl]carbamoyl]phenyl]-2-methyl-benzamide; M.29.11.j) 4-cyano-3-[(4-cyano-2-methyl-benzoyl)amino]-N-[2,6-dichloro-4-[1,2,2,3,3,3-hexafluoro-1-(trifluoromethyl)propyl]phenyl]-2-fluoro-benzamide; M.29.11.k) N-[5-[[2-chloro-6-cyano-4-[1,2,2,3,3,3-hexafluoro-1-(trifluoromethyl)propyl]phenyl]carbamoyl]-2-cyanophenyl]-4-cyano-2-methyl-benzamide; M.29.11.l) N-[5-[[2-bromo-6-chloro-4-[2,2,2-trifluoro-1-hydroxy-1-(trifluoromethyl)ethyl]phenyl]carbamoyl]-2-cyano-phenyl]-4-cyano-2-methyl-benzamide; M.29.11.m) N-[5-[[2-bromo-6-chloro-4-[1,2,2,3,3,3-hexafluoro-1-(trifluoromethyl) propyl]phenyl]carbamoyl]-2-cyano-phenyl]-4-cyano-2-methyl-benzamide; M.29.11.n) 4-cyano-N-[2-cyano-5-[[2,6-dichloro-4-[1,2,2,3,3,3-hexafluoro-1-(trifluoromethyl) propyl]phenyl]carbamoyl]phenyl]-2-methyl-benzamide; M.29.11.o) 4-cyano-N-[2-cyano-5-[[2,6-dichloro-4-[1,2,2,2-tetrafluoro-1-(trifluoromethyl)ethyl]phenyl]carbamoyl] phenyl]-2-methyl-benzamide; M.29.11.p) N-[5-[[2-bromo-6-chloro-4-[1,2,2,2-tetrafluoro-1-(trifluoromethyl)ethyl] phenyl]carbamoyl]-2-cyano-phenyl]-4-cyano-2-methyl-benzamide; or a compound selected from the of M.29.12, wherein the compound M.29.12a) to M.29.12m): M.29.12.a) 2-(1,3-Dioxan-2-yl)-6-[2-(3-pyridinyl)-5-thiazolyl]-pyridine; M.29.12.b) 2-[6-[2-(5-Fluoro-3-pyridinyl)-5-thiazolyl]-2-pyridinyl]-pyrimidine; M.29.12.c) 2-[6-[2-(3-Pyridinyl)-5-thiazolyl]-2-pyridinyl]-pyrimidine; M.29.12.d) N-M ethyl-sulfonyl-6-[2-(3-pyridyl)thiazol-5-yl]pyridine-2-carboxamide; M.29.12.e) N-Methylsulfonyl-6-[2-(3-pyridyl)thiazol-5-yl]pyridine-2-carboxamide;

M.29.12.f) N-Ethyl-N-[4-methyl-2-(3-pyridyl)thiazol-5-yl]-3-methylthio-propanamide; M.29.12.g) N-Methyl-N-[4-methyl-2-(3-pyridyl)thiazol-5-yl]-3-methylthio-propanamide; M.29.12.h) N,2-Dimethyl-N-[4-methyl-2-(3-pyridyl)

thiazol-5-yl]-3-methylthio-propanamide; M.29.12.i) N-Ethyl-2-methyl-N-[4-methyl-2-(3-pyridyl)thiazol-5-yl]-3-methylthio-propanamide; M.29.12.j) N-[4-Chloro-2-(3-pyridyl)thiazol-5-yl]-N-ethyl-2-methyl-3-methylthio-propanamide; M.29.12.k) N-[4-Chloro-2-(3-pyridyl)thiazol-5-yl]-N,2-dimethyl-3-methylthio-propanamide; M.29.12.l) N-[4-Chloro-2-(3-pyridyl)thiazol-5-yl]-N-methyl-3-methyl-thio-propanamide; M.29.12.m) N-[4-Chloro-2-(3-pyridyl)thiazol-5-yl]-N-ethyl-3-methylthio-propanamide; or the compounds M.29.14a) 1-[(6-Chloro-3-pyridinyl)methyl]-1,2,3,5,6,7-hexahydro-5-methoxy-7-methyl-8-nitroimidazo[1,2-a]pyridine; or M.29.14b) 1-[(6-Chloropyridin-3-yl)methyl]-7-methyl-8-nitro-1,2,3,5,6,7-hexahydroimidazo[1,2-a]pyridin-5-ol; or the compounds M.29.16a) 1-isopropyl-N,5-dimethyl-N-pyridazin-4-yl-pyrazole-4-carboxamide; or M.29.16b) 1-(1,2-dimethylpropyl)-N-ethyl-5-methyl-N-pyridazin-4-yl-pyrazole-4-carboxamide; M.29.16c) N,5-dimethyl-N-pyridazin-4-yl-1-(2,2,2-trifluoro-1-methyl-ethyl)pyrazole-4-carboxamide; M.29.16d) 1-[1-(1-cyanocyclopropyl)ethyl]-N-ethyl-5-methyl-N-pyridazin-4-yl-pyrazole-4-carboxamide; M.29.16e) N-ethyl-1-(2-fluoro-1-methyl-propyl)-5-methyl-N-pyridazin-4-yl-pyrazole-4-carboxamide; M.29.16f) 1-(1,2-dimethylpropyl)-N,5-dimethyl-N-pyridazin-4-yl-pyrazole-4-carboxamide; M.29.16g) 1-[1-(1-cyanocyclopropyl)ethyl]-N,5-dimethyl-N-pyridazin-4-yl-pyrazole-4-carboxamide; M.29.16h) N-methyl–1-(2-fluoro-1-methyl-propyl]-5-methyl-N-pyridazin-4-yl-pyrazole-4-carboxamide;

M.29.16i) 1-(4,4-difluorocyclohexyl)-N-ethyl-5-methyl-N-pyridazin-4-yl-pyrazole-4-carboxamide; or M.29.16j) 1-(4,4-difluorocyclohexyl)-N,5-dimethyl-N-pyridazin-4-yl-pyrazole-4-carboxamide, or M.29.17 a compound selected from the compounds M.29.17a) to M.29.17j): M.29.17a) N-(1-methylethyl)-2-(3-pyridinyl)-2H-indazole-4-carboxamide; M.29.17b) N-cyclopropyl-2-(3-pyridinyl)-2H-indazole-4-carboxamide; M.29.17c) N-cyclohexyl-2-(3-pyridinyl)-2H-indazole-4-carboxamide; M.29.17d) 2-(3-pyridinyl)-N-(2,2,2-trifluoroethyl)-2H-indazole-4-carboxamide; M.29.17e) 2-(3-pyridinyl)-N-[(tetrahydro-2-furanyl)methyl]-2H-indazole-5-carboxamide; M.29.17f) methyl 2-[[2-(3-pyridinyl)-2H-indazol-5-yl]carbonyl]hydrazinecarboxylate; M.29.17g) N-[(2,2-difluorocyclopropyl)methyl]-2-(3-pyridinyl)-2H-indazole-5-carboxamide; M.29.17h) N-(2,2-difluoropropyl)-2-(3-pyridinyl)-2H-indazole-5-carboxamide; M.29.17i) 2-(3-pyridinyl)-N-(2-pyrimidinylmethyl)-2H-indazole-5-carboxamide; M.29.17j) N-[(5-methyl-2-pyrazinyl)methyl]-2-(3-pyridinyl)-2H-indazole-5-carboxamide, or M.29.18 a compound selected from the compounds M.29.18a) to M.29.18d): M.29.18a) N-[3-chloro-1-(3-pyridyl)pyrazol-4-yl]-N-ethyl-3-(3,3,3-trifluoropropylsulfanyl)propanamide; M.29.18b) N-[3-chloro-1-(3-pyridyl)pyrazol-4-yl]-N -ethyl-3-(3,3,3-trifluoropropylsulfinyl)propanamide; M.29.18c) N-[3-chloro-1-(3-pyridyl)pyrazol-4-yl]-3-[(2,2-difluorocyclopropyl)methylsulfanyl]-N-ethyl-propanamide;

M.29.18d) N-[3-chloro-1-(3-pyridyl)pyrazol-4-yl]-3-[(2,2-difluorocyclopropyl)methylsulfinyl]-N-ethyl-propanamide; or the compound M.29.19 sarolaner, or the compound M.29.20 lotilaner.

The commercially available compounds of the M listed above may be found in The Pesticide Manual, 16th Edition, C. MacBean, British Crop Protection Council (2013) among other publications. The online Pesticide Manual is updated regularly and is accessible through http://bcpcdata.com/pesticide-manual.html.

Another online data base for pesticides providing the ISO common names is http://www.alanwood.net/pesticides.

The M.4 neonicotinoid cycloxaprid is known from WO2010/069266 and WO2011/069456, the neonicotinoid M.4A.2, sometimes also to be named as guadipyr, is known from WO2013/003977, and the neonicotinoid M.4A.3 (approved as paichongding in China) is known from WO2007/101369. The metaflumizone analogue M.22B.1 is described in CN10171577 and the analogue M.22B.2 in CN102126994. The phthalamides M.28.1 and M.28.2 are both known from WO2007/101540. The anthranilamide M.28.3 is described in WO2005/077934. The hydrazide compound M.28.4 is described in WO2007/043677. The anthranilamides M.28.5a) to M.28.5d) and M.28.5h) are described in WO 2007/006670, WO2013/024009 and WO2013/024010, the anthranilamide M.28.5i) is described in WO2011/085575, M.28.5j) in WO2008/134969, M.28.5k) in US2011/046186 and M.28.5l) in WO2012/034403. The diamide compound M.28.6 can be found in WO2012/034472. The spiroketal-substituted cyclic ketoenol derivative M.29.3 is known from WO2006/089633 and the biphenyl-substituted spirocyclic ketoenol derivative M.29.4 from WO2008/067911. The triazoylphenylsulfide M.29.5 is described in WO2006/043635, and biological control agents on the basis of *Bacillus firmus* are described in WO2009/124707. The compounds M.29.6a) to M.29.6i) listed under M.29.6 are described in WO2012/029672, and M.29.6j) and M.29.6k) in WO2013/129688. The nematicide M.29.8 is known from WO2013/055584. The isoxazoline M.29.9.a) is described in WO2013/050317. The isoxazoline M.29.9.b) is described in WO2014/126208. The pyridalyl-type analogue M.29.10 is known from WO2010/060379. The carboxamides broflanilide and M.29.11.b) to M.29.11.h) are described in WO2010/018714, and the carboxamides M.29.11i) to M.29.11.p) in WO2010/127926. The pyridylthiazoles M.29.12.a) to M.29.12.c) are known from WO2010/006713, M.29.12.d) and M.29.12.e) are known from WO2012/000896, and M.29.12.f) to M.29.12.m) from WO2010/129497. The compounds M.29.14a) and M.29.14b) are known from WO2007/101369. The pyrazoles M.29.16.a) to M.29.16h) are described in WO2010/034737, WO2012/084670, and WO2012/143317, respectively, and the pyrazoles M.29.16i) and M.29.16j) are described in U.S. 61/891,437. The pyridinylindazoles M.29.17a) to M.29.17.j) are described in WO2015/038503. The pyridylpyrazoles M.29.18a) to M.29.18d) are described in US2014/0213448. The isoxazoline M.29.19 is described in WO2014/036056. The isoxazoline M.29.20 is known from WO2014/090918.

The following list of fungicides, in conjunction with which the compounds of the present invention can be used, is intended to illustrate the possible combinations but does not limit them:

A) Respiration Inhibitors

Inhibitors of complex III at $Q_o$ site (e. g. strobilurins): azoxystrobin (A.1.1), coumethoxystrobin (A.1.2), coumoxystrobin (A.1.3), dimoxystrobin (A.1.4), enestroburin (A.1.5), fenaminstrobin (A.1.6), fenoxystrobin/flufenoxystrobin (A.1.7), fluoxastrobin (A.1.8), kresoxim-methyl (A.1.9), mandestrobin (A.1.10), metominostrobin (A.1.11), orysastrobin (A.1.12), picoxy.strobin (A.1.13), pyraclostrobin (A.1.14), pyrametostrobin (A.1.15), pyraoxystrobin (A.1.16), trifloxystrobin (A.1.17), 2-(2-(3-(2,6-dichlorophenyl)-1-methyl-allylideneami nooxymethyl)-phenyl)-2-methoxyimino-N-methyl-acetamide (A.1.18), pyribencarb (A.1.19), triclopyricarb/chlorodincarb (A.1.20), famoxadone (A.1.21), fenamidone (A.1.21), methyl-N-[2-[(1,4-dimethyl-5-phenyl-pyrazol-3-yl)oxylmethyl]phenyl]-N-methoxy-carbamate (A.1.22), 1-[3-chloro-2-[[1-(4-chlorophenyl)-1H-pyrazol-3-yl]oxymethyl]phenyl]-4-methyl-tetrazol-5-one (A.1.23), 1-[3-bromo-2-[[1-(4-chlorophenyl)pyrazol-3-yl]oxymethyl]phenyl]-4-methyl-tetrazol-5-one (A.1.24), 1-[2-[[1-(4-chlorophenyl)pyrazol-3-yl]oxymethyl]-3-methyl-phenyl]-4-methyl-tetrazol-5-one (A.1.25), 1-[2-[[1-(4-chlorophenyl)pyrazol-3-yl]oxymethyl]-3-fluoro-phenyl]-4-methyl-tetrazol-5-one (A.1.26), 1-[2-[[1-(2,4-dichlorophenyl)pyrazol-3-yl]oxymethyl]-3-fluoro-phenyl]-4-methyl-tetrazol-5-one (A.1.27), 1-[2-[[4-(4-chlorophenyl)thiazol-2-yl]oxymethyl]-3-methyl-phenyl]-4-methyl-tetrazol-5-one (A.1.28), 1-[3-chloro-2-[[4-(p-tolyl)thiazol-2-yl]oxymethyl]phenyl]-4-methyl-tetrazol-5-one (A.1.29), 1-[3-cyclopropyl-2-[[2-methyl-4-(1-methylpyrazol-3-yl)phenoxy]methyl]phenyl]-4-methyl-tetrazol-5-one (A.1.30), 1-[3-(difluoromethoxy)-2-[[2-methyl-4-(1-methylpyrazol-3-yl)phenoxy]methyl]phenyl]-4-methyl-tetrazol-5-one (A.1.31), 1-methyl-4-[3-methyl-2-[[2-methyl-4-(1-methylpyrazol-3-yl)phenoxy]methyl]phenyl]tetrazol-5-one (A.1.32), 1-methyl-4-[3-methyl-2-[[1-[3-(trifluoromethyl)phenyl]-ethylideneamino]oxymethyl]phenyl]tetrazol-5-one (A.1.33), (Z,2E)-5-[1-(2,4-dichlorophenyl)pyrazol-3-yl]oxy-2-methoxyimino-N,3-dimethyl-pent-3-enamide (A.1.34), (Z,2E)-5-[1-(4-chlorophenyl)pyrazol-3-yl]oxy-2-methoxyimino-N,3-dimethyl-pent-3-enamide (A.1.35), (Z,2E)-5-[1-(4-chloro-2-fluoro-phenyl)pyrazol-3-yl]oxy-2-methoxyimino-N,3-dimethyl-pent-3-enamide (A.1.36), inhibitors of complex III at $Q_i$ site: cyazofamid (A.2.1), amisulbrom (A.2.2), [(3S,6S,7R,8R)-8-benzyl-3-[(3-acetoxy-4-methoxy-pyridine-2-carbonyl)amino]-6-methyl-4,9-dioxo-1,5-dioxonan-7-yl] 2-methylpropanoate (A.2.3), [(3S,6S,7R,8R)-8-benzyl-3-[[3-(acetoxymethoxy)-4-methoxypyridine-2-carbonyl]amino]-6-methyl-4,9-dioxo-1,5-dioxonan-7-yl] 2-methylpropanoate (A.2.4), [(3S,6S,7R,8R)-8-benzyl-3-[(3-isobutoxycarbonyloxy-4-methoxy-pyridine-2-carbonyl)amino]-6-methyl-4,9-dioxo-1,5-dioxonan-7-yl] 2-methylpropanoate (A.2.5), [(3S,6S,7R,8R)-8-benzyl-3-[[3-(1,3-benzodioxol-5-ylmethoxy)-4-methoxy-pyridine-2-carbonyl]amino]-6-methyl-4,9-dioxo-1,5-dioxonan-7-yl] 2-methylpropanoate (A.2.6); (3S,6S,7R,8R)-3-[[(3-hydroxy-4-methoxy-2-pyridinyl)carbonyl]amino]-6-methyl-4,9-dioxo-8-(phenylmethyl)-1,5-dioxonan-7-yl 2-methylpropanoate (A.2.7), (3S,6S,7R,8R)-8-benzyl-3-[3-[(isobutyryloxy)methoxy]-4-methoxypicolinamido]-6-methyl-4,9-dioxo-1,5-dioxonan-7-yl isobutyrate (A.2.8);

inhibitors of complex II (e. g. carboxamides): benodanil (A.3.1), benzovindiflupyr (A.3.2), bixafen (A.3.3), boscalid (A.3.4), carboxin (A.3.5), fenfuram (A.3.6), fluopyram (A.3.7), flutolanil (A.3.8), fluxapyroxad (A.3.9), furametpyr (A.3.10), isofetamid (A.3.11), isopyrazam (A.3.12), mepronil (A.3.13), oxycarboxin (A.3.14), penflufen (A.3.14), penthiopyrad (A.3.15), sedaxane (A.3.16), tecloftalam (A.3.17), thifluzamide (A.3.18), N-(4'-trifluoromethylthiobiphenyl-2-yl)-3-difluoromethyl-1-methyl-1H-pyrazole-4-carboxamide (A.3.19), N-(2-(1,3,3-trimethyl-butyl)-phenyl)-1,3-dimethyl-5-fluoro-1H-pyrazole-4-carboxamide (A.3.20), 3-(difluoromethyl)-1-methyl-N-(1,1,3-trimethylindan-4-yl)pyrazole-4-carboxamide (A.3.21), 3-(trifluoromethyl)-1-methyl-N-(1,1,3-trimethylindan-4-yl)pyrazole-4-carboxamide (A.3.22), 1,3-dimethyl-N-(1,1,3-trimethylindan-4-yl)pyrazole-4-carboxamide (A.3.23), 3-(trifluoromethyl)-1,5-dimethyl-N-(1,1,3-trimethylindan-4-yl)pyrazole-4-carboxamide (A.3.24), 1,3,5-trimethyl-N-(1,1,3-trimethylindan-4-yl)pyrazole-4-carboxamide (A.3.25), N-(7-fluoro-1,1,3-trimethyl-indan-4-yl)-1,3-dimethyl-pyrazole-4-carboxamide (A.3.26), N-[2-(2,4-dichlorophenyl)-2-methoxy-1-methylethyl]-3-(difluoromethyl)-1-methyl-pyrazole-4-carboxamide (A.3.27);

other respiration inhibitors (e. g. complex I, uncouplers): diflumetorim (A.4.1), (5,8-difluoroquinazolin-4-yl)-{2-[2-fluoro-4-(4-trifluoromethylpyridin-2-yloxy)-phenyl]-ethyl}-amine (A.4.2); nitrophenyl derivates: binapacryl (A.4.3), dinobuton (A.4.4), dinocap (A.4.5), fluazinam (A.4.6); ferimzone (A.4.7); organometal compounds: fentin salts, such as fentin-acetate (A.4.8), fentin chloride (A.4.9) or fentin hydroxide (A.4.10); ametoctradin (A.4.11); and silthiofam (A.4.12);

B) Sterol biosynthesis inhibitors (SBI fungicides)

C14 demethylase inhibitors (DMI fungicides): triazoles: azaconazole (B.1.1), bitertanol (B.1.2), bromuconazole (B.1.3), cyproconazole (B.1.4), difenoconazole (B.1.5), diniconazole (B.1.6), diniconazole-M (B.1.7), epoxiconazole (B.1.8), fenbuconazole (B.1.9), fluquinconazole (B.1.10), flusilazole (B.1.11), flutriafol (B.1.12), hexaconazole (B.1.13), imibenconazole (B.1.14), ipconazole (B.1.15), metconazole (B.1.17), myclobutanil (B.1.18), oxpoconazole (B.1.19), paclobutrazole (B.1.20), penconazole (B.1.21), propiconazole (B.1.22), prothioconazole (B.1.23), simeconazole (B.1.24), tebuconazole (B.1.25), tetraconazole (B.1.26), triadimefon (B.1.27), triadimenol (B.1.28), triticonazole (B.1.29), uniconazole (B.1.30), 1-[rel-(2S,3R)-3-(2-chlorophenyl)-2-(2,4-difluorophenyl)-oxiranylmethyl]-5-thiocyanato-1H-[1,2,4]triazolo (B.1.31), 2-[rel-(2S;3R)-3-(2-chlorophenyl)-2-(2,4-difluorophenyl)-oxiranylmethyl]-2H-[1,2,4]triazole-3-thiol (B.1.32), 2-[2-chloro-4-(4-chlorophenoxy)phenyl]-1-(1,2,4-triazol-1-yl)pentan-2-ol (B.1.33), 1-[4-(4-chlorophenoxy)-2-(trifluoromethyl)phenyl]-1-cyclopropyl-2-(1,2,4-triazol-1-yl)ethanol (B.1.34), 2-[4-(4-chlorophenoxy)-2-(trifluoromethyl)phenyl]-1-(1,2,4-triazol-1-yl)butan-2-ol (B.1.35), 2-[2-chloro-4-(4-chlorophenoxy)phenyl]-1-(1,2,4-triazol-1-yl)butan-2-ol (B.1.36), 2-[4-(4-chlorophenoxy)-2-(trifluoromethyl)phenyl]-3-methyl-1-(1,2,4-triazol-1-yl)butan-2-ol (B.1.37), 2-[4-(4-chlorophenoxy)-2-(trifluoromethyl)phenyl]-1-(1,2,4-triazol-1-yl)propan-2-ol (B.1.38), 2-[2-chloro-4-(4-chlorophenoxy)phenyl]-3-methyl-1-(1,2,4-triazol-1-yl)butan-2-ol (B.1.39), 2-[4-(4-chlorophenoxy)-2-(trifluoromethyl)phenyl]-1-(1,2,4-triazol-1-yl)pentan-2-ol (B.1.40), 2-[4-(4-fluorophenoxy)-2-(trifluoromethyl)phenyl]-1-(1,2,4-triazol-1-yl)propan-2-ol (B.1.41), 2-[2-chloro-4-(4-chlorophenoxy)phenyl]-1-(1,2,4-triazol-1-yl)pent-3-yn-2-ol (B.1.51); imidazoles: imazalil (B.1.42), pefurazoate (B.1.43), prochloraz (B.1.44), triflumizol (B.1.45); pyrimidines, pyridines and piperazines: fenarimol (B.1.46), nuarimol (B.1.47), pyrifenox (B.1.48), triforine (B.1.49), [3-(4-chloro-2-fluoro-phenyl)-5-(2,4-difluorophenyl)isoxazol-4-yl]-(3-pyridyl)methanol (B.1.50);

Delta14-reductase inhibitors: aldimorph (B.2.1), dodemorph (B.2.2), dodemorph-acetate (B.2.3), fenpropimorph (B.2.4), tridemorph (B.2.5), fenpropidin (B.2.6), piperalin (B.2.7), spiroxamine (B.2.8);

Inhibitors of 3-keto reductase: fenhexamid (B.3.1);

C) Nucleic acid synthesis inhibitors phenylamides or acyl amino acid fungicides: benalaxyl (C.1.1), benalaxyl-M (C.1.2), kiralaxyl (C.1.3), metalaxyl (C.1.4), metalaxyl-M (mefenoxam, C.1.5), ofurace (C.1.6), oxadixyl (C.1.7);

others: hymexazole (C.2.1), octhilinone (C.2.2), oxolinic acid (C.2.3), bupirimate (C.2.4), 5-fluorocytosine (C.2.5), 5-fluoro-2-(p-tolylmethoxy)pyrimidin-4-amine (C.2.6), 5-fluoro-2-(4-fluorophenylmethoxy)pyrimidin-4-amine (C.2.7);

D) Inhibitors of cell division and cytoskeleton tubulin inhibitors, such as benzimidazoles, thiophanates: benomyl (D1.1), carbendazim (D1.2), fuberidazole (D1.3), thiabendazole (D1.4), thiophanate-methyl (D1.5); triazolopyrimidines: 5-chloro-7-(4-methylpiperidin-1-yl)-6-(2,4,6-trifluorophenyl)-[1,2,4]triazolo[1,5-a]pyrimidine (D1.6);

other cell division inhibitors: diethofencarb (D2.1), ethaboxam (D2.2), pencycuron (D2.3), fluopicolide (D2.4), zoxamide (D2.5), metrafenone (D2.6), pyriofenone (D2.7);

E) Inhibitors of amino acid and protein synthesis methionine synthesis inhibitors (anilino-pyrimidines): cyprodinil (E.1.1), mepanipyrim (E.1.2), pyrimethanil (E.1.3);

protein synthesis inhibitors: blasticidin-S (E.2.1), kasugamycin (E.2.2), kasugamycin hydrochloride-hydrate (E.2.3), mildiomycin (E.2.4), streptomycin (E.2.5), oxytetracyclin (E.2.6), polyoxine (E.2.7), validamycin A (E.2.8);

F) Signal transduction inhibitors

MAP/histidine kinase inhibitors: fluoroimid (F.1.1), iprodione (F.1.2), procymidone (F.1.3), vinclozolin (F.1.4), fenpiclonil (F.1.5), fludioxonil (F.1.6);

G protein inhibitors: quinoxyfen (F.2.1);

G) Lipid and membrane synthesis inhibitors

Phospholipid biosynthesis inhibitors: edifenphos (G.1.1), iprobenfos (G.1.2), pyrazophos (G.1.3), isoprothiolane (G.1.4);

lipid peroxidation: dicloran (G.2.1), quintozene (G.2.2), tecnazene (G.2.3), tolclofos-methyl (G.2.4), biphenyl (G.2.5), chloroneb (G.2.6), etridiazole (G.2.7);

phospholipid biosynthesis and cell wall deposition: dimethomorph (G.3.1), flumorph (G.3.2), mandipropamid (G.3.3), pyrimorph (G.3.4), benthiavalicarb (G.3.5), iprovalicarb (G.3.6), valifenalate (G.3.7) and N-(1-(1-(4-cyano-phenyl)ethanesulfonyl)-but-2-yl) carbamic acid-(4-fluorophenyl) ester (G.3.8);

compounds affecting cell membrane permeability and fatty acides: propamocarb (G.4.1);

fatty acid amide hydrolase inhibitors: oxathiapiprolin (G.5.1), 2-{3-[2-(1-{[3,5-bis(difluoromethyl-1H-pyrazol-1-yl]acetyl}piperidin-4-yl)-1,3-thiazol-4-yl]-4,5-dihydro-1,2-oxazol-5-yl}phenyl methanesulfonate (G.5.2), 2-{3-[2-(1-{[3,5-bis(difluoromethyl)-1H-pyrazol-1-yl]acetyl}piperidin-4-yl) 1,3-thiazol-4-yl]-4,5-dihydro-1,2-oxazol-5-yl}-3-chlorophenyl methanesulfonate (G.5.3);

H) Inhibitors with Multi Site Action inorganic active substances: Bordeaux mixture (H.1.1), copper acetate (H.1.2), copper hydroxide (H.1.3), copper oxychloride (H.1.4), basic copper sulfate (H.1.5), sulfur (H.1.6);

thio- and dithiocarbamates: ferbam (H.2.1), mancozeb (H.2.2), maneb (H.2.3), metam (H.2.4), metiram (H.2.5), propineb (H.2.6), thiram (H.2.7), zineb (H.2.8), ziram (H.2.9);

organochlorine compounds (e. g. phthalimides, sulfamides, chloronitriles): anilazine (H.3.1), chlorothalonil (H.3.2), captafol (H.3.3), captan (H.3.4), folpet (H.3.5), dichlofluanid (H.3.6), dichlorophen (H.3.7), hexachlorobenzene (H.3.8), pentachlorphenole (H.3.9) and its salts, phthalide (H.3.10), tolylfluanid (H.3.11), N-(4-chloro-2-nitro-phenyl)-N-ethyl-4-methylbenzenesulfonamide (H.3.12);

guanidines and others: guanidine (H.4.1), dodine (H.4.2), dodine free base (H.4.3), guazatine (H.4.4), guazatine-acetate (H.4.5), iminoctadine (H.4.6), iminoctadine-triacetate (H.4.7), iminoctadine-tris(albesilate) (H.4.8), dithianon (H.4.9), 2,6-dimethyl-1H,5H[1,4]dithiino[2,3-c:5,6-c']dipyrrole-1,3,5,7(2H,6H)-tetraone (H.4.10);

I) Cell wall synthesis inhibitors inhibitors of glucan synthesis: validamycin (I.1.1), polyoxin B (I.1.2);

melanin synthesis inhibitors: pyroquilon (I.2.1), tricyclazole (I.2.2), carpropamid (I.2.3), dicyclomet (I.2.4), fenoxanil (I.2.5);

J) Plant defence inducers acibenzolar-S-methyl (J.1.1), probenazole (J.1.2), isotianil (J.1.3), tiadinil (J.1.4), prohexadione-calcium (J.1.5); phosphonates: fosetyl (J.1.6), fosetyl-aluminum (J.1.7), phosphorous acid and its salts (J.1.8), potassium or sodium bicarbonate (J.1.9);

K) Unknown mode of action bronopol (K.1.1), chinomethionat (K.1.2), cyflufenamid (K.1.3), cymoxanil (K.1.4), dazomet (K.1.5), debacarb (K.1.6), diclomezine (K.1.7), difenzoquat (K.1.8), difenzoquat-methylsulfate (K.1.9), diphenylamin (K.1.10), fenpyrazamine (K.1.11), flumetover (K.1.12), flusulfamide (K.1.13), flutianil (K.1.14), methasulfocarb (K.1.15), nitrapyrin (K.1.16), nitrothal-isopropyl (K.1.18), oxathiapiprolin (K.1.19), tolprocarb (K.1.20), oxin-copper (K.1.21), proquinazid (K.1.22), tebufloquin (K.1.23), tecloftalam (K.1.24), triazoxide (K.1.25), 2-butoxy-6-iodo-3-propylchromen-4-one (K.1.26), 2-[3,5-bis(difluoromethyl)-1H-pyrazol-1-yl]-1-[4-(4-{5-[2-(prop-2-yn-1-yloxy)phenyl]-4,5-dihydro-1,2-oxazol-3-yl}-1,3-thiazol-2-yl)piperidin-1-yl]ethanone (K.1.27), 2-[3,5-bis(difluoromethyl)-1H-pyrazol-1-yl]-1-[4-(4-{5-[2-fluoro-6-(prop-2-yn-1-yloxy)phenyl]-4,5-dihydro-1,2-oxazol-3-yl}-1,3-thiazol-2-yl)piperidin-1-yl]ethanone (K.1.28), 2-[3,5-bis(difluoromethyl)-1H-pyrazol-1-yl]-1-[4-(4-{5-[2-chloro-6-(prop-2-yn-1-yloxy)phenyl]-4,5-dihydro-1,2-oxazol-3-yl}-1,3-thiazol-2-yl)piperidin-1-yl]ethanone (K.1.29), N-(cyclopropylmethoxyimino-(6-difluoromethoxy-2,3-difluoro-phenyl)-methyl)-2-phenyl acetamide (K.1.30), N'-(4-(4-chloro-3-trifluoromethyl-phenoxy)-2,5-dimethyl-phenyl)-N-ethyl-N-methyl formamidine (K.1.31), N'-(4-(4-fluoro-3-trifluoromethyl-phenoxy)-2,5-dimethyl-phenyl)-N-ethyl-N-methyl formamidine (K.1.32), N'-(2-methyl-5-trifluoromethyl-4-(3-trimethylsilanyl-propoxy)-phenyl)-N-ethyl-N-methyl formamidine (K.1.33), N'-(5-difluoromethyl-2-methyl-4-(3-trimethylsilanylpropoxy)-phenyl)-N-ethyl-N-methyl formamidine (K.1.34), methoxy-acetic acid 6-tert-butyl-8-fluoro-2,3-dimethylquinolin-4-yl ester (K.1.35), 3-[5-(4-methylphenyl)-2,3-dimethyl-isoxazolidin-3-yl]-pyridine (K.1.36), 3-[5-(4-chloro-phenyl)-2,3-dimethyl-isoxazolidin-3-yl]-pyridine (pyrisoxazole) (K.1.37), N-(6-methoxy-pyridin-3-yl) cyclopropanecarboxylic acid amide (K.1.38), 5-chloro-1-(4,6-dimethoxy-pyrimidin-2-yl)-2-methyl-1H-benzoimidazole (K.1.39), 2-(4-chloro-phenyl)-N-[4-(3,4-dimethoxy-phenyl)-isoxazol-5-yl]-2-prop-2-ynyloxy-acetamide, ethyl (Z)-3-amino-2-cyano-3-phenyl-prop-2-enoate (K.1.40), picarbutrazox (K.1.41), pentyl N-[6-[[(Z)-[(1-methyl-tetrazol-5-yl)-phenyl-methylene]amino]oxymethyl]-2-pyridyl]carbamate (K.1.42), 2-[2-[(7,8-difluoro-2-methyl-3-quinolyl)oxy]-6-fluoro-phenyl]propan-2-ol (K.1.43), 2-[2-fluoro-6-[(8-fluoro-2-methyl-3-quinolyl)oxy]phen-yl]propan-2-ol (K.1.44), 3-(5-fluoro-3,3,4,4-tetramethyl-3,4-dihydroisoquinolin-1-yl)quinoline (K.1.45), 3-(4,4-difluoro-3,3-dimethyl-3,4-dihydroisoquinolin-1-yl)quinoline (K.1.46), 3-(4,4,5-trifluoro-3,3-dimethyl-3,4-dihydroisoquinolin-1-yl) quinoline (K.1.47), 9-fluoro-2,2-dimethyl-5-(3-quinolyl)-3H-1,4-benzoxazepine (K.1.48).

The fungicides described by common names, their preparation and their activity e.g. against harmful fungi is known (cf.: http://www.alanwood.net/pesticides/); these substances are commercially available.

The fungicides described by IUPAC nomenclature, their preparation and their pesticidal activity is also known (cf. Can. J. Plant Sci. 48(6), 587-94, 1968; EP-A 141 317; EP-A 152 031; EP-A 226 917; EP-A 243 970; EP-A 256 503; EP-A 428 941; EP-A 532 022; EP-A 1 028 125; EP-A 1 035 122; EP-A 1 201 648; EP-A 1 122 244, JP 2002316902; DE 19650197; DE 10021412; DE 102005009458; U.S. Pat. Nos. 3,296,272; 3,325,503; WO 98/46608; WO 99/14187; WO 99/24413; WO 99/27783; WO 00/29404; WO 00/46148; WO 00/65913; WO 01/54501; WO 01/56358; WO 02/22583; WO 02/40431; WO 03/10149; WO 03/11853; WO 03/14103; WO 03/16286; WO 03/53145; WO 03/61388; WO 03/66609; WO 03/74491; WO 04/49804; WO 04/83193; WO 05/120234; WO 05/123689; WO 05/123690; WO 05/63721; WO 05/87772; WO 05/87773; WO 06/15866; WO 06/87325; WO 06/87343; WO 07/82098; WO 07/90624, WO 11/028657, WO2012/168188, WO 2007/006670, WO 2011/77514; WO13/047749, WO 10/069882, WO 13/047441, WO 03/16303, WO 09/90181, WO 13/007767, WO 13/010862, WO 13/127704, WO 13/024009, WO 13/024010 and WO 13/047441, WO 13/162072, WO 13/092224, WO 11/135833).

Biopesticides

Suitable mixing partners for the compounds of the present invention also include biopesticides.

Biopesticides have been defined as a form of pesticides based on micro-organisms (bacteria, fungi, viruses, nematodes, etc.) or natural products (compounds, such as metabolites, proteins, or extracts from biological or other natural sources) (U.S. Environmental Protection Agency: http://www.epa.gov/pesticides/biopesticides/). Biopesticides fall into two major classes, microbial and biochemical pesticides:

(1) Microbial pesticides consist of bacteria, fungi or viruses (and often include the metabolites that bacteria and fungi produce). Entomopathogenic nematodes are also classified as microbial pesticides, even though they are multicellular.

(2) Biochemical pesticides are naturally occurring substances or or structurally-similar and functionally identical to a naturally-occurring substance and extracts from biological sources that control pests or provide other crop protection uses as defined below, but have non-toxic mode of actions (such as growth or developmental regulation, attractants, repellents or defence activators (e.g. induced resistance) and are relatively non-toxic to mammals.

Biopesticides for use against crop diseases have already established themselves on a variety of crops. For example, biopesticides already play an important role in controlling downy mildew diseases. Their benefits include: a 0-Day Pre-Harvest Interval, the ability to use under moderate to severe disease pressure, and the ability to use in mixture or in a rotational program with other registered pesticides.

A major growth area for biopesticides is in the area of seed treatments and soil amendments. Biopesticidal seed treatments are e.g. used to control soil borne fungal pathogens that cause seed rots, damping-off, root rot and seedling blights. They can also be used to control internal seed borne fungal pathogens as well as fungal pathogens that are on the surface of the seed. Many biopesticidal products also show capacities to stimulate plant host defenses and other physiological processes that can make treated crops more resistant to a variety of biotic and abiotic stresses or can regulate plant growth. Many biopesticidal products also show capacities to stimulate plant health, plant growth and/or yield enhancing activity.

The following list of biopesticides, in conjunction with which the compounds of the present invention can be used, is intended to illustrate the possible combinations but does not limit them:

L) Biopesticides

L1) Microbial pesticides with fungicidal, bactericidal, viricidal and/or plant defense activator activity: *Ampelomyces quisqualis, Aspergillus flavus, Aureobasidium pullulans, Bacillus altitudinis, B. amyloliquefaciens, B. megaterium, B. mojavensis, B. mycoides, B. pumillus, B. simplex, B. solisalsi B. subtilis, B. subtilis* var. *amyloliquefaciens, Candida oleophila, C. saitoana, Clavibacter michiganensis* (bacteriophages), *Coniothyrium miniltans, Cryphonectria parasitica, Cryptococcus albidus, Dilophosphora alopecur Fusarium oxysporum, Clonostachys rosea F. catenulate* (also named *Gliocladium catenulatum*), *Gliocladium roseum, Lysobacterantibioticus, L. enzymogenes, Metschnikowia fructicola, Microdochium dimerum, Microsphaeropsis ochracea, Muscodor albus, Paenibacillus alvei, Paenibacillus polymyxa, Pantoea vagans, Penicillium bilaiae, Phlebiopsis gigantea, Pseudomonas* sp., *Pseudomonas chloraphis, Pseudozyma flocculosa, Pichia anomala, Pythium oligandrum, Sphaerodes mycoparasitica, Streptomyces griseovirdis, S. lydicus, S. violaceusniger, Talaromyces flavus, Trichoderma asperelloides, T. asperellum, T. atroviride, T. fertile, T. gamsii, T. harmatum, T. harzianum, T. polysporum, T. stromaticum, T. virens, T. viride, Typhula phacorrhiza, Ulocladium oudemansii Verticillum dahlla*, zucchini yellow mosaic virus (avirulent strain);

L2) Biochemical pesticides with fungicidal, bactericidal, viricidal and/or plant defense activator activity: harpin protein, *Reynoutria sachalinensis* extract;

L3) Microbial pesticides with insecticidal, acaricidal, molluscidal and/or nematicidal activity: *Agrobacterium radiobacter, Bacillus cereus, B. firmus, B. thuringiensis, B. thuringiensis* ssp. *aizawai*, B. t. ssp. *israelensis*, B. t. ssp. *galleriae*, B. t. ssp. *kurstaki*, B. t. ssp. *tenebrionis, Beauveria bassiana, B. brongniartii, Burkholderia* spp., *Chromobacterium subtsugae, Cydia pomonella* granulovirus (CpGV),

*Cryptophlebia leucotreta* granulovirus (CrleGV), *Flavobacterium* spp., *Helicoverpa armigera* nucleopolyhedrovirus (HearNPV), *Hellcoverpa zea* nucleopolyhedrovirus (HzNPV), *Helicoverpa zea* single capsid nucleopolyhedrovirus (HzSNPV), *Heterorhabditis bacteriophora, Isaria fumosorosea, Lecanicillum longisporum, L. muscarilum, Metarhizium anisopllae, Metarhizium anisoplliae var. anisopllae, M. anisopllae* var. *acridum, Nomuraea rileyi, Paecilomyces fumosoroseus, P. lilacinus, Paenibacillus popillae, Pasteuria* spp., *P. nishizawae, P. penetrans, P. ramosa, P. thornea, P. usgae, Pseudomonas fluorescens, Spodoptera littoralis* nucleopolyhedrovirus (SpliNPV), *Steinernema carpocapsae, S. feltiae, S. kraussei, Streptomyces galbus, S. microflavus;*

L4) Biochemical pesticides with insecticidal, acaricidal, molluscidal, pheromone and/or nematicidal activity: L-carvone, citral, (E,Z)-7,9-dodecadien-1-yl acetate, ethyl formate, (E,Z)-2,4-ethyl decadienoate (pear ester), (Z,Z,E)-7,11,13-hexadecatrienal, heptyl butyrate, isopropyl myristate, lavanulyl senecioate, cis-jasmone, 2-methyl 1-butanol, methyl eugenol, methyl jasmonate, (E,Z)-2,13-octadecadien-1-ol, (E,Z)-2,13-octadecadien-1-ol acetate, (E,Z)-3,13-octadecadien-1-ol, R-1-octen-3-ol, pentatermanone, (E,Z,Z)-3,8,11-tetradecatrienyl acetate, (Z,E)-9,12-tetradecadien-1-yl acetate, Z-7-tetradecen-2-one, Z-9-tetradecen-1-yl acetate, Z-11-tetradecenal, Z-11-tetradecen-1-ol, extract of *Chenopodium ambrosiodes*, Neem oil, Quillay extract;

L5) Microbial pesticides with plant stress reducing, plant growth regulator, plant growth promoting and/or yield enhancing activity: *Azospirllum amazonense, A. brasilense, A. lipoferum, A. irakense, A. halopraeferens, Bradyrhizobium* spp., *B. elkanii, B. japonicum, B. liaoningense, B. lupini, Delftia acidovorans, Glomus intraradices, Mesorhizobium* spp., *Rhizobium leguminosarum* bv. *phaseoli*, R. I. bv. *trifolii*, R. I. bv. *viciae, R. tropici, Sinorhizobium meliloti.*

The biopesticides from L1) and/or L2) may also have insecticidal, acaricidal, molluscidal, pheromone, nematicidal, plant stress reducing, plant growth regulator, plant growth promoting and/or yield enhancing activity. The biopesticides from L3) and/or L4) may also have fungicidal, bactericidal, viricidal, plant defense activator, plant stress reducing, plant growth regulator, plant growth promoting and/or yield enhancing activity. The biopesticides from L5) may also have fungicidal, bactericidal, viricidal, plant defense activator, insecticidal, acaricidal, molluscidal, pheromone and/or nematicidal activity.

Many of these biopesticides have been deposited under deposition numbers mentioned herein (the prefices such as ATCC or DSM refer to the acronym of the respective culture collection, for details see e. g. here: http://www.wfcc.info/ccinfo/collection/by_acronym/), are referred to in literature, registered and/or are commercially available: mixtures of *Aureobasidium pullulans* DSM 14940 and DSM 14941 isolated in 1989 in Konstanz, Germany (e. g. blastospores in BlossomProtect® from bio-ferm GmbH, Austria), *Azospirllum brasilense* Sp245 originally isolated in wheat reagion of South Brazil (Passo Fundo) at least prior to 1980 (BR 11005; e. g. GELFIX® Gramineas from BASF Agricultural Specialties Ltd., Brazil), *A. brasilense* strains Ab-V5 and Ab-V6 (e. g. in AzoMax from Novozymes BioAg Produtos papra Agricultura Ltda., Quattro Barras, Brazil or Simbiose-Maiz® from Simbiose-Agro, Brazil; Plant Soil 331, 413-425, 2010), *Bacillus amyloliquefaciens* strain AP-188 (NRRL B-50615 and B-50331; U.S. Pat. No. 8,445,255); *B. amyloliquefaciens* spp. *plantarum* D747 isolated from air in Kikugawa-shi, Japan (US 20130236522 A1; FERM BP-8234; e. g. Double Nickel™ 55 WDG from Certis LLC, USA), *B. amyloliquefaciens* spp. *plantarum* FZB24 isolated from soil in Brandenburg, Germany (also called SB3615; DSM 96-2; J. Plant Dis. Prot. 105, 181-197, 1998; e. g. Taegro® from Novozyme Biologicals, Inc., USA), *B. amyloliquefaciens* ssp. *plantarum* FZB42 isolated from soil in Brandenburg, Germany (DSM 23117; J. Plant Dis. Prot. 105, 181-197, 1998; e. g. RhizoVital® 42 from AbiTEP GmbH, Germany), *B. amyloliquefaciens* ssp. *plantarum* MBI600 isolated from faba bean in Sutton Bonington, Nottinghamshire, U.K. at least before 1988 (also called 1430; NRRL B-50595; US 2012/0149571 A1; e. g. Integral® from BASF Corp., USA), *B. amyloliquefaciens* spp. *plantarum* QST-713 isolated from peach orchard in 1995 in California, U.S.A. (NRRL B-21661; e. g. Serenade® MAX from Bayer Crop Science LP, USA), *B. amyloliquefaciens* spp. *plantarum* TJ1000 isolated in 1992 in South Dakoda, U.S.A. (also called 1 BE; ATCC BAA-390; CA 2471555 A1; e. g. QuickRoots™ from TJ Technologies, Watertown, S. Dak., USA), *B. firmus* CNCM I-1582, a variant of parental strain EIP-N1 (CNCM I-1556) isolated from soil of central plain area of Israel (WO 2009/126473, U.S. Pat. No. 6,406,690; e. g. Votivo® from Bayer CropScience LP, USA), *B. pumilus* GHA 180 isolated from apple tree rhizosphere in Mexico (IDAC 260707-01; e. g. PROMIX® BX from Premier Horticulture, Quebec, Canada), *B. pumilus* INR-7 otherwise referred to as BU-F22 and BU-F33 isolated at least before 1993 from cucumber infested by *Erwinia tracheiphila* (NRRL B-50185, NRRL B-50153; U.S. Pat. No. 8,445,255), *B. pumilus* QST 2808 was isolated from soil collected in Pohnpei, Federated States of Micronesia, in 1998 (NRRL B-30087; e. g. Sonata® or Ballad® Plus from Bayer Crop Science LP, USA), *B. simplex* ABU 288 (NRRL B50304; U.S. Pat. No. 8,445,255), *B. subtilis* FB17 also called UD 1022 or UD10-22 isolated from red beet roots in North America (ATCC PTA-11857; System. Appl. Microbiol. 27, 372-379, 2004; US 2010/0260735; WO 2011/109395); *B. thuringiensis* ssp. *aizawai* ABTS-1857 isolated from soil taken from a lawn in Ephraim, Wis., U.S.A., in 1987 (also called ABG-6346; ATCC SD1372; e. g. XenTari® from BioFa AG, Minsingen, Germany), B. t. ssp. *kurstaki* ABTS-351 identical to HD-1 isolated in 1967 from diseased Pink Bollworm black larvae in Brownsville, Tex., U.S.A. (ATCC SD-1275; e. g. Dipel® DF from Valent BioSciences, IL, USA), B. t. ssp. *tenebrionis* NB-176-1, a mutant of strain NB-125, a wild type strain isolated in 1982 from a dead pupa of the beetle *Tenebrio molitor* (DSM 5480; EP 585 215 B1; e. g. Novodor® from Valent BioSciences, Switzerland), *Beauveria bassiana* GHA (ATCC 74250; e. g. BotaniGard® 22WGP from Laverlam Int. Corp., USA), *B. bassiana* JW-1 (ATCC 74040; e. g. Naturalis® from CBC (Europe) S.r.l., Italy), *Bradyrhizobium elkanii* strains SEMIA 5019 (also called 29W) isolated in Rio de Janeiro, Brazil and SEMIA 587 isolated in 1967 in the State of Rio Grande do Sul, from an area previously inoculated with a North American isolate, and used in commercial inoculants since 1968 (Appl. Environ. Microbiol. 73(8), 2635, 2007; e. g. GELFIX 5 from BASF Agricultural Specialties Ltd., Brazil), *B. japonicum* 532c isolated from Wisconsin field in U.S.A. (Nitragin 61A152; Can. J. Plant. Sci. 70, 661-666, 1990; e. g. in Rhizoflo®, Histick®, Hicoat® Super from BASF Agricultural Specialties Ltd., Canada), *B. japonicum* E-109 variant of strain USDA 138 (INTA E109, SEMIA 5085; Eur. J. Soil Biol. 45, 28-35, 2009; Biol. Fertil. Soils 47, 81-89, 2011); *B. japonicum* strains deposited at SEMIA known from Appl. Environ. Microbiol. 73(8), 2635, 2007: SEMIA 5079 isolated from soil in Cerrados region, Brazil by Embrapa-Cerrados used in commercial inoculants since 1992 (CPAC 15; e. g. GELFIX 5 or ADHERE 60 from BASF Agricultural Specialties Ltd., Brazil), *B. japonicum* SEMIA 5080 obtained under lab conditions by Embrapa-Cerrados in Brazil and used in commercial inoculants since 1992, being a natural variant of SEMIA 586 (CB1809) originally isolated in U.S.A. (CPAC 7; e. g. GELFIX 5 or ADHERE 60 from BASF Agricultural Specialties Ltd., Brazil); *Burkholderia* sp. A396 isolated from soil in Nikko, Japan, in 2008 (NRRL B-50319; WO 2013/032693; Marrone Bio Innovations, Inc., USA), *Coniothyrium minitans* CON/M/91-08 isolated from oilseed rape (WO 1996/021358; DSM 9660; e. g. Contans® WG, Intercept® WG from Bayer CropScience AG, Germany), harpin (alphabeta) protein (Science 257, 85-88, 1992; e. g. Messenger™ or HARP-N-Tek from Plant Health Care plc, U.K.), *Helicoverpa armigera* nucleopolyhedrovirus (HearNPV) (J. Invertebrate Pathol. 107, 112-126, 2011; e. g. Helicovex® from Adermatt Biocontrol, Switzerland; Diplomata® from Koppert, Brazil; Vivus® Max from AgBiTech Pty Ltd., Queensland, Australia), *Helicoverpa zea* single capsid nucleopolyhedrovirus (HzSNPV) (e. g. Gemstar® from Certis LLC, USA), *Helicoverpa zea* nucleopolyhedrovirus ABA-NPV-U (e. g. Heligen® from AgBiTech Pty Ltd., Queensland, Australia), *Heterorhabditis bacteriophora* (e. g. Nemasys® G from BASF Agricultural Specialities Limited, UK), *Isaria fumosorosea* Apopka-97 isolated from mealy bug on gynura in Apopka, Fla., U.S.A. (ATCC 20874; Biocontrol Science Technol. 22(7), 747-761, 2012; e. g. PFR-97™ or PreFeRal® from Certis LLC, USA), *Metarhizium anisopliae* var. *anisopliae* F52 also called 275 or V275 isolated from codling moth in Austria (DSM 3884, ATCC 90448; e. g. Met52® Novozymes Biologicals BioAg Group, Canada), *Metschnikowia fructicola* 277 isolated from grapes in the central part of Israel (U.S. Pat. No. 6,994,849; NRRL Y-30752; e. g. formerly Shemer® from Agrogreen, Israel), *Paecilomyces ilacinus* 251 isolated from infected nematode eggs in the Philippines (AGAL 89/030550; WO1991/02051; Crop Protection 27, 352-361, 2008; e. g. BioAct® from Bayer CropScience AG, Germany and MeloCon® from Certis, USA), Pasteuria nishizawae Pn1 isolated from a soybean field in the mid-2000s in Illinois, U.S.A. (ATCC SD-5833; Federal Register 76(22), 5808, Feb. 2, 2011; e.g. Clariva™ PN from Syngenta Crop Protection, LLC, USA), *Penicillium bilaiae* (also called *P. bilaii*) strains ATCC 18309 (=ATCC 74319), ATCC 20851 and/or ATCC 22348 (=ATCC 74318) originally isolated from soil in Alberta, Canada (Fertilizer Res. 39, 97-103, 1994; Can. J. Plant Sci. 78(1), 91-102, 1998; U.S. Pat. No. 5,026,417, WO 1995/017806; e. g. Jump Start®, Provide® from Novozymes Biologicals BioAg Group, Canada), *Reynoutria sachalinensis* extract (EP 0307510 B1; e. g. Regalia® SC from Marrone BioInnovations, Davis, Calif., USA or Milsana® from BioFa AG, Germany), *Steinernema carpocapsae* (e. g. Millenium® from BASF Agricultural Specialities Limited, UK), *S. feltiae* (e. g. Nemashield® from BioWorks, Inc., USA; Nemasys® from BASF Agricultural Specialities Limited, UK), *Streptomyces microflavus* NRRL B-50550 (WO 2014/124369; Bayer CropScience, Germany), *T. harzianum* T-22 also called KRL-AG2 (ATCC 20847; BioControl 57, 687-696, 2012; e. g. Plantshield® from BioWorks Inc., USA or SabrEx™ from Advanced Biological Marketing Inc., Van Wert, Ohio, USA).

According to the invention, the solid material (dry matter) of the biopesticides (with the exception of oils such as Neem oil) are considered as active components (e.g. to be obtained after drying or evaporation of the extraction or suspension medium in case of liquid formulations of the microbial pesticides).

In accordance with the present invention, the weight ratios and percentages used herein for a biological extract such as Quillay extract are based on the total weight of the dry content (solid material) of the respective extract(s).

The total weight ratios of compositions comprising at least one microbial pesticide in the form of viable microbial cells including dormant forms, can be determined using the amount of CFU of the respective microorganism to calculate the total weight of the respective active component with the following equation that $1\times10^{10}$ CFU equals one gram of total weight of the respective active component. Colony forming unit is measure of viable microbial cells, in particular fungal and bacterial cells. In addition, here "CFU" may also be understood as the number of (juvenile) individual nematodes in case of (entomopathogenic) nematode biopesticides, such as *Steinernema feltiae*.

When mixtures comprising microbial pesticides are employed in crop protection, the application rates preferably range from about $1\times106$ to $5\times1015$ (or more) CFU/ha, preferably from about $1\times108$ to about $1\times1013$ CFU/ha, and even more preferably from about $1\times109$ to about $1\times1012$ CFU/ha. In the case of (entomopathogenic) nematodes as microbial pesticides (e. g. *Steinernema feltiae*), the application rates preferably range inform about $1\times105$ to $1\times1012$ (or more), more preferably from $1\times108$ to $1\times1011$, even more preferably from $5\times108$ to $1\times1010$ individuals (e. g. in the form of eggs, juvenile or any other live stages, preferably in an infective juvenile stage) per ha.

When mixtures comprising microbial pesticides are employed in seed treatment, the application rates with respect to plant propagation material preferably range from about $1\times106$ to $1\times1012$ (or more) CFU/seed. Preferably, the concentration is about $1\times106$ to about $1\times109$ CFU/seed. In the case of the microbial pesticides II, the application rates with respect to plant propagation material also preferably range from about $1\times107$ to $1\times1014$ (or more) CFU per 100 kg of seed, preferably from $1\times109$ to about $1\times1012$ CFU per 100 kg of seed.

The invention also relates to agrochemical compositions comprising an auxiliary and at least one compound of the present invention or a mixture thereof.

An agrochemical composition comprises a pesticidally effective amount of a compound of the present invention or a mixture thereof. The term "pesticidally effective amount" is defined below.

The compounds of the present invention or the mixtures thereof can be converted into customary types of agrochemical compositions, e. g. solutions, emulsions, suspensions, dusts, powders, pastes, granules, pressings, capsules, and mixtures thereof. Examples for composition types are suspensions (e.g. SC, OD, FS), emulsifiable concentrates (e.g. EC), emulsions (e.g. EW, EO, ES, ME), capsules (e.g. CS, ZC), pastes, pastilles, wettable powders or dusts (e.g. WP, SP, WS, DP, DS), pressings (e.g. BR, TB, DT), granules (e.g. WG, SG, GR, FG, GG, MG), insecticidal articles (e.g. LN), as well as gel formulations for the treatment of plant propagation materials such as seeds (e.g. GF). These and further compositions types are defined in the "Catalogue of pesticide formulation types and international coding system", Technical Monograph No. 2, 6th Ed. May 2008, CropLife International.

The compositions are prepared in a known manner, such as described by Mollet and Grubemann, Formulation technology, Wiley VCH, Weinheim, 2001; or Knowles, New developments in crop protection product formulation, Agrow Reports DS243, T&F Informa, London, 2005.

Examples for suitable auxiliaries are solvents, liquid carriers, solid carriers or fillers, surfactants, dispersants, emulsifiers, wetters, adjuvants, solubilizers, penetration enhancers, protective colloids, adhesion agents, thickeners, humectants, repellents, attractants, feeding stimulants, compatibilizers, bactericides, anti-freezing agents, anti-foaming agents, colorants, tackifiers and binders.

Suitable solvents and liquid carriers are water and organic solvents, such as mineral oil fractions of medium to high boiling point, e.g. kerosene, diesel oil; oils of vegetable or animal origin; aliphatic, cyclic and aromatic hydrocarbons, e. g. toluene, paraffin, tetrahydronaphthalene, alkylated naphthalenes; alcohols, e.g. ethanol, propanol, butanol, benzylalcohol, cyclo-hexanol; glycols; DMSO; ketones, e.g. cyclohexanone; esters, e.g. lactates, carbonates, fatty acid esters, gamma-butyrolactone; fatty acids; phosphonates; amines; amides, e.g. N-methylpyrrolidone, fatty acid dimethylamides; and mixtures thereof.

Suitable solid carriers or fillers are mineral earths, e.g. silicates, silica gels, talc, kaolins, limestone, lime, chalk, clays, dolomite, diatomaceous earth, bentonite, calcium sulfate, magnesium sulfate, magnesium oxide; polysaccharide powders, e.g. cellulose, starch; fertilizers, e.g. ammonium sulfate, ammonium phosphate, ammonium nitrate, ureas; products of vegetable origin, e.g. cereal meal, tree bark meal, wood meal, nutshell meal, and mixtures thereof.

Suitable surfactants are surface-active compounds, such as anionic, cationic, nonionic and amphoteric surfactants, block polymers, polyelectrolytes, and mixtures thereof. Such surfactants can be used as emusifier, dispersant, solubilizer, wetter, penetration enhancer, protective colloid, or adjuvant. Examples of surfactants are listed in McCutcheon's, Vol. 1: Emulsifiers & Detergents, McCutcheon's Directories, Glen Rock, USA, 2008 (International Ed. or North American Ed.).

Suitable anionic surfactants are alkali, alkaline earth or ammonium salts of sulfonates, sulfates, phosphates, carboxylates, and mixtures thereof. Examples of sulfonates are alkylaryl-sulfonates, diphenylsulfonates, alpha-olefin sulfonates, lignine sulfonates, sulfonates of fatty acids and oils, sulfonates of ethoxylated alkylphenols, sulfonates of alkoxylated arylphenols, sulfonates of condensed naphthalenes, sulfonates of dodecyl- and tridecylbenzenes, sulfonates of naphthalenes and alkyl-naphthalenes, sulfosuccinates or sulfosuccinamates. Examples of sulfates are sulfates of fatty acids and oils, of ethoxylated alkylphenols, of alcohols, of ethoxylated alcohols, or of fatty acid esters. Examples of phosphates are phosphate esters. Examples of carboxylates are alkyl carboxylates, and carboxylated alcohol or alkylphenol ethoxylates.

Suitable nonionic surfactants are alkoxylates, N-substituted fatty acid amides, amine oxides, esters, sugar-based surfactants, polymeric surfactants, and mixtures thereof. Examples of alkoxylates are compounds such as alcohols, alkylphenols, amines, amides, arylphenols, fatty acids or fatty acid esters which have been alkoxylated with 1 to 50 equivalents. Ethylene oxide and/or propylene oxide may be employed for the alkoxylation, preferably ethylene oxide. Examples of N-substituted fatty acid amides are fatty acid glucamides or fatty acid alkanolamides. Examples of esters are fatty acid esters, glycerol esters or monoglycerides. Examples of sugar-based surfactants are sorbitans, ethoxylated sorbitans, sucrose and glucose esters or alkylpolyglucosides. Examples of polymeric surfactants are homo- or copolymers of vinylpyrrolidone, vinyl-alcohols, or vinylacetate.

Suitable cationic surfactants are quaternary surfactants, for example quaternary ammonium compounds with one or two hydrophobic groups, or salts of long-chain primary amines. Suitable amphoteric surfactants are alkylbetains and imidazolines. Suitable block polymers are block polymers of the A-B or A-B-A type comprising blocks of polyethylene oxide and polypropylene oxide, or of the A-B—C type comprising alkanol, polyethylene oxide and polypropylene oxide. Suitable polyelectrolytes are polyacids or polybases. Examples of polyacids are alkali salts of polyacrylic acid or polyacid comb polymers. Examples of polybases are polyvinylamines or polyethyleneamines.

Suitable adjuvants are compounds, which have a neglectable or even no pesticidal activity themselves, and which improve the biological performance of the compounds of the present invention on the target. Examples are surfactants, mineral or vegetable oils, and other auxilaries. Further examples are listed by Knowles, Adjuvants and additives, Agrow Reports DS256, T&F Informa UK, 2006, chapter 5.

Suitable thickeners are polysaccharides (e.g. xanthan gum, carboxymethylcellulose), anorganic clays (organically modified or unmodified), polycarboxylates, and silicates.

Suitable bactericides are bronopol and isothiazolinone derivatives such as alkylisothiazolinones and benzisothiazolinones.

Suitable anti-freezing agents are ethylene glycol, propylene glycol, urea and glycerin.

Suitable anti-foaming agents are silicones, long chain alcohols, and salts of fatty acids.

Suitable colorants (e.g. in red, blue, or green) are pigments of low water solubility and water-soluble dyes. Examples are inorganic colorants (e.g. iron oxide, titan oxide, iron hexacyanoferrate) and organic colorants (e.g. alizarin-, azo- and phthalocyanine colorants).

Suitable tackifiers or binders are polyvinylpyrrolidons, polyvinylacetates, polyvinyl alcohols, polyacrylates, biological or synthetic waxes, and cellulose ethers.

Examples for composition types and their preparation are:
i) Water-soluble concentrates (SL, LS)
10-60 wt % of a compound I according to the invention and 5-15 wt % wetting agent (e.g. alcohol alkoxylates) are dissolved in water and/or in a water-soluble solvent (e.g. alcohols) up to 100 wt %. The active substance dissolves upon dilution with water.

ii) Dispersible concentrates (DC)
5-25 wt % of a compound I according to the invention and 1-10 wt % dispersant (e. g. polyvinylpyrrolidone) are dissolved in up to 100 wt % organic solvent (e.g. cyclohexanone). Dilution with water gives a dispersion.

iii) Emulsifiable concentrates (EC)
15-70 wt % of a compound I according to the invention and 5-10 wt % emulsifiers (e.g. calcium dodecylbenzenesulfonate and castor oil ethoxylate) are dissolved in up to 100 wt % water-insoluble organic solvent (e.g. aromatic hydrocarbon). Dilution with water gives an emulsion.

iv) Emulsions (EW, EO, ES)
5-40 wt % of a compound I according to the invention and 1-10 wt % emulsifiers (e.g. calcium dodecylbenzenesulfonate and castor oil ethoxylate) are dissolved in 20-40 wt % water-insoluble organic solvent (e.g. aromatic hydrocarbon). This mixture is introduced into up to 100 wt % water by means of an emulsifying machine and made into a homogeneous emulsion. Dilution with water gives an emulsion.

v) Suspensions (SC, OD, FS)

In an agitated ball mill, 20-60 wt % of a compound I according to the invention are comminuted with addition of 2-10 wt % dispersants and wetting agents (e.g. sodium lignosulfonate and alcohol ethoxylate), 0.1-2 wt % thickener (e.g. xanthan gum) and up to 100 wt % water to give a fine active substance suspension. Dilution with water gives a stable suspension of the active substance. For FS type composition up to 40 wt % binder (e.g. polyvinylalcohol) is added.

vi) Water-dispersible granules and water-soluble granules (WG, SG)

50-80 wt % of a compound I according to the invention are ground finely with addition of up to 100 wt % dispersants and wetting agents (e.g. sodium lignosulfonate and alcohol ethoxylate) and prepared as water-dispersible or water-soluble granules by means of technical appliances (e. g. extrusion, spray tower, fluidized bed). Dilution with water gives a stable dispersion or solution of the active substance.

vii) Water-dispersible powders and water-soluble powders (WP, SP, WS)

50-80 wt % of a compound I according to the invention are ground in a rotor-stator mill with addition of 1-5 wt % dispersants (e.g. sodium lignosulfonate), 1-3 wt % wetting agents (e.g. alcohol ethoxylate) and up to 100 wt % solid carrier, e.g. silica gel. Dilution with water gives a stable dispersion or solution of the active substance.

viii) Gel (GW, GF)

In an agitated ball mill, 5-25 wt % of a compound I according to the invention are comminuted with addition of 3-10 wt % dispersants (e.g. sodium lignosulfonate), 1-5 wt % thickener (e.g. carboxymethylcellulose) and up to 100 wt % water to give a fine suspension of the active substance. Dilution with water gives a stable suspension of the active substance.

ix) Microemulsion (ME)

5-20 wt % of a compound I according to the invention are added to 5-30 wt % organic solvent blend (e.g. fatty acid dimethylamide and cyclohexanone), 10-25 wt % surfactant blend (e.g. alcohol ethoxylate and arylphenol ethoxylate), and water up to 100%. This mixture is stirred for 1 h to produce spontaneously a thermodynamically stable microemulsion.

x) Microcapsules (CS)

An oil phase comprising 5-50 wt % of a compound I according to the invention, 0-40 wt % water insoluble organic solvent (e.g. aromatic hydrocarbon), 2-15 wt % acrylic monomers (e.g. methylmethacrylate, methacrylic acid and a di- or triacrylate) are dispersed into an aqueous solution of a protective colloid (e.g. polyvinyl alcohol). Radical polymerization initiated by a radi-cal initiator results in the formation of poly(meth)acrylate microcapsules. Alternatively, an oil phase comprising 5-50 wt % of a compound I according to the invention, 0-40 wt % water insolu-ble organic solvent (e.g. aromatic hydrocarbon), and an isocyanate monomer (e.g. diphenylme-thene-4,4'-diisocyanatae) are dispersed into an aqueous solution of a protective colloid (e.g. polyvinyl alcohol). The addition of a polyamine (e.g. hexamethylenediamine) results in the formation of a polyurea microcapsule. The monomers amount to 1-10 wt %. The wt % relate to the total CS composition.

xi) Dustable powders (DP, DS)

1-10 wt % of a compound I according to the invention are ground finely and mixed intimately with up to 100 wt % solid carrier, e.g. finely divided kaolin.

xii) Granules (GR, FG)

0.5-30 wt % of a compound I according to the invention is ground finely and associated with up to 100 wt % solid carrier (e.g. silicate). Granulation is achieved by extrusion, spray-drying or the fluidized bed.

xiii) Ultra-low volume liquids (UL)

1-50 wt % of a compound I according to the invention are dissolved in up to 100 wt % organic solvent, e.g. aromatic hydrocarbon.

The compositions types i) to xi) may optionally comprise further auxiliaries, such as 0.1-1 wt % bactericides, 5-15 wt % anti-freezing agents, 0.1-1 wt % anti-foaming agents, and 0.1-1 wt % colorants.

The agrochemical compositions generally comprise between 0.01 and 95%, preferably between 0.1 and 90%, and most preferably between 0.5 and 75%, by weight of active substance. The active substances are employed in a purity of from 90% to 100%, preferably from 95% to 100% (according to NMR spectrum).

Various types of oils, wetters, adjuvants, fertilizer, or micronutrients, and other pesticides (e.g. herbicides, insecticides, fungicides, growth regulators, safeners) may be added to the active substances or the compositions comprising them as premix or, if appropriate not until immediately prior to use (tank mix). These agents can be admixed with the compositions according to the invention in a weight ratio of 1:100 to 100:1, preferably 1:10 to 10:1.

The user applies the composition according to the invention usually from a predosage device, a knapsack sprayer, a spray tank, a spray plane, or an irrigation system. Usually, the agrochemical composition is made up with water, buffer, and/or further auxiliaries to the desired application concentration and the ready-to-use spray liquor or the agrochemical composition according to the invention is thus obtained. Usually, 20 to 2000 liters, preferably 50 to 400 liters, of the ready-to-use spray liquor are applied per hectare of agricultural useful area.

According to one embodiment, individual components of the composition according to the invention such as parts of a kit or parts of a binary or ternary mixture may be mixed by the user himself in a spray tank and further auxiliaries may be added, if appropriate.

In a further embodiment, either individual components of the composition according to the invention or partially premixed components, e. g. components comprising compounds of the present invention and/or mixing partners as defined above, may be mixed by the user in a spray tank and further auxiliaries and additives may be added, if appropriate.

In a further embodiment, either individual components of the composition according to the invention or partially premixed components, e. g. components comprising compounds of the present invention and/or mixing partners as defined above, can be applied jointly (e.g. after tank mix) or consecutively.

The compounds of the present invention are suitable for use in protecting crops, plants, plant propagation materials, such as seeds, or soil or water, in which the plants are growing, from attack or infestation by animal pests. Therefore, the present invention also relates to a plant protection method, which comprises contacting crops, plants, plant propagation materials, such as seeds, or soil or water, in which the plants are growing, to be protected from attack or infestation by animal pests, with a pesticidally effective amount of a compound of the present invention.

The compounds of the present invention are also suitable for use in combating or controlling animal pests. Therefore, the present invention also relates to a method of combating or controlling animal pests, which comprises contacting the animal pests, their habitat, breeding ground, or food supply, or the crops, plants, plant propagation materials, such as seeds, or soil, or the area, material or environment in which the animal pests are growing or may grow, with a pesticidally effective amount of a compound of the present invention.

The compounds of the present invention are effective through both contact and ingestion. Furthermore, the compounds of the present invention can be applied to any and all developmental stages, such as egg, larva, pupa, and adult.

The compounds of the present invention can be applied as such or in form of compositions comprising them as defined above. Furthermore, the compounds of the present invention can be applied together with a mixing partner as defined above or in form of compositions comprising said mixtures as defined above. The components of said mixture can be applied simultaneously, jointly or separately, or in succession, that is immediately one after another and thereby creating the mixture "in situ" on the desired location, e.g. the plant, the sequence, in the case of separate application, generally not having any effect on the result of the control measures.

The application can be carried out both before and after the infestation of the crops, plants, plant propagation materials, such as seeds, soil, or the area, material or environment by the pests.

Suitable application methods include inter alia soil treatment, seed treatment, in furrow application, and foliar application. Soil treatment methods include drenching the soil, drip irrigation (drip application onto the soil), dipping roots, tubers or bulbs, or soil injection. Seed treatment techniques include seed dressing, seed coating, seed dusting, seed soaking, and seed pelleting. In furrow applications typically include the steps of making a furrow in cultivated land, seeding the furrow with seeds, applying the pesticidally active compound to the furrow, and closing the furrow. Foliar application refers to the application of the pesticidally active compound to plant foliage, e.g. through spray equipment. For foliar applications, it can be advantageous to modify the behavior of the pests by use of pheromones in combination with the compounds of the present invention. Suitable pheromones for specific crops and pests are known to a skilled person and publicly available from databases of pheromones and semiochemicals, such as http://www.pherobase.com.

As used herein, the term "contacting" includes both direct contact (applying the compounds/compositions directly on the animal pest or plant—typically to the foliage, stem or roots of the plant) and indirect contact (applying the compounds/compositions to the locus, i.e. habitat, breeding ground, plant, seed, soil, area, material or environment in which a pest is growing or may grow, of the animal pest or plant).

The term "animal pest" includes arthropods, gastropods, and nematodes. Preferred animal pests according to the invention are arthropods, preferably insects and arachnids, in particular insects. Insects, which are of particular relevance for crops, are typically referred to as crop insect pests.

The term "crop" refers to both, growing and harvested crops.

The term "plant" includes cereals, e.g. durum and other wheat, rye, barley, triticale, oats, rice, or maize (fodder maize and sugar maize/sweet and field corn); beet, e.g. sugar beet or fodder beet; fruits, such as pomes, stone fruits or soft fruits, e.g. apples, pears, plums, peaches, nectarines, almonds, cherries, papayas, strawberries, raspberries, blackberries or gooseberries; leguminous plants, such as beans, lentils, peas, alfalfa or soybeans; oil plants, such as rapeseed (oilseed rape), turnip rape, mustard, olives, sunflowers, coconut, cocoa beans, castor oil plants, oil palms, ground nuts or soybeans; cucurbits, such as squashes, pumpkins, cucumber or melons; fiber plants, such as cotton, flax, hemp or jute; citrus fruit, such as oranges, lemons, grapefruits or mandarins; vegetables, such as eggplant, spinach, lettuce (e.g. iceberg lettuce), chicory, cabbage, asparagus, cabbages, carrots, onions, garlic, leeks, tomatoes, potatoes, cucurbits or sweet peppers; lauraceous plants, such as avocados, cinnamon or camphor; energy and raw material plants, such as corn, soybean, rapeseed, sugar cane or oil palm; tobacco; nuts, e.g. walnuts; pistachios; coffee; tea; bananas; vines (table grapes and grape juice grape vines); hop; sweet leaf (also called Stevia); natural rubber plants or ornamental and forestry plants, such as flowers (e.g. carnation, petunias, geranium/pelargoniums, pansies and impatiens), shrubs, broad-leaved trees (e.g. poplar) or evergreens, e.g. conifers; eucalyptus; turf; lawn; grass such as grass for animal feed or ornamental uses. Preferred plants include potatoes sugar beets, tobacco, wheat, rye, barley, oats, rice, corn, cotton, soybeans, rapeseed, legumes, sunflowers, coffee or sugar cane; fruits; vines; ornamentals; or vegetables, such as cucumbers, tomatoes, beans or squashes.

The term "plant" is to be understood as including wild type plants and plants, which have been modified by either conventional breeding, or mutagenesis or genetic engineering, or by a combination thereof.

Plants, which have been modified by mutagenesis or genetic engineering, and are of particular commercial importance, include alfalfa, rapeseed (e.g. oilseed rape), bean, carnation, chicory, cotton, eggplant, eucalyptus, flax, lentil, maize, melon, papaya, petunia, plum, poplar, potato, rice, soybean, squash, sugar beet, sugarcane, sunflower, sweet pepper, tobacco, tomato, and cereals (e.g. wheat), in particular maize, soybean, cotton, wheat, and rice. In plants, which have been modified by mutagenesis or genetic engineering, one or more genes have been mutagenized or integrated into the genetic material of the plant. The one or more mutagenized or integrated genes are preferably selected from pat, epsps, cry1Ab, bar, cry1Fa2, cry1Ac, cry34Ab1, cry35AB1, cry3A, cryF, cry1F, mcry3a, cry2Ab2, cry3Bb1, cry1A.105, dfr, barnase, vip3Aa20, barstar, als, bxn, bp40, asn1, and ppo5. The mutagenesis or integration of the one or more genes is performed in order to improve certain properties of the plant. Such properties, also known as traits, include abiotic stress tolerance, altered growth/yield, disease resistance, herbicide tolerance, insect resistance, modified product quality, and pollination control. Of these properties, herbicide tolerance, e.g. imidazolinone tolerance, glyphosate tolerance, or glufosinate tolerance, is of particular importance. Several plants have been rendered tolerant to herbicides by mutagenesis, for example Clearfield® oilseed rape being tolerant to imidazolinones, e.g. imazamox. Alternatively, genetic engineering methods have been used to render plants, such as soybean, cotton, corn, beets and oil seed rape, tolerant to herbicides, such as glyphosate and glufosinate, some of which are commercially available under the trade names RoundupReady® (glyphosate) and LibertyLink® (glufosinate). Furthermore, insect resistance is of importance, in particular lepidopteran insect resistance and coleopteran insect resistance. Insect resistance is typically achieved by modifying plants by integrating cry and/or vip genes, which were isolated from *Bacillus*

*thuringiensis* (Bt), and code for the respective Bt toxins. Genetically modified plants with insect resistance are commercially available under trade names including Wide-Strike®, Bollgard®, Agrisure®, Herculex®, YieldGard®, Genuity®, and Intacta®. Plants may be modified by mutagenesis or genetic engineering either in terms of one property (singular traits) or in terms of a combination of properties (stacked traits). Stacked traits, e.g. the combination of herbicide tolerance and insect resistance, are of increasing importance. In general, all relevant modified plants in connection with singular or stacked traits as well as detailed information as to the mutagenized or integrated genes and the respective events are available from websites of the organizations "International Service for the Acquisition of Agri-biotech Applications (ISAAA)" (http://www.isaaa.org/gmapprovaldatabase) and "Center for Environmental Risk Assessment (CERA)" (http://cera-gmc.org/GMCropDatabase).

It has surprisingly been found that the pesticidal activity of the compounds of the present invention may be enhanced by the insecticidal trait of a modified plant. Furthermore, it has been found that the compounds of the present invention are suitable for preventing insects to become resistant to the insecticidal trait or for combating pests, which already have become resistant to the insecticidal trait of a modified plant. Moreover, the compounds of the present invention are suitable for combating pests, against which the insecticidal trait is not effective, so that a complementary insecticidal activity can advantageously be used.

The term "plant propagation material" refers to all the generative parts of the plant such as seeds and vegetative plant material such as cuttings and tubers (e.g. potatoes), which can be used for the multiplication of the plant. This includes seeds, roots, fruits, tubers, bulbs, rhizomes, shoots, sprouts and other parts of plants. Seedlings and young plants, which are to be transplanted after germination or after emergence from soil, may also be included. These plant propagation materials may be treated prophylactically with a plant protection compound either at or before planting or transplanting.

The term "seed" embraces seeds and plant propagules of all kinds including but not limited to true seeds, seed pieces, suckers, corms, bulbs, fruit, tubers, grains, cuttings, cut shoots and the like, and means in a preferred embodiment true seeds.

In general, "pesticidally effective amount" means the amount of active ingredient needed to achieve an observable effect on growth, including the effects of necrosis, death, retardation, prevention, and removal, destruction, or otherwise diminishing the occurrence and activity of the target organism. The pesticidally effective amount can vary for the various compounds/compositions used in the invention. A pesticidally effective amount of the compositions will also vary according to the prevailing conditions such as desired pesticidal effect and duration, weather, target species, locus, mode of application, and the like.

In the case of soil treatment, in furrow application or of application to the pests dwelling place or nest, the quantity of active ingredient ranges from 0.0001 to 500 g per 100 m$^2$, preferably from 0.001 to 20 g per 100 m$^2$.

For use in treating crop plants, e.g. by foliar application, the rate of application of the active ingredients of this invention may be in the range of 0.0001 g to 4000 g per hectare, e.g. from 1 g to 2 kg per hectare or from 1 g to 750 g per hectare, desirably from 1 g to 100 g per hectare, more desirably from 10 g to 50 g per hectare, e.g., 10 to 20 g per hectare, 20 to 30 g per hectare, to 40 g per hectare, or 40 to 50 g per hectare.

The compounds of the present invention are particularly suitable for use in the treatment of seeds in order to protect the seeds from insect pests, in particular from soil-living insect pests, and the resulting seedling's roots and shoots against soil pests and foliar insects. The present invention therefore also relates to a method for the protection of seeds from insects, in particular from soil insects, and of the seedling's roots and shoots from insects, in particular from soil and foliar insects, said method comprising treating the seeds before sowing and/or after pregermination with a compound of the present invention. The protection of the seedling's roots and shoots is preferred. More preferred is the protection of seedling's shoots from piercing and sucking insects, chewing insects and nematodes.

The term "seed treatment" comprises all suitable seed treatment techniques known in the art, such as seed dressing, seed coating, seed dusting, seed soaking, seed pelleting, and in-furrow application methods. Preferably, the seed treatment application of the active compound is carried out by spraying or by dusting the seeds before sowing of the plants and before emergence of the plants.

The present invention also comprises seeds coated with or containing the active compound. The term "coated with and/or containing" generally signifies that the active ingredient is for the most part on the surface of the propagation product at the time of application, although a greater or lesser part of the ingredient may penetrate into the propagation product, depending on the method of application. When the said propagation product is (re)planted, it may absorb the active ingredient.

Suitable seed is for example seed of cereals, root crops, oil crops, vegetables, spices, ornamentals, for example seed of durum and other wheat, barley, oats, rye, maize (fodder maize and sugar maize/sweet and field corn), soybeans, oil crops, crucifers, cotton, sunflowers, bananas, rice, oilseed rape, turnip rape, sugarbeet, fodder beet, eggplants, potatoes, grass, lawn, turf, fodder grass, tomatoes, leeks, pumpkin/squash, cabbage, iceberg lettuce, pepper, cucumbers, melons, *Brassica* species, melons, beans, peas, garlic, onions, carrots, tuberous plants such as potatoes, sugar cane, tobacco, grapes, petunias, geranium/pelargoniums, pansies and impatiens.

In addition, the active compound may also be used for the treatment of seeds from plants, which have been modified by mutagenisis or genetic engineering, and which e.g. tolerate the action of herbicides or fungicides or insecticides. Such modified plants have been described in detail above.

Conventional seed treatment formulations include for example flowable concentrates FS, solutions LS, suspoemulsions (SE), powders for dry treatment DS, water dispersible powders for slurry treatment WS, water-soluble powders SS and emulsion ES and EC and gel formulation GF. These formulations can be applied to the seed diluted or undiluted. Application to the seeds is carried out before sowing, either directly on the seeds or after having pregerminated the latter. Preferably, the formulations are applied such that germination is not included.

The active substance concentrations in ready-to-use formulations, which may be obtained after two-to-tenfold dilution, are preferably from 0.01 to 60% by weight, more preferably from 0.1 to 40% by weight.

In a preferred embodiment a FS formulation is used for seed treatment. Typically, a FS formulation may comprise 1-800 g/l of active ingredient, 1-200 g/l Surfactant, 0 to 200 g/l antifreezing agent, 0 to 400 g/l of binder, 0 to 200 g/l of a pigment and up to 1 liter of a solvent, preferably water.

Especially preferred FS formulations of the compounds of the present invention for seed treatment usually comprise from 0.1 to 80% by weight (1 to 800 g/l) of the active ingredient, from 0.1 to 20% by weight (1 to 200 g/l) of at least one surfactant, e.g. 0.05 to 5% by weight of a wetter and from 0.5 to 15% by weight of a dispersing agent, up to 20% by weight, e.g. from 5 to 20% of an anti-freeze agent, from 0 to 15% by weight, e.g. 1 to 15% by weight of a pigment and/or a dye, from 0 to 40% by weight, e.g. 1 to 40% by weight of a binder (sticker/adhesion agent), optionally up to 5% by weight, e.g. from 0.1 to 5% by weight of a thickener, optionally from 0.1 to 2% of an anti-foam agent, and optionally a preservative such as a biocide, antioxidant or the like, e.g. in an amount from 0.01 to 1% by weight and a filler/vehicle up to 100% by weight.

In the treatment of seed, the application rates of the compounds of the invention are generally from 0.1 g to 10 kg per 100 kg of seed, preferably from 1 g to 5 kg per 100 kg of seed, more preferably from 1 g to 1000 g per 100 kg of seed and in particular from 1 g to 200 g per 100 kg of seed, e.g. from 1 g to 100 g or from 5 g to 100 g per 100 kg of seed.

The invention therefore also relates to seed comprising a compound of the present invention, or an agriculturally useful salt thereof, as defined herein. The amount of the compound of the present invention or the agriculturally useful salt thereof will in general vary from 0.1 g to 10 kg per 100 kg of seed, preferably from 1 g to 5 kg per 100 kg of seed, in particular from 1 g to 1000 g per 100 kg of seed. For specific crops such as lettuce the rate can be higher.

The invention also relates to composition comprising seed and a compound of the present invention, or an agriculturally useful salt thereof, as defined herein. The amount of the compound of the present invention or the agriculturally useful salt thereof will in general vary from 0.1 g to kg per 100 kg of seed, preferably from 1 g to 5 kg per 100 kg of seed, in particular from 1 g to 1000 g per 100 kg of seed. For specific crops such as lettuce the rate can be higher.

The compounds of the present invention may also be used for improving the health of a plant. Therefore, the present invention also relates to a method for improving plant health by treating a plant, plant propagation material and/or the locus where the plant is growing or is to grow with an effective and non-phytotoxic amount of a compound of the present invention.

As used herein "an effective and non-phytotoxic amount" means that the compound is used in a quantity which allows to obtain the desired effect but which does not give rise to any phytotoxic symptom on the treated plant or on the plant grown from the treated propagule or treated soil.

The terms "plant" and "plant propagation material" are defined above.

"Plant health" is defined as a condition of the plant and/or its products which is determined by several aspects alone or in combination with each other such as yield (for example increased biomass and/or increased content of valuable ingredients), quality (for example improved content or composition of certain ingredients or shelf life), plant vigour (for example improved plant growth and/or greener leaves ("greening effect"), tolerance to abiotic (for example drought) and/or biotic stress (for example disease) and production efficiency (for example, harvesting efficiency, processability).

The above identified indicators for the health condition of a plant may be interdependent and may result from each other. Each indicator is defined in the art and can be determined by methods known to a skilled person.

The compounds of the invention are also suitable for use against non-crop insect pests. For use against said non-crop pests, compounds of the present invention can be used as bait composition, gel, general insect spray, aerosol, as ultra-low volume application and bed net (impregnated or surface applied). Furthermore, drenching and rodding methods can be used.

As used herein, the term "non-crop insect pest" refers to pests, which are particularly relevant for non-crop targets, such as ants, termites, wasps, flies, ticks, mosquitos, crickets, or cockroaches.

The bait can be a liquid, a solid or a semisolid preparation (e.g. a gel). The bait employed in the composition is a product, which is sufficiently attractive to incite insects such as ants, termites, wasps, flies, mosquitos, crickets etc. or cockroaches to eat it. The attractiveness can be manipulated by using feeding stimulants or sex pheromones. Food stimulants are chosen, for example, but not exclusively, from animal and/or plant proteins (meat-, fish- or blood meal, insect parts, egg yolk), from fats and oils of animal and/or plant origin, or mono-, oligo- or poly-organosaccharides, especially from sucrose, lactose, fructose, dextrose, glucose, starch, pectin or even molasses or honey. Fresh or decaying parts of fruits, crops, plants, animals, insects or specific parts thereof can also serve as a feeding stimulant. Sex pheromones are known to be more insect specific. Specific pheromones are described in the literature (e.g. http://www.pherobase.com), and are known to those skilled in the art.

For use in bait compositions, the typical content of active ingredient is from 0.001 weight % to weight %, desirably from 0.001 weight % to 5% weight % of active compound.

Formulations of the compounds of the present invention as aerosols (e.g in spray cans), oil sprays or pump sprays are highly suitable for the non-professional user for controlling pests such as flies, fleas, ticks, mosquitos or cockroaches. Aerosol recipes are preferably composed of the active compound, solvents, furthermore auxiliaries such as emulsifiers, perfume oils, if appropriate stabilizers, and, if required, propellants.

The oil spray formulations differ from the aerosol recipes in that no propellants are used.

For use in spray compositions, the content of active ingredient is from 0.001 to 80 weights %, preferably from 0.01 to 50 weight % and most preferably from 0.01 to 15 weight %.

The compounds of the present invention and its respective compositions can also be used in mosquito and fumigating coils, smoke cartridges, vaporizer plates or long-term vaporizers and also in moth papers, moth pads or other heat-independent vaporizer systems.

Methods to control infectious diseases transmitted by insects (e.g. malaria, dengue and yellow fever, lymphatic filariasis, and leishmaniasis) with compounds of the present invention and its respective compositions also comprise treating surfaces of huts and houses, air spraying and impregnation of curtains, tents, clothing items, bed nets, tsetse-fly trap or the like. Insecticidal compositions for application to fibers, fabric, knitgoods, nonwovens, netting material or foils and tarpaulins preferably comprise a mixture including the insecticide, optionally a repellent and at least one binder.

The compounds of the present invention and its compositions can be used for protecting wooden materials such as trees, board fences, sleepers, frames, artistic artifacts, etc. and buildings, but also construction materials, furniture, leathers, fibers, vinyl articles, electric wires and cables etc. from ants and/or termites, and for controlling ants and termites from doing harm to crops or human being (e.g. when the pests invade into houses and public facilities).

Customary application rates in the protection of materials are, for example, from 0.001 g to 2000 g or from 0.01 g to 1000 g of active compound per m$^2$ treated material, desirably from 0.1 g to 50 g per m$^2$.

Insecticidal compositions for use in the impregnation of materials typically contain from 0.001 to 95 weight %, preferably from 0.1 to 45 weight %, and more preferably from 1 to 25 weight % of at least one repellent and/or insecticide.

The compounds of the the present invention are especially suitable for efficiently combating animal pests such as arthropods, gastropods and nematodes including but not limited to:

insects from the order of Lepidoptera, for example *Achroia grisella*, *Acleris* spp. such as *A. fimbriana*, *A. gloverana*, *A. varilana*; *Acrolepiopsis assectella*, *Acronicta major*, *Adoxophyes* spp. such as *A. cyrtosema*, *A. orana*; *Aedia leucomelas*, *Agrotis* spp. such as *A. exclamationis*, *A. fucosa*, *A. ipsion*, *A. orthogoma*, *A. segetum*, *A. subterranea*; *Alabama argillacea*, *Aleurodicus dispersus*, *Alsophila pometaria*, *Ampelophaga rubiginosa*, *Amyelois transitella*, *Anacampsis sarcitella*, *Anagasta kuehniella*, *Anarsia lineatella*, *Anisota senatorla*, *Antheraea pernyi*, *Anticarsia* (=*Thermesia*) spp. such as *A. gemmatalis*; *Apamea* spp., *Aproaerema modicella*, *Archips* spp. such as *A. argyrospila*, *A. fuscocupreanus*, *A. rosana*, *A. xyloseanus*; *Argyresthia conjugella*, *Argyroploce* spp., *Argyrotaenia* spp. such as *A. velutinana*; *Athetis mindara*, *Austroasca viridigrisea*, *Autographa gamma*, *Autographa nigrisigna*, *Barathra brassicae*, *Bedellia* spp., *Bonagota salubricola*, *Borbo cinnara*, *Bucculatrix thurberlella*, *Bupalus pinlarlus*, *Busseola* spp.; *Cacoecia* spp. such as *C. murinana*, *C. podana*; *Cactoblastis cactorum*, *Cadra cautella*, *Calingo brazilliensis*, *Caloptlills theivora*, *Capua reticulana*, *Carposina* spp. such as *C. niponensis*, *C. sasakii*; *Cephus* spp., *Chaetocnema aridula*, *Cheimatobia brumata*, *Chilo* spp. such as *C. Indicus*, *C. suppressalis*, *C. partellus*; *Choreutis parlana*, *Choristoneura* spp. such as *C. confictana*, *C. fumiferana*, *C. longicellana*, *C. murinana*, *C. occidentalis*, *C. rosaceana*; *Chrysodeixis* (=*Pseudoplusia*) spp. such as *C. eriosoma*, *C. includens*; *Cirphis unipuncta*, *Clysia ambiguella*, *Cnaphalocerus* spp., *Cnaphalocrocis medinalis*, *Cnephasia* spp., *Cochylis hospes*, *Coleophora* spp., *Colias eurytheme*, *Conopomorpha* spp., *Conotrachelus* spp., *Copitarsia* spp., *Corcyra cephalonica*, *Crambus caliginosellus*, *Crambus teterrellus*, *Crocidosema* (=*Epinotia*) *aporema*, *Cydalima* (=*Diaphania*) *perspectalis*, *Cydia* (=*Carpocapsa*) spp. such as *C. pomonella*, *C. latiferreana*; *Dalaca noctuides*, *Datana integerrima*, *Dasychira pinlcola*, *Dendrolimus* spp. such as *D. pini*, *D. spectabilis*, *D. silbiricus*; *Desmia funeralis*, *Diaphania* spp. such as *D. nitidalis*, *D. hyalinata*; *Diatraea grandiosella*, *Diatraea saccharalis*, *Diphthera festiva*, *Earias* spp. such as *E. insulana*, *E. vittella*, *Ecdytolopha aurantianu*, *Egira* (=*Xylomyges*) *curialis*, *Elasmopalpus lignosellus*, *Eldana saccharina*, *Endopiza viteana*, *Ennomos subsignaria*, *Eoreuma loftini*, *Ephestia* spp. such as *E. cautella*, *E. elutella*, *E. kuehniella*; *Epinotia aporema*, *Epiphyas postvittana*, *Erannis tiliaria*, *Erionota thrax*, *Etiella* spp., *Eulia* spp., *Eupoecilia ambiguella*, *Euproctis chrysorrhoea*, *Euxoa* spp., *Evetria boullana*, *Faronta albillinea*, *Feltia* spp. such as *F. subterranean*, *Galleria mellonella*, *Gracillaria* spp., *Grapholita* spp. such as *G. funebrana*, *G. molesta*, *G. inopinata*; *Halysidota* spp., *Harrisina americana*, *Hedylepta* spp., *Hellcoverpa* spp. such as *H. armigera* (=*Hellothis armigera*), *H. zea* (=*Hellothis zea*); *Hellothis* spp. such as *H. assulta*, *H. subflexa*, *H. virescens*; *Hellula* spp. such as *H. undalis*, *H. rogatalis*; *Helocoverpa gelotopoeon*, *Hemileuca ollviae*, *Herpetogramma licarsisalis*, *Hibernia defoliaria*, *Hofmannophilla pseudospretella*, *Homoeosoma electellum*, *Homona magnanima*, *Hypena scabra*, *Hyphantria cunea*, *Hyponomeuta padella*, *Hyponomeuta malinellus*, *Kakivoria flavofasciata*, *Keiferia lycopersicella*, *Lambdina fiscellaria fiscellaria*, *Lambdina fiscellaria lugubrosa*, *Lamprosema indicata*, *Laspeyresla molesta*, *Leguminivora glycinivorella*, *Lerodea eufala*, *Leucinodes orbonalis*, *Leucoma sallcis*, *Leucoptera* spp. such as *L. coffeella*, *L. scitella*; *Leuminivora lycinivorella*, *Lithocolletis blancardella*, *Lithophane antennata*, *Llattia octo* (=*Amyna axis*), *Lobesia botrana*, *Lophocampa* spp., *Loxagrotis alblcosta*, *Loxostege* spp. such as *L. sticticalis*, *L. cereralis*; *Lymantria* spp. such as *L. dispar*, *L. monacha*; *Lyonetia cerkella*, *Lyonetia prunifoliella*, *Malacosoma* spp. such as *M. americanum*, *M. callfornicum*, *M. constrictum*, *M. neustria*; *Mamestra* spp. such as *M. brassicae*, *M. configurata*; *Marmstra brassicae*, *Manduca* spp. such as *M. quinquemaculata*, *M. sexta*; *Marasmia* spp, *Marmara* spp., *Maruca testulalis*, *Megalopyge lanata*, *Melanchra picta*, *Melanitis leda*, *Mocis* spp. such as *M. lapites*, *M. repanda*; *Mocis latipes*, *Monochroa fragariae*, *Mythimna separata*, *Nemapogon cloacella*, *Neoleucinodes elegantalis*, *Nepytia* spp., *Nymphula* spp., *Oiketicus* spp., *Omilodes indicata*, *Omphisa anastomosalis*, *Operophtera brumata*, *Orgyia pseudotsugata*, *Oria* spp., *Orthaga thyrisalis*, *Ostrinia* spp. such as *O. nubilalis*; *Oulema oryzae*, *Paleacrita vernata*, *Panolis flammea*, *Parnara* spp., *Papaipema nebris*, *Papiilo cresphontes*, *Paramyelois transitella*, *Paranthrene regalis*, *Paysandisia archon*, *Pectinophora* spp. such as *P. gossyplella*; *Peridroma saucia*, *Perilleucoptera* spp., such as *P. coffeella*; *Phalera bucephala*, *Phryganidia callfornica*, *Phthorimaea* spp. such as *P. operculella*; *Phyllocnistis citrella*, *Phyllonorycter* spp. such as *P. blancardella*, *P. crataegella*, *P. issik*, *P. ringoniella*; *Pieris* spp. such as *P. brassicae*, *P. rapae*, *P. napi*; *Pilocrocis tripunctata*, *Plathypena scabra*, *Platynota* spp. such as *P. flavedana*, *P. idaeusalis*, *P. stultana*; *Platyptilia carduidactyla*, *Plebejus argus*, *Plodia interpunctella*, *Plusia* spp, *Plutella macullpennis*, *Plutella xylostella*, *Pontia protodica*, *Prays* spp., *Prodenia* spp., *Proxenus lepigone*, *Pseudaletia* spp. such as *P. sequax*, *P. unipuncta*, *Pyrausta nubilalis*, *Rachiplusia nu*, *Richia alblcosta*, *Rhizobius ventralis*, *Rhyacionia frustrana*, *Sabulodes aegrotata*, *Schizura concinna*, *Schoenobius* spp., *Schreckensteinia festaellella*, *Scirpophaga* spp. such as *S. incertulas*, *S. innotata*; *Scotia segetum*, *Sesamia* spp. such as *S. inferens*, *Seudyra subflava*, *Sitotroga cerealella*, *Sparganothis pilleriana*, *Spilonota lechriaspis*, *S. ocellana*, *Spodoptera* (=*Lamphygma*) spp. such as *S. cosmoides*, *S. eridania*, *S. exigua*, *S. frugiperda*, *S. latisfascia*, *S. llttoralis*, *S. lltura*, *S. omithogall*; *Stigmella* spp., *Stomopteryx subseclvella*, *Strymon bazochii*, *Sylepta derogata*, *Synanthedon* spp. such as *S. exitiosa*, *Tecia solanivora*, *Telehin llcus*, *Thaumatopoea pityocampa*, *Thaumatotibia* (=*Cryptophlebia*) *leucotreta*, *Thaumetopoea pityocampa*, *Thecla* spp., *Theresimima ampelophaga*, *Thyrintelna* spp, *Tildenia inconspicuella*, *Tinea* spp. such as *T. cloacella*, *T. pellionella*; *Tineola bisselliella*, *Tortrix* spp. such as *T. viridana*; *Trichophaga tapetzella*, *Trichoplusia* spp. such as *T. ni*; *Tuta* (=*Scrobipalpula*) *absoluta*, *Udea* spp. such as *U. rubigalis*, *U. rubigalis*; *Virachola* spp., *Yponomeuta padella*, and *Zeiraphera canadensis*;

insects from the order of Coleoptera, for example *Acalymma vittatum, Acanthoscehdes obtectus, Adoretus* spp., *Agelastica alni, Agrilus* spp. such as *A. anxlus, A. planipennis, A. sinuatus; Agrlotes* spp. such as *A. fuscicollis, A. lineatus, A. obscurus; Alphltobius diaperinus, Amphimallus solstitialis, Anisandrus dispar, Anisoplila austriaca, Anobium punctatum, Anomala corpulenta, Anomala rufocuprea, Anoplophora* spp. such as *A. glabripennis; Anthonomus* spp. such as *A. eugenii, A. grandls, A. pomorum; Anthrenus* spp., *Aphthona euphoridae, Apion* spp., *Apogonia* spp., *Athous haemorrhoidalis, Atomaria* spp. such as *A. linearis; Attagenus* spp., *Aulacophora femoralis, Blastophagus piniperda, Blitophaga undata, Bruchidius obtectus, Bruchus* spp. such as *B. lentis, B. pisorum, B. rufimanus; Byctiscus betulae, Callidiellum rufipenne, Callopistria floridensis, Callosobruchus chinensis, Cameraria ohridella, Cassida nebulosa, Cerotoma trifurcata, Cetonia aurata, Ceuthorhynchus* spp. such as *C. assimills, C. napi; Chaetocnema tibialis, Cleonus mendicus, Conoderus* spp. such as *C. vespertinus; Conotrachelus ne nuphar, Cosmopolites* spp., *Costelytra zealandica, Crioceris asparagi, Cryptolestes ferrugineus, Cryptorhynchus lapathi, Ctenicera* spp. such as *C. destructor; Curculio* spp., *Cylindrocopturus* spp., *Cyclocephala* spp., *Dactylispa balyi, Dectes texanus, Dermestes* spp., *Diabrotica* spp. such as *D. undecimpunctata, D. speciosa, D. longicornis, D. semipunctata, D. virgifera; Diaprepes abbreviates, Dichocrocis* spp., *Dicladispa armigera, Diloboderus abderus, Diocalandra frumenti (Diocalandra stigmaticollis), Enaphalodes rufulus, Epilachna* spp. such as *E. varivestis, E. vigintioctomaculata; Epitrix* spp. such as *E. hirtipennis, E. similaris; Eutheola humllis, Eutinobothrus brasiliensis, Faustinus cubae, Gibbium psylloides, Gnathocerus cornutus, Hellula undalis, Heteronychus arator, Hylamorpha elegans, Hylobius abietis, Hylotrupes bajulus, Hypera* spp. such as *H. brunneipennis, H. postica; Hypomeces squamosus, Hypothenemus* spp., *Ips typographus, Lachnosterna consanguinea, Lasioderma serricorne, Latheticus oryzae, Lathridius* spp., *Lema* spp. such as *L. bilineata, L. melanopus; Leptinotarsa* spp. such as *L. decem lineata; Leptispa pygmaea, Limonius californicus, Lissorhoptrus oryzophilus, Lixus* spp., *Luperodes* spp., *Lyctus* spp. such as *L. bruneus; Liogenys fuscus, Macrodactylus* spp. such as *M. subspinosus, Maladera matrida, Megaplatypus mutates, Megascelis* spp., *Melanotus communis, Meligethes* spp. such as *M. aeneus; Melolontha* spp. such as *M. hippocastani, M. melolontha; Metamasius hemipterus, Microtheca* spp., *Migdolus* spp. such as *M. fryanus, Monochamus* spp. such as *M. alternatus; Naupactus xanthographus, Niptus hololeucus, Oberia brevs, Oemona hirta, Oryctes rhinoceros, Oryzaephilus surinamensis, Oryzaphagus oryzae, Otiorrhynchus sulcatus, Otiorrhynchus ovatus, Otiorrhynchus sulcatus, Oulema melanopus, Oulema oryzae, Oxycetonia jucunda, Phaedon* spp. such as *P. brassicae, P. cochleariae; Phoracantha recurva, Phyllobius pyri, Phyllopertha horticola, Phyllophaga* spp. such as *P. helleri; Phyllotreta* spp. such as *P. chrysocephala, P. nemorum, P. striolata, P. vittula; Phyllopertha horticola, Popillia japonica, Premnotrypes* spp., *Psacothea hilaris, Psylliodes chrysocephala, Prostephanus truncates, Psylliodes* spp., *Ptinus* spp., *Pulga saltona, Rhizopertha dominica, Rhynchophorus* spp. such as *R. billineatus, R. ferrugineus, R. palmarum, R. phoenicis, R. vulneratus; Saperda candida, Scolytus schevyrewi, Scyphophorus acupunctatus, Sitona lineatus, Sitophilus* spp. such as *S. granaria, S. oryzae, S. zeamais; Sphenophorus* spp. such as *S. levis; Stegobium paniceum, Sternechus* spp. such as *S. subsignatus; Strophomorphus ctenotus, Symphyletes* spp., *Tanymecus* spp., *Tenebrio molitor, Tenebrioides mauretanicus, Tribolium* spp. such as *T. castaneum; Trogoderma* spp., *Tychius* spp., *Xylotrechus* spp. such as *X. pyrrhoderus;* and, *Zabrus* spp. such as *Z. tenebrioides,* insects from the order of Diptera for example *Aedes* spp. such as *A. aegypti, A. albopictus, A. vexans; Anastrepha ludens, Anopheles* spp. such as *A. albimanus, A. crucians, A. freeborni, A. gambiae, A. leucosphyrus, A. maculipennis, A. minimus, A. quadrimaculatus, A. sinensis; Bactrocera invadens, Bibio hortulanus, Calliphora erythrocephala, Calliphora vicina, Ceratitis capitata, Chrysomyia* spp. such as *C. bezziana, C. hominivorax, C. macellaria; Chrysops atlanticus, Chrysops dlscalis, Chrysops silacea, Cochliomyia* spp. such as *C. hominivorax; Contarinia* spp. *such as C. sorghicola; Cordylobia anthropophaga, Culex* spp. such as *C. nigripalpus, C. pipiens, C. quinquefasciatus, C. tarsalis, C. tritaeniorhynchus; Culicoides furens, Culiseta inornata, Culiseta melanura, Cuterebra* spp., *Dacus cucurbitae, Dacus oleae, Dasineura brassicae, Dasineura oxycoccana, Delia* spp. such as *D. antique, D. coarctata, D. platura, D. radicum; Dermatobia hominis, Drosophila* spp. such as *D. suzukii Fannia* spp. such as *F. canicularis; Gastraphilus* spp. such as *G. intestinalis; Geomyza tipunctata, Glossina* spp. such as *G. fuscipes, G. morsitans, G. palpalis, G. tachinoides; Haematobia irritans, Haplodiplosis equestris, Hippelates* spp., *Hylemyia* spp. such as *H. platura; Hypoderma* spp. such as *H. lineata; Hyppobosca* spp., *Hydrellia philippina, Leptoconops torrens, Liriomyza* spp. such as *L. sativae, L. trifolii; Lucilia* spp. such as *L. caprina, L. cuprina, L. sericata; Lycoria pectoralis, Mansonia titillanus, Mayetiola* spp. such as *M. destructor; Musca* spp. such as *M. autumnalis, M. domestica; Muscina stabulans, Oestrus* spp. such as *O. ovis; Opomyza florum, Oscinella* spp. such as *O. frit; Orseolia oryzae, Pegomya hysocyami Phlebotomus argentipes, Phorbia* spp. such as *P. antiqua, P. brassicae, P. coarctata; Phytomyza gymnostoma, Prosimulium mixtum, Psila rosae, Psorophora columbiae, Psorophora discolor, Rhagoletis* spp. such as *R. cerasi, R. cingulate, R. indifferens, R. mendax, R. pomonella; Rivellia quadrifasciata, Sarcophaga* spp. such as *S. haemorrhoidalis; Simulium vittatum, Sitodiplosis mosellana, Stomoxys* spp. such as *S. calcitrans; Tabanus* spp. such as *T. atratus, T. bovinus, T. lineola, T. similis; Tannia* spp., *Thecodiplosis japonensis, Tipula oleracea, Tipula paludosa,* and *Wohlfahrtia* spp;

insects from the order of Thysanoptera for example, *Baliothrips biformis, Dichromothrips corbetti, Dichromothrips* ssp., *Echinothrips americanus, Enneothrips flavens, Frankliniella* spp. *such as F. fusca, F. occidentalis, F. tritici; Heliothrips* spp., *Hercinothrips femoralis, Kakothrips* spp., *Microcephalothrips abdominalis, Neohydatothrips samayunkur, Pezothrips kellyanus, Rhipiphorothrips cruentatus, Scirtothrips* spp. such as *S. citri, S. dorsallis, S. perseae; Stenchaetothrips* spp, *Taeniothrips cardamoni, Taeniothrips inconsequens, Thrips* spp. such as *T. imagines, T. hawaiiensis, T. oryzae, T. palmi, T. parvispinus, T. tabaci;* insects from the order of Hemiptera for example, *Acizzia jamatonica, Acrosternum* spp. such as *A. hilare; Acyrthosipon* spp. such as *A. onobrychis, A. pisum; Adelges laricis, Adelges tsugae, Adelphocoris* spp., such as *A. rapidus, A. superbus; Aeneolamia* spp., *Agonoscena* spp., *Aulacorthum solani, Aleurocanthus woglumi, Aleurodes* spp., *Aleurodicus disperses, Aleurolobus barodensis, Aleurothrixus* spp., *Amrasca* spp., *Anasa tristis, Antestiopsis* spp., *Anuraphis cardui Aonidiella* spp., *Aphanostigma pir Aphidula nasturtii Aphis* spp. such as *A. craccivora, A. fabae, A. forbesi, A. gossypi A. grossulariae, A. maidiradicis, A. pomi A. sambuci, A. schneider A. spiraecola; Arboridia apicalis, Arillus* critatus, Aspidiella spp., Aspidiotus spp., Atanus spp., Aulacaspis yasumatsu Aulacorthum solani, Bactericera cockerelli (Paratrioza cockerelli), Bemisia spp. such as B. argentifolli B. tabaci (Aleurodes tabaci); Blissus spp. such as B. leucopterus; Brachycaudus spp. such as B. cardui B. helichrysi, B. persicae, B. prunicola; Brachycolus spp., Brachycorynella asparagi, Brevicoryne brassicae, Cacopsylla spp. such as C. fulguralis, C. pyricola (Psylla piri); Calligypona marginata, Calocoris spp., Campylomma livida, Capitophorus horni, Carneocephala fulgida, Cavelerius spp., Ceraplastes spp., Ceratovacuna lanigera, Ceroplastes ceriferus, Cerosipha gossypii, Chaetosiphon fragaefolii, Chionaspis tegalensis, Chlorita onukii, Chromaphis juglandicola, Chrysomphalus ficus, Cilcadulina mbila, Cimex spp. such as C. hemipterus, C. lectularlus; Coccomytilus halli, Coccus spp. such as C. hesperlidum, C. pseudomagnollarum; Corythucha arcuata, Creontiades dilutus, Cryptomyzus ribls, Chrysomphalus aonidum, Cryptomyzus ribls, Ctenarytaina spatulata, Cyrtopeltis notatus, Dalbulus spp., Dasynus piperls, Dialeurodes spp. such as D. citrifolii; Dalbulus maidls, Diaphorina spp. such as D. citri; Diaspis spp. such as D. bromellae; Dichelops furcatus, Diconocoris hewetti, Doralis spp., Dreyfusia nordmannianae, Dreyfusia piceae, Drosicha spp., Dysaphis spp. such as D. plantaginea, D. pyri, D. radicola; Dysaulacorthum pseudosolani, Dysdercus spp. such as D. cingulatus, D. intermedius; Dysmicoccus spp., Edessa spp., Geocoris spp., Empoasca spp. such as E. fabae, E. solana; Epidiaspis leperii, Eriosoma spp. such as E. lanigerum, E. pyricola; Erythroneura spp., Eurygasterspp. such as E. integriceps; Euscelis bilobatus, Euschistus spp. such as E. heros, E. impictiventris, E. servus; Forinia theae, Geococcus coffeae, Glycaspis brimblecombe Halyomorpha spp. such as H. halys; Helliopeltis spp., Homalodisca vitripennis (=H. coagulata), Horcias nobilellus, Hyalopterus pruni, Hyperomyzus lactucae, lcerya spp. such as I. purchase; ldioicerus spp., ldioscopus spp., Laodelphax striatellus, Lecanium spp., Lecanoideus floccissimus, Lepidosaphes spp. such as L. ulmi, Leptocorisa spp., Leptoglossus phyllopus, Lipaphis erysimlLygus spp. such as L. hesperus, L. lineolaris, L. pratensis; Maconellcoccus hirsutus, Marchallna hellenica, Macropes excavatus, Macrosiphum spp. such as M. rosae, M. avenae, M. euphorbiae; Macrosteles quadrillneatus, Mahanarva fimbriolata, Megacopta cribraria, Megoura viciae, Melanaphis pyrarius, Melanaphis sacchari, Melanocalis (=Tinocalis) caryaefoliae, Metcaflella spp., Metopolophium diirhodum, Monella costalis, Monelliopsis pecanls, Myzocallis coryli, Murgantia spp., Myzus spp. such as M. ascalonicus, M. cerasi, M. nicotianae, M. persicae, M. varians; Nasonovia ribis-nigr Neotoxoptera formosana, Neomegalotomus spp, Nephotettixspp. such as N. malayanus, N. nigropictus, N. parvus, N. vlrescens; Nezara spp. such as N. viridula; Nilaparvata lugens, Nysius huttoni, Oebalus spp. such as O. pugnax; Oncometopia spp., Orthezia praelonga, Oxycaraenus hyalinipennis, Parabemisia myricae, Parlatoria spp., Parthenolecanium spp. such as P. corni, P. persicae; Pemphigus spp. such as P. bursarlus, P. popullvenae; Peregrinus maidls, Perkinsiella saccharicida, Phenacoccus spp. such as P. aceris, P. gossypii; Phloeomyzus passerinil Phorodon humui, Phylloxera spp. such as P. devastatrix, Piesma quadrata, Piezodorus spp. such as P. guildnii; Pinnaspis aspidstrae, Planococcus spp. such as P. citri, P. ficus; Prosapia bicincta, Protopulvinaria pyriformls, Psallus seriatus, Pseudacysta persea, Pseudaulacaspis pentagona, Pseudococcus spp. such as P. comstocki; Psylla spp. such as P. mali; Pteromalus spp., Pulvinaria amygdali, Pyrlla spp., Quadraspidiotus spp., such as Q. perniciosus; Quesada gigas, Rastrococcus spp., Reduvius senllis, Rhizoecus americanus, Rhodnius spp., Rhopalomyzus ascalonicus, Rhopalosiphum spp. such as R. pseudobrassicas, R. insertum, R. maidls, R. padi; Sagatodes spp., Sahibergella singularis, Saissetia spp., Sappaphis mala, Sappaphis mali, Scaptocoris spp., Schapholdes titanus, Schizaphis gramlinum, Schizoneura lanuginosa, Scotinophora spp., Selenaspidus articulatus, Slioblon avenae, Sogata spp., Sogatella furclifera, Solubea insularis, Spissistllus festinus (=Stictocephala festlna), Stephanitis nashi, Stephanitis pyrloides, Stephanitis takeyai, Tenalaphara malayensis, Tetraleurodes perseae, Therloaphis maculate, Thyanta spp. such as T. accerra, T. perditor; Tibraca spp., Tomaspis spp., Toxoptera spp. such as T. aurantii; Trialeurodes spp. such as T. abutionea, T. ricini, T. vaporariorum; Triatoma spp., Trioza spp., Typhlocyba spp., Unaspis spp. such as U. citri, U. yanonensis; and Viteus vitifolii, Insects from the order Hymenoptera for example Acanthomyops interjectus, Athalia rosae, Atta spp. such as A. capiguara, A. cephalotes, A. cephalotes, A. laevigata, A. robusta, A. sexdens, A. texana, Bombus spp., Brachymyrmexspp., Camponotus spp. such as C. floridanus, C. pennsylvanicus, C. modoc, Cardiocondyla nuda, Challibion sp, Crematogasterspp., Dasymutilla occidentalis, Diprion spp., Dollichovespula maculata, Dorymyrmex spp., Dryocosmus kuriphilus, Formica spp., Hoplocampa spp. such as H. minuta, H. testudinea; Iridomyrmex humillis, Lasius spp. such as L. niger, Linepithema humile, Liometopum spp., Leptocybe invasa, Monomorium spp. such as M. pharaonis, Monomorium, Nylandria fulva, Pachycondyla chinensis, Paratrechina longicornis, Paravespula spp., such as P. germanica, P. pennsylvanica, P. vulgaris; Pheidole spp. such as P. megacephala; Pogonomyrmex spp. such as P. barbatus, P. callfornicus, Polistes rubiginosa, Prenolepis impairs, Pseudomyrmex gracilis, Schelipron spp., Sirex cyaneus, Solenopsis spp. such as S. geminata, S. invicta, S. molesta, S. richter S. xyloni, Sphecius speciosus, Sphex spp., Tapinoma spp. such as T. melanocephalum, T. sessile; Tetramorium spp. such as T. caespitum, T. bicarinatum, Vespa spp. such as V. crabro; Vespula spp. such as V. squamosal; Wasmannia auropunctata, Xylocopa sp;

Insects from the order Orthoptera for example Acheta domesticus, Calliptamus italicus, Chortoicetes terminifera, Ceuthophilus spp., Diastrammena asynamora, Dociostaurus maroccanus, Gryllotalpa spp. such as G. africana, G. gryllotalpa; Gryllus spp., Hieroglyphus daganensis, Kraussaria angulifera, Locusta spp. such as L. migratoria, L. pardalina; Melanoplus spp. such as M. bivittatus, M. femurrubrum, M. mexicanus, M. sanguinipes, M. spretus; Nomadacris septemfasciata, Oedaleus senegalensis, Scapteriscus spp., Schistocerca spp. such as S. ameri cana, S. gregaria, Stemopelmatus spp., Tachycines asynamorus, and Zonozerus variegatus;

Pests from the Class Arachnida for example Acari, e.g. of the families Argasidae, Ixodidae and Sarcoptidae, such as Amblyomma spp. (e.g. A. americanum, A. variegatum, A. maculatum), Argas spp. such as A. persicu), Boophilus spp. such as B. annulatus, B. decoloratus, B. microplus, Dermacentorspp. such as D. silvarum, D. andersoni, D. variabilis, Hyalomma spp. such as H. truncatum, Ixodes spp. such as I. ricinus, I. rubicundus, I. scapularis, I. holocyclus, I. pacificus, Rhipicephalus sanguineus, Omithodorus spp. such as O. moubata, O. hermsi, O. turicata, Omithonyssus bacoti, Otobius megnini, Dermanyssus gallinae, Psoroptes spp. such as P. ovis, Rhipicephalus spp. such as R. sanguineus, R. appendiculatus, Rhipicephalus evertsi Rhizoglyphus spp., Sarcoptes spp. such as S. Scabier; and Family Eriophyidae including *Aceria* spp. such as *A. sheldoni, A. anthocoptes, Acallitus* spp., *Aculops* spp. such as *A. lycopersici, A. pelekassi; Aculus* spp. such as *A. schlechtendali; Colomerus vitis, Epitrimerus pyri, Phyllocoptruta oleivora; Eriophytes ribis* and *Eriophyes* spp. such as *Eriophyes sheldon*, Family Tarsonemidae including *Hemitarsonemus* spp., *Phytonemus pallidus* and *Polyphagotarsonemus latus, Stenotarsonemus* spp. *Steneotarsonemus spinki*; Family Tenuipalpidae including *Brevipalpus* spp. such as *B. phoenicis*; Family Tetranychidae including *Eotetranychus* spp., *Eutetranychus* spp., *Oligonychus* spp., *Petrobia latens, Tetranychus* spp. such as *T. cinnabarinus, T. evansi, T. kanzawai T, pacificus, T. phaseulus, T. telarius* and *T. urticae; Bryobia praetiosa; Panonychus* spp. such as *P. ulmi, P. citr Metatetranychus* spp. and *Oligonychus* spp. such as *O. pratensis, O. perseae, Vasates lycopersici; Raoiella indica*, Family Carpoglyphidae including *Carpoglyphus* spp.; *Penthaleidae* spp. such as *Halotydeus destructor*; Family Demodicidae with species such as *Demodex* spp.; Family Trombicidea including *Trombicula* spp.; Family Macronyssidae including *Ornothonyssus* spp.; Family Pyemotidae including *Pyemotes tritici; Tyrophagus putrescentiae*; Family Acaridae including *Acarus siro*; Family Araneida including *Latrodectus mactans, Tegenaria agrestis, Chiracanthium* sp, *Lycosa* sp *Achaearanea tepidariorum* and *Loxosceles reclusa;*

Pests from the Phylum Nematoda, for example, plant parasitic nematodes such as root-knot nematodes, *Meloidogyne* spp. such as *M. hapla, M. incognita, M. javanica; cyst*-forming nematodes, *Globodera* spp. such as *G. rostochiensis; Heterodera* spp. such as *H. avenae, H. glycines, H. schachtii, H. trifolii*; Seed gall nematodes, *Anguina* spp.; Stem and foliar nematodes, *Aphelenchoides* spp. such as *A. besseyi;* Sting nematodes, *Belonolaimus* spp. such as *B. longicaudatus;* Pine nematodes, *Bursaphelenchus* spp. such as *B. lignicolus, B. xylophilus*; Ring nematodes, *Criconema* spp., *Criconemella* spp. such as *C. xenopllax* and *C. ornata*; and, *Criconemoides* spp. such as *Criconemoides informis; Mesocriconema* spp.; Stem and bulb nematodes, *Ditylenchus* spp. such as *D. destructor, D. dipsaci*; Awl nematodes, *Dolichodorus* spp.; Spiral nematodes, *Heliocotylenchus multicinctus*; Sheath and sheathoid nematodes, *Hemicycliophora* spp. and *Hemicriconemoides* spp.; *Hirshmanniella* spp.; Lance nematodes, *Hoploaimus* spp.; False rootknot nematodes, *Nacobbus* spp.; Needle nematodes, *Longidorus* spp. such as *L. elongatus*; Lesion nematodes, *Pratylenchus* spp. such as *P. brachyurus, P. neglectus, P. penetrans, P. curvitatus, P. goodeyi*; Burrowing nematodes, *Radopholus* spp. such as *R. similis; Rhadopholus* spp.; *Rhodopholus* spp.; Reniform nematodes, *Rotylenchus* spp. such as *R. robustus, R. reniformis; Scutellonema* spp.; Stubby-root nematode, *Trichodorus* spp. such as *T. obtusus, T. primitivus; Paratrichodorus* spp. such as *P. minor*; Stunt nematodes, *Tylenchorhynchus* spp. such as *T. claytoni T. dubius*; Citrus nematodes, *Tylenchulus* spp. such as *T. semipenetrans*; Dagger nematodes, *Xiphinema* spp.; and other plant parasitic nematode species;

Insects from the order Isoptera for example *Calotermes flavicollis, Coptotermes* spp. such as *C. formosanus, C. gestroi C. acinaciformis; Cornitermes cumulans, Cryptotermes* spp. such as *C. brevis, C. cavifrons; Globitermes sulfureus, Heterotermes* spp. such as *H. aureus, H. longiceps, H. tenuis; Leucotermes flavipes, Odontotermes* spp., *Incisitermes* spp. such as *I. minor, I. Snydei; Marginitermes hubbardi, Mastotermes* spp. such as *M. darwiniensis Neocapritermes* spp. such as *N. opacus, N. parvus; Neotermes* spp., *Procornitermes* spp., *Zootermopsis* spp. *such as Z angusticollis, Z nevadensis, Reticulitermes* spp. such as *R. hesperus, R. tibialis, R. speratus, R. flaviles, R. grasse R. lucifugus, R. santonensis, R. virginicus; Termes natalensis,*

Insects from the order Blattaria for example *Blatta* spp. such as *B. orientalis, B. lateralis; Blattella* spp. such as *B. asahinae, B. germanica; Leucophaea maderae, Panchlora nivea, Periplaneta* spp. such as *P. americana, P. australasiae, P. brunnea, P. fuligginosa, P. japonica; Supella longipalpa, Parcoblatta pennsylvanica, Eurycotis floridana, Pycnoscelus surinamensis,*

Insects from the order Siphonoptera for example *Cediopsylla simples, Ceratophyllus* spp., *Ctenocephalides* spp. such as *C. felis, C. canis, Xenopsylla cheopis, Pulex irritans, Trichodectes canis, Tunga penetrans,* and *Nosopsyllus fasciatus,*

Insects from the order Thysanura for example *Lepisma saccharina, Ctenolepisma urbana,* and *Thermobia domestica,*

Pests from the class Chilopoda for example *Geophilus* spp., *Scutigera* spp. such as *Scutigera coleoptrata;*

Pests from the class Diplopoda for example *Blaniulus guttulatus, Julus* spp., *Narceus* spp., Pests from the class Symphyla for example *Scutigerella immaculata,*

Insects from the order Dermaptera, for example *Forficula auricularia,*

Insects from the order Collembola, for example *Onychiurus* spp., such as *Onychiurus armatus,*

Pests from the order Isopoda for example, Armadillidium vulgare, Oniscus asellus, Porcellio scaber, Insects from the order Phthiraptera, for example *Damalinia* spp., *Pediculus* spp. such as *Pediculus humanus capitis, Pediculus humanus corporis, Pediculus humanus humanus; Pthirus pubis, Haematopinus* spp. such as *Haematopinus eurysternus, Haematopinus suis; Linognathus* spp. such as *Linognathus vituli, Bovicola bovis, Menopon gallinae, Menacanthus stramineus* and *Solenopotes capillatus, Trichodectes* spp., Examples of further pest species which may be controlled by compounds of formula (I) include: from the Phylum Mollusca, class Bivalvia, for example, *Dreissena* spp.; class Gastropoda, for example, *Arion* spp., *Biomphalaria* spp., *Bulinus* spp., *Deroceras* spp., *Galba* spp., *Lymnaea* spp., *Oncomelania* spp., *Pomacea canalicllata, Succinea* spp.; from the class of the helminths, for example, *Ancylostoma duodenale, Ancylostoma ceylanicum, Acylostoma braziliensis, Ancylostoma* spp., *Ascaris lumbricoides, Ascaris* spp., *Brugia malayli, Brugia timori, Bunostomum* spp., *Chabertia* spp., *Clonorchis* spp., *Cooperia* spp., *Dicrocoellium* spp., *Dictyocaulus filaria, Diphyllobothrium latum, Dracunculus medinensis, Echinococcus granulosus, Echinococcus multiocularis, Enterobius vermicularis, Faciola* spp., *Haemonchus* spp. such as *Haemonchus contortus; Heterakis* spp., *Hymenolepis nana, Hyostrongulus* spp., *Loa Loa, Nematodirus* spp., *Oesophagostomum* spp., *Opisthorchis* spp., *Onchocerca volvulus, Ostertagia* spp., *Paragonimus* spp., *Schistosomen* spp., *Strongyloides fuelleborni, Strongyloides stercoralis, Stronyloides* spp., *Taenia saginata, Taenia solium, Trichinella spiralis, Trichinella nativa, Trichinella britov Trichinella nelsoni, Trichinella pseudopsiralis, Trichostrongulus* spp., *Trichuris trichiura, Wuchereria bancrofti*

The compounds of the present invention are suitable for use in treating or protecting animals against infestation or infection by parasites. Therefore, the present invention also relates to the use of a compound of the present invention for the manufacture of a medicament for the treatment or protection of animals against infestation or infection by parasites. Furthermore, the present invention relates to a method of treating or protecting animals against infestation and infection by parasites, which comprises orally, topically or parenterally administering or applying to the animals a parasiticidally effective amount of a compound of the present invention.

The present invention also relates to the non-therapeutic use of compounds of the present invention for treating or protecting animals against infestation and infection by parasites. Moreover, the present invention relates to a non-therapeutic method of treating or protecting animals against infestation and infection by parasites, which comprises applying to a locus a parasiticidally effective amount of a compound of the present invention.

The compounds of the present invention are further suitable for use in combating or controlling parasites in and on animals. Furthermore, the present invention relates to a method of combating or controlling parasites in and on animals, which comprises contacting the parasites with a parasitically effective amount of a compound of the present invention.

The present invention also relates to the non-therapeutic use of compounds of the present invention for controlling or combating parasites. Moreover, the present invention relates to a nontherapeutic method of combating or controlling parasites, which comprises applying to a locus a parasiticidally effective amount of a compound of the present invention.

The compounds of the present invention can be effective through both contact (via soil, glass, wall, bed net, carpet, blankets or animal parts) and ingestion (e.g. baits). Furthermore, the compounds of the present invention can be applied to any and all developmental stages.

The compounds of the present invention can be applied as such or in form of compositions comprising the compounds of the present invention.

The compounds of the present invention can also be applied together with a mixing partner, which acts against pathogenic parasites, e.g. with synthetic coccidiosis compounds, polyetherantibiotics such as Amprolium, Robenidin, Toltrazuril, Monensin, Salinomycin, Maduramicin, Lasalocid, Narasin or Semduramicin, or with other mixing partners as defined above, or in form of compositions comprising said mixtures.

The compounds of the present invention and compositions comprising them can be applied orally, parenterally or topically, e.g. dermally. The compounds of the present invention can be systemically or non-systemically effective.

The application can be carried out prophylactically, therapeutically or non-therapeutically. Furthermore, the application can be carried out preventively to places at which occurrence of the parasites is expected.

As used herein, the term "contacting" includes both direct contact (applying the compounds/compositions directly on the parasite, including the application directly on the animal or excluding the application directly on the animal, e.g. at it's locus for the latter) and indirect contact (applying the compounds/compositions to the locus of the parasite). The contact of the parasite through application to its locus is an example of a non-therapeutic use of the compounds of the present invention.

The term "locus" means the habitat, food supply, breeding ground, area, material or environment in which a parasite is growing or may grow outside of the animal.

As used herein, the term "parasites" includes endo- and ectoparasites. In some embodiments of the present invention, endoparasites can be preferred. In other embodiments, ectoparasites can be preferred. Infestations in warm-blooded animals and fish include, but are not limited to, lice, biting lice, ticks, nasal bots, keds, biting flies, muscoid flies, flies, myiasitic fly larvae, chiggers, gnats, mosquitoes and fleas.

The compounds of the present invention are especially useful for combating parasites of the following orders and species, respectively:

fleas (Siphonaptera), e.g. *Ctenocephalides felis, Ctenocephalides canis, Xenopsylla cheopis, Pulex irritans, Tunga penetrans, and Nosopsyllus fasciatus*; cockroaches (Blattaria—Blattodea), e.g. *Battella germanica, Battella asahinae, Periplaneta americana, Periplaneta japonica, Periplaneta brunnea, Periplaneta fuligginosa, Periplaneta australasiae, and Blatta orientalis*; flies, mosquitoes (Diptera), e.g. *Aedes aegypti, Aedes albopictus, Aedes vexans, Anastrepha ludens, Anopheles maculipennis, Anopheles crucians, Anopheles albimanus, Anopheles gambiae, Anopheles freeborni, Anopheles leucosphyrus, Anopheles minimus, Anopheles quadrimaculatus, Calliphora vicina, Chrysomya bezziana, Chrysomya hominivorax, Chrysomya macellaria, Chrysops discalis, Chrysops silacea, Chrysops atlanticus, Cochliomyia hominivorax, Cordylobia anthropophaga, Culicoides furens, Culex pipiens, Culex nigripalpus, Culex quinquefasciatus, Culex tarsalis, Culiseta inornata, Culiseta melanura, Dermatobia hominis, Fannia caniculars, Gasterophilus intestinalis, Glossina morsitans, Glossina palpalis, Glossina fuscipes, Glossina tachinoides, Haematobia irritans, Haplodiplosis equestris, Hippelates spp., Hypoderma lineata, Leptoconops torrens, Lucilia caprina, Lucilia cuprina, Lucilia sericata, Lycoria pectoralis, Mansonia spp., Musca domestica, Muscina stabulans, Oestrus ovis, Phlebotomus argentipes, Psorophora columbiae, Psorophora discolor, Prosimulium mixtum, Sarcophaga haemorrhoidalis, Sarcophaga sp., Simulium vittatum, Stomoxys calcitrans, Tabanus bovinus, Tabanus atratus, Tabanus lineola, and Tabanus similis*; lice (Phthiraptera), e.g. *Pediculus humanus capitis, Pediculus humanus corporis, Pthirus pubis, Haematopinus eurysternus, Haematopinus suis, Linognathus vituli, Bovicola bovis, Menopon gallinae, Menacanthus stramineus and Solenopotes capillatus*; ticks and parasitic mites (Parasitiformes): ticks (Ixodida), e.g. *Ixodes scapulars, Ixodes holocyclus, Ixodes pacificus, Rhiphicephalus sanguineus, Dermacentor andersoni, Dermacentor variabilis, Amblyomma americanum, Ambryomma maculatum, Ornithodoros hermsi, Ornithodorus turicata* and parasitic mites (Mesostigmata), e.g. *Ornithonyssus bacoti* and *Dermanyssus gallinae*; Actinedida (Prostigmata) und Acaridida (Astigmata), e.g. *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., and *Laminosioptes* spp; Bugs (Heteropterida): *Cimex lectularlus, Cimex hemipterus, Reduvius senilis, Triatoma* spp., *Rhodnius* ssp., *Panstrongylus* ssp., and *Arilus critatus*, Anoplurida, e.g. *Haematopinus* spp., *Linognathus* spp., *Pediculus* spp., *Phtirus* spp., and *Solenopotes* spp.; Mallophagida (suborders Arnblycerina and Ischnocerina), e.g. *Trimenopon* spp., *Menopon* spp., *Trinoton* spp., *Bovicola* spp., *Werneckiella* spp., *Lepikentron* spp., *Trichodectes* spp., and *Felicola* spp.; Roundworms Nematoda: Wipeworms and Trichinosis (Trichosyringida), e.g. Trichinellidae (*Trichinella* spp.), (Trichuridae) *Trichuris* spp., *Capillaria* spp.; Rhabditida, e.g. *Rhabditis* spp., *Strongyloides* spp., *Helicephalobus* spp.; Strongylida, e.g. *Strongylus* spp., *Ancylostoma* spp., *Necator americanus*,

*Bunostomum* spp. (Hookworm), *Trichostrongylus* spp., *Haemonchus contortus, Ostertagia* spp., *Cooperia* spp., *Nematodirus* spp., *Dictyocaulus* spp., *Cyathostoma* spp., *Oesophagostomum* spp., *Stephanurus dentatus, Ollulanus* spp., *Chabertia* spp., *Stephanurus dentatus, Syngamus trachea, Ancylostoma* spp., *Uncinaria* spp., *Globocephalus* spp., *Necator* spp., *Metastrongylus* spp., *Muellerius capllaris, Protostrongylus* spp., *Angiostrongylus* spp., *Parelaphostrongylus* spp., *Aleurostrongylus abstrusus*, and *Dioctophyma renale*; Intestinal roundworms (Ascaridida), e.g. *Ascaris lumbricoides, Ascaris suum, Ascaridia galli, Parascaris equorum, Enterobius vermicularis* (Threadworm), *Toxocara canis, Toxascaris leonine, Skrjabinema* spp., *and Oxyuris equi*; Camallanida, e.g. *Dracunculus medinensis* (guinea worm); Spirurida, e.g. *Thelazia* spp., *Wuchereria* spp., *Brugia* spp., *Onchocerca* spp., *Dirofilari* spp. a, *Dipetalonema* spp., *Setaria* spp., *Elaeophora* spp., *Spirocerca lupi*, and *Habronema* spp.; Thorny headed worms (Acanthocephala), e.g. *Acanthocephalus* spp., *Macracanthorhynchus hirudinaceus* and *Oncicola* spp.; Planarians (Plathelminthes): Flukes (Trematoda), e.g. *Faciola* spp., *Fascioloides magna, Paragonimus* spp., *Dicrocoelium* spp., *Fasciolopsis buski, Clonorchis sinensis, Schistosoma* spp., *Trichobilharzia* spp., *Alaria alata, Paragonimus* spp., *and Nanocyetes* spp.; Cercomeromorpha, in particular Cestoda (Tapeworms), e.g. *Diphyllobothrium* spp., *Tenia* spp., *Echinococcus* spp., *Dipylidium caninum, Multiceps* spp., *Hymenolepis* spp., *Mesocestoides* spp., *Vampirolepis* spp., *Moniezia* spp., *Anoplocephala* spp., *Sirometra* spp., *Anoplocephala* spp., *and Hymenolepis* spp.

As used herein, the term "animal" includes warm-blooded animals (including humans) and fish. Preferred are mammals, such as cattle, sheep, swine, camels, deer, horses, pigs, poultry, rabbits, goats, dogs and cats, water buffalo, donkeys, fallow deer and reindeer, and also in fur-bearing animals such as mink, chinchilla and raccoon, birds such as hens, geese, turkeys and ducks and fish such as fresh- and salt-water fish such as trout, carp and eels. Particularly preferred are domestic animals, such as dogs or cats.

In general, "parasiticidally effective amount" means the amount of active ingredient needed to achieve an observable effect on growth, including the effects of necrosis, death, retardation, prevention, and removal, destruction, or otherwise diminishing the occurrence and activity of the target organism. The parasiticidally effective amount can vary for the various compounds/compositions used in the invention. A parasiticidally effective amount of the compositions will also vary according to the prevailing conditions such as desired parasiticidal effect and duration, target species, mode of application, and the like.

Generally, it is favorable to apply the compounds of the present invention in total amounts of 0.5 mg/kg to 100 mg/kg per day, preferably 1 mg/kg to 50 mg/kg per day.

For oral administration to warm-blooded animals, the formula I compounds may be formulated as animal feeds, animal feed premixes, animal feed concentrates, pills, solutions, pastes, suspensions, drenches, gels, tablets, boluses and capsules. In addition, the formula I compounds may be administered to the animals in their drinking water. For oral administration, the dosage form chosen should provide the animal with 0.01 mg/kg to 100 mg/kg of animal body weight per day of the formula I compound, preferably with 0.5 mg/kg to 100 mg/kg of animal body weight per day.

Alternatively, the formula I compounds may be administered to animals parenterally, for example, by intraruminal, intramuscular, intravenous or subcutaneous injection. The formula I compounds may be dispersed or dissolved in a physiologically acceptable carrier for subcutaneous injection. Alternatively, the formula I compounds may be formulated into an implant for subcutaneous administration. In addition the formula I compound may be transdermally administered to animals. For parenteral administration, the dosage form chosen should provide the animal with 0.01 mg/kg to 100 mg/kg of animal body weight per day of the formula I compound.

The formula I compounds may also be applied topically to the animals in the form of dips, dusts, powders, collars, medallions, sprays, shampoos, spot-on and pour-on formulations and in ointments or oil-in-water or water-in-oil emulsions. For topical application, dips and sprays usually contain 0.5 ppm to 5,000 ppm and preferably 1 ppm to 3,000 ppm of the formula I compound. In addition, the formula I compounds may be formulated as ear tags for animals, particularly quadrupeds such as cattle and sheep.

Suitable preparations are:
Solutions such as oral solutions, concentrates for oral administration after dilution, solutions for use on the skin or in body cavities, pouring-on formulations, gels;
Emulsions and suspensions for oral or dermal administration; semi-solid preparations;
Formulations wherein the active compound is processed in an ointment base or in an oil-in-water or water-in-oil emulsion base;
Solid preparations such as powders, premixes or concentrates, granules, pellets, tablets, boluses, capsules; aerosols and inhalants, and active compound-containing shaped articles.

Compositions suitable for injection are prepared by dissolving the active ingredient in a suitable solvent and optionally adding further auxiliaries such as acids, bases, buffer salts, preservatives, and solubilizers. Suitable auxiliaries for injection solutions are known in the art. The solutions are filtered and filled sterile.

Oral solutions are administered directly. Concentrates are administered orally after prior dilution to the use concentration. Oral solutions and concentrates are prepared according to the state of the art and as described above for injection solutions, sterile procedures not being necessary.

Solutions for use on the skin are trickled on, spread on, rubbed in, sprinkled on or sprayed on. Solutions for use on the skin are prepared according to the state of the art and according to what is described above for injection solutions, sterile procedures not being necessary.

Gels are applied to or spread on the skin or introduced into body cavities. Gels are prepared by treating solutions which have been prepared as described in the case of the injection solutions with sufficient thickener that a clear material having an ointment-like consistency results. Suitable thickeners are known in the art.

Pour-on formulations are poured or sprayed onto limited areas of the skin, the active compound penetrating the skin and acting systemically. Pour-on formulations are prepared by dissolving, suspending or emulsifying the active compound in suitable skin-compatible solvents or solvent mixtures. If appropriate, other auxiliaries such as colorants, bioabsorption-promoting substances, antioxidants, light stabilizers, adhesives are added. Suitable such auxiliaries are known in the art.

Emulsions can be administered orally, dermally or as injections. Emulsions are either of the water-in-oil type or of the oil-in-water type. They are prepared by dissolving the active compound either in the hydrophobic or in the hydrophilic phase and homogenizing this with the solvent of the other phase with the aid of suitable emulsifiers and, if appropriate, other auxiliaries such as colorants, absorption-promoting substances, preservatives, antioxidants, light stabilizers, viscosity-enhancing substances. Suitable hydrophobic phases (oils), suitable hydrophilic phases, suitable emulsifiers, and suitable further auxiliaries for emulsions are known in the art.

Suspensions can be administered orally or topically/dermally. They are prepared by suspending the active compound in a suspending agent, if appropriate with addition of other auxiliaries such as wetting agents, colorants, bioabsorption-promoting substances, preservatives, antioxidants, light stabilizers. Suitable suspending agents, and suitable other auxiliaries for suspensions including wetting agents are known in the art.

Semi-solid preparations can be administered orally or topically/dermally. They differ from the suspensions and emulsions described above only by their higher viscosity.

For the production of solid preparations, the active compound is mixed with suitable excipients, if appropriate with addition of auxiliaries, and brought into the desired form. Suitable auxiliaries for this purpose are known in the art.

The compositions which can be used in the invention can comprise generally from about 0.001 to 95% of the compound of the present invention.

Ready-to-use preparations contain the compounds acting against parasites, preferably ectoparasites, in concentrations of 10 ppm to 80 percent by weight, preferably from 0.1 to 65 percent by weight, more preferably from 1 to 50 percent by weight, most preferably from 5 to 40 percent by weight.

Preparations which are diluted before use contain the compounds acting against ectoparasites in concentrations of 0.5 to 90 percent by weight, preferably of 1 to 50 percent by weight.

Furthermore, the preparations comprise the compounds of formula I against endoparasites in concentrations of 10 ppm to 2 percent by weight, preferably of 0.05 to 0.9 percent by weight, very particularly preferably of 0.005 to 0.25 percent by weight.

Topical application may be conducted with compound-containing shaped articles such as collars, medallions, ear tags, bands for fixing at body parts, and adhesive strips and foils.

Generally it is favorable to apply solid formulations which release compounds of the present invention in total amounts of 10 mg/kg to 300 mg/kg, preferably 20 mg/kg to 200 mg/kg, most preferably 25 mg/kg to 160 mg/kg body weight of the treated animal in the course of three weeks.

EXAMPLES

Preparation Examples

With appropriate modification of the starting materials, the procedures as described in the preparation examples below were used to obtain further compounds of formula I. The compounds obtained in this manner are listed in the table X that follows, together with physical data.

Compounds can be characterized e.g. by coupled High Performance Liquid Chromatography/mass spectrometry (HPLC/MS), by $^1$H-NMR and/or by their melting points.

Analytical HPLC/MS—Method 1: Agilent Eclipse Plus C18, 50×4.6 mm, ID 5 μm; Elution: A=10 mM Amm. Formate (0.1% Formic Acid), B=Acetonitrile (0.1% Formic Acid), Flow=1.25 ml/min. at 40° C.; Gradient: 10% B to 100% B—1.5 min, hold for 1 min, 1 min—100% B. Run Time=3.5 min.

Analytical HPLC/MS—Method 2: Kinetex XB C18 1.7μ 50×2.1 mm; A=Water+0.1% TFA, B=Acetonitrile, Flow=0.8 ml/min—1.0 ml/min in 1.5 min. at 60° C.; Gradient: 5% B to 100% B—1.5 min.

$^1$H-NMR: The signals are characterized by chemical shift (ppm, . . . [delta]) vs. tetramethylsilane respectively, CDCl$_3$ for $^{13}$C-NMR, by their multiplicity and by their integral (relative number of hydrogen atoms given). The following abbreviations are used to characterize the multiplicity of the signals: m=multiplet, h=heptet, q=quartet, t=triplet, d=doublet and s=singlet.

Abbreviations used are: d for day(s), h for hour(s), min for minute(s), r.t./room temperature for 20-25° C., R$_t$ for retention time; DMSO for dimethyl sulfoxide, OAc for acetate, EtOAc for ethyl acetate, THF for tetrahydrofuran, t-BuOH for tert-butanol, dppfPdCl for [1,1'-Bis(diphenylphosphino) ferrocene]dichloropalladium(II), DIPEA for diisopropylethylamine, DCM for dichloromethane and DMAP for 4-Dimethylaminopyridine Example 1

1-(2,6-dimethyl phenyl)-3-[(E)-[1-methyl-3-[[4-(trifluoromethoxy)phenoxy] methyl]indazol-6-yl] methyleneamino]thiourea (C-1 of Table X)

Step 1: Methyl 6-bromo-1-methyl-indazole-3-carboxylate

To a solution of methyl 6-bromo-1H-indazole-3-carboxylate (1.3 gm) in Acetonitrile (20 ml) and DMF (3 ml) was added Potassium carbonate (3.52 gm) at ambient temperature. Then Methyl iodide (1.27 ml) was added to the reaction mixture at 0° C. Reaction mixture was stirred at room temperature for 16 h. Progress of reaction was monitored by TLC. After completion of reaction, reaction mixture was diluted with water (80 ml) and followed by extraction with ethyl acetate (50 ml×3). The combined organic extracts were dried over Na$_2$SO$_4$, filtered and concentrated under reduced pressure. The crude product was purified by flash chromatography (eluting in 5-30% ethyl acetate in heptane as a mobile phase) to afford of title compound (0.750 g). HPLC/MS (method 1): R$_t$: 1.876 min; MS: m/z=269.10 (M+1). $^1$H NMR (300 MHz, Chloroform-d) δ 8.11 (d, J=8.6 Hz, 1H), 7.68 (s, 1H), 7.44 (dd, J=8.6, 1.3 Hz, 1H), 7.28 (s, 1H), 4.16 (s, 3H), 4.06 (s, 3H).

Step 2: (6-bromo-1-methyl-indazol-3-yl)methanol

To a solution of Methyl 6-bromo-1-methyl-indazole-3-carboxylate (0.750 gm) in 10 ml of THF was added Di-isobutyl aluminium hydride (8.36 ml) at −78° C. Then reaction mixture was stirred at room temperature for 16 h. Progress of reaction was monitored by TLC. After completion of reaction, reaction mixture was quenched with sat. NH$_4$Cl solution and with 1N HCl solution. Aqueous layer was extracted with ethyl acetate (30 ml×3). The combined organic extracts were dried over Na$_2$SO$_4$, filtered and concentrated under reduced pressure. The crude product was purified by flash chromatography (eluting in 5-50% ethyl acetate in heptane as a mobile phase) to afford the title compound (0.500 g). HPLC/MS (method 1): R$_t$: 1.567 min; MS: m/z=243.0 (M+1). $^1$H NMR (300 MHz, Chloroform-d) δ 7.67 (d, J=8.5 Hz, 1H), 7.56 (s, 1H), 7.31-7.21 (m, 2H), 5.01 (s, 2H), 4.00 (s, 3H).

Step 3: 6-bromo-3-(chloromethyl)-1-methyl-indazole

To a solution of (6-bromo-1-methyl-indazol-3-yl)methanol (0.500 g) in THF (10 ml) was added Phosphorus oxychloride (0.25 ml g) under inert atmosphere. Reaction mixture was heated at 70° C. for 3 h. Progress of reaction was monitored by TLC. After completion of reaction, reaction mixture was concentrated under reduced pressure. The crude product was purified by flash chromatography (eluting in 5-30% ethyl acetate in heptane as a mobile phase) to afford the title compound (0.450 g). HPLC/MS (method 1): $R_t$: 2.053 min; MS: m/z=261.0 (M+1). $^1$H NMR (300 MHz, Chloroform-d) δ 7.77 (d, J=8.6 Hz, 1H), 7.67 (s, 1H), 7.40 (dd, J=8.6, 1.3 Hz, 1H), 5.01 (s, 2H), 4.11 (s, 3H), 3.66 (t, J=6.6 Hz, 4H), 3.53 (t, J=6.0 Hz, 8H), 1.95 (dt, J=14.4, 6.6 Hz, 4H), 1.80 (dt, J=12.7, 6.2 Hz, 4H), 1.71 (t, J=2.8 Hz, 4H).

Step 4: 6-bromo-1-methyl-3-[[4-(trifluoromethoxy)phenoxy]methyl]indazole

To a solution of 4-(trifluoromethoxy)phenol (0.27 ml) in DMF (5 ml) was added Potassium tertbutoxide (0.398 gm). Reaction mixture was stirred for 10 min at room temperature. Then 6-bromo-3-(chloromethyl)-1-methyl-indazole (0.460 gm) dissolved in 3 ml of DMF was added to the reaction mixture. Reaction mixture was stirred for 5 h at room temperature. Progress of reaction was monitored by TLC. After completion of reaction, reaction mixture was diluted with water (30 ml) and followed by extraction with ethyl acetate (30 ml×3). The combined organic extracts were dried over $Na_2SO_4$, filtered and concentrated under reduced pressure. The crude product was purified by flash chromatography (eluting in 5-30% ethyl acetate in heptane as a mobile phase) to afford the title compound (0.610 g). HPLC/MS (method 1): $R_t$: 2.347 min; MS: m/z=403.0 (M+1). $^1$H NMR (300 MHz, Chloroform-d) δ 7.72-7.63 (m, 1H), 7.61-7.54 (m, 1H), 7.26 (s, 2H), 7.14 (d, J=8.6 Hz, 2H), 7.03 (d, J=9.2 Hz, 2H), 5.38 (s, 2H), 4.03 (s, 3H).

Step 5: 1-methyl-3-[[4-(trifluoromethoxy)phenoxy]methyl]-6-vinyl-indazole

To a degassed solution of 6-bromo-1-methyl-3-[[4-(trifluoromethoxy)phenoxy] methyl]indazole (0.600 g) in Toluene (5 ml). was added Tributyl(vinyl)tin (0.52 ml) and 1,1'-Bis(diphenylphosphino)ferrocene]palladium(II) chloride (0.066 gm). Reaction mixture was heated at 110° C. for 2 h. Progress of reaction was monitored by TLC. After completion of reaction, reaction mixture was diluted with water (20 ml) and extracted with ethyl acetate (30 ml×2). The combined organic extracts were dried over $Na_2SO_4$, filtered and concentrated under reduced pressure. The crude product was purified by flash chromatography (eluting in 0-30% ethyl acetate in heptane as a mobile phase) to afford the title compound (0.260 g). HPLC/MS (method 1): $R_t$: 2.382 min; MS: m/z=349.2 (M+1). H NMR (300 MHz, Chloroform-d) δ 7.75 (d, J=8.7 Hz, 1H), 7.36-7.27 (m, 2H), 7.14 (d, J=8.7 Hz, 2H), 7.09-7.00 (m, 2H), 6.89-6.77 (m, 1H), 5.86 (d, J=17.5 Hz, 1H), 5.43-5.30 (m, 3H), 4.07 (s, 3H).

Step 6: 1-methyl-3-[[4-(trifluoromethoxy)phenoxy]methyl]indazole-6-carbaldehyde To a solution of 1-methyl-3-[[4-(trifluoromethoxy)phenoxy]methyl]-6-vinyl-indazole (0.341 g) in 1,4 Dioxane (5 ml) and Water (2 ml) was added Osmium tetraoxide (0.015 g) at 0° C. and reaction was stirred at the same temperature for 5 min. Then Sodium periodate (0.461 gm) was added. The reaction mixture was stirred for 3 h at room temperature. Progress of reaction was monitored by TLC. After completion of reaction, reaction mixture was quenched in aqueous Sodium sulfite solution (20 ml) and followed by extraction with ethyl acetate (30 ml×2). The combined organic extracts were dried over $Na_2SO_4$, filtered and concentrated under reduced pressure. The crude product was purified by flash chromatography (eluting in 5-50% ethyl acetate in heptane as a mobile phase) to afford the title compound (0.084 g). HPLC/MS (method 1): $R_t$: 2.075 min; MS: m/z=351.25 (M+1). $^1$H NMR (300 MHz, Chloroform-d) δ 10.18 (s, 1H), 7.98 (d, J=5.7 Hz, 2H), 7.73 (d, J=8.7 Hz, 1H), 7.22-7.02 (m, 5H), 6.86 (dd, J=13.5, 9.0 Hz, 1H), 5.46 (s, 2H), 4.19 (s, 3H), 3.73 (s, 5H), 3.59 (t, J=6.6 Hz, 1H), 3.51-3.41 (m, 3H), 1.76 (dd, J=64.8, 6.8 Hz, 13H), 1.42-1.24 (m, 5H), 0.94 (t, J=7.3 Hz, 2H).

Step 7: 1-(2,6-dimethylphenyl)-3-[(E)-[1-methyl-3-[[4-(trifluoromethoxy)phenoxy] methyl]indazol-6-yl]methyleneamino]thiourea (C-1 of Table X)

A mixture of 1-methyl-3-[[4-(trifluoromethoxy)phenoxy] methyl]indazole-6-carbaldehyde (0.250 g) and 1-amino-3-(2,6-dimethylphenyl) thiourea (0.139 g) in EtOH (5 ml) was heated at 80° C. for 3 h. The progress of reaction was monitored by TLC. Reaction mixture was cooled and concentrated under reduced pressure. Then reaction mass was diluted with water (15 ml) and extracted with ethyl acetate (25 ml×2). The combined organic solvent was dried over $Na_2SO_4$, filtered and concentrated under reduced pressure. The crude product was purified by flash chromatography (eluting in 0-5% Methanol in Dichloromethane as a mobile phase) to afford the title compound (0.160 g). HPLC/MS (method 1): $R_t$: 2.20 min; MS: m/z=528.90 (M+1). $^1$H NMR (300 MHz, DMSO-$d_6$) δ 11.88 (s, 1H), 9.91 (s, 1H), 8.27 (s, 1H), 8.06 (s, 1H), 7.86 (d, J=17.2 Hz, 2H), 7.31 (d, J=8.8 Hz, 2H), 7.23-7.10 (m, 5H), 5.45 (s, 2H), 4.10 (s, 3H), 2.21 (s, 6H).

Example 2

(2Z)-3-(2,6-dimethylphenyl)-2-[(E)-[1-methyl-3-[[4-(trifluoromethoxy)phenoxy] methyl]indazol-6-yl] methylenehydrazono]thiazolidin-4-one (C-2 of Table X)

To a solution of 1-(2,6-dimethylphenyl)-3-[(E)-[1-methyl-3-[[4-(trifluoromethoxy) phenoxy] methyl]indazol-6-yl]methyleneamino]thiourea (0.160 g) in Ethanol (5.0 ml) were added NaOAc (0.100 g) and Methyl bromo acetate (0.139 g) at room temperature. Then the reaction mixture was stirred at 28° C. for 16 h. Progress of the reaction was monitored by TLC. The reaction mixture was diluted with Water (15 ml) and extracted with Ethyl acetate (25 ml×2). The combined organic solvent was dried over $Na_2SO_4$, filtered and concentrated under reduced pressure. The crude product was purified by flash chromatography (eluting in 0-5% Methanol in Dichloromethane as a mobile phase) to afford the title compound (0.074 g). HPLC/MS (method 1): $R_t$: 2.33 min; MS: m/z=568.3 (M+1). $^1$H NMR (300 MHz, DMSO-$d_6$) δ 8.45 (s, 1H), 7.89 (d, J=8.3 Hz, 2H), 7.66 (d, J=8.8 Hz, 1H), 7.42-7.13 (m, 8H), 5.45 (s, 2H), 4.29 (s, 2H), 4.06 (s, 3H), 2.12 (s, 6H).

Example 3

1-(2-isopropylphenyl)-3-[(E)-[1-methyl-3-[[4-(trifluoromethoxy)phenoxy]methyl] indazol-6-yl]methyleneamino]thiourea (C-3 of Table X)

A mixture of 1-methyl-3-[[4-(trifluoromethoxy)phenoxy]methyl]indazole-6-carbaldehyde (0.085 g) and 1-amino-3-(2-isopropylphenyl)thiourea (0.051 g) in EtOH (5 ml) was heated at 80° C. for 3 h. The progress of reaction was monitored by TLC. Reaction mixture was cooled and concentrated under reduced pressure. Then reaction mixture was diluted with Water (15 ml) and extracted with Ethyl acetate (25 ml×2). The combined organic solvent was dried over $Na_2SO_4$, filtered and concentrated under reduced pressure. The crude product was purified by flash chromatography (eluting in 10-50% EtOAc in Heptane as a mobile phase) to afford the title compound (0.131 g). HPLC/MS (method 1): $R_t$: 2.31 min; MS: m/z=542.3 (M+1). $^1$H NMR (300 MHz, DMSO-$d_6$) δ 11.91 (s, 1H), 10.02 (s, 1H), 8.28 (s, 1H), 8.03 (s, 1H), 8.01-7.87 (m, 1H), 7.82 (d, J=8.6 Hz, 1H), 7.42-7.13 (m, 8H), 5.45 (s, 2H), 4.09 (s, 3H), 3.20-3.07 (m, 1H), 1.20 (d, J=6.9 Hz, 6H).

Example 4

(2Z)-3-(2-isopropylphenyl)-2-[(E)-[1-methyl-3-[[4-(trifluoromethoxy)phenoxy] methyl]indazol-6-yl]methylenehydrazono]thiazolidin-4-one (C-4 of Table X)

To a solution of 1-(2-isopropylphenyl)-3-[(E)-[1-methyl-3-[[4-(trifluoromethoxy) phenoxy]methyl]indazol-6-yl] methyleneamino]thiourea (0.170 g, 0.314 mmol) in ethanol (5.0 ml) were added NaOAc (0.103 g, 1.256 mmol) and methyl bromo acetate (0.144 g, 0.942 mmol) at room temperature. Then the reaction mixture was stirred at 28° C. for 16 h. Progress of the reaction was monitored by TLC. The reaction mixture was diluted with Water (15 ml) and extracted with Ethyl acetate (25 ml×2). The combined organic solvent was dried over $Na_2SO_4$, filtered and concentrated under reduced pressure. The crude product was purified by flash chromatography (eluting in 10-50% EtOAc in Heptane as a mobile phase) to afford the title compound (0.183 g). HPLC/MS (method 1): $R_t$: 2.36 min; MS: m/z=582.4 (M+1). $^1$H NMR (300 MHz, DMSO-$d_6$) δ 8.43 (s, 1H), 7.89 (d, J=9.2 Hz, 2H), 7.67 (d, J=8.8 Hz, 1H), 7.50 (q, J=7.8, 7.2 Hz, 2H), 7.41-7.14 (m, 6H), 5.45 (s, 2H), 4.44-4.10 (m, 2H), 4.06 (s, 3H), 2.86-2.74 (m, 1H), 1.16 (dd, J=9.0, 7.0 Hz, 7H).

Example 5

[(2S,3R,4R,5S,6S)-3,4,5-trimethoxy-6-methyl-tetrahydropyran-2-yl] N-[1-methyl-3-[[4-(trifluoromethoxy)benzoyl]amino]indazol-6-yl]carbamate (C-5 of Table X)

Step 1. N-(6-bromo-1-methyl-indazol-3-yl)-4-(trifluoromethoxy)benzamide

To a solution of 3-amino-6-bromo-1-methyl-1H-indazole (1.00 g), DMAP (0.058 g) and DIPEA (3.8 ml) in THF (10 ml) at 0° C. was added 4-trifluoromethoxybenzoylchloride (0.80 g) and the reaction was allowed to slowly warm to room temperature and stirred for 16 h. The reaction mixture was poured into water, extracted with EtOAc and the organic layer was washed with brine, dried over $MgSO_4$, filtered and concentrated under reduced pressure. Purification by column chromatography using a gradient of EtOAc and Cyclohexane afforded the title compound (1.38 g). $^1$H NMR (400 MHz, CDCl$_3$) δ 8.52 (s, 1H), 8.05-7.94 (m, 3H), 7.51 (d, J=1.7 Hz, 1H), 7.38-7.31 (m, 2H), 7.28-7.21 (m, 2H), 3.93 (s, 3H).

Step 2. Methyl 1-methyl-3-[[4-(trifluoromethoxy)benzoyl]amino]indazole-6-carboxylate A solution of N-(6-bromo-1-methyl-indazol-3-yl)-4-(trifluoromethoxy)benzamide (1.08 g), DIPEA (1.1 ml) and dppfPdCl$_2$ (191 mg) in Methanol at 60° C. under an atmosphere of CO (g) (1 atm) was stirred for 16 h. The reaction mixture was poured into water and extracted with CH$_2$Cl$_2$ and the organic layer was dried over MgSO$_4$, filtered and concentrated under reduced pressure and used without further purification (1.32 g). HPLC/MS (method 2): $R_t$=1.15 min, MS: m/z=394(M+).

Step 3. 1-Methyl-3-[[4-(trifluoromethoxy)benzoyl]amino]indazole-6-carboxylic Acid A suspension of methyl 1-methyl-3-[[4-(trifluoromethoxy)benzoyl]amino]indazole-6-carboxylate (1.63 g) and LiOH.H$_2$O in THF/Water (3:1, 60 ml) was stirred at room temperature for 16 h. The reaction was then quenched with aq. HCl (1 M) and the resultant precipitate was isolated by filtration, washing with ice water then dried (0.95 g). $^1$H NMR (400 MHz, DMSO-d$_6$) δ 13.12 (s, 1H), 11.07 (s, 1H), 8.28-8.16 (m, 3H), 7.84 (d, J=8.6 Hz, 1H), 7.66 (dd, J=8.6, 1.3 Hz, 1H), 7.59-7.52 (m, 2H), 4.10 (s, 3H).

Step 4. 1-Methyl-3-[[4-(trifluoromethoxy)benzoyl]amino]indazole-6-carbonyl Azide A suspension of 1-methyl-3-[[4-(trifluoromethoxy)benzoyl]amino]indazole-6-carboxylate (0.45 g) in Thionyl chloride (3 ml,) and DMF (2 drops) was stirred and heated at reflux for 4 h during which time a solution formed. The reaction mixture was concentrated under reduced pressure, re-dissolved in CH$_2$Cl$_2$ then concentrated. The crude solid (0.49 g) was suspended in Acetone (4 ml) at 0° C. and a solution of NaN$_3$ (0.19 g) in Water (6.5 ml) was slowly added. After stirring for 16 h while slowly allowing the reaction mixture to warm to room temperature, the resultant precipitate (0.19 g over 2 steps) was isolated by filtration and washed with water.

Step 5. [(2S,3R,4R,5S,6S)-3,4,5-trimethoxy-6-methyl-tetrahydropyran-2-yl] N-[1-methyl-3-[[4-(trifluoromethoxy)benzoyl]amino]indazol-6-yl]carbamate (C-5 of Table X)

A stirred solution of 1-methyl-3-[[4-(trifluoromethoxy) benzoyl]amino]indazole-6-carbonyl azide (0.140 g) in Toluene (6 ml) was heated at 100° C. for 2 h then cooled to room temperature and concentrated under reduced pressure. The resultant oil was dissolved in Acetonitrile (6 ml), (3R,4R,5S,6S)-3,4,5-trimethoxy-6-methyl-tetrahydropyran-2-ol (0.11 g) and Cs$_2$CO$_3$ (0.056 g) were added and the suspension was stirred at room temperature for 16 h. The reaction mixture was poured into water and extracted with EtOAc and the organic layer was dried over MgSO$_4$, filtered and concentrated under reduced pressure. Purification by column chromatography using a gradient of EtOAc and cyclohexane afforded the title compound (40 mg). ¹H NMR (500 MHz, CDCl₃) δ 8.13 (s, 1H), 7.83 (d, J=8.5 Hz, 2H), 7.48-7.40 (m, 2H), 7.25 (d, J=8.4 Hz, 2H), 6.94 (dd, J=8.8, 1.7 Hz, 1H), 6.24 (d, J=2.0 Hz, 1H), 4.09 (s, 3H), 3.71 (dq, J=12.9, 5.1, 3.8 Hz, 1H), 3.70 (s, 1H), 3.61-3.46 (m, 11H), 3.22 (t, J=9.4 Hz, 1H), 2.05 (s, 1H), 1.42 (s, 1H), 1.32 (d, J=6.2 Hz, 3H), 1.28 (dt, J=19.0, 6.7 Hz, 1H).

Example 6

[(2S,3R,4R,5S,6S)-3,4,5-trimethoxy-6-methyl-tetrahydropyran-2-yl] N-[1-methyl-3-[[4-(trifluoromethoxy)phenyl]carbamoyl]indazol-6-yl]carbamate (C-6 of Table X)

Step 1: Methyl 1-methyl-3-[[4-(trifluoromethoxy)phenyl]carbamoyl]indazole-6-carboxylate A solution of methyl 3-bromo-1-methyl-indazole-6-carboxylate (0.90 g), 4-(trifluoromethoxy)aniline (0.89 g), DIPEA (1.4 ml) and Pd(dppf)Cl₂ (0.24 g) in dimethylacetamide (60 ml) was heated at 80° C. with stirring under an atmosphere of CO (g) (5 atm) for 19 h. The reaction mixture was allowed to cool to room temperature, then extracted with ethyl acetate washing with water, dried over MgSO₄, filtered, and concentrated under reduced pressure. Purification by silica gel chromatography using a gradient of ethyl acetate/cyclohexane afforded the title compound (0.65 g). HPLC/MS (method 2): $R_t$: 1.32 min; MS: m/z=394 (M+1).

Step 2: 1-methyl-3-[[4-(trifluoromethoxy)phenyl]carbamoyl]indazole-6-carboxylic Acid A solution of methyl 1-methyl-3-[[4-(trifluoromethoxy)phenyl]carbamoyl]indazole-6-carboxylate (0.83 g) and LiOH.H₂O (0.13 g) in THF (15 ml) and H₂O (5 ml) was stirred at room temperature for 16 h. The reaction mixture was then poured onto an ice-cold solution of aq. HCl (1 M) and the resultant precipitate was isolated by filtration washing with cold water. The wet solid was dried by co-distillation with toluene (3×) then precipitation from diisopropylether (0.40 g) and used without further purification.

Step 3: 1-methyl-3-[[4-(trifluoromethoxy)phenyl]carbamoyl]indazole-6-carbonyl Azide To a solution of 1-methyl-3-[[4-(trifluoromethoxy)phenyl]carbamoyl]indazole-6-carboxylic acid (0.40 g) in CH₂Cl₂ at 0° C. was added oxalyl chloride (0.11 ml) followed by 1 drop of DMF. The reaction mixture was warmed to room temperature and stirred for 3 h then concentrated to dryness. The resultant crude oil was suspended in acetone (7 ml) then added to a stirred solution of NaN₃ (0.18 g) at 0° C. The reaction mixture was stirred for 16 h at room temperature, then the resultant precipitate was isolated by filtration washing with cold water and dried to afford the title compound (285 mg). HPLC/MS (method 2): $R_t$: 1.33 min; MS: m/z=405 (M+1).

Step 4: [(2S,3R,4R,5S,6S)-3,4,5-trimethoxy-6-methyl-tetrahydropyran-2-yl] N-[1-methyl-3-[[4-(trifluoromethoxy)phenyl]carbamoyl]indazol-6-yl]carbamate (C-6 of Table X)

A suspension of 1-methyl-3-[[4-(trifluoromethoxy)phenyl]carbamoyl]indazole-6-carbonyl azide (0.14 g) in Toluene was heated at 80° C. for 2 h, cooled to r.t. then concentrated. The resultant crude oil was dissolved in CH₃CN (6 ml) at r.t. then Cs₂CO₃ (56 mg) and (3R,4R,5S,6S)-3,4,5-trimethoxy-6-methyl-tetrahydropyran-2-ol (0.11 g) were added. After 16 h, the reaction mixture was concentrated and partitioned between ethyl acetate and aq. NaHCO₃. The organic layer was dried over MgSO₄, filtered, and concentration. Purification by silica gel chromatography using a gradient of ethyl acetate/cyclohexane afforded the title compound (70 mg). HPLC/MS (method 2): $R_t$: 1.25 min; MS: m/z=584 (M+1). ¹H NMR (400 MHz, CDCl₃) δ 8.84 (s, 1H), 8.29 (d, J=8.7 Hz, 1H), 8.10-8.04 (m, 1H), 7.82-7.73 (m, 2H), 7.23 (d, J=8.6 Hz, 2H), 6.99 (s, 1H), 6.92 (dd, J=8.7, 1.8 Hz, 1H), 6.23 (d, J=2.0 Hz, 1H), 4.10 (s, 2H), 3.77-3.65 (m, 2H), 3.61-3.47 (m, 8H), 3.22 (t, J=9.4 Hz, 1H), 1.34 (d, J=6.2 Hz, 2H).

Example 7

6-[(E)-[(2-isopropylphenyl)carbamothioylhydrazono]methyl]-1-methyl-N-[4-(trifluoromethoxy)phenyl]indazole-3-carboxamide (C-7 of Table X)

Step 1: 6-bromo-1H-indazole-3-carbaldehyde

A solution of 6-bromoindole (6 g) in Acetone (200 ml) was cooled to 0° C. under inert atmosphere. To the solution was added NaNO₂ (16.89 g) in Water (30 ml) and 2N Aq. HCl (70 ml) drop wise at 0° C. under inert atmosphere. Reaction mixture was stirred at room temperature for 1 h. Progress of reaction was monitored by TLC. After completion of the reaction, the solvents were evaporated under vacuum and precipitated product was filtered through a filter paper. Product was washed with cold DCM (50 ml) and dried under reduced pressure to afford the title compound (6.5 g). HPLC/MS (method 1): $R_t$: 1.699 min; MS: m/z=225 (M−1).

Step 2: 6-bromo-1-methyl-indazole-3-carbaldehyde

To a solution of 6-bromo-1H-indazole-3-carbaldehyde (3 g) in dry THF (30 ml) were added methyl iodide (2.27 g) and K₂CO₃ (2.76 g) under inert atmosphere. Reaction mixture was stirred at room temperature for 12 h. Progress of reaction was monitored by TLC. After completion, the reaction mixture was diluted with Water (60 ml) and extracted with Ethyl acetate (80 ml×2). The combined organic extracts were dried over Na₂SO₄, filtered and concentrated under reduced pressure. The crude product was purified by flash chromatography (eluting in 15-20% ethyl acetate in heptane as a mobile phase) to afford (2.1 g) of the title compound. HPLC/MS (method 1): $R_t$: 1.898 min; MS: m/z=238.2 (M+1).

Step 3: 6-bromo-1-methyl-indazole-3-carboxylic Acid

To a solution of 6-bromo-1-methyl-indazole-3-carbaldehyde (1 g) in CH₃CN (10 ml) and Water (4 ml) was added KMnO₄ (1.32 g) at room temperature. The reaction mixture was stirred for 12 h. Progress of reaction was monitored by TLC. After completion, the reaction mixture was poured in ice cold water and filtered through a celite bed. Celite bed was washed with water and pH of filtrate was adjusted up to ~3-4 using Aq. 1N HCl solution. The precipitated product was filtered through a filter paper and dried under reduced pressure to afford (0.8 g) of title the compound. HPLC/MS (method 1): $R_t$: 1.569 min; MS: m/z=253 (M−1).

Step 4: 6-bromo-1-methyl-N-[4-(trifluoromethoxy)phenyl]indazole-3-carboxamide To a solution of 6-bromo-1-methyl-indazole-3-carboxylic acid (0.8 g) in dry DCM (10 ml) were added 4-trifluromethoxy aniline (0.61 g) and Triethyl amine (1.04 g) at 0° C. under inert atmosphere. Reaction mixture was stirred at room temperature for 5 min and then Propyl phosphonic anhydride solution (5.98 g, 50% in ethyl acetate) was added to the reaction mixture. Reaction mixture was continued to stir for 12 h at room temperature. Progress of reaction was monitored by TLC. After completion, the reaction mixture was diluted with Water (50 ml) and extracted with Ethyl acetate (60 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (1.2 g) of the title compound. HPLC/MS (method 1): $R_t$: 2.186 min; MS: m/z=413.9 (M−1).

Step 5: 1-methyl-N-[4-(trifluoromethoxy)phenyl]-6-vinyl-indazole-3-carboxamide A solution of 6-bromo-1-methyl-N-[4-(trifluoromethoxy)phenyl]indazole-3-carboxamide (1 g) in dry Toluene (10 ml) was purged with Nitrogen for 10 min. To the solution was added Pd(dppf)C2 (0.106 g) and Nitrogen purging was continued for another 10 min. Then Tributyl vinyl tin (1.148 g) was added to the solution. The reaction mixture was stirred for 3 h at 110° C. Progress of reaction was monitored by TLC. After completion, the reaction mixture was allow to cool to room temperature, then diluted with Water (50 ml) and extracted with Ethyl acetate (60 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.450 g) of the title compound. HPLC/MS (method 1): $R_t$: 2.196 min; MS: m/z=362.15 (M+1).

Step 6: 6-formyl-1-methyl-N-[4-(trifluoromethoxy)phenyl]indazole-3-carboxamide A solution of 1-methyl-N-[4-(trifluoromethoxy)phenyl]-6-vinyl-indazole-3-carboxamide (0.450 g) in 1,4-dioxane (5 ml) and Water (2 ml) was cooled to 0° C. under inert atmosphere. To the stirred solution $OsO_4$ (0.005 g) and $NaIO_4$ (0.584 g) were added under inert atmosphere. The reaction mixture was stirred at room temperature for 4 h. Progress of reaction was monitored by TLC. After completion, the reaction mixture was diluted with Water (10 ml), quenched with Aq. sodium sulfite solution (10 ml) and extracted with Ethyl acetate (20 ml×2). The combined organic extracts were dried over $Na_2SO_4$, filtered and concentrated under reduced pressure. The crude product was purified by flash chromatography (eluting in 20-22% ethyl acetate in heptane as a mobile phase) to afford (0.300 g) of the title compound. HPLC/MS (method 1): $R_t$: 2.098 min; MS: m/z=362.0 (M−1).

Step 7: 6-[(E)-[(2-isopropylphenyl)carbamothioylhydrazono]methyl]-1-methyl-N-[4-(trifluoromethoxy)phenyl]indazole-3-carboxamide (C-7 of Table X)

1-amino-3-(2-isopropylphenyl)thiourea (0.173 g) was added to a solution of 6-formyl-1-methyl-N-[4-(trifluoromethoxy)phenyl]indazole-3-carboxamide (0.3 g) in Ethanol (3 ml) at room temperature under inert atmosphere. The reaction mixture was stirred for 3 h at 85° C. Progress of reaction was monitored by TLC. After completion, the reaction mixture was cooled to room temperature and the precipitated product was filtered through a filter paper. The residue was washed with cold EtOH (2 ml), triturated with Pentane (5 ml) and dried under reduced pressure to afford (0.280 g) of the title compound. HPLC/MS (method 1): $R_t$: 2.229 min; MS: m/z=553.3 (M−1). $^1$H NMR (500 MHz, DMSO-$d_6$) δ 11.96 (s, 1H), 10.62 (s, 1H), 10.07 (s, 1H), 8.32 (s, 1H), 8.22-8.15 (m, 2H), 8.09 (d, J=8.6 Hz, 1H), 8.06-7.99 (m, 2H), 7.37 (t, J=8.8 Hz, 3H), 7.32 (ddd, J=8.0, 6.0, 2.7 Hz, 1H), 7.29-7.20 (m, 2H), 4.25 (s, 3H), 3.16 (hept, J=6.9 Hz, 1H), 1.21 (d, J=6.9 Hz, 6H).

Example 8

6-[(E)-[(Z)-[3-(2-isopropylphenyl)-4-oxo-thiazolidin-2-ylidene]hydrazono]methyl]-1-methyl-N-[4-(trifluoromethoxy)phenyl]indazole-3-carboxamide (C-8 of Table X)

To a stirred solution of 6-[(E)-[(2-isopropylphenyl)carbamothioylhydrazono]methyl]-1-methyl-N-[4-(trifluoromethoxy)phenyl]indazole-3-carboxamide (0.24 g) in EtOH (5 ml) were added NaOAc (0.071 g) and Methyl bromo acetate (0.099 g) at room temperature. The reaction mixture was continued to stir at room temperature for 12 h. Progress of reaction was monitored by TLC. After completion, the reaction mixture was diluted with Water (20 ml) and extracted with Ethyl acetate (25 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.2 g) of the title compound. HPLC/MS (method 1): $R_t$: 2.325 min; MS: m/z=595.1 (M+1). $^1$H NMR (500 MHz, DMSO-$d_6$) δ 10.63 (s, 1H), 8.47 (s, 1H), 8.26 (d, J=8.5 Hz, 1H), 8.06-7.98 (m, 3H), 7.83 (d, J=8.5 Hz, 1H), 7.56-7.45 (m, 2H), 7.40-7.32 (m, 3H), 7.29 (dd, J=7.9, 1.2 Hz, 1H), 4.32-4.22 (m, 1H), 4.22 (s, 3H), 4.17 (d, J=17.3 Hz, 1H), 2.81 (hept, J=6.9 Hz, 1H), 1.16 (dd, J=16.7, 6.8 Hz, 6H).

Example 9

[(E)-[1-methyl-3-[[4-(trifluoromethoxy)phenyl]carbamoyl]indazol-6-yl] methyleneamino]N-(2-isopropylphenyl)carbamate (C-9 of Table X)

Step 1: 6-[(E)-hydroxyiminomethyl]-1-methyl-N-[4-(trifluoromethoxy)phenyl]indazole-3-carboxamide Hydroxyl amine hydrochloride (0.191 g) and Sodium acetate (0.226 g) were added to a solution of 6-formyl-1-methyl-N-[4-(trifluoromethoxy)phenyl]indazole-3-carboxamide (0.25 g) in EtOH (3 ml) at room temperature under inert atmosphere. The reaction mixture was stirred for 3 h at 85° C. Progress of reaction was monitored by TLC. After completion, the reaction mixture was cooled to room temperature, diluted with Water (25 ml) and extracted with Ethyl acetate (30 ml×2). The combined organic extracts were dried over $Na_2SO_4$, filtered and concentrated under reduced pressure. The crude product was purified by flash chromatography (eluting in 25-30% ethyl acetate in heptane as a mobile phase) to afford (0.275 g) of the title compound. HPLC/MS (method 1): $R_t$: 1.941 min; MS: m/z=379 (M+1).

Step 2: [(E)-[1-methyl-3-[[4-(trifluoromethoxy)phenyl]carbamoyl]indazol-6-yl]methyleneamino]N-(2-isopropylphenyl)carbamate (C-9 of Table X)

1-isocyanato-2-isopropyl-benzene (0.143 g) and Triethyl amine (0.150 g) were added to a solution of 6-[(E)-hydroxyiminomethyl]-1-methyl-N-[4-(trifluoromethoxy) phenyl] indazole-3-carboxamide (0.28 g) in Toluene (3 ml) at room temperature under inert atmosphere. The reaction mixture was stirred at room temperature for 12 h. Progress of reaction was monitored by TLC. After completion, the reaction mass was diluted with Water (25 ml) and extracted with Ethyl acetate (30 ml×2). The combined organic extracts were dried over $Na_2SO_4$, filtered and concentrated under reduced pressure. The crude product was purified by Prep. HPLC to afford (0.170 g) of the title compound. HPLC/MS (method 1): $R_t$: 2.250 min; MS: m/z=538.2 (M−1). $^1$H NMR (500 MHz, DMSO-$d_6$) δ 10.66 (s, 1H), 9.36 (s, 1H), 8.81 (s, 1H), 8.30 (d, J=8.5 Hz, 1H), 8.25 (s, 1H), 8.06-7.99 (m, 2H), 7.90 (dd, J=8.6, 1.2 Hz, 1H), 7.41-7.34 (m, 3H), 7.38-7.20 (m, 2H), 4.27 (s, 3H), 3.23 (p, J=6.9 Hz, 1H), 1.20 (d, J=6.8 Hz, 6H).

Example 10:1-(2-isopropyl phenyl)-3-[(E)-[1-methyl-3-[[4-(trifluoromethoxy) anilino]methyl] indazol-6-yl]methyleneamino]thiourea (C-10 of Table X)

Step 1: 6-(1,3-dioxolan-2-yl)-1-methyl-N-[4-(trifluoromethoxy)phenyl]indazole-3-carboxamide To a stirred solution of 6-formyl-1-methyl-N-[4-(trifluoromethoxy)phenyl]indazole-3-carboxamide (1.4 g) in Toluene (14 ml) were added Ethylene glycol (0.718 g) and p-Toluenesulfonic acid (0.073 g) at room temperature under inert atmosphere. The reaction mixture was stirred for 12 h at 110° C. Progress of reaction was monitored by TLC. After completion, the reaction mixture was cooled to room temperature, diluted with Water (20 ml), quenched with Aq. sodium bicarbonate solution (20 ml) and extracted with Ethyl acetate (60 ml×2). The combined organic extracts were dried over $Na_2SO_4$, filtered and concentrated under reduced pressure. The crude product was purified by flash chromatography (eluting in 20-22% ethyl acetate in heptane as a mobile phase) to afford (1.1 g) of the title compound. HPLC/MS (method 1): $R_t$: 2.038 min; MS: m/z=408.15 (M+1).

Step 2: N-[[6-(1,3-dioxolan-2-yl)-1-methyl-indazol-3-yl]methyl]-4-(trifluoromethoxy) aniline To a stirred solution of 6-(1,3-dioxolan-2-yl)-1-methyl-N-[4-(trifluoromethoxy) phenyl]indazole-3-carboxamide (0.5 g) in dry DCM (10 ml) was added DIBAL-H (0.610 g) at 0° C. under inert atmosphere. Reaction mixture was stirred at room temperature for 2 h. Again (0.610 g) of DIBALH was added to the reaction mixture. The reaction mixture was then stirred for 12 h at 45° C. Progress of reaction was monitored by TLC. After completion, the reaction mixture was diluted with Water (20 ml), quenched with Aq. 1N HCl solution and extracted with Ethyl acetate (30 ml×2). The combined organic extracts were dried over $Na_2SO_4$, filtered and concentrated under reduced pressure. The crude product was purified by flash chromatography (eluting in 22-25% ethyl acetate in heptane as a mobile phase) to afford (0.25 g) of the title compound. HPLC/MS (method 1): $R_t$: 2.022 min; MS: m/z=394.1 (M+1).

Step 3: 1-methyl-3-[[4-(trifluoromethoxy)anilino] methyl]indazole-6-carbaldehyde To a solution of N-[[6-(1,3-dioxolan-2-yl)-1-methyl-indazol-3-yl]methyl]-4-(trifluoromethoxy)aniline (0.25 g) in Acetone (3 ml) was added p-Toluenesulfonic acid (0.012 g) and the reaction mixture was stirred at room temperature for 12 h. Progress of reaction was monitored by TLC. After completion, the reaction mixture was diluted with Water (15 ml), quenched with Aq. sodium bicarbonate solution (10 ml) and extracted with Ethyl acetate (30 ml×2). The combined organic extracts were dried over $Na_2SO_4$, filtered and concentrated under reduced pressure. The crude product was purified by flash chromatography (eluting in 25-30% ethyl acetate in heptane as a mobile phase) to afford (0.1 g) of the title compound. HPLC/MS (method 1): $R_t$: 2.018 min; MS: m/z=350.0 (M+1).

Step 4: 1-(2-isopropylphenyl)-3-[(E)-[1-methyl-3-[[4-(trifluoromethoxy)anilino] methyl] indazol-6-yl] methyleneamino]thiourea (C-10 of Table X)

1-amino-3-(2-isopropylphenyl)thiourea (0.06 g) was added to a solution of 1-methyl-3-[[4-(trifluoromethoxy) anilino]methyl]indazole-6-carbaldehyde (0.1 g) in EtOH (2 ml) at room temperature under inert atmosphere. Then the reaction mixture was stirred for 3 h at 85° C. Progress of reaction was monitored by TLC. After completion, the reaction mixture was cooled to r.t. and the precipitated product was filtered through a filter paper. The residue washed with cold EtOH (2 ml), triturated with Pentane (5 ml) and dried under reduced pressure to afford (0.07 g) of the title compound. HPLC/MS (method 1): $R_t$: 2.217 min; MS: m/z=541.3 (M+1). $^1$H NMR (300 MHz, DMSO-$d_6$) δ 11.88 (s, 1H), 9.99 (s, 1H), 8.25 (s, 1H), 7.94 (s, 1H), 7.84 (s, 2H), 7.46-7.20 (m, 2H), 7.02 (d, J=8.4 Hz, 2H), 6.71 (d, J=8.9 Hz, 2H), 6.65-6.47 (m, 1H), 4.56 (d, J=5.8 Hz, 2H), 4.039 (s, 3H), 3.13 (p, J=7.0 Hz, 1H), 1.19 (d, J=6.9 Hz, 6H).

Example 11

(2Z)-3-(2-isopropylphenyl)-2-[(E)-[1-methyl-3-[[4-(trifluoromethoxy) anilino] methyl]indazol-6-yl] methylenehydrazono]thiazolidin-4-one (C-11 of Table X)

To a stirred solution of 1-(2-isopropylphenyl)-3-[(E)-[1-methyl-3-[[4-(trifluoromethoxy) anilino]methyl]indazol-6-yl]methyleneamino]thiourea (0.170 g) in EtOH (4 ml) were added NaOAc (0.052 g) and Methyl bromo acetate (0.072 g) at room temperature. The reaction mixture was continued to stir at room temperature for 12 h. Progress of reaction was monitored by TLC. After completion, reaction mixture was diluted with Water (20 ml) and extracted in Ethyl acetate (30 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.065 g) of the title compound. HPLC/MS (method 1): $R_t$: 2.240 min; MS: m/z=581.3 (M+1). $^1$H NMR (500 MHz, DMSO-$d_6$) δ 8.40 (s, 1H), 7.90 (d, J=8.5 Hz, 1H), 7.84 (s, 1H), 7.59 (dd, J=8.6, 1.2 Hz, 1H), 7.50 (dtd, J=14.9, 7.9, 1.6 Hz, 2H), 7.34 (td, J=7.6, 1.7 Hz, 1H), 7.27

(dd, J=7.9, 1.4 Hz, 1H), 7.03 (d, J=8.6 Hz, 2H), 6.77-6.68 (m, 2H), 6.57 (s, 1H), 4.56 (s, 2H), 4.26 (d, J=17.2 Hz, 1H), 4.20-4.09 (m, 1H), 4.01 (s, 3H), 2.80 (p, J=6.8 Hz, 1H), 1.15 (dd, J=13.5, 6.8 Hz, 6H).

Example 12

1-(2-isopropylphenyl)-3-[(E)-[1-methyl-3-[1-[4-(trifluoromethoxy)phenoxy] ethyl]indazol-6-yl] methyleneamino]thiourea (C-12 of Table X)

Step 1: 1-(6-bromo-1-methyl-indazol-3-yl)ethanol

To a stirred solution of 6-bromo-1-methyl-indazole-3-carbaldehyde (1.5 g) in dry THF (15 ml) was added methyl magnesium bromide (0.823 g, 1M in THF) at 0° C. under inert atmosphere. Reaction temperature was slowly raised to room temperature. Reaction mixture was continued to stir at room temperature for 2 h. Progress of reaction was monitored by TLC. After completion, the reaction mixture was quenched with Aq. ammonium chloride solution (25 ml) and extracted with Ethyl acetate (30 ml×2). The combined organic extracts were dried over $Na_2SO_4$, filtered and concentrated under reduced pressure. The crude product was purified by flash chromatography (eluting in 20-22% ethyl acetate in heptane as a mobile phase) to afford (0.750 g) of the title compound. HPLC/MS (method 1): $R_t$: 1.602 min; MS: m/z=255.05 (M+1).

Step 2: 6-bromo-1-methyl-3-[1-[4-(trifluoromethoxy)phenoxy]ethyl]indazole

In a microwave vial, 4-trifluromethoxy phenol (0.168 g) and triphenyl phosphine (0.217 g) were added to a solution of 1-(6-bromo-1-methyl-indazol-3-yl)ethanol (0.2 g) in dry THF (2 ml) under inert atmosphere and cooled to 0° C. The reaction mixture was stirred at 0° C. for 5 min and then DBAD (0.217 g) was added to the reaction mixture. Reaction mixture was continued to stir at 42° C. for 2 h. Progress of reaction was monitored by TLC. After completion, the reaction mixture was diluted with Water (10 ml) and extracted with Ethyl acetate (10 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.2 g) of the title compound. HPLC/MS (method 1): $R_t$: 2.400 min; MS: m/z=416.9 (M+1).

Step 3: 1-methyl-3-[1-[4-(trifluoromethoxy)phenoxy]ethyl]-6-vinyl-indazole

A solution of 6-bromo-1-methyl-3-[1-[4-(trifluoromethoxy) phenoxy]ethyl]indazole (0.2 g) in dry Toluene (2 ml) was purged with Nitrogen for 10 min. To the solution was added Pd(dppf)Cl$_2$ (0.021 g) and Nitrogen purging was continued for another 10 min. Then Tributyl vinyl tin (0.229 g) was added to the solution and the reaction mixture was heated at 110° C. for 3 h. Progress of reaction was monitored by TLC. After completion, the reaction mixture was cooled to room temperature, diluted with Water (10 ml) and extracted with Ethyl acetate (20 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.150 g) of the title compound. HPLC/MS (method 1): $R_t$: 2.287 min; MS: m/z=363.15 (M+1).

Step 4: 1-methyl-3-[1-[4-(trifluoromethoxy)phenoxy]ethyl]indazole-6-carbaldehyde To a stirred solution of 1-methyl-3-[1-[4-(trifluoromethoxy)phenoxy]ethyl]-6-vinyl-indazole (0.15 g) in 1,4-dioxane (2 ml) and Water (1 ml), OsO$_4$ (0.002 g) and NaIO$_4$ (0.194 g) were added at 0° C. under inert atmosphere. Reaction mixture was stirred at room temperature for 3 h. Progress of reaction was monitored by TLC. After completion, reaction mixture was diluted with Water (10 ml), quenched with Aq. Sodium sulfite solution (10 ml) and extracted with Ethyl acetate (20 ml×2). The combined organic extracts were dried over $Na_2SO_4$, filtered and concentrated under reduced pressure. The crude product was purified by flash chromatography (eluting in 20-22% ethyl acetate in heptane as a mobile phase) to afford (0.05 g) of the title compound. HPLC/MS (method 1): $R_t$: 2.112 min; MS: m/z=365.1 (M+1).

Step 5: 1-(2-isopropylphenyl)-3-[(E)-[1-methyl-3-[1-[4-(trifluoromethoxy) phenoxy] ethyl]indazol-6-yl]methyleneamino]thiourea (C-12 of Table X)

To a solution of 1-methyl-3-[1-[4-(trifluoromethoxy)phenoxy]ethyl]indazole-6-carbaldehyde (0.05 g) in EtOH (1 ml) was added 1-amino-3-(2-isopropylphenyl)thiourea (0.029 g) at room temperature under inert atmosphere. Then the reaction mixture was stirred for 3 h at 85° C. Progress of reaction was monitored by TLC. After completion, the reaction mixture was cooled to room temperature and the precipitated product was filtered through a filter paper. The residue was washed with cold EtOH (2 ml), triturated with Pentane (5 ml) and dried under reduced pressure to afford (0.05 g) of the title compound. HPLC/MS (method 1): $R_t$: 2.272 min; MS: m/z=554.2 (M−1). $^1$H NMR (500 MHz, DMSO-d$_6$) δ 11.89 (s, 1H), 9.99 (s, 1H), 8.25 (s, 1H), 7.97 (s, 1H), 7.89-7.78 (m, 2H), 7.37 (d, J=7.7 Hz, 1H), 7.31 (dt, J=8.1, 4.0 Hz, 1H), 7.27-7.15 (m, 4H), 7.13-7.06 (m, 2H), 5.92 (q, J=6.5 Hz, 1H), 4.05 (s, 3H), 3.13 (p, J=6.9 Hz, 1H), 1.76 (d, J=6.5 Hz, 3H), 1.22-1.12 (m, 6H).

Example 13

(2Z)-3-(2-isopropylphenyl)-2-[(E)-[1-methyl-3-[1-[4-(trifluoromethoxy) phenoxy]ethyl]indazol-6-yl] methylenehydrazono]thiazolidin-4-one (C-13 of Table X)

A mixture of 1-(2-isopropylphenyl)-3-[(E)-[1-methyl-3-[1-[4-(trifluoromethoxy) phenoxy]ethyl]indazol-6-yl]methyleneamino]thiourea (0.320 g), NaOAc (0.095 g) and Methyl bromo acetate (0.132 g) in EtOH (6.0 ml) was stirred at room temperature for 12 h. Progress of reaction was monitored by TLC. After completion, the reaction mixture was diluted with Water (25 ml) and extracted with Ethyl acetate (30 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.15 g) of the title compound. HPLC/MS (method 1): $R_t$: 2.342 min; MS: m/z=596.25 (M+1). $^1$H NMR (500 MHz, DMSO-d$_6$) δ 8.39 (s, 1H), 7.90 (d, J=8.5 Hz, 1H), 7.85 (s, 1H), 7.62 (d, J=8.5 Hz, 1H), 7.49 (dt, J=14.9, 7.8 Hz, 2H), 7.34 (t, J=7.5 Hz, 1H), 7.30-7.19 (m, 3H), 7.09 (d, J=8.7 Hz, 2H), 5.91 (q, J=6.4 Hz, 1H), 4.26 (d, J=17.3 Hz, 1H), 4.14 (d, J=17.6 Hz, 1H), 4.02 (s, 3H), 2.79 (p, J=6.9 Hz, 1H), 1.75 (d, J=6.5 Hz, 3H), 1.19-1.08 (m, 6H).

Example 14

(2Z)-2-(2-isopropylphenyl)imino-3-[(E)-[1-methyl-3-[1-[4-(trifluoromethoxy) phenoxy]ethyl]indazol-6-yl]methyleneamino]thiazolidin-4-one (C-14 of Table X)

A mixture of 1-methyl-3-[1-[4-(trifluoromethoxy)phenoxy]ethyl]indazole-6-carbaldehyde (0.2 g) and (2Z)-3-amino-2-(2-isopropylphenyl)imino-thiazolidin-4-one (0.137 g) in Acetic acid (2 ml) was stirred at room temperature for 3 h. Progress of reaction was monitored by TLC. After completion, the reaction mixture was diluted with Water (15 ml) and extracted with Ethyl acetate (25 ml×2). The combined organic extracts were dried over $Na_2SO_4$, filtered and concentrated under reduced pressure. The crude product was purified by flash chromatography (eluting in 25-30% ethyl acetate in heptane as a mobile phase) to afford (0.075 g) of the title compound. HPLC/MS (method 1): $R_t$: 2.399 min; MS: m/z=596.25 (M+1). $^1$H NMR (500 MHz, DMSO-$d_6$) δ 9.28 (s, 1H), 8.17 (d, J=1.2 Hz, 1H), 8.06 (d, J=8.5 Hz, 1H), 7.81 (dd, J=8.6, 1.3 Hz, 1H), 7.36 (dd, J=7.7, 1.6 Hz, 1H), 7.32-7.20 (m, 3H), 7.21-7.13 (m, 3H), 6.93 (dd, J=7.7, 1.4 Hz, 1H), 6.01 (q, J=6.5 Hz, 1H), 4.21 (s, 2H), 4.15 (s, 3H), 3.05 (hept, J=6.9 Hz, 1H), 1.83 (d, J=6.4 Hz, 3H), 1.19 (d, J=6.9 Hz, 6H).

Example 15

1-(2-isopropylphenyl)-3-[(E)-[1-methyl-3-[[4-(trifluoromethoxy) phenoxy] methyl]pyrazolo[4,3-c] pyridin-6 yl]methyleneamino]thiourea (C-15 of Table X)

Step 1: 4,6-dichloro-N-methoxy-N-methyl-pyridine-3-carboxamide

To a solution of 4,6-dichloropyridine-3-carboxylic acid (5.0 g) in DMF (100 ml) EDC.HCl (4.85 g), N-Methylmorpholine (3.43 ml) and N, O-Dimethylhydroxylamine (3.04 g) were added and the reaction mixture was stirred for 16 h at room temperature. Progress of reaction was monitored by TLC. After completion, the reaction mixture was diluted with Water (100 ml) and extracted with Ethyl acetate (50 ml×3). The combined organic extracts were dried over $Na_2SO_4$, filtered and concentrated under reduced pressure. The crude product was purified by flash chromatography (eluting in 0-50% ethyl acetate in heptane as a mobile phase) to afford (5.7 g) of the title compound as a solid. LC/MS (method 1): $R_t$: 1.59 min; MS: m/z=235.0 (M+1).

Step 2: 1-(4,6-dichloro-3-pyridyl)ethenone

To a stirred solution of 4,6-dichloro-N-methoxy-N-methyl-pyridine-3-carboxamide (5.7 gm) in THF (40 ml) was added Methyl magnesium bromide (16.16 gm) at 0° C. The reaction mass was stirred for 16 h at room temperature. Progress of reaction was monitored by TLC. After completion, the reaction mixture was diluted with saturated solution of Ammonium chloride (100 ml) and extracted with Ethyl acetate (50 ml×3). The combined organic extracts were dried over $Na_2SO_4$, filtered and concentrated under reduced pressure. The crude product was purified by flash chromatography (eluting in 0-50% ethyl acetate in heptane as a mobile phase) to afford (4.0 g) of the title compound. HPLC/MS (method 1): $R_t$: 1.73 min; MS: m/z=231.0 (M+1).

Step 3: 6-chloro-1,3-dimethyl-pyrazolo[4,3-c]pyridine

To a stirred solution of 1-(4,6-dichloro-3-pyridyl)ethanone (4.0 gm) in Methanol (25 ml) was added Methyl hydrazine (2.28 gm) at 0 CC. Then the reaction mixture was heated at 50° C. for 2 h. Progress of reaction was monitored by TLC. After completion, the reaction mixture was concentrated under reduced pressure, diluted with Water (100 ml) and extracted with Ethyl acetate (30 ml×3). The combined organic extracts were dried over $Na_2SO_4$, filtered and concentrated under reduced pressure. The crude product was purified by flash chromatography (eluting in 0-20% ethyl acetate in heptane as a mobile phase) to afford (1.6 gm) of the title compound. HPLC/MS (method 1): $R_t$: 1.52 min; MS: m/z=182.1 (M+1).

Step 4: 3-(bromomethyl)-6-chloro-1-methyl-pyrazolo[4,3-c]pyridine

To a stirred solution of 6-chloro-1,3-dimethyl-pyrazolo[4,3-c]pyridine (3.1 gm) in $CCl_4$ (25 ml) was added N-Bromosuccinimide (3.66 gm) and Benzoyl peroxide (0.332 gm) at room temperature. Then reaction mixture was heated at 78° C. for 16 h. Progress of reaction was monitored by TLC. After completion, the reaction mixture was concentrated under reduced pressure, diluted with Water (100 ml) and extracted with Ethyl acetate (30 ml×3). The combined organic extracts were dried over $Na_2SO_4$, filtered and concentrated under reduced pressure. The crude product was purified by flash chromatography (eluting in 0-20% ethyl acetate in heptane as a mobile phase) to afford (1.6 g) of the title compound. HPLC/MS (method 1): $R_t$: 1.69 min; MS: m/z=302.95 (M+1).

Step 5: 6-chloro-1-methyl-3-[[4-(trifluoromethoxy)phenoxy]methyl]pyrazolo[4,3-c]pyridine To a stirred solution of 4-(trifluoromethoxy)phenol (0.342 ml) in DMF (5 ml) was added Potassium tert-butoxide (0.323 gm) at room temperature under inert atmosphere. After 10 min, 3-(bromomethyl)-6-chloro-1-methyl-pyrazolo[4,3-c]pyridine (0.5 g) was added to the reaction mixture and the reaction mixture was stirred at r.t. for 5 h. Progress of reaction was monitored by TLC. After completion, the reaction mixture was diluted with Water (25 ml) and extracted with Ethyl acetate (30 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.470 g) of the title compound. HPLC/MS (method 1): $R_t$: 2.099 min; MS: m/z=358 (M+1).

Step 6: 1-methyl-3-[[4-(trifluoromethoxy)phenoxy]methyl]-6-vinyl-pyrazolo[4,3-c]pyridine A stirred solution of 6-chloro-1-methyl-3-[[4-(trifluoromethoxy)phenoxy]methyl] pyrazolo[4,3-c]pyridine (0.47 g) in dry 1,4-dioxane (5 ml) was purged with Nitrogen for 10 min. To the solution Pd(dppf)C2 (0.058 g) was added and Nitrogen purging was continued for another 10 min. Tributyl vinyl tin (0.625 g) was added to the reaction mixture and heated at 110° C. for 12 h with stirring. Progress of reaction was monitored by TLC. After completion, the reaction mixture was cooled to room temperature, diluted with Water (30 ml) and extracted with Ethyl acetate (40 ml×2). The combined organic extracts were dried over $Na_2SO_4$, filtered and concentrated under reduced pressure. The crude product was purified by flash chromatography (eluting in 20-25% ethyl acetate in heptane as a mobile phase) to afford (0.2 g) of the title compound. HPLC/MS (method 1): $R_t$: 1.921 min; MS: m/z=350.3 (M+1).

Step 7: 1-methyl-3-[[4-(trifluoromethoxy)phenoxy] methyl]pyrazolo[4,3-c]pyridine-6-carbaldehyde To a stirred solution of 1-methyl-3-[[4-(trifluoromethoxy) phenoxy]methyl]-6-vinyl-pyrazolo[4,3-c]pyridine (0.2 g) in 1,4-dioxane (2 ml), $OsO_4$ (0.003 g) and $NaIO_4$ (0.268 g) were added at 0° C. under inert atmosphere. The reaction mixture was continued to stir at room temperature for 3 h. Progress of reaction was monitored by TLC. After completion, the reaction mixture was diluted with Water (10 ml), quenched with Aq. Sodium sulfite solution (10 ml) and extracted with Ethyl acetate (20 ml×2). The combined organic extracts were dried over $Na_2SO_4$, filtered and concentrated under reduced pressure. The crude product was purified by flash chromatography (eluting in 20-22% ethyl acetate in heptane as a mobile phase) to afford (0.055 g) of the title compound. HPLC/MS (method 1): $R_t$: 1.905 min; MS: m/z=352.1 (M+1).

Step 8: 1-(2-isopropylphenyl)-3-[(E)-[1-methyl-3-[[4-(trifluoromethoxy) phenoxy] methyl]pyrazolo[4,3-c]pyridin-6-yl]methyleneamino]thiourea (C-15 of Table X)

A mixture of 1-methyl-3-[[4-(trifluoromethoxy)phenoxy] methyl]pyrazolo[4,3-c]pyridine-6-carbaldehyde (0.053 g) and 1-amino-3-(2-isopropylphenyl)thiourea (0.033 g) in EtOH (2 ml) was heated at 85° C. for 3 h under inert atmosphere. Progress of reaction was monitored by TLC. After completion, the reaction mixture was cooled to room temperature and the precipitated product was filtered through a filter paper. The residue was washed with cold EtOH (2 ml), triturated with Pentane (5 ml) and dried under reduced pressure to afford (0.045 g) of the title compound. HPLC/MS (method 1): $R_t$: 2.115 min; MS: m/z=541.25 (M−1). $^1$H NMR (500 MHz, DMSO-$d_6$) δ 14.46 (s, 1H), 12.06 (s, 1H), 10.26 (s, 1H), 10.03 (s, 1H), 9.17 (s, 1H), 8.57 (s, 1H), 8.36 (s, 1H), 8.21 (d, J=7.4 Hz, 1H), 7.55 (s, 1H), 7.40 (d, J=7.7 Hz, 1H), 7.34 (d, J=8.8 Hz, 6H), 7.32-7.18 (m, 7H), 5.60 (s, 1H), 5.54 (s, 2H), 4.15 (s, 2H), 4.09 (s, 3H), 3.38 (s, 1H), 3.32 (s, 7H), 3.19-3.08 (m, 1H), 2.58 (d, J=18.8 Hz, 1H), 2.43 (s, OH), 1.31 (d, J=9.7 Hz, 1H), 1.19 (dd, J=22.4, 6.8 Hz, 14H).

Example 16

(2Z)-3-(2-isopropylphenyl)-2-[(E)-[1-methyl-3-[[4-(trifluoromethoxy) phenoxy]methyl]pyrazolo[4,3-c] pyridin-6-yl]methylenehydrazono]thiazolidin-4-one (C-16 of Table X)

A mixture of 1-(2-isopropylphenyl)-3-[(E)-[1-methyl-3-[[4-(trifluoromethoxy) phenoxy] methyl]pyrazolo[4,3-c] pyridin-6-yl]methyleneamino]thiourea (0.045 g), NaOAc (0.014 g) and Methyl bromo acetate (0.019 g) in EtOH (2 ml) was stirred at room temperature for 12 h. Progress of reaction was monitored by TLC. After completion, the reaction mixture was diluted with Water (15 ml) and extracted with Ethyl acetate (20 ml×2). The combined organic extracts were dried over $Na_2SO_4$, filtered and concentrated under reduced pressure. The crude product was purified by flash chromatography (eluting in 25-30% ethyl acetate in heptane as a mobile phase) to afford (0.022 g) of the title compound. HPLC/MS (method 1): $R_t$: 2.221 min; MS: m/z=583.6 (M+1). $^1$H NMR (500 MHz, DMSO-$d_6$) δ 9.25 (s, 1H), 8.35 (s, 1H), 8.16 (s, 1H), 7.61-7.44 (m, 2H), 7.41-7.26 (m, 4H), 7.26-7.18 (m, 2H), 5.55 (s, 2H), 4.30 (d, J=17.4 Hz, 1H), 4.19 (d, J=17.4 Hz, 1H), 4.14 (s, 3H), 2.94-2.72 (m, 1H), 1.16 (dd, J=13.6, 6.9 Hz, 6H).

Example 17

4-fluoro-6-[[[(2-isopropylphenyl)carbamothioylhydrazono]methyl]—1-methyl-N-[4-(trifluoromethoxy) phenyl]indazole-3-carboxamide (C-17 of Table X)

Step 1: Ethyl 2-(4-bromo-2,6-difluoro-phenyl)-2-oxo-acetate

To a mixture of 1-bromo-3,5-difluoro-benzene (1 g) in THF (5 ml) cooled to −78° C. was added a solution of Lithium bis(trimethylsilyl)amide (1.04 g) in THF. Diethyl oxalate (0.87 g) was added and the mixture stirred for 4 h. A saturated solution of ammonium chloride was added and the mixture extracted with Ethyl acetate, the extracts washed with a saturated solution of Sodium chloride, dried over anhydrous Sodium sulphate and evaporated under reduced pressure. The resultant solid was subjected to silica gel flash column chromatography eluting with a gradient of Ethyl acetate and Heptane to get the title compound (0.61 g). $^1$H NMR (500 MHz, DMSO-$d_6$) δ 7.71 (d, J=8.3 Hz, 2H), 4.29 (d, J=7.1 Hz, 2H), 1.22 (t, J=7.1 Hz, 3H).

Step 2: Ethyl 6-bromo-4-fluoro-1-methyl-indazole-3-carboxylate

A mixture of Ethyl 2-(4-bromo-2,6-difluoro-phenyl)-2-oxo-acetate (0.1 g), Methyl hydrazine sulfate (0.10 g) and Triethyl amine (0.089 g) in N-Methylpyrollidinone (3 ml) was heated at 80° C. for 1 h. The mixture was diluted with water and extracted with Ethyl acetate. The organic extracts were separated, washed with a saturated solution of Sodium chloride, dried over anhydrous Sodium sulphate and evaporated in vacuo. The residue obtained was subjected to silica gel flash column chromatography eluting with a gradient of Ethyl acetate and Heptane to afford the title compound (0.07 g). $^1$H NMR (500 MHz, DMSO-$d_6$) δ 8.00 (d, J=1.1 Hz, 1H), 7.34 (dd, J=10.1, 1.2 Hz, 1H), 4.36 (q, J=7.1 Hz, 2H), 4.14 (s, 3H), 1.34 (t, J=7.1 Hz, 3H).

Step 3: 6-bromo-4-fluoro-1-methyl-indazole-3-carboxylic Acid

Ethyl 6-bromo-4-fluoro-1-methyl-indazole-3-carboxylate (2.4 g) and Lithium hydroxide (1.0 g) in a mixture of THF (15 ml) and Water was stirred at room temperature for 3 h. The reaction mixture was neutralized with 2M Hydrochloric acid solution. The precipitated solids were filtered, washed with water and pentane and dried to afford the title compound (2.16 g). $^1$H NMR (500 MHz, DMSO-$d_6$); $^1$H NMR (500 MHz, DMSO-d$_6$) δ 13.14 (s, 1H), 8.00 (s, 1H), 7.33 (d, J=10.0 Hz, 1H), 4.13 (s, 3H).

Step 4: 6-bromo-4-fluoro-1-methyl-N-[4-(trifluoromethoxy)phenyl]indazole-3-carboxamide A mixture of 6-bromo-4-fluoro-1-methyl-indazole-3-carboxylic acid (0.06 g, 0.22 mmol), 4-(trifluoromethoxy) aniline (0.04 g), 1-[Bis(dimethylamino) methylene]-1H-1,2,3-triazolo[4,5-b]pyridinium 3-oxid hexafluorophosphate (0.167 g) and N,N diisopropyl ethyl amine (0.057 g) in DMF (3 ml) was stirred at room temperature for 16 h. The mixture was poured into a mixture of ice and water and the precipitated solids were filtered, washed with water and pentane and dried to obtain the title compound (0.07 g). HPLC/MS (method 1): R$_t$: 2.22 min, m/z=431.6 (M+1); $^1$H NMR (500 MHz, DMSO-d$_6$) δ 10.70 (s, 1H), 8.05 (s, 1H), 7.95 (d, J=8.7 Hz, 2H), 7.36 (t, J=8.1 Hz, 3H), 4.19 (s, 3H).

Step 5: 4-fluoro-1-methyl-N-[4-(trifluoromethoxy)phenyl]-6-vinyl-indazole-3-carboxamide 6-bromo-4-fluoro-N,1-dimethyl-N-[4-(trifluoromethoxy) phenylindazole-3-carboxamide (0.2 g), [1,1'-Bis(diphenylphosphino) ferrocene] dichloropalladium(II) (0.017 g) and Tri-n-butyl-vinyl tin (0.220 g) in 1,4-Dioxane (4 ml) was heated at 100° C. for 3 h. The mixture was filtered through Celite then the filtrate, diluted with water and extracted with Ethyl acetate. The organic extracts were dried over anhydrous Sodium sulphate and evaporated under reduced pressure and the residue obtained was subjected to flash column chromatography using a gradient of Ethyl acetate and Heptane to afford the title compound (0.1 g). HPLC/MS (method 1): R$_t$: 2.18 min; m/z=390.2 (M+1); $^1$H NMR (500 MHz, DMSO-d$_6$): δ 10.64 (s, 1H), 7.96 (d, J=8.6 Hz, 2H), 7.69 (s, 1H), 7.36 (dd, J=16.9, 10.2 Hz, 3H), 6.89 (dd, J=17.6, 10.9 Hz, 1H), 6.09 (d, J=17.6 Hz, 1H), 5.46 (d, J=10.9 Hz, 1H), 4.20 (s, 3H).

Step 6: 4-fluoro-6-formyl-1-methyl-N-[4-(trifluoromethoxy)phenyl]indazole-3-carboxamide A mixture of 4-fluoro-N,1-dimethyl-N-[4-(trifluoromethoxy)phenyl]-6-vinyl-indazole-3-carboxamide (0.1 g), Osmium tetroxide (0.004 g) and Sodium periodate (0.17 g) in 1,4-Dioxane (4 ml) and water (1 ml) was stirred at room temperature for 12 h. Sodium sulfite solution (0.5%) was added and the mixture extracted with Ethyl acetate. The organic extracts were dried over anhydrous Sodium sulfate, concentrated under reduced pressure and the residue obtained was subjected to silica gel flash column chromatography to get the title compound (0.07 g); HPLC/MS (method 1): R$_t$: 1.961 min; m/z=392.1 (M+1); $^1$H NMR (500 MHz, DMSO-d$_6$): δ 10.77 (s, 1H), 10.14 (d, J=2.1 Hz, 1H), 8.39 (d, J=0.9 Hz, 1H), 8.01-7.92 (m, 2H), 7.47 (dd, J=10.4, 1.0 Hz, 1H), 7.42-7.34 (m, 2H), 4.32 (s, 3H).

Step 7: 4-fluoro-6-[[(2-isopropylphenyl)carbamothioylhydrazono]methyl]-1-methyl-N-[4-(trifluoromethoxy)phenyl]indazole-3-carboxamide (C-17 of Table X)

A mixture of 4-fluoro-6-formyl-N,1-dimethyl-N-[4-(trifluoromethoxy)phenyl]indazole-3-carboxamide (0.065 g) and 1-amino-3-(2-isopropylphenyl)thiourea (0.037 g) in Ethanol (3 ml) was heated at 80° C. for 6 h. The mixture was concentrated under reduced pressure and residue was subjected to Silica gel flash column chromatography eluting with a gradient of Dichloromethane and Methanol to afford the title compound (0.026 g). HPLC/MS (method 1): R$_t$: 2.237 min; m/z=573.2 (M+1); $^1$H NMR (500 MHz, DMSO-d$_6$) δ 12.01 (s, 1H), 10.69 (s, 1H), 10.20 (s, 1H), 8.28 (s, 1H), 8.10 (d, J=12.1 Hz, 1H), 8.01-7.91 (m, 3H), 7.42-7.29 (m, 4H), 7.25 (td, J=7.5, 1.5 Hz, 1H), 7.19 (dd, J=7.8, 1.4 Hz, 1H), 4.24 (s, 3H), 3.15 (hept, J=7.0 Hz, 1H), 1.21 (d, J=6.9 Hz, 6H).

Example 18

4-fluoro-6-[[(2-isopropylphenyl)carbamothioylhydrazono]methyl]-N,1-dimethyl-N-[4-(trifluoromethoxy)phenyl]indazole-3-carboxamide (C-18 of Table X)

Step 1: 6-bromo-4-fluoro-N,1-dimethyl-N-[4-(trifluoromethoxy)phenyl]indazole-3-carboxamide To a stirred solution of 6-bromo-4-fluoro-1-methyl-N-[4-(trifluoromethoxy)phenyl] indazole-3-carboxamide (0.3 g) in DMF (3 ml) at 0° C. was added Sodium hydride (0.02 g) and stirred for 15 min. Methyl iodide (0.128 g) was subsequently added and the mixture was stirred at room temperature for 12 h. Saturated Ammonium chloride solution was added and the mixture extracted with Ethyl acetate. The organic extracts were dried over anhydrous Sodium sulfate, concentrated under reduced pressure and the residue subjected to silica gel flash column chromatography to get the title compound (0.26 g). HPLC/MS (method 1): R$_t$: 2.14 min; m/z=447.3 (M+1); $^1$H NMR (500 MHz, CDCl$_3$) δ 7.28 (d, J=12.9 Hz, 2H), 7.19 (s, 1H), 7.05 (d, J=8.2 Hz, 2H), 6.96 (d, J=9.4 Hz, 1H), 3.88 (s, 3H), 3.54 (s, 3H).

Step 2: 4-fluoro-N,1-dimethyl-N-[4-(trifluoromethoxy)phenyl]-6-vinyl-indazole-3-carboxamide A mixture of 6-bromo-4-fluoro-N,1-dimethyl-N-[4-(trifluoromethoxy)phenylindazole-3-carboxamide (0.35 g), 1,1'-Bis(diphenylphosphino) ferrocene] dichloropalladium(II) (0.03 g) and Tri-n-butyl vinyl tin (0.37 g) in 1,4-Dioxane (6 ml) was heated at 100° C. for 3 h. The reaction mixture was filtered through celite and the filtrate, diluted with water and extracted with Ethyl acetate. The organic extracts were dried over anhydrous Sodium sulphate and evaporated under reduced pressure and the resultant residue was subjected to Silica gel flash column chromatography to get the title compound (0.27 g). LC/MS (method 1): R$_t$: 2.09 min, m/z=390.4 (M+1); $^1$H NMR (500 MHz, DMSO-d$_6$) δ 7.52 (s, 1H), 7.42-7.16 (m, 5H), 6.82 (dd, J=17.5, 10.9 Hz, 1H), 6.02 (d, J=17.6 Hz, 1H), 5.41 (d, J=11.0 Hz, 1H), 3.91 (d, J=18.0 Hz, 3H), 3.45 (s, 3H).

Step 3: 4-fluoro-6-formyl-N,1-dimethyl-N-[4-(trifluoromethoxy)phenyl]indazole-3-carboxamide A mixture of 4-fluoro-N,1-dimethyl-N-[4-(trifluoromethoxy)phenyl]-6-vinyl-indazole-3-carboxamide (0.4 g), Osmium tetroxide (0.013 g), Sodium periodate (0.65 g) in 1,4-Dioxane (6 ml) and water (3 ml) was stirred at r.t. for 12 h. Sodium sulfite solution (0.5%) was added and the mixture extracted with Ethyl acetate. The organic extracts were dried over anhydrous Sodium sulfate and concentrated under reduced pressure and the residue obtained was subjected to silica gel flash column chromatography to afford the title compound (0.3 g). HPLC/MS (method 1): R$_t$: 1.9 min; m/z=396 (M+1); $^1$H NMR (500 MHz, DMSO-d$_6$) δ

10.07 (d, J=2.1 Hz, 1H), 8.24 (s, 1H), 7.43-7.18 (m, 5H), 4.12-3.99 (s, 3H), 3.47 (s, 3H).

Step 4: 4-fluoro-6-[[(2-isopropylphenyl)carbamothioylhydrazono]methyl]-N,1-dimethyl-N-[4-(trifluoromethoxy)phenyl]indazole-3-carboxamide (C-18 of Table X)

A mixture of 4-fluoro-6-formyl-N,1-dimethyl-N-[4-(trifluoromethoxy)phenyl]indazole-3-carboxamide (0.29 g) and 1-amino-3-(2-isopropylphenyl)thiourea (0.16 g) in THF (10 ml) was heated at 60° C. for 2 h. The mixture was evaporated in vacuo and the residue was subjected to silica gel flash column chromatography eluting with a gradient of Dichloromethane and Methanol to get the desired compound (0.3 g). HPLC/MS (method 1): $R_t$: 2.15 min, m/z=587.2 (M+1); $^1$H NMR (500 MHz, DMSO-$d_6$) δ 11.96 (s, 1H), 10.15 (s, 1H), 8.21 (s, 1H), 7.98 (d, J=12.1 Hz, 1H), 7.76 (s, 1H), 7.45-6.90 (m, 8H), 3.97 (s, 3H), 3.45 (s, 3H), 3.13 (p, J=6.8 Hz, 1H), 1.20 (d, J=6.9 Hz, 6H).

Example 19: 4-fluoro-6-[[(Z)-[3-(2-isopropylphenyl)-4-oxo-thiazolidin-2-ylidene]hydrazono]methyl]-N,1-dimethyl-N-[4-(trifluoromethoxy)phenyl]indazole-3-carboxamide (C-19 of Table X)

A mixture of 4-fluoro-6-[(E)-[(2-isopropylphenyl)carbamothioylhydrazono]methyl]-N,1-dimethyl-N-[4-(trifluoromethoxy)phenyl]indazole-3-carboxamide (0.18 g), Sodium acetate (0.05 g) and Methyl bromo acetate (0.187 g) in THF (4 ml) was heated at 40° C. for 6 h. The mixture was diluted with Water and extracted with Ethyl acetate, the organic extracts dried over Sodium sulphate, concentrated under reduced pressure and the residue subjected to silica gel flash column chromatography to obtain the title compound (0.12 g). HPLC/MS (method 1): $R_t$: 2.299 min; m/z=627.4 (M+1)+; $^1$H NMR (500 MHz, DMSO-$d_6$) δ 8.39 (d, J=1.5 Hz, 1H), 7.75 (s, 1H), 7.49 (dtd, J=15.0, 7.9, 1.6 Hz, 2H), 7.38-7.24 (m, 7H), 4.28 (d, J=17.4 Hz, 1H), 4.16 (d, J=17.3 Hz, 1H), 3.94 (s, 3H), 3.45 (s, 3H), 2.79 (h, J=6.8 Hz, 1H), 1.15 (dd, J=10.6, 6.8 Hz, 6H).

Example 20

1-(2-isopropylphenyl)-3-[(E)-[1-methyl-3-[(E)-2-[4-(trifluoromethoxy)phenyl]vinyl] indazol-6-yl]methyleneamino]thiourea (C-20 of Table X)

Step 1: 1H-indazol-6-ylmethanol

To a stirred solution of methyl 1H-indazole-6-carboxylate (6 g) in THF (150 ml) was added 1 M LiAlH$_4$ solution in THF (34.7 ml) at 0° C. Reaction mixture was stirred at room temperature for 16 h. The reaction mixture was quenched with NaOH solution and extracted with Ethyl acetate. The crude was filtered through celite and the organic layer was separated, washed with brine, dried over anhydrous Na$_2$SO$_4$ and concentrated under reduced pressure to afford the title compound (4.5 g). HPLC/MS (method 1): $R_t$:1.114 min; m/z=149 (M+1).

Step 2: 1H-indazole-6-carbaldehyde

To the stirred solution of 1H-indazol-6-ylmethanol (1.5 g) in DCM (15 ml) and THF (15 ml) was added Dess Martin Periodinane (4.29 g) and stirred at room temperature for 16 h. DCM was added and filtered through celite. Filtrate was evaporated under vacuum to afford the title compound (1.3 g). HPLC/MS (method 1): $R_t$:1.290 min; m/z=146 (M+1).

Step 3: 3-iodo-1H-indazole-6-carbaldehyde

To a stirred solution of 1H-indazole-6-carbaldehyde (2.4 g) in DMF (20 ml), K$_2$CO$_3$ (5.6 g) and I$_2$ (7.5 g) were added. Reaction mixture was stirred at room temperature for 2 h. After completion, reaction mixture was diluted with Sodium thiosulphate solution and stirred for 10 min, solid was precipitated. Solid was filtered and dried under vacuum to afford the title compound (3.8 g). HPLC/MS (method 1): $R_t$:1.624 min; m/z=271 (M−1).

Step 4: 3-iodo-1-methyl-indazole-6-carbaldehyde

To a stirred solution of 3-iodo-1H-indazole-6-carbaldehyde (3.2 g) in THF (50 ml), K$_2$CO$_3$ (3.2 g) and MeI (2.5 g) were added. Reaction mixture was stirred at room temperature for 16 h. After completion, reaction mixture was quenched with Water, extracted with Ethyl acetate, concentrated under reduced pressure and the residue subjected to silica gel flash column chromatography to obtain the title compound (1.2 g). $^1$H NMR (500 MHz, DMSO-$d_6$) δ 10.16 (s, 1H), 8.37 (s, 1H), 7.80-7.47 (m, 2H), 4.18 (s, 3H).

Step 5: 1-methyl-3-[(E)-2-[4-(trifluoromethoxy)phenyl]vinyl]indazole-6-carbaldehyde To a stirred solution of 3-iodo-1-methyl-indazole-6-carbaldehyde (0.15 g) in DMF (1 ml), 1-(trifluoromethoxy)-4-vinyl-benzene (0.118 g) and DIPEA (0.141 g) were added. The reaction mixture was purged with Ar gas for 10 min and Pd(OAc)$_2$ (0.012 g), Tri(o-tolyl)phosphine (0.048 g) were added. Reaction mixture was heated at 110° C. for 24 h. After completion, the reaction mixture was diluted with Water and extracted with Ethyl acetate, the organic extracts dried over sodium sulphate, concentrated under reduced pressure and the residue subjected to silica gel flash column chromatography to obtain the title compound (0.04 g).

Step 6: 1-(2-isopropylphenyl)-3-[(E)-[1-methyl-3-[(E)-2-[4-(trifluoromethoxy) phenyl] vinyl]indazol-6-yl]methyleneamino]thiourea (C-20 of Table X)

A mixture of 1-methyl-3-[(E)-2-[4-(trifluoromethoxy) phenyl] vinyl] indazole-6-carbaldehyde (0.1 g) and 1-amino-3-(2-isopropylphenyl)thiourea (0.03 g) in EtOH (1 ml) was heated at 90° C. for 2 h. Solid precipitated after 2 h. The solid was filtered, washed with cold EtOH and dried under vacuum to afford the title compound (0.093 g). HPLC/MS (method 1): $R_t$: 2.323 min; m/z=538 (M+1). $^1$H NMR (500 MHz, DMSO-$d_6$) δ 10.02 (s, 1H), 8.29 (s, 1H), 8.17 (d, J=8.6 Hz, 1H), 8.04 (s, 1H), 7.94 (d, J=8.5 Hz, 1H), 7.90-7.81 (m, 2H), 7.58 (d, J=16.6 Hz, 1H), 7.53 (d, J=16.6 Hz, 1H), 7.37 (m, J=7.8, 3.9 Hz, 3H), 7.31 (s, 1H), 7.27-7.20 (m, 2H), 4.11 (s, 3H), 3.20-3.08 (m, 1H), 1.20 (d, J=6.9 Hz, 6H).

Example 21

(2Z)-3-(2-isopropylphenyl)-2-[(E)-[1-methyl-3-[(E)-2-[4-(trifluoromethoxy)phenyl] vinyl]indazol-6-yl] methylenehydrazono]thiazolidin-4-one (C-21 of Table X)

A mixture of 1-(2-isopropylphenyl)-3-[(E)-[1-methyl-3-[(E)-2-[4-(trifluoromethoxy) phenyl] vinyl]indazol-6-yl]

methyleneamino]thiourea (0.08 g), NaOAc (0.049 g) and Methyl bromo acetate (0.046 g) in EtOH (5 ml) was heated at 40° C. for 8 h. After completion, the reaction mixture was diluted with Water and extracted with Ethyl acetate, the organic extracts dried over Sodium sulphate, concentrated under reduced pressure and the residue subjected to silica gel flash column chromatography to obtain the title compound (0.060 g). H PLC/MS (method 1): $R_t$: 2.377 min; m/z=578 (M+1). 6 $^1$H NMR (500 MHz, DMSO-$d_6$) δ 8.46 (s, 1H), 8.25 (d, J=8.6 Hz, 1H), 7.92 (s, 1H), 7.90-7.83 (m, 2H), 7.73 (dd, J=8.7, 1.2 Hz, 1H), 7.60-7.45 (m, 4H), 7.44-7.32 (m, 3H), 7.28 (dd, J=7.8, 1.4 Hz, 1H), 4.28 (d, J=17.2 Hz, 1H), 4.16 (d, J=17.3 Hz, 1H), 4.08 (s, 3H), 2.82 (h, J=6.7 Hz, 1H), 1.17 (dd, J=16.6, 6.8 Hz, 6H).

Example 22

1-(2-isopropylphenyl)-3-[(E)-[3-[[4-(trifluoromethoxy)phenoxy]methyl]-1,2-benzothiazol-6-yl]methyleneamino]thiourea (C-22 of Table X)

Step 1: (6-bromo-1,2-benzothiazol-3-yl)methanol

To a stirred solution of ethyl 6-bromo-1,2-benzothiazole-3-carboxylate (0.6 g) in THF (6 ml) and EtOH (3 ml), LiBH$_4$ (0.069 g) was added drop wise at 0° C. under inert atmosphere. Reaction mixture was stirred at 00° C. for 2 h. Progress of reaction was monitored by TLC. After completion, the reaction mixture was diluted with Water (30 ml) and quenched with Aq. 5% NaOH solution, extracted with Ethyl acetate (40 ml×2). The combined organic extracts were dried over Na$_2$SO$_4$, filtered and concentrated under reduced pressure. The crude product was purified by flash chromatography (eluting in 20-22% ethyl acetate in heptane as a mobile phase) to afford (0.380 g) of the title compound. HPLC/MS (method 1): $R_t$: 1.680 min; MS: m/z=246 (M+1).

Step 2: 6-bromo-3-[[4-(trifluoromethoxy)phenoxy]methyl]-1,2-benzothiazole

To a stirred solution of (6-bromo-1,2-benzothiazol-3-yl)methanol (1.1 g) in dry THF (11 ml), 4-trifluromethoxy phenol (0.963 g) and triphenyl phosphine (1.182 g) were added at 00° C. under inert atmosphere. Reaction mixture was continued to stir at 00° C. for 5 min and then DBAD (1.038 g) was added. Then the reaction mixture was stirred at 42° C. for 2 h in microwave. Progress of reaction was monitored by TLC. After completion, the reaction mixture was diluted with Water (50 ml) and extracted with Ethyl acetate (60 ml×2). The combined organic extracts were dried over Na$_2$SO$_4$, filtered and concentrated under reduced pressure. The crude product was purified by flash chromatography (eluting in 8-10% ethyl acetate in heptane as a mobile phase) to afford (1 g) of the title compound. HPLC/MS (method 1): $R_t$: 2.428 min; MS: m/z=404 (M−1).

Step 3: 3-[[4-(trifluoromethoxy)phenoxy]methyl]-6-vinyl-1,2-benzothiazole

A solution of 6-bromo-3-[[4-(trifluoromethoxy)phenoxy]methyl]-1,2-benzothiazole (0.9 g) in dry Toluene (10 ml) was purged with Nitrogen for 10 min. To the solution Pd(dppf)Cl$_2$ (0.098 g) was added and purging was continued for another 10 min. Tributyl vinyl tin (0.847 g) was added to the reaction mixture and heated at 110° C. for 3 h. Progress of reaction was monitored by TLC. After completion, the reaction mixture was cooled to room temperature, diluted with Water (50 ml) and extracted with Ethyl acetate (60 ml×2). The combined organic extracts were dried over Na$_2$SO$_4$, filtered and concentrated under reduced pressure. The crude product was purified by flash chromatography (eluting in 15-20% ethyl acetate in heptane as a mobile phase) to afford (0.660 g) of the title compound. HPLC/MS (method 1): $R_t$: 2.391 min; MS: m/z=352 (M+1).

Step 4: 3-[[4-(trifluoromethoxy)phenoxy]methyl]-1,2-benzothiazole-6-carbaldehyde To a stirred solution of 3-[[4-(trifluoromethoxy)phenoxy]methyl]-6-vinyl-1,2-benzothiazole (0.660 g) in 1,4-dioxane (6 ml) and Water (2 ml), OsO$_4$ (0.007 g) and NaIO$_4$ (0.880 g) were added at 0° C. under inert atmosphere. The reaction mixture was stirred at room temperature for 3 h. Progress of reaction was monitored by TLC. After completion, the reaction mixture was diluted with Water (20 ml), quenched with Aq. Sodium sulfite solution (15 ml) and extracted with Ethyl acetate (40 ml×2). The combined organic extracts were dried over Na$_2$SO$_4$, filtered and concentrated under reduced pressure. The crude product was purified by flash chromatography (eluting in 20-22% ethyl acetate in heptane as a mobile phase) to afford (0.170 g) of the title compound. HPLC/MS (method 1): $R_t$: 2.108 min; MS: m/z=354.4 (M+1).

Step 5: 1-(2-isopropylphenyl)-3-[(E)-[3-[[4-(trifluoromethoxy)phenoxy]methyl]-1,2-benzothiazol-6-yl]methyleneamino]thiourea (C-22 of Table X)

A mixture of 3-[[4-(trifluoromethoxy)phenoxy]methyl]-1,2-benzothiazole-6-carbaldehyde (0.17 g) and 1-amino-3-(2-isopropylphenyl)thiourea (0.101 g) in EtOH (2 ml) was heated at 85° C. for 3 h. Progress of reaction was monitored by TLC. After completion, the reaction mixture was cooled to room temperature and the precipitated product was filtered through a filter paper. The residue was washed with cold EtOH (2 ml), triturated with Pentane (5 ml) and dried under reduced pressure to afford (0.165 g) of the title compound. HPLC/MS (method 1): $R_t$: 2.347 min; MS: m/z=545.1 (M+1). $^1$H NMR (500 MHz, DMSO-$d_6$) δ 11.97 (s, 1H), 10.12 (s, 1H), 8.63 (s, 1H), 8.31-8.19 (m, 3H), 7.41-7.29 (m, 4H), 7.28-7.15 (m, 4H), 5.63 (s, 2H), 3.14 (h, J=6.9 Hz, 1H), 1.20 (d, J=6.9 Hz, 6H).

Example 23: (2Z)-3-(2-isopropylphenyl)-2-[(E)-[3-[[4-(trifluoromethoxy)phenoxy] methyl]-1,2-benzothiazol-6-yl]methylenehydrazono]thiazolidin-4-one (C-23 of Table X)

A mixture of 1-(2-isopropylphenyl)-3-[(E)-[3-[[4-(trifluoromethoxy)phenoxy]methyl]-1,2-benzothiazol-6-yl]methyleneamino]thiourea (0.115 g), NaOAc (0.035 g) and Methyl bromo acetate (0.048 g) in EtOH (2.0 ml) was stirred at room temperature for 12 h. Progress of reaction was monitored by TLC. After completion the reaction mixture was diluted with Water (15 ml) and extracted with Ethyl acetate (20 ml×2). The combined organic extracts were dried over Na$_2$SO$_4$, filtered and concentrated under reduced pressure. The crude product was purified by flash chromatography (eluting in 20-25% ethyl acetate in heptane as a mobile phase) to afford (0.060 g) of the title compound. HPLC/MS (method 1): $R_t$: 2.419 min; MS: m/z=585.2 (M+1). $^1$H NMR (500 MHz, DMSO-$d_6$) δ 8.50 (d, J=7.1 Hz, 2H), 8.31 (d, J=8.5 Hz, 1H), 7.95 (dd, J=8.5, 1.3 Hz, 1H), 7.55-7.44 (m, 2H), 7.38-7.25 (m, 4H), 7.23-7.16 (m, 2H), 5.62 (s, 2H), 4.29 (d, J=17.4 Hz, 1H), 4.17 (d, J=17.3 Hz, 1H), 2.80 (h, J=6.9 Hz, 1H), 1.16 (dd, J=12.6, 6.8 Hz, 6H).

Example 24

1-(2-isopropylphenyl)-3-[(E)-[3-[[4-(trifluoromethoxy)phenoxy]methyl]-1,2-benzoxazol-6-yl]methyleneamino]thiourea (C-24 of Table X)

Step 1: (6-bromo-1,2-benzoxazol-3-yl) Methanol

To a stirred solution of ethyl 6-bromo-1,2-benzoxazole-3-carboxylate (1.1 g) in THF (10 ml) and EtOH (3 ml), LiBH$_4$ (0.133 g) was added drop wise at 0° C. under inert atmosphere. The reaction mixture was stirred at 0° C. for 2 h. Reaction was monitored by TLC. After the completion, the reaction mixture was diluted with Water (20 ml), quenched with 5% NaOH solution and extracted with Ethyl acetate (30 ml×2). The combined organic extracts were dried over Na$_2$SO$_4$, filtered and concentrated under reduced pressure. The crude product was purified by flash chromatography (eluting in 15-20% ethyl acetate in heptane as a mobile phase) to afford (0.8 g) of the title compound. HPLC/MS (method 1): R$_t$: 1.587 min; MS: m/z=229 (M+1).

Step 2: 6-bromo-3-[[4-(trifluoromethoxy)phenoxy]methyl]-1,2-benzoxazole

To a stirred solution of (6-bromo-1,2-benzoxazol-3-yl) methanol (0.5 g) in dry THF (5 ml), 4-triflurometnoxy phenol (0.469 g) and Triphenyl phosphine (0.575 g) were added at 0° C. under inert atmosphere. The reaction mixture was stirred at 0° C. for 5 min and then DBAD (0.505 g) was added. Then the reaction mixture was stirred at 35° C. for 2 h in microwave. Progress of reaction was monitored by TLC. After completion, the reaction mixture was diluted with Water (20 ml) and extracted with Ethyl acetate (30 ml×2). The combined organic extracts were dried over Na$_2$SO$_4$, filtered and concentrated under reduced pressure. The crude product was purified by flash chromatography (eluting in 10-12% ethyl acetate in heptane as a mobile phase) to afford (1.5 g) of the title compound. HPLC/MS (method 1): R$_t$: 2.296 min; MS: m/z=389 (M+1).

Step 3: 3-[[4-(trifluoromethoxy)phenoxy]methyl]-6-vinyl-1,2-benzoxazole

A solution of 6-bromo-3-[[4-(trifluoromethoxy)phenoxy] methyl]-1,2-benzoxazole (1.5 g) in dry Toluene (15 ml) was purged with Nitrogen for 10 min. To the solution Pd(dppf) C2 (0.170 g) was added and purging was continued for another 10 min. Tributyl vinyl tin (1.838 g) was added to the reaction mixture and heated at 105° C. for 3 h. Progress of reaction was monitored by TLC. After completion, the reaction mixture was cooled to room temperature, diluted with Water (40 ml) and extracted with Ethyl acetate (50 ml×2). The combined organic extracts were dried over Na$_2$SO$_4$, filtered and concentrated under reduced pressure. The crude product was purified by flash chromatography (eluting in 15-20% ethyl acetate in heptane as a mobile phase) to afford (1.4 g) of the title compound. HPLC/MS (method 1): R$_t$: 1.929 min; MS: m/z=332.1 (M+1).

Step 4: 3-[[4-(trifluoromethoxy)phenoxy]methyl]-1,2-benzoxazole-6-carbaldehyde

To a stirred solution of 3-[[4-(trifluoromethoxy)phenoxy] methyl]-6-vinyl-1,2-benzoxazole (2 g) in 1,4-dioxane (16 ml) and Water (4 ml), OsO$_4$ (0.030 g) and NaIO$_4$ (2.795 g) were added at 0° C. under inert atmosphere. The reaction mixture was stirred at room temperature for 3 h. Progress of reaction was monitored by TLC. After completion, the reaction mixture was diluted with Water (50 ml), quenched with Aq. sodium sulfite solution (20 ml) and extracted with Ethyl acetate (60 ml×2). The combined organic extracts were dried over Na$_2$SO$_4$, filtered and concentrated under reduced pressure. The crude product was purified by flash chromatography (eluting in 25-30% ethyl acetate in heptane as a mobile phase) to afford (0.6 g) of the title compound, which was further used without characterization.

Step 5: 1-(2-isopropylphenyl)-3-[(E)-[3-[[4-(trifluoromethoxy)phenoxy]methyl]-1,2-benzoxazol-6-yl]methyleneamino]thiourea (C-24 of Table X)

A mixture of 3-[[4-(trifluoromethoxy)phenoxy]methyl]-1,2-benzoxazole-6-carbaldehyde (0.2 g) and 1-amino-3-(2-isopropylphenyl)thiourea (0.124 g) in EtOH (2 ml) was heated at 85° C. for 3 h. Progress of reaction was monitored by TLC. After completion the reaction mixture was cooled to room temperature and the precipitated product was filtered through a filter paper. The residue was washed with cold EtOH (2 ml), triturated with Pentane (5 ml) and dried under reduced pressure to afford (0.180 g) of the title compound. H PLC/MS (method 1): R$_t$: 2.276 min; MS: m/z=529.3 (M+1). $^1$H NMR (500 MHz, DMSO-d$_6$) δ 11.99 (s, 1H), 10.19 (s, 1H), 8.44 (s, 1H), 8.27 (s, 1H), 8.00-7.92 (m, 2H), 7.35 (dddd, J=16.6, 15.0, 7.8, 1.6 Hz, 4H), 7.28-7.16 (m, 4H), 5.65 (s, 2H), 3.13 (h, J=6.9 Hz, 1H), 1.19 (d, J=6.9 Hz, 6H).

Example 25

(2Z)-3-(2-isopropylphenyl)-2-[(E)-[3-[[4-(trifluoromethoxy)phenoxy]methyl]-1,2-benzoxazol-6-yl]methylenehydrazono]thiazolidin-4-one (C-25 of Table X)

A mixture of 1-(2-isopropylphenyl)-3-[(E)-[3-[[4-(trifluoromethoxy)phenoxy] methyl]-1,2-benzoxazol-6-yl]methyleneamino]thiourea (0.125 g), NaOAc (0.029 g) and methyl bromo acetate (0.054 g) in EtOH (3 ml) was stirred at room temperature for 12 h. Progress of reaction was monitored by TLC. After completion, the reaction mixture was diluted with Water (15 ml) and extracted with Ethyl acetate (20 ml×2). The combined organic extracts were dried over Na$_2$SO$_4$, filtered and concentrated under reduced pressure. The crude product was purified by flash chromatography (eluting in 20-25% ethyl acetate in heptane as a mobile phase) to afford (0.11 g) of the title compound. HPLC/MS (method 1): R$_t$: 2.335 min; MS: m/z=569.3 (M+1). $^1$H NMR (500 MHz, DMSO-d$_6$) δ 8.56 (s, 1H), 8.11-8.05 (m, 2H), 7.93 (dd, J=8.3, 1.1 Hz, 1H), 7.61-7.50 (m, 2H), 7.45-7.36 (m, 3H), 7.40-7.30 (m, 1H), 7.33-7.24 (m, 2H), 5.71 (s, 2H), 4.35 (d, J=17.3 Hz, 1H), 4.22 (d, J=17.3 Hz, 1H), 2.85 (h, J=6.8 Hz, 1H), 1.21 (dd, J=11.0, 6.8 Hz, 6H).

Example 26

(E)-1-[3-[[4-(trifluoromethoxy)phenoxy]methyl]-1,2-benzoxazol-6-yl]-N-[(2S,3R,4S,5S,6S)-3,4,5-trimethoxy-6-methyl-tetrahydropyran-2-yl]oxymethanimine (C-26 of Table X)

A mixture of 3-[[4-(trifluoromethoxy)phenoxy]methyl]-1,2-benzoxazole-6-carbaldehyde (0.15 g) and O-[(2S,3R,4S, 5S,6S)-3,4,5-trimethoxy-6-methyl-tetrahydropyran-2-yl] hydroxylamine (0.108 g) in EtOH (2 ml) was heated at 85° C. for 4 h. Progress of reaction was monitored by TLC. After completion, the reaction mixture was evaporated under reduced pressure and the crude product was purified by flash chromatography (eluting in 35-40% ethyl acetate in heptane as a mobile phase). to afford (0.045 g) of the title compound. HPLC/MS (method 1): $R_t$: 2.179 min; MS: m/z=539.25 (M−1). $^1$H NMR (500 MHz, DMSO-$d_6$) δ 8.60 (s, 1H), 8.02 (d, J=8.4 Hz, 2H), 7.78 (dd, J=8.2, 1.2 Hz, 1H), 7.38-7.31 (m, 2H), 7.27-7.19 (m, 2H), 5.66 (s, 2H), 5.56 (d, J=2.1 Hz, 1H), 3.82 (dd, J=3.2, 2.1 Hz, 1H), 3.60-3.50 (m, 1H), 3.47-3.36 (m, 9H), 3.06 (t, J=9.2 Hz, 1H), 1.17 (d, J=6.2 Hz, 3H).

Example 27

[(2S,3R,4S,5S,6S)-3,4,5-trimethoxy-6-methyl-tetrahydropyran-2-yl] N-[3-[[4-(trifluoromethoxy)phenoxy]methyl]-1,2-benzoxazol-6-yl]carbamate (C-27 of Table X)

Step 1: 3-[[4-(trifluoromethoxy)phenoxy]methyl]-1, 2-benzoxazole-6-carboxylic Acid To a solution of 3-[[4-(trifluoromethoxy)phenoxy] methyl]-1,2-benzoxazole-6-carbaldehyde (0.35 g) in CH$_3$CN (4 ml) and Water (1.5 ml), KMnO$_4$ (0.328 g) was added and the reaction mixture was stirred at room temperature for 12 h. Progress of reaction was monitored by TLC. After completion, the reaction mixture was poured in ice cold water and filtered through a celite bed. Celite bed was washed with water and pH of filtrate was adjusted up to ~3-4 using Aq. 1N HCl solution. The precipitated product was filtered through a filter paper and dried under reduced pressure to afford (0.360 g) of the title compound. HPLC/MS (method 1): $R_t$: 1.947 min; MS: m/z=352 (M−1).

Step 2: [[3-[[4-(trifluoromethoxy)phenoxy]methyl]-1,2-benzoxazole-6-carbonyl]iminio-lambda5-azanylidene]azanide To a stirred solution of -[[4-(trifluoromethoxy)phenoxy] methyl]-1,2-benzoxazole-6-carboxylic acid (0.31 g) in Acetone (4 ml), Triethyl amine (0.124 g) and Ethyl chloroformate (0.143 g) were added at 0° C. The reaction mixture was stirred at room temperature for 2 h and then NaN$_3$ (0.068 g) in Water (1 ml) was added and the reaction was continued to stir at room temperature for 12 h. Progress of reaction was monitored by TLC. After completion, the reaction mixture was diluted with water (10 ml) and extracted with DCM (20 ml×2). The combined organic extracts were dried over Na$_2$SO$_4$, filtered and concentrated under reduced pressure to afford (0.3 g) of the title compound, which was further used without characterization.

Step 3: [(2S,3R,4S,5S,6S)-3,4,5-trimethoxy-6-methyl-tetrahydropyran-2-yl] N-[3-[[4-(trifluoromethoxy)phenoxy]methyl]-1,2-benzoxazol-6-yl] carbamate (C-27 of Table X)

A mixture of [[3-[[4-(trifluoromethoxy)phenoxy]methyl]-1,2-benzoxazole-6-carbonyl] iminio-lambda5-azanylidene] azanide (0.3 g) and (3R,4R,5S,6S)-3,4,5-trimethoxy-6-methyl-tetrahydropyran-2-ol (0.164 g) in CH$_3$CN (3 ml) was heated at 85° C. for 2 h. Then the reaction mixture was cooled to 0° C. and Cesium carbonate (0.085 g) was added.

Reaction mixture was further stirred for 12 h at room temperature. Progress of reaction was monitored by TLC. After completion, the solvent of the reaction mixture was concentrated under reduced pressure. The residue was purified by flash chromatography (eluting in 25-30% ethyl acetate in heptane as a mobile phase) to afford (0.026 g) of the title compound. HPLC/MS (method 1): $R_t$: 2.127 min; MS: m/z=557.3 (M+1). $^1$H NMR (500 MHz, DMSO-$d_6$) δ 10.40 (s, 1H), 8.04 (s, 1H), 7.91 (d, J=8.7 Hz, 1H), 7.47 (dd, J=8.7, 1.6 Hz, 1H), 7.40 (d, J=8.7 Hz, 2H), 7.27 (d, J=9.1 Hz, 2H), 6.06 (d, J=2.1 Hz, 1H), 5.64 (s, 2H), 3.83 (t, J=2.7 Hz, 1H), 3.69 (dt, J=12.4, 6.3 Hz, 1H), 3.57 (dd, J=9.3, 3.2 Hz, 1H), 3.53-3.44 (m, 9H), 3.10-3.14 (t, 1H), 1.27-1.19 (m, 3H).

Example 64

Synthesis of 6-[[[(2-isopropylanilino)-methylsulfanyl-methylene]hydrazono] methyl]-1-methyl-N-[4-(trifluoromethoxy)phenyl]indazole-3-carboxamide (C-64 of Table X)

To a mixture of 6-[[[(2-isopropylphenyl)carbamothioylhydrazono]methyl]-1-methyl-N-[4-(trifluoromethoxy)phenyl] indazole-3-carboxamide (0.15 g) in Ethanol (10 ml) were added Sodium acetate (0.075 g) and Methyl iodide (0.18 g). The mixture was heated at 68° C. for 4 h. The mixture was subsequently cooled to ambient temperature, diluted with water and extracted with Ethyl acetate. The Ethyl acetate extracts were washed with brine, dried over anhydrous Sodium sulphate and evaporated under reduced pressure. The resultant residue was purified by silica gel flash column chromatography using a gradient of Ethyl acetate and Heptane as eluent to afford the title compound (0.06 g). HPLC/MS (method 1): $R_t$: 2.48 min; m/z=569 (M+1); $^1$H NMR (500 MHz, CDCl$_3$) δ 8.85 (s, 1H), 8.61 (s, 1H), 8.40 (d, J=8.5 Hz, 1H), 8.26 (s, 1H), 7.85 (dd, J=8.5, 1.2 Hz, 1H), 7.81-7.74 (m, 2H), 7.72 (d, J=4.4 Hz, 1H), 7.34 (m, 3H), 7.23 (m, 3H), 4.18 (s, 3H), 3.29 (m, 1H), 2.48 (s, 3H), 1.29 (d, J=6.9 Hz, 6H).

Example 65

Synthesis of 6-[[[3-(2-isopropylphenyl)thiazolidin-2-ylidene]hydrazono] methyl]-1-methyl-N-[4-(trifluoromethoxy)phenyl]indazole-3-carboxamide (C-65 of Table X)

To a stirred solution of 6-[[[(2-isopropylphenyl)carbamothioylhydrazono]methyl]-1-methyl-N-[4-(trifluoromethoxy) phenyl]indazole-3-carboxamide (0.2 g) in Acetone (10 ml) were added potassium carbonate (0.1 g) and 1-bromo-2-chloro ethane (0.12 g). The mixture was heated at 65° C. for 3 h. The mixture was cooled to ambient temperature, diluted with brine solution and extracted with Ethyl acetate. The Ethylacetate extracts were washed with brine, dried over Sodium sulphate and concentrated under reduced pressure and the resultant residue subjected to Silica gel flash column chromatography to get the title compound (0.1 g). HPLC/MS (method 1): $R_t$: 2.34 min; m/z=581 (M+1); $^1$H NMR (300 MHz, CDCl$_3$) δ 8.85 (s, 1H), 8.40-8.24 (m, 2H), 7.84-7.69 (m, 3H), 7.62 (s, 1H), 7.45-7.38 (m, 1H), 7.38-7.30 (m, 1H), 7.30-7.20 (m, 4H), 4.14 (s, 3H), 4.11-4.00 (m, 1H), 4.00-3.85 (m, 1H), 3.45-3.26 (m, 2H), 3.12 (m, 1H), 1.25 (dd, J=15.0, 6.9 Hz, 6H).

Example 66

Synthesis of 6-[[[3-(2-isopropylphenyl)-1,3-thiazinan-2-ylidene] hydrazono] methyl]-1-methyl-N-[4-(trifluoromethoxy)phenyl]indazole-3-carboxamide (C-66 of Table X)

To a stirred solution of 6-[[(2-isopropylphenyl)carbamothioylhydrazono]methyl]-1-methyl-N-[4-(trifluoromethoxy)phenyl]indazole-3-carboxamide in acetone were added Potassium carbonate (0.2 g) and 1-bromo-3-chloro propane (0.103 g). The mixture was heated at 66° C. for 12 h. The reaction mixture was subsequently cooled to ambient temperature, diluted with brine solution and extracted with Ethyl acetate. The organic extracts were washed with brine, dried over Sodium sulphate and concentrated under reduced pressure. The resultant residue was subjected to silica gel flash column chromatography using a gradient of Ethyl acetate and Heptane as eluent to afford the title compound (0.09 g). HPLC/MS (method 1): R$_t$: 2.46 min; m/z=595 (M+1); $^1$H NMR (500 MHz, CDCl$_3$) δ 8.83 (s, 1H), 8.31 (d, J=8.5 Hz, 1H), 8.14 (s, 1H), 7.79-7.74 (m, 2H), 7.72 (dd, J=8.5, 1.1 Hz, 1H), 7.59 (s, 1H), 7.39 (dd, J=7.8, 1.6 Hz, 1H), 7.33 (m, 1H), 7.29-7.24 (m, 1H), 7.23 (d, J=8.6 Hz, 2H), 7.19 (dd, J=7.7, 1.4 Hz, 1H), 4.12 (s, 3H), 3.84-3.62 (m, 1H), 3.54 (m, 1H), 3.11 (m, 3H), 2.36 (m, 2H), 1.23 (d, J=6.9 Hz, 6H).

Examples of compound of formula I given in table X were prepared using the method analogous to preparation of the above examples or by derivatization of the above examples or intermediates thereof, or using the method analogous to the methods mentioned in the general procedure.

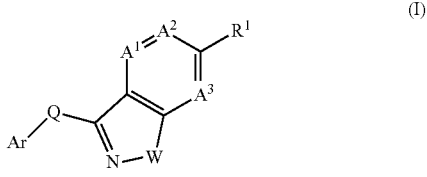

(I)

TABLE X

| No | Ar-Q | R$^1$ | HPLC/MS | Rt min |
|---|---|---|---|---|
| C-1 | 4-(trifluoromethoxy)phenoxyethyl | 2,6-dimethylphenyl thiosemicarbazone | 528.9 (method 1) | 2.20 |
| C-2 | 4-(trifluoromethoxy)phenoxyethyl | 3-(2,6-dimethylphenyl)-4-oxothiazolidin-2-ylidene hydrazone | 568.3 (method 1) | 2.33 |
| C-3 | 4-(trifluoromethoxy)phenoxyethyl | 2-isopropylphenyl thiosemicarbazone | 542.3 (method 1) | 2.31 |

TABLE X-continued

| No | Ar-Q | (core structure) | R¹ | HPLC/ MS | Rt min |
|---|---|---|---|---|---|
| C-4 | 4-(trifluoromethoxy)phenoxyethyl | 1-methyl-1H-indazol-3,6-diyl | 3-(2-isopropylphenyl)-4-oxothiazolidin-2-ylidene hydrazone | 582.4 (method 1) | 2.36 |
| C-5 | 4-(trifluoromethoxy)benzamide | 1-methyl-1H-indazol-3,6-diyl | trimethoxy methylpyranyl carbamate | — | — |
| C-6 | 4-(trifluoromethoxy)phenyl acetamide | 1-methyl-1H-indazol-3,6-diyl | trimethoxy methylpyranyl carbamate | 584 (method 2) | 1.25 |
| C-7 | 4-(trifluoromethoxy)phenyl acetamide | 1-methyl-1H-indazol-3,6-diyl | N-(2-isopropylphenyl)thiosemicarbazone | 553.3 (method 1) | 2.22 |
| C-8 | 4-(trifluoromethoxy)phenyl acetamide | 1-methyl-1H-indazol-3,6-diyl | 3-(2-isopropylphenyl)-4-oxothiazolidin-2-ylidene hydrazone | 595.1 (method 1) | 2.32 |
| C-9 | 4-(trifluoromethoxy)phenyl acetamide | 1-methyl-1H-indazol-3,6-diyl | O-((2-isopropylphenyl)carbamoyl) oxime | 538.2 (method 10) | 2.25 |

TABLE X-continued
| No | Ar-Q | | R¹ | HPLC/ MS | Rt min |
|---|---|---|---|---|---|
| C-10 | 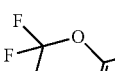 | 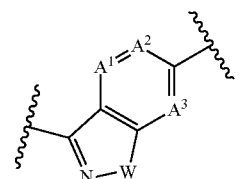 | 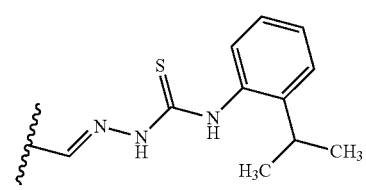 [SMILES: */C=N/NC(=S)Nc1ccccc1C(C)C] | 541.3 (method 1) | 2.21 |
| C-11 | 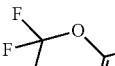 | 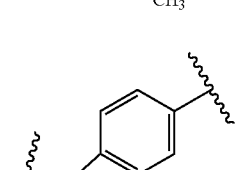 | 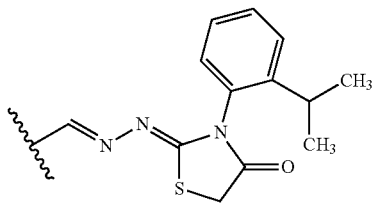 [SMILES: */C=N/N=C1\SCC(=O)N1c1ccccc1C(C)C] | 581.3 (method 1) | 2.24 |
| C-12 | 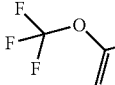 | 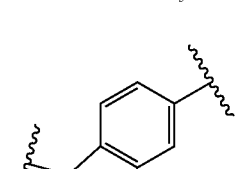 | 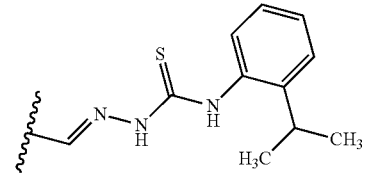 [SMILES: */C=N/NC(=S)Nc1ccccc1C(C)C] | 554.2 (method 1) | 2.27 |
| C-13 | 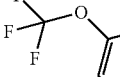 | 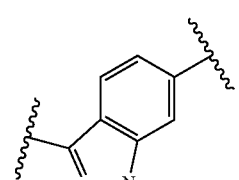 | 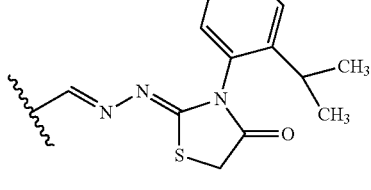 | 596.2 (method 1) | 2.34 |
| C-14 |  | 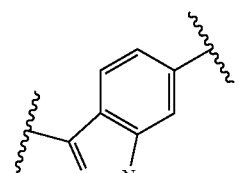 | 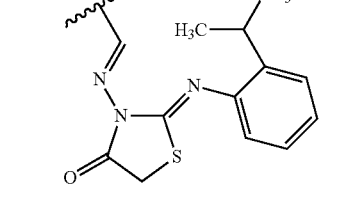 | 596.2 (method 1) | 2.39 |
| C-15 | 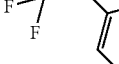 | 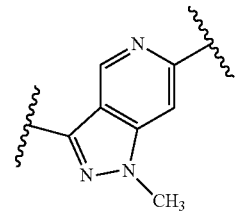 [SMILES: *c1cc2c(cn1)c(*)nn2C] | 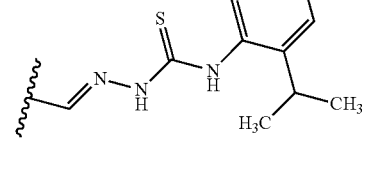 | 541.2 (method 1) | 2.11 |

TABLE X-continued
| No | Ar-Q | (core) | R¹ | HPLC/MS | Rt min |
|---|---|---|---|---|---|
| C-16 | 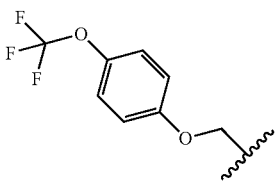 [SMILES: *COc1ccc(OC(F)(F)F)cc1] | 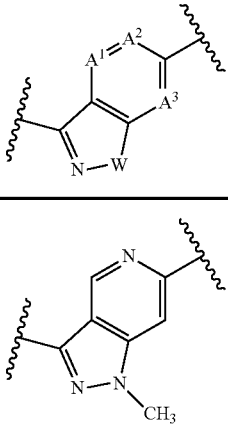 | 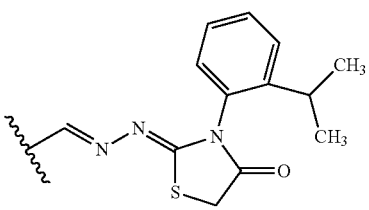 [SMILES: */C=N/N=C1\SCC(=O)N1c1ccccc1C(C)C] | 583.6 (method 1) | 2.22 |
| C-17 | 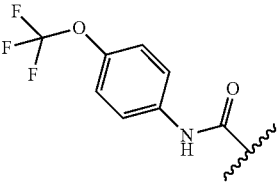 [SMILES: *C(=O)Nc1ccc(OC(F)(F)F)cc1] | 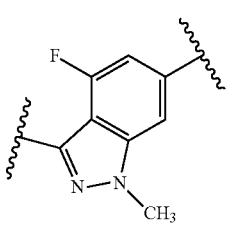 [SMILES: *c1cc(F)c2c(*)nn(C)c2c1] | 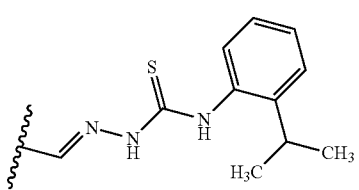 [SMILES: */C=N/NC(=S)Nc1ccccc1C(C)C] | 573.2 (method 1) | 2.23 |
| C-18 | 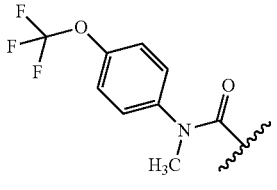 [SMILES: *C(=O)N(C)c1ccc(OC(F)(F)F)cc1] | 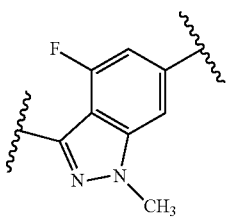 [SMILES: *c1cc(F)c2c(*)nn(C)c2c1] | 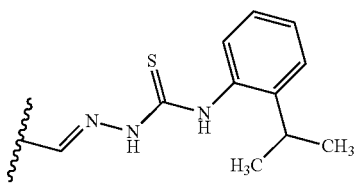 [SMILES: */C=N/NC(=S)Nc1ccccc1C(C)C] | 587.2 (method 1) | 2.15 |
| C-19 | 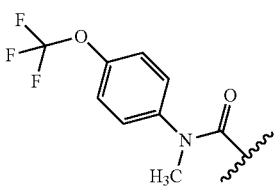 | 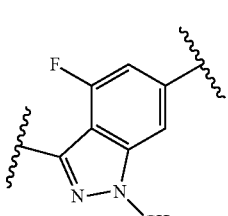 | 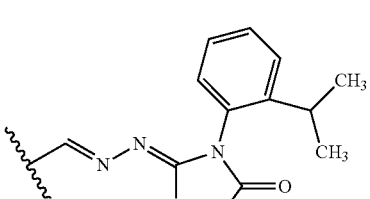 | 627.4 (method 1) | 2.29 |
| C-20 | 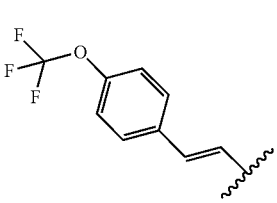 [SMILES: */C=C/c1ccc(OC(F)(F)F)cc1] | 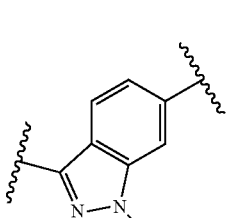 | 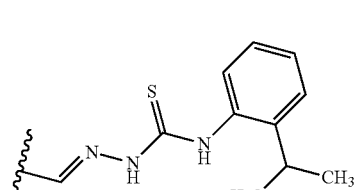 | 538 (method 1) | 2.32 |
| C-21 | 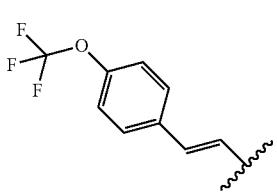 [SMILES: */C=C/c1ccc(OC(F)(F)F)cc1] | 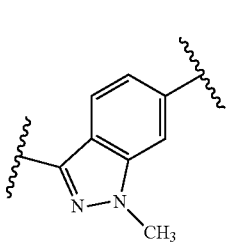 | 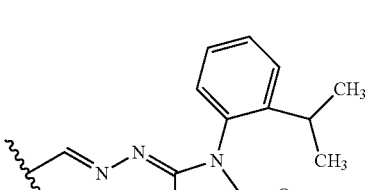 | 578 (method 1) | 2.37 |

TABLE X-continued

| No | Ar-Q | (core) | R¹ | HPLC/MS | Rt min |
|---|---|---|---|---|---|
| C-22 | 4-(trifluoromethoxy)phenoxy-CH₂- | benzisothiazol-6-yl | -CH=N-NH-C(=S)-NH-(2-isopropylphenyl) | 545.1 (method 1) | 2.34 |
| C-23 | 4-(trifluoromethoxy)phenoxy-CH₂- | benzisothiazol-6-yl | -CH=N-N=C(thiazolidin-4-one)-N-(2-isopropylphenyl) | 585.2 (method 1) | 2.41 |
| C-24 | 4-(trifluoromethoxy)phenoxy-CH₂- | benzisoxazol-6-yl | -CH=N-NH-C(=S)-NH-(2-isopropylphenyl) | 529.3 (method 1) | 2.27 |
| C-25 | 4-(trifluoromethoxy)phenoxy-CH₂- | benzisoxazol-6-yl | -CH=N-N=C(thiazolidin-4-one)-N-(2-isopropylphenyl) | 569.3 (method 1) | 2.33 |
| C-26 | 4-(trifluoromethoxy)phenoxy-CH₂- | benzisoxazol-6-yl | -CH=N-O-(2,3,4-tri-O-methyl-6-deoxy-pyranosyl) | 539.2 (method 1) | 2.17 |
| C-27 | 4-(trifluoromethoxy)phenoxy-CH₂- | benzisoxazol-6-yl | -NH-C(=O)-O-(2,3,4-tri-O-methyl-6-deoxy-pyranosyl) | 557.3 (method 1) | 2.12 |

TABLE X-continued
| No | Ar-Q | | R¹ | HPLC/ MS | Rt min |
|---|---|---|---|---|---|
| C-28 | 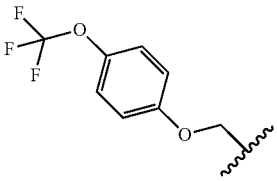 [SMILES: *COc1ccc(OC(F)(F)F)cc1] | 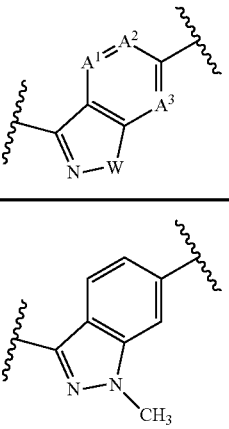 | 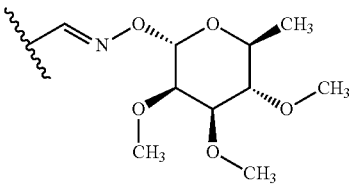 | 554.3 (method 1) | 2.26 |
| C-29 | 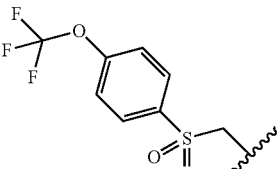 | 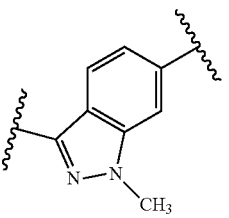 | 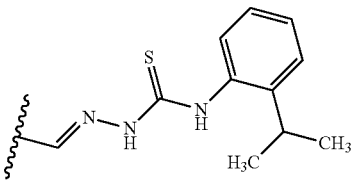 [SMILES: */C=N/NC(=S)Nc1ccccc1C(C)C] | 590.3 (method 1) | 2.13 |
| C-30 | 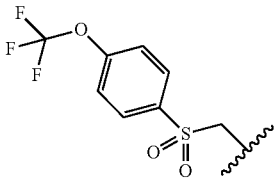 [SMILES: *CS(=O)(=O)c1ccc(OC(F)(F)F)cc1] | 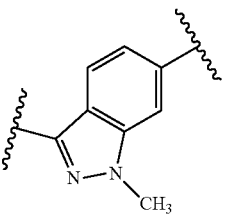 [SMILES: *c1ccc2c(*)nn(C)c2c1] | 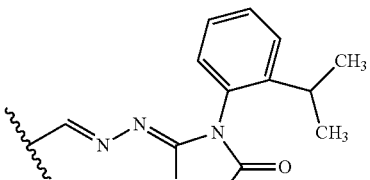 | 630.6 (method 1) | 2.11 |
| C-31 | 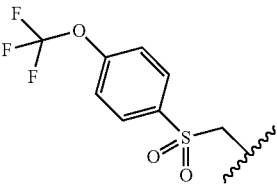 [SMILES: *CS(=O)(=O)c1ccc(OC(F)(F)F)cc1] | 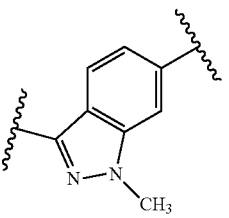 | 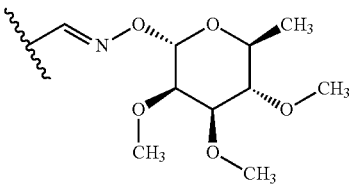 [SMILES: */C=N/O[C@@H]1O[C@@H](C)[C@H](OC)[C@@H](OC)[C@H]1OC] | 602.5 (method 1) | 1.97 |
| C-32 | 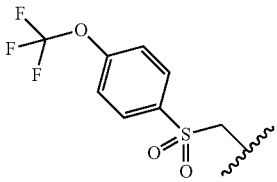 [SMILES: *CS(=O)(=O)c1ccc(OC(F)(F)F)cc1] | 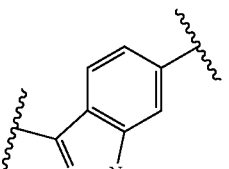 | 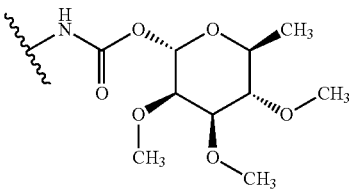 [SMILES: *NC(=O)O[C@@H]1O[C@@H](C)[C@H](OC)[C@@H](OC)[C@H]1OC] | 618.2 (method 1) | 1.93 |
| C-33 | 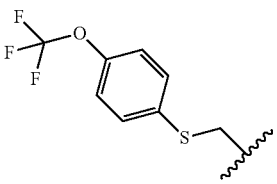 | 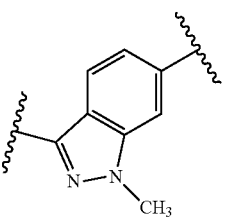 | 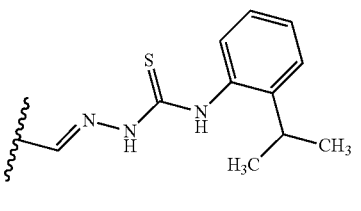 [SMILES: */C=N/NC(=S)Nc1ccccc1C(C)C] | 556.2 (method 1) | 2.36 |

TABLE X-continued
| No | Ar-Q | (core) | R¹ | HPLC/MS | Rt min |
|---|---|---|---|---|---|
| C-34 | 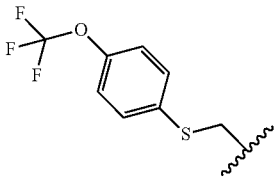 | 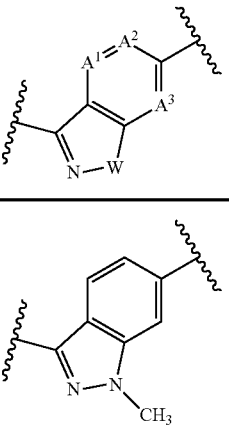 | 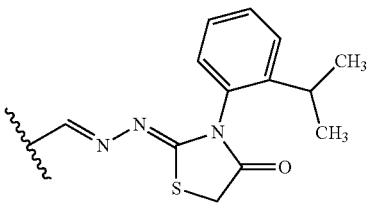 [SMILES: */C=N/N=C1\SCC(=O)N1c1ccccc1C(C)C] | 598.3 (method 1) | 2.4 |
| C-35 | 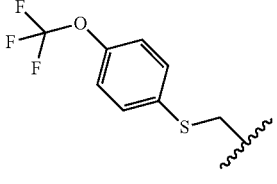 | 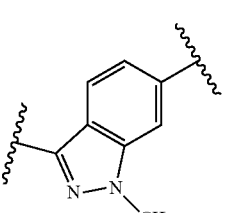 | 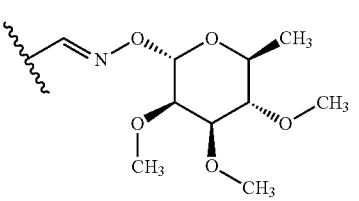 [SMILES: */C=N/O[C@@H]1O[C@@H](C)[C@H](OC)[C@@H](OC)[C@H]1OC] | 570.3 (method 1) | 2.31 |
| C-36 | 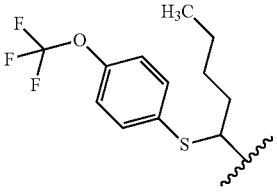 [SMILES: *C(CCCC)Sc1ccc(OC(F)(F)F)cc1] | 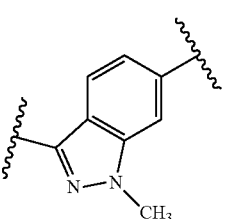 | 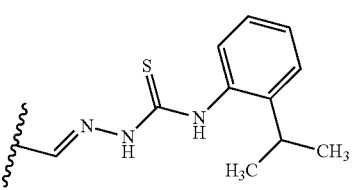 [SMILES: */C=N/NC(=S)Nc1ccccc1C(C)C] | 612 (method 1) | 2.65 |
| C-37 | 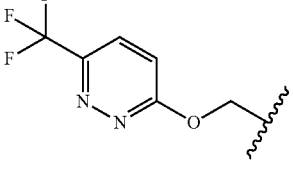 | 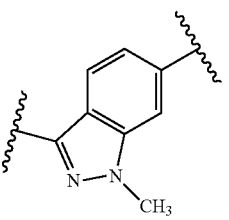 | 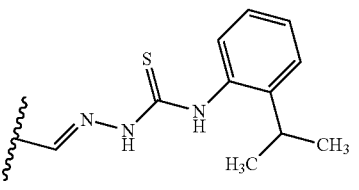 [SMILES: */C=N/NC(=S)Nc1ccccc1C(C)C] | 528.3 (method 1) | 2.12 |
| C-38 | 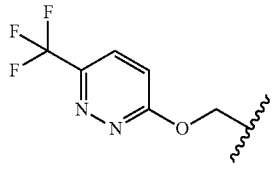 [SMILES: *COc1ccc(C(F)(F)F)nn1] | 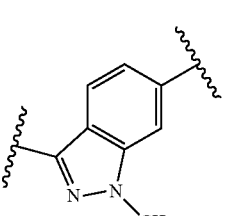 | 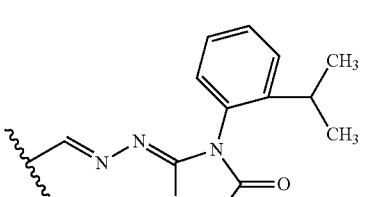 | 568.3 (method 1) | 2.16 |
| C-39 | 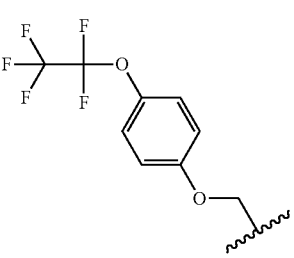 [SMILES: *COc1ccc(OC(F)(F)C(F)(F)F)cc1] | 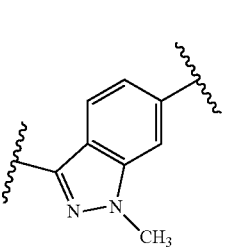 | 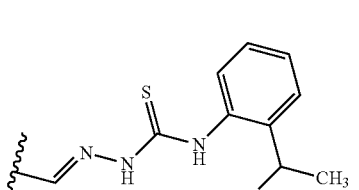 | 592.3 (method 1) | 2.36 |

TABLE X-continued

| No | Ar-Q | R¹ | HPLC/MS | Rt min |
|---|---|---|---|---|
| C-40 | 4-(pentafluoroethoxy)phenoxyethyl | 1-methyl-indazol-3,6-diyl / thiazolidinone hydrazone with 2-isopropylphenyl | 632.4 (method 1) | 2.43 |
| C-41 | 4-(trifluoromethoxy)phenoxyethyl | 1-ethyl-indazol-3,6-diyl / thiosemicarbazone with 2-isopropylphenyl | 554.3 (method 1) | 2.34 |
| C-42 | 4-(trifluoromethoxy)phenoxyethyl | 1-ethyl-indazol-3,6-diyl / thiazolidinone hydrazone with 2-isopropylphenyl | 596.3 (method 1) | 2.38 |
| C-43 | 4-(trifluoromethoxy)phenyl-NHC(O)- | 1-ethyl-indazol-3,6-diyl / thiosemicarbazone with 2-isopropylphenyl | 567.2 (method 1) | 2.27 |
| C-44 | 4-(trifluoromethoxy)phenyl-NHC(O)- | 1-ethyl-indazol-3,6-diyl / thiazolidinone hydrazone with 2-isopropylphenyl | 609.3 (method 1) | 2.32 |
| C-45 | 4-(trifluoromethoxy)phenyl-NHC(O)- | 1-(2,2-difluoroethyl)-indazol-3,6-diyl / thiosemicarbazone with 2-isopropylphenyl | 603.2 (method 1) | 2.22 |

TABLE X-continued
| No | Ar-Q | 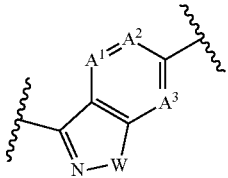 | R¹ | HPLC/MS | Rt min |
|---|---|---|---|---|---|
| C-46 |  | 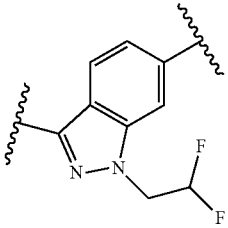 [SMILES: *c1ccc2c(*)nn(CC(F)F)c2c1] | 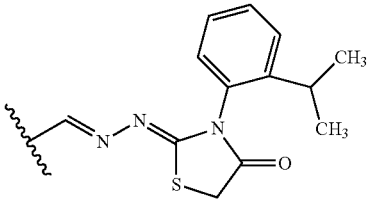 [SMILES: */C=N/N=C1\SCC(=O)N1c1ccccc1C(C)C] | 645.1 (method 1) | 2.32 |
| C-47 |  | 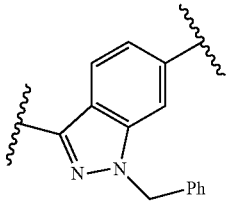 [SMILES: *c1ccc2c(*)nn(Cc3ccccc3)c2c1] | 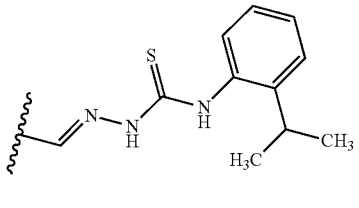 [SMILES: */C=N/NC(=S)Nc1ccccc1C(C)C] | 631.3 (method 1) | 2.34 |
| C-48 |  | 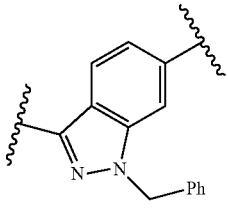 [SMILES: *c1ccc2c(*)nn(Cc3ccccc3)c2c1] | 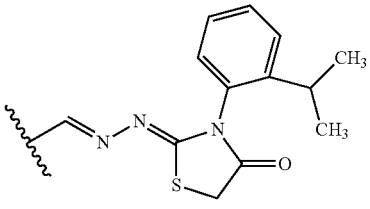 [SMILES: */C=N/N=C1\SCC(=O)N1c1ccccc1C(C)C] | 671.3 (method 1) | 2.39 |
| C-49 |  | 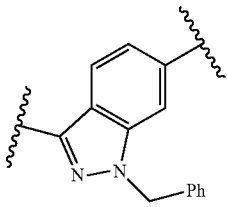 [SMILES: *c1ccc2c(*)nn(Cc3ccccc3)c2c1] | 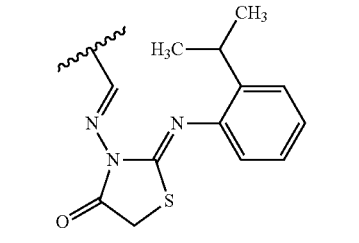 [SMILES: */C=N/N1C(=O)CS/C1=N\c1ccccc1C(C)C] | 671.1 (method 1) | 2.46 |
| C-50 |  | 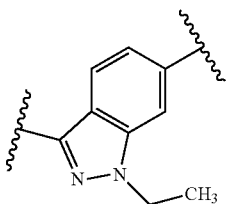 | 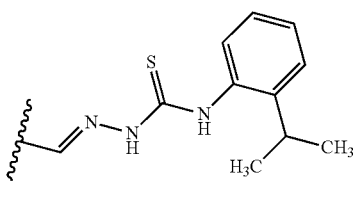 [SMILES: */C=N/NC(=S)Nc1ccccc1C(C)C] | 583.1 (method 1) | 2.40 |

TABLE X-continued

| No | Ar-Q | (core) | R¹ | HPLC/MS | Rt min |
|---|---|---|---|---|---|
| C-51 | 4-(trifluoromethoxy)phenyl-NH-C(O)- | 1-isopropyl-indazole-3,6-diyl | -CH=N-N=C(thiazolidinone)-N(2-isopropylphenyl) | 623.1 (method 1) | 2.42 |
| C-52 | 4-(trifluoromethoxy)phenyl-NH-C(O)- | 1-isopropyl-indazole-3,6-diyl | -CH=N-N(thiazolidinone)=N-(2-isopropylphenyl) | 623.1 (method 1) | 2.46 |
| C-53 | 4-(trifluoromethoxy)phenoxymethyl- | 1H-indazole-3,6-diyl | -CH=N-NH-C(=S)-NH-(2-isopropylphenyl) | 528.1 (method 1) | 2.16 |
| C-54 | 4-(trifluoromethoxy)phenoxymethyl- | 1H-indazole-3,6-diyl | -CH=N-N=C(thiazolidinone)-N-(2-isopropylphenyl) | 566.1 (method 1) | 2.20 |
| C-55 | 4-(trifluoromethoxy)phenyl-NH-C(O)- | 1-methyl-indazole-3,6-diyl | -NH-C(O)-O-(trimethoxy-propoxy-methyl-pyranose) | 611.2 (method 2) | 1.37 |

TABLE X-continued

| No | Ar-Q | (core) | R¹ | HPLC/MS | Rt min |
|---|---|---|---|---|---|
| C-56 | 4-(trifluoromethoxy)-N-methyl-phenylacetamide | 1-methyl-1H-indazol-3,6-diyl | carbamate of 2,3,4-tri-O-methyl-6-deoxy sugar | 597.2 (method 2) | 1.26 |
| C-57 | 4-(trifluoromethoxy)benzyloxy | 1-methyl-1H-indazol-3,6-diyl | carbamate of 2,3,4-tri-O-methyl-6-deoxy sugar | 570.2 (method 2) | 1.31 |
| C-58 | 4-(trifluoromethoxy)benzyloxy | 1-methyl-1H-indazol-3,6-diyl | carbamate of 2,4-di-O-methyl-3-O-propyl-6-deoxy sugar | 598.2 (method 2) | 1.41 |
| C-59 | 4-(trifluoromethoxy)benzylthio | 1-methyl-1H-indazol-3,6-diyl | carbamate of 2,3,4-tri-O-methyl-6-deoxy sugar | 586. (method 2) | 1.34 |
| C-60 | 4-(trifluoromethoxy)benzyloxy | benzo[d]isoxazol-3,6-diyl | carbamate of 2,3,4-tri-O-methyl-6-deoxy sugar | 557.1 (method 2) | 1.36 |

TABLE X-continued
| No | Ar-Q | | R¹ | HPLC/ MS | Rt min |
|---|---|---|---|---|---|
| C-61 | 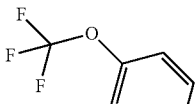 | 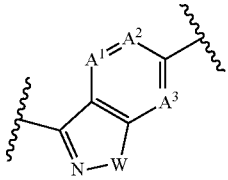 | 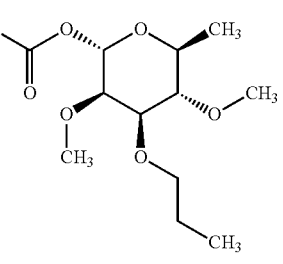 | 585.2 (method 2) | 1.39 |
| C-62 | 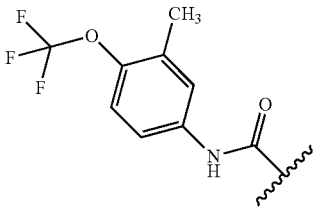 [SMILES: *C(=O)Nc1ccc(OC(F)(F)F)c(C)c1] | 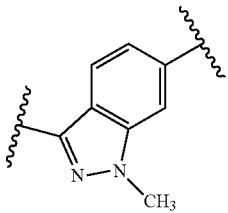 [SMILES: *c1ccc2c(*)nn(C)c2c1] | 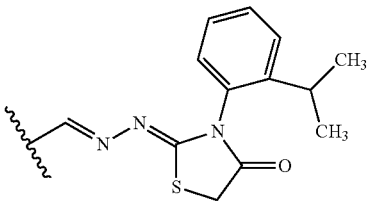 [SMILES: */C=N/N=C1\SCC(=O)N1c1ccccc1C(C)C] | 609.2 (method 2) | 1.48 |
| C-63 | 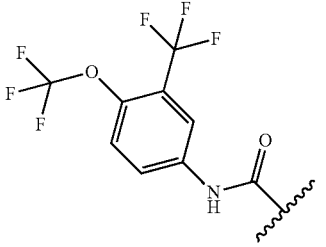 [SMILES: *C(=O)Nc1ccc(OC(F)(F)F)c(C(F)(F)F)c1] | 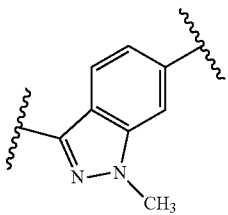 | 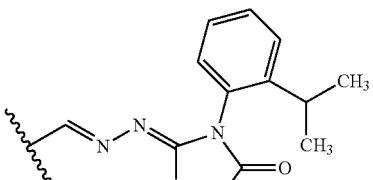 | 663.1 (method 2) | 1.51 |
| C-64 | 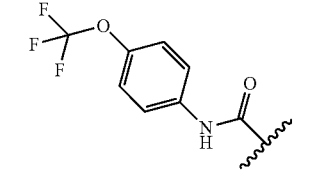 [SMILES: *C(=O)Nc1ccc(OC(F)(F)F)cc1] | 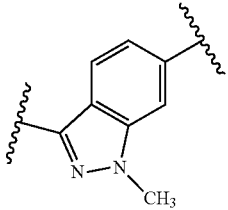 [SMILES: *c1ccc2c(*)nn(C)c2c1] | 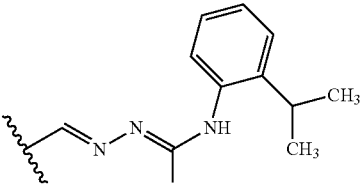 | 569.2 (method 1) | 2.48 |
| C-65 | 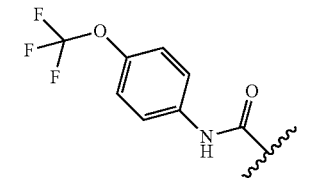 [SMILES: *C(=O)Nc1ccc(OC(F)(F)F)cc1] | 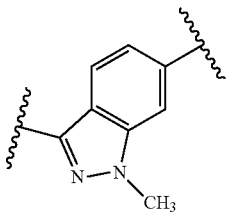 | 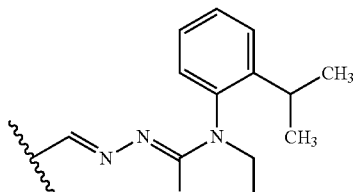 | 595.6 (method 1) | 2.46 |

TABLE X-continued

| No | Ar-Q | R¹ | HPLC/ MS | Rt min |
|---|---|---|---|---|
| C-66 | 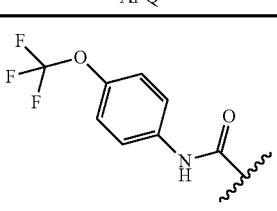 | 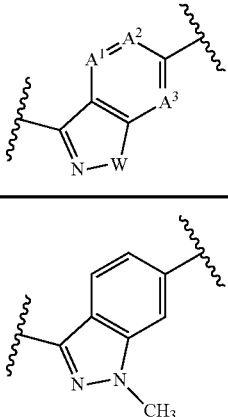 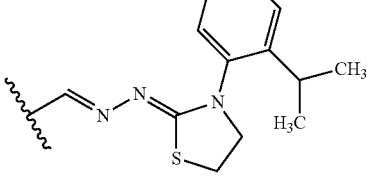 | 581.2 (method 1) | 2.37 |

BIOLOGICAL EXAMPLES

Example B1: Action on Yellow Fever Mosquito (*Aedes aegypti*)

For evaluating control of yellow fever mosquito (*Aedes aegypti*) the test unit consisted of 96-well-microtiter plates containing 200 μl of tap water per well and 5-15 freshly hatched *A. aegypti* larvae.

The active compounds were formulated using a solution containing 75% (v/v) water and 25% (v/v) DMSO. Different concentrations of formulated compounds or mixtures were sprayed onto the insect diet at 2.5 μl, using a custom built micro atomizer, at two replications.

After application, microtiter plates were incubated at 28+1° C., 80+5% RH for 2 days. Larval mortality was then visually assessed.

In this test, compounds C-1, C-2, C-3, C-4, C-5, C-6, C-7, C-8, C-12, C-13, C-14, C-15, C-19, C-25, C-30, C-38, C-39, C-40, C-41, C-42, C-43, C-44, C-46, C-51, C-57 and C-58 at 800 ppm showed at least 75% mortality in comparison with untreated controls.

Example B2: Action on Orchid thrips (*Dichromothrips corbetti*)

*Dichromothrips corbetti* adults used for bioassay were obtained from a colony maintained continuously under laboratory conditions. For testing purposes, the test compound is diluted in a 1:1 mixture of acetone:water (vol:vol), plus Kinetic® HV at a rate of 0.01% v/v.

*Thrips* potency of each compound was evaluated by using a floral-immersion technique. All petals of individual, intact orchid flowers were dipped into treatment solution and allowed to dry in Petri dishes. Treated petals were placed into individual re-sealable plastic along with about adult *thrips*. All test arenas were held under continuous light and a temperature of about 28° C. for duration of the assay. After 3 days, the numbers of live *thrips* were counted on each petal. The percent mortality was recorded 72 hours after treatment.

In this test, compounds C-1, C-2, C-3, C-4, C-6, C-12, C-13, C-14, C-15, C-19, C-28, C-30, C37, C-38, C-39, C-40, C-41, C-42, C-43, C-44, C-45, C-46, C-51, C-52 and C-56 at 500 ppm showed at least 75% mortality in comparison with untreated controls.

Example B3: Action on Boll Weevil (*Anthonomus grandis*)

For evaluating control of boll weevil (*Anthonomus grandis*) the test unit consisted of 96-well-microtiter plates containing an insect diet and 5-10 *A. grandis* eggs.

The compounds were formulated using a solution containing 75% v/v water and 25% v/v DMSO. Different concentrations of formulated compounds were sprayed onto the insect diet at 5 μl, using a custom built micro atomizer, at two replications.

After application, microtiter plates were incubated at about 25±1° C. and about 75±5% relative humidity for 5 days. Egg and larval mortality was then visually assessed.

In this test, compounds C-1, C-2, C-3, C-4, C-5, C-6, C-7, C-8, C-12, C-15, C-17, C-18, C-19, C-22, C-23, C-24, C-25, C-28, C-29, C-30, C-33, C-34, C-37, C-38, C-39, C-40, C-41, C-42, C-43, C-44, C-45, C-46, C-50, C-51, C-55, C-56, C-57, C-58 and C-60 at 800 ppm showed at least 75% mortality in comparison with untreated controls.

Example B4: Action on Silverleaf Whitefly (*Bemisia argentifoli*) (Adults)

The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 5 or 10 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Cotton plants at the cotyledon stage (one plant per pot) were sprayed by an automated electrostatic plant sprayer equipped with an atomizing spray nozzle. The plants were dried in the sprayer fume hood and then removed from the sprayer. Each pot was pla-ced into a plastic cup and about 10 to 12 whitefly adults (approximately 3-5 days old) were introduced. The insects were collected using an aspirator and a nontoxic Tygon® tubing connected to a barrier pipette tip. The tip, containing the collected insects, was then gently inserted into the soil containing the treated plant, allowing insects to crawl out of the tip to reach the foliage for feeding.

Cups were covered with a reusable screened lid. Test plants were maintained in a growth room at about 25° C. and about 20-40% relative humidity for 3 days, avoiding direct exposure to fluorescent light (24 hour photoperiod) to prevent trapping of heat inside the cup. Mortality was assessed 3 days after treatment, compared to untreated control plants.

In this test, compounds C-3, C-6, C-12, C-13, C-14, C-28, C-39, C-40, C-42, C-55 and C-56 at 300 ppm showed at least 75% mortality in comparison with untreated controls.

Example B5: Action on Tobacco Budworm (*Heliothis virescens*)

For evaluating control of tobacco budworm (*Heliothis virescens*) the test unit consisted of 96-well-microtiter plates containing an insect diet and 15-25 *H. virescens* eggs.

The compounds were formulated using a solution containing 75% v/v water and 25% v/v DMSO. Different concentrations of formulated compounds were sprayed onto the insect diet at 10 µl, using a custom built micro atomizer, at two replications.

After application, microtiter plates were incubated at about 28±1° C. and about 80±5% relative humidity for 5 days. Egg and larval mortality was then visually assessed.

In this test, compounds C-1, C-2, C-3, C-6, C-7, C-8, C-12, C-13, C-14, C-15, C-17, C-18, C-19, C-22, C-23, C-24, C-25, C-29, C-30, C-33, C-34, C-37, C-38, C-39, C-40, C-41, C-42, C-43, C-44, C-45, C-46, C-47, C-50, C-51, C-55, C-56, C-57, C-58 and C-61 at 800 ppm showed at least 75% mortality in comparison with untreated controls.

Example B6: Action on Diamond Back Moth (*Plutella xylostella*)

The active compound is dissolved at the desired concentration in a mixture of 1:1 (vol:vol) distilled water:acetone. Surfactant (Kinetic® HV) is added at a rate of 0.01% (vol/vol). The test solution is prepared at the day of use.

Leaves of cabbage were dipped in test solution and air-dried. Treated leaves were placed in petri dishes lined with moist filter paper and inoculated with ten 3$^{rd}$ instar larvae. Mortality was recorded 72 hours after treatment. Feeding damages were also recorded using a scale of 0-100%.

In this test, compounds C-1, C-2, C-3, C-4, C-6, C-7, C-8, C-12, C-13, C-14, C-15, C-18, C-19, C-22, C-23, C-24, C-25, C-28, C-30, C-34, C-37, C-38, C-39, C-40, C-41, C-42, C-43, C-44, C-45, C-46, C-50, C-51, C-52, C-55, C-56, C-57, C-58, C-60 and C-61 at 500 ppm showed at least 75% mortality in comparison with untreated controls.

Example B7: Action on Southern Armyworm (*Spodoptera eridania*), 2nd Instar Larvae The active compounds were formulated by a Tecan liquid handler in 100% cyclohexanone as a 10,000 ppm solution supplied in tubes. The 10,000 ppm solution was serially diluted in 100% cyclohexanone to make interim solutions. These served as stock solutions for which final dilutions were made by the Tecan in 50% acetone:50% water (v/v) into 10 or 20 ml glass vials. A nonionic surfactant (Kinetic®) was included in the solution at a volume of 0.01% (v/v). The vials were then inserted into an automated electrostatic sprayer equipped with an atomizing nozzle for application to plants/insects.

Lima bean plants (variety Sieva) were grown 2 plants to a pot and selected for treatment at the 1$^{st}$ true leaf stage. Test solutions were sprayed onto the foliage by an automated electrostatic plant sprayer equipped with an atomizing spray nozzle. The plants were dried in the sprayer fume hood and then removed from the sprayer. Each pot was placed into perforated plastic bags with a zip closure. About 10 to 11 armyworm larvae were placed into the bag and the bags zipped closed. Test plants were maintained in a growth room at about 25° C. and about 20-40% relative humidity for 4 days, avoiding direct exposure to fluorescent light (24 hour photoperiod) to prevent trapping of heat inside the bags. Mortality and reduced feeding were assessed 4 days after treatment, compared to untreated control plants.

In this test, compounds C-1, C-3, C-6, C-7, C-8, C-12, C-13, C-14, C-15, C-17, C-18, C-19, C-22, C-23, C-38, C-39, C-40, C-42, C-43, C-44, C-45, C-46, C-51, C-55, C-57 and C-58 at 300 ppm showed at least 75% mortality in comparison with untreated controls.

We claim:
1. A compound of formula (I)

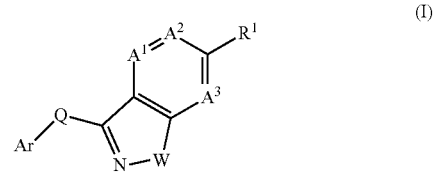

wherein
$A^1$ is N or $CR^A$;
$A^2$ is N or $CR^B$;
$A^3$ is N or $CR^{B1}$;
W is O, $S(=O)_m$, or $NR^6$;
$R^A$, $R^B$ and $R^{B1}$ independently of each other are H, halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C(=O)$—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, $C(=O)$—$NR^bR^c$, $C(=O)$—$R^d$, $SO_2NR^bR^c$, or $S(=O)_mR^e$, phenyl, phenoxy, phenylcarbonyl, phenylthio, or —$CH_2$-phenyl, wherein the phenyl rings are unsubstituted or substituted with $R^f$;
Q is —$C(R^4R^5)$—O—, —$C(=O)$—O—, —$S(=O)_m$—$C(R^7R^8)$—, —$N(R^2)$—$S(=O)_m$—, —$N(R^2)$—C($R^9R^{10}$)—, —$C(=O)$—$C(R^{19}R^{20})$—, —$N(R^2)$—C(=O)—, —$C(R^{13}R^{14})$—$C(R^{15}R^{16})$—, or —$C(R^{17})=C(R^{18})$—; wherein Ar is bound to either side of Q;
m is 0, 1, or 2;
$R^2$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)$—$OR^a$, $C_1$-$C_6$-alkylene-$NR^bR^c$, $C_1$-$C_6$-alkylene-CN, $C(=O)$—$NR^bR^c$, $C(=O)$—$R^d$, SO$_2$NR$^b$R$^c$, S($=$O)$_m$R$^e$, phenyl, or —CH$_2$-phenyl, wherein the phenyl rings are unsubstituted or substituted with R$^f$;

R$^4$, R$^5$, R$^7$, R$^8$, R$^9$, R$^{10}$, R$^{13}$, R$^{14}$, R$^{15}$, R$^{16}$, R$^{17}$, R$^{18}$, R$^{19}$, R$^{20}$ are, identical or different, H, halogen, C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, wherein the alkyl, alkoxy, alkenyl, alkynyl, cycloalkyl and cycloalkoxy moieties are unsubstituted or substituted with halogen, C($=$O)—OR$^a$, C$_1$-C$_6$-alkylene-NR$^b$R$^c$, C$_1$-C$_6$-alkylene-CN, C($=$O)—NR$^b$R$^c$, C($=$O)—R$^d$, SO$_2$NR$^b$R$^c$, S($=$O)$_m$R$^e$, phenyl, or —CH$_2$-phenyl, wherein the phenyl rings are unsubstituted or substituted with R$^f$;

R$^6$ is H, C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_3$-C$_6$-cycloalkoxy-C$_1$-C$_4$-alkyl, wherein the alkyl, alkoxy, alkenyl, alkynyl, cycloalkyl and cycloalkoxy moieties are unsubstituted or substituted with halogen, C($=$O)—OR$^a$, C$_1$-C$_6$-alkylene-NR$^b$R$^c$, C$_1$-C$_6$-alkylene-CN, C($=$O)—NR$^b$R$^c$, C($=$O)—R$^d$, SO$_2$NR$^b$R$^c$, S($=$O)$_m$R$^e$, phenyl, —CH$_2$—C($=$O)—OR$^a$, or —CH$_2$-phenyl, wherein the phenyl rings are unsubstituted or substituted with R$^f$;

Ar is phenyl or 5- or 6-membered hetaryl, which are unsubstituted or substituted with R$^{Ar}$, wherein R$^{Ar}$ is halogen, N$_3$, OH, CN, NO$_2$, —SCN, —SF$_5$, C$_1$-C$_6$-alkyl, C$_1$-C$_6$-alkoxy, C$_2$-C$_6$-alkenyl, tri-C$_1$-C$_6$-alkylsilyl, C$_2$-C$_6$-alkynyl, C$_1$-C$_6$-alkoxy-C$_1$-C$_4$-alkyl, C$_1$-C$_6$-alkoxy-C$_1$-C$_4$-alkoxy, C$_3$-C$_6$-cycloalkyl, C$_3$-C$_6$-cycloalkoxy, C$_3$-C$_6$-cycloalkyl-C$_1$-C$_4$-alkyl, C$_3$-C$_6$-cycloalkoxy-C$_1$-C$_4$-alkyl, wherein the alkyl, alkoxy, alkenyl, alkynyl, cycloalkyl and cycloalkoxy moieties are unsubstituted or substituted with halogen, C($=$O)—OR$^a$, NR$^b$R$^c$, C$_1$-C$_6$-alkylene-NR$^b$R$^c$, O—C$_1$-C$_6$-alkylene-NR$^b$R$^c$, C$_1$-C$_6$-alkylene-CN, NH—C$_1$-C$_6$-alkylene-NR$^b$R$^c$, C($=$O)—NR$^b$R$^c$, C($=$O)—R$^d$, SO$_2$NR$^b$R$^c$, or S($=$O)$_m$R$^e$, phenyl, phenoxy, phenylcarbonyl, phenylthio or —CH$_2$-phenyl, wherein phenyl rings are unsubstituted or substituted with R$^f$;

R$^1$ is a moiety of formula YZT-1 to YZT-9, wherein

denotes attachment to the 9 membered hetaryl;

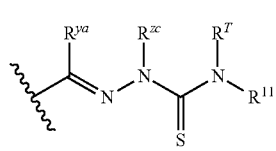

YZT-1

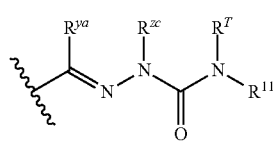

YZT-2

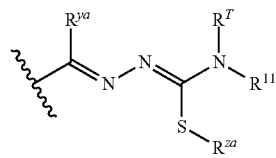

YZT-3

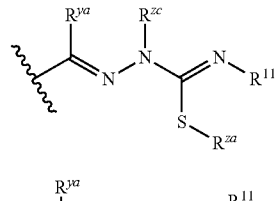

YZT-4

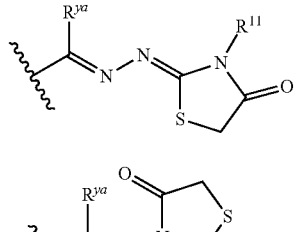

YZT-5

YZT-6

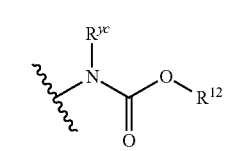

YZT-7

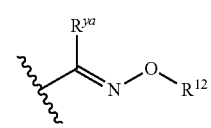

YZT-8

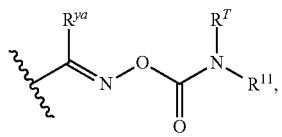

YZT-9

R$^{11}$ is C$_1$-C$_6$-alkyl, C$_2$-C$_6$-alkenyl, C$_2$-C$_6$-alkynyl, C$_1$-C$_6$-alkoxy-C$_1$-C$_4$-alkyl, C$_3$-C$_6$-cycloalkyl, C$_3$-C$_6$-cycloalkyl-C$_1$-C$_4$-alkyl, C$_1$-C$_4$-alkyl-C$_3$-C$_6$-cycloalkoxy, wherein the alkyl, alkoxy, alkenyl, alkynyl, cycloalkyl and cycloalkoxy moieties are unsubstituted or substituted with halogen, C$_1$-C$_6$-alkylene-NR$^b$R$^c$, C$_1$-C$_6$-alkylene-CN, C($=$O)—NR$^b$R$^c$, C($=$O)—R$^d$, aryl, aryl-carbonyl, aryl-C$_1$-C$_4$-alkyl, aryloxy-C$_1$-C$_4$-alkyl, hetaryl, carbonyl-hetaryl, hetaryl-C$_1$-C$_4$-alkyl or hetaryloxy-C$_1$-C$_4$-alkyl, wherein the phenyl rings are unsubstituted or substituted with R$^9$ and wherein the hetaryl is a 5- or 6-membered monocyclic hetaryl or a 8-, 9- or 10-membered bicyclic hetaryl;

$R^{12}$ is a radical of the formula $A^1$;

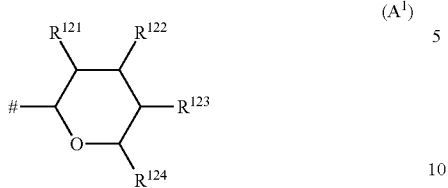

wherein # indicates the point of attachment to T;

$R^{121}$, $R^{122}$, $R^{123}$ are, identical or different, H, halogen, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_1$-$C_6$-alkoxy, $C_2$-$C_6$-alkenyloxy, $C_2$-$C_6$-alkynyloxy, $C_1$-$C_6$-alkoxy-$C_1$-$C_4$-alkoxy, $C_1$-$C_6$-alkylcarbonlyoxy, $C_1$-$C_6$-alkenylcarbonlyoxy, $C_3$-$C_6$-cycloalkylcarbonlyoxy, wherein the alkyl, alkoxy, alkenyl, alkenyloxy, alkynyl, alkynyloxy and cycloalkyl moieties are unsubstituted or substituted with halogen, or $NR^bR^c$, or one of $R^{121}$, $R^{122}$, $R^{123}$ may also be oxo;

$R^{124}$ is H, $C_1$-$C_6$-alkyl, $C_1$-$C_6$-alkoxy-$C_1$-$C_4$-alkyl, $C_1$-$C_6$-alkoxy, or $C_2$-$C_6$-alkenyloxy, wherein the alkyl, alkoxy, alkenyl and alkenyloxy moieties are unsubstituted or substituted with halogen;

and where $R^{ya}$ is H, halogen, $C_1$-$C_6$-alkyl, $C_1$-$C_6$-alkoxy, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_1$-$C_4$-alkyl-$C_3$-$C_6$-cycloalkyl, $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen, $C(=O)$—$OR^a$, $C_1$-$C_6$-alkylene-$NR^bR^c$, $C_1$-$C_6$-alkylene-CN, $C(=O)$—$NR^bR^c$, $C(=O)$—$R^d$, $SO_2NR^bR^c$, $S(=O)_mR^e$, phenyl, or —$CH_2$—phenyl, wherein the phenyl rings are unsubstituted or substituted with $R^f$;

$R^{yc}$, $R^{zc}$ are, identical or different, H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkyl, or $C_1$-$C_4$-alkyl-$C_3$-$C_6$-cycloalkoxy, wherein the alkyl, alkoxy, alkenyl, alkynyl, cycloalkyl and cycloalkoxy moieties are unsubstituted or substituted with halogen;

$R^T$ is H, $C_1$-$C_6$-alkyl, $C_2$-$C_6$-alkenyl, $C_2$-$C_6$-alkynyl, $C_1$-$C_4$-alkyl-$C_1$-$C_6$-alkoxy, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)$—$OR^a$, $C_1$-$C_6$-alkylene-$NR^bR^c$, $C_1$-$C_6$-alkylene-CN, $C(=O)$—$NR^bR^c$, $C(=O)$—$R^d$, $SO_2NR^bR^c$, $S(=O)_mR^e$, phenyl, or —$CH_2$—phenyl, wherein the phenyl rings are unsubstituted or substituted with $R^f$;

$R^{zc}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C=N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with Rh;

$R^{za}$ is H, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_4$-alkyl-$C_1$-$C_6$-alkoxy, $C_3$-$C_6$-cycloalkyl, $C_1$-$C_4$-alkyl-$C_3$-$C_6$-cycloalkoxy, $C_1$-$C_4$-alkyl-$C_3$-$C_6$-cycloalkyl, wherein the alkyl, alkoxy, alkenyl, alkynyl, cycloalkyl and cycloalkoxy moieties are unsubstituted or substituted with halogen, $C_1$-$C_6$-alkylene-$NR^bR^c$, $C_1$-$C_6$-alkylene-CN, $C(=O)$—$NR^bR^c$, $C(=O)$—$R^d$, phenyl, phenylcarbonyl, or —$CH_2$-phenyl, wherein the phenyl rings are unsubstituted or substituted with $R^f$;

$R^{za}$ together with $R^T$ if present, may form $C_1$-$C_6$-alkylene or a linear $C_2$-$C_6$-alkenylene group, where in the linear $C_1$-$C_6$-alkylene and the linear $C_2$-$C_6$-alkenylene a $CH_2$ moiety may be replaced by a carbonyl or a C=N—R' and/or wherein 1 or 2 $CH_2$ moieties may be replaced by O or S and/or wherein the linear $C_1$-$C_6$-alkylene and the linear $C_2$-$C_6$-alkenylene may be unsubstituted or substituted with $R^h$;

$R^a$, $R^b$ and $R^c$ are, identical or different, H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C_1$-$C_6$-alkylene-CN, phenyl, or —$CH_2$-phenyl, wherein the phenyl rings are unsubstituted or substituted with $R^f$;

$R^d$ is H, $C_1$-$C_6$-alkyl, $C_2$-$C_6$-alkenyl, $C_2$-$C_6$-alkynyl, $C_1$-$C_6$-alkoxy-$C_1$-$C_4$-alkyl, $C_3$-$C_6$-cycloalkyl, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, phenyl, or —$CH_2$-phenyl, wherein the phenyl rings are unsubstituted or substituted with $R^f$;

$R^e$ is $C_1$-$C_6$-alkyl, $C_3$-$C_6$-cycloalkyl, $C_3$-$C_6$-cycloalkyl-$C_1$-$C_4$-alkyl, wherein the alkyl, cycloalkyl moieties are unsubstituted or substituted with halogen, phenyl and —$CH_2$-phenyl, wherein the phenyl rings are unsubstituted or substituted with $R^f$;

$R^f$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl-$C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, $C(=O)$—$OR^a$, $NR^bR^c$, $C_1$-$C_6$-alkylene-$NR^bR^c$, O—$C_1$-$C_6$-alkylene-$NR^bR^c$, $C_1$-$C_6$-alkylene-CN, NH—$C_1$-$C_6$-alkylene-$NR^bR^c$, $C(=O)$—$NR^bR^c$, $C(=O)$—$R^d$, $SO_2NR^bR^c$, or $S(=O)_mR^e$;

$R^g$ is halogen, $N_3$, OH, CN, $NO_2$, —SCN, —$SF_5$, $C_1$-$C_6$-alkyl, $C_1$-$C_6$-alkoxy, $C_2$-$C_6$-alkenyl, tri-$C_1$-$C_6$-alkylsilyl, $C_2$-$C_6$-alkynyl, $C_1$-$C_6$-alkoxy-$C_1$-$C_4$-alkyl, $C_1$-$C_6$-alkoxy-$C_1$-$C_4$-alkoxy, $C_3$-$C_6$-cycloalkyl, $C_3$-$C_6$-cycloalkoxy, $C_3$-$C_6$-cycloalkyl- $C_1$-$C_4$-alkyl, $C_3$-$C_6$-cycloalkoxy-$C_1$-$C_4$-alkyl, wherein the alkyl, alkoxy, alkenyl, alkynyl, cycloalkyl and cycloalkoxy moieties are unsubstituted or substituted with halogen, C(=O)—OR$^a$, NR$^b$R$^c$, $C_1$-$C_6$-alkylene-NR$^b$R$^c$, O—$C_1$-$C_6$-alkylene-NR$^b$R$^c$, $C_1$-$C_6$-alkylene-CN, NH—$C_1$-$C_6$-alkylene-NR$^b$R$^c$, C(=O)—NR$^b$R$^c$, C(=O)—R$^d$, SO$_2$NR$^b$R$^c$, or S(=O)$_m$R$^e$;

R$^h$ is halogen, OH, $C_1$-$C_6$-alkyl, $C_3$-$C_6$-cycloalkyl, or CN;

with a proviso that when Z is a single bond, R$^T$ is other than H;

and the N-oxides, stereoisomers, tautomers and agriculturally or veterinarily acceptable salts thereof.

2. The compound of claim 1, wherein W is O, A$^1$ is CR$^A$, A$^2$ is CR$^B$, and A$^3$ is N.

3. The compound of claim 1, wherein W is NR$^6$, A$^1$ is CR$^A$, A$^2$ is CR$^B$, and A$^3$ is N.

4. The compound of claim 1, wherein W is O, A$^1$ is CR$^A$, A$^2$ is CR$^B$, and A$^3$ is CR$^{B1}$.

5. The compound of claim 1, wherein W is NR$^6$, A$^1$ is CR$^A$, A$^2$ is CR$^B$, and A$^3$ is CR$^{B1}$.

6. The compound of claim 1, wherein W is N, A$^1$ is N, A$^2$ is N, and A$^3$ is CR$^{B1}$.

7. The compound of claim 1, wherein W is S(=O)$_m$, A$^1$ is CR$^A$, A$^2$ is CR$^B$, and A$^3$ is CR$^{B1}$.

8. The compound of claim 1, wherein Ar is selected from formulas Ar-1 to Ar-16:

Ar-1

Ar-2

Ar-3

Ar-4

Ar-5

Ar-6

-continued

Ar-7
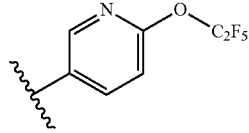

Ar-8
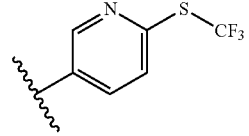

Ar-9
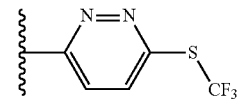

Ar-10
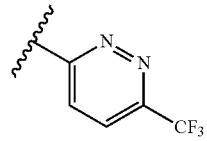

Ar-11
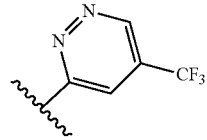

Ar-12
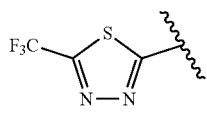

Ar-13
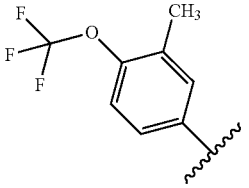

Ar-14
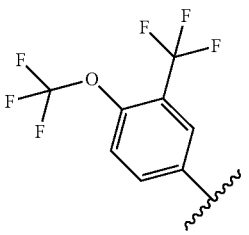

Ar-15
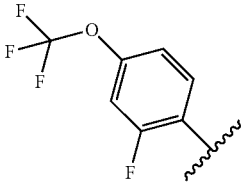

-continued

Ar-16

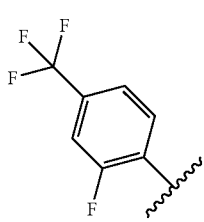

9. A composition, comprising a compound of claim 1, an N-oxide or an agriculturally acceptable salt thereof, and a further active substance.

10. A method for combating or controlling invertebrate pests, which method comprises contacting said pest or its food supply, habitat or breeding grounds with a pesticidally effective amount of at least a compound of claim 1.

11. A method for protecting growing plants from attack or infestation by invertebrate pests, which method comprises contacting a plant, or soil or water wherein the plant is growing, with a pesticidally effective amount of at least a compound of claim 1.

12. Seed treated with a compound of claim 1, or the enantiomers, diastereomers or salts thereof, in an amount of from 0.1 g to 10 kg per 100 kg of seed.

13. A method for treating or protecting an animal from infestation or infection by invertebrate pests which comprises bringing the animal in contact with a pesticidally effective amount of at least one compound of claim 1, a stereoisomer thereof and/or at least one veterinarily acceptable salt thereof.

14. The method of claim 10, wherein W is O, $A^1$ is $CR^A$, $A^2$ is $CR^B$, and $A^3$ is N.

15. The method of claim 10, wherein W is $NR^6$, $A^1$ is $CR^A$, $A^2$ is $CR^B$, and $A^3$ is N.

16. The method of claim 10, wherein W is O, $A^1$ is $CR^A$, $A^2$ is $CR^B$, and $A^3$ is $CR^{B1}$.

17. The method of claim 10, wherein W is $NR^6$, $A^1$ is $CR^A$, $A^2$ is $CR^B$, and $A^3$ is $CR^{B1}$.

18. The method of claim 10, wherein W is $NR^6$, $A^1$ is N, $A^2$ is N, and $A^3$ is $CR^{B1}$.

19. The method of claim 10, wherein W is $S(=O)_m$, $A^1$ is $CR^A$, $A^2$ is $CR^B$, and $A^3$ is $CR^{B1}$.

20. The method of claim 10, wherein Ar is selected from formulas Ar-1 to Ar-16:

Ar-1

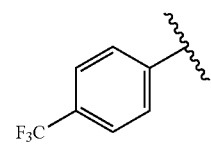

Ar-2

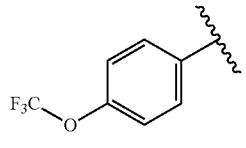

Ar-3

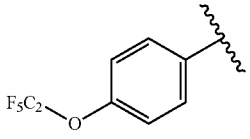

-continued

Ar-4

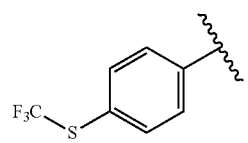

Ar-5

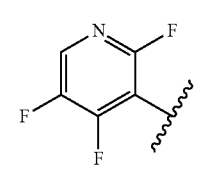

Ar-6

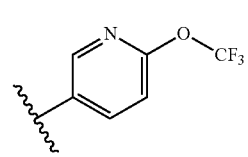

Ar-7

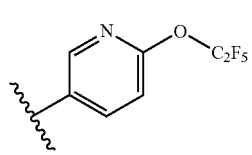

Ar-8

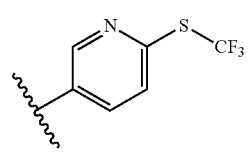

Ar-9

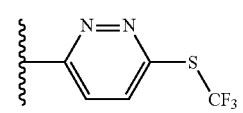

Ar-10

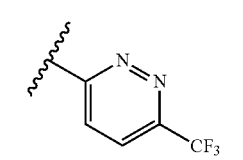

Ar-11

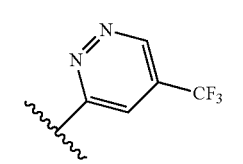

Ar-12

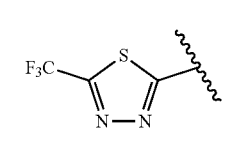

Ar-13

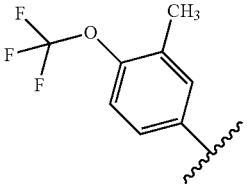

-continued
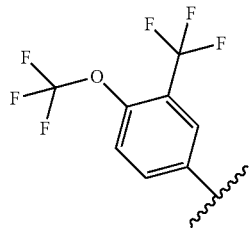
Ar-14
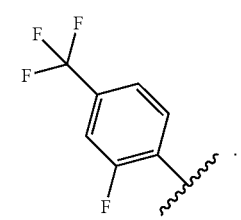
Ar-15
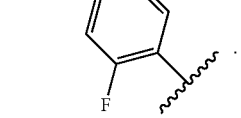
Ar-16
* * * * *